US009409906B2

(12) United States Patent
Sauvageau et al.

(10) Patent No.: US 9,409,906 B2
(45) Date of Patent: Aug. 9, 2016

(54) PYRIMIDO[4,5-B]INDOLE DERIVATIVES AND USE THEREOF IN THE EXPANSION OF HEMATOPOIETIC STEM CELLS

(71) Applicant: UNIVERSITÉ DE MONTRÉAL, Montréal (CA)

(72) Inventors: Guy Sauvageau, Montréal (CA); Yves Gareau, Notre-Dame de l'Ile-Perrot (CA); Réjean Ruel, Saint-Lambert (CA); Stéphane Gingras, Montréal (CA); Iman Fares, Montréal (CA)

(73) Assignee: UNIVERSITE DE MONTREAL, Montreal, Quebec (CA)

( * ) Notice: Subject to any disclaimer, the term of this patent is extended or adjusted under 35 U.S.C. 154(b) by 0 days.

(21) Appl. No.: 14/374,953

(22) PCT Filed: Jan. 25, 2013

(86) PCT No.: PCT/CA2013/050052
§ 371 (c)(1),
(2) Date: Jul. 28, 2014

(87) PCT Pub. No.: WO2013/110198
PCT Pub. Date: Aug. 1, 2013

(65) Prior Publication Data
US 2015/0011543 A1 Jan. 8, 2015

Related U.S. Application Data

(60) Provisional application No. 61/591,521, filed on Jan. 27, 2012.

(51) Int. Cl.
C07D 471/04 (2006.01)
C07D 487/04 (2006.01)
A61K 35/28 (2015.01)

(52) U.S. Cl.
CPC .............. C07D 471/04 (2013.01); A61K 35/28 (2013.01); C07D 487/04 (2013.01)

(58) Field of Classification Search
CPC ..... C07D 471/04; C07D 487/04; A61K 35/28
See application file for complete search history.

(56) References Cited

U.S. PATENT DOCUMENTS

| 7,795,024 B2 | 9/2010 | Madlambayan et al. |
| 2012/0238751 A1 | 9/2012 | Bensen et al. |

FOREIGN PATENT DOCUMENTS

| CA | 2 464 934 | * | 5/2003 | ........... C07D 487/04 |
| CA | 2464934 A1 | | 5/2003 | |
| GB | 1262864 | | 2/1972 | |
| WO | 93/20078 A1 | | 10/1993 | |
| WO | 95/19970 A1 | | 7/1995 | |
| WO | 97/02266 A1 | | 1/1997 | |
| WO | 98/42708 A2 | | 10/1998 | |
| WO | 00/28987 A1 | | 5/2000 | |
| WO | 00/35446 A1 | | 6/2000 | |
| WO | 00/66112 A1 | | 11/2000 | |
| WO | 00/66585 A1 | | 11/2000 | |
| WO | 01/17349 A1 | | 3/2001 | |
| WO | 01/21180 A1 | | 3/2001 | |
| WO | 01/34585 A1 | | 5/2001 | |
| WO | 01/39773 A1 | | 7/2001 | |
| WO | 01/89457 A2 | | 11/2001 | |
| WO | 02/49413 A2 | | 6/2002 | |
| WO | 02/085343 A1 | | 10/2002 | |
| WO | 02/089746 A2 | | 11/2002 | |
| WO | 03/037898 A1 | | 5/2003 | |
| WO | 03/103686 A1 | | 12/2003 | |
| WO | 2004/054515 A2 | | 7/2004 | |
| WO | 2004/058764 A1 | | 7/2004 | |
| WO | WO 2004/058764 | * | 7/2004 | ........... C07D 487/04 |
| WO | 2005/037825 A2 | | 4/2005 | |
| WO | 2006/116733 A2 | | 11/2006 | |
| WO | 2007/009120 A2 | | 1/2007 | |
| WO | 2007/022269 A2 | | 2/2007 | |
| WO | 2007/145227 A1 | | 12/2007 | |
| WO | 2008/028645 A1 | | 3/2008 | |
| WO | 2008/055233 A1 | | 5/2008 | |
| WO | 2008/073748 A1 | | 6/2008 | |
| WO | 2008079965 A1 | | 7/2008 | |
| WO | 2009/004329 A1 | | 1/2009 | |
| WO | WO 2009/004329 | * | 1/2009 | ........... C07D 471/14 |
| WO | 2010/006032 A1 | | 1/2010 | |
| WO | 2010059401 A2 | | 5/2010 | |

(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Reader, J.C. et al., Structure-Guided Evolution of Potent and Selective CHK1 Inhibitors through Scaffold Morphing. Journal of Med Chem Am Chem Soc. vol. 54. No. 24. 2011. pp. 8328-8342.
Boitano, AE. et al., "Aryl Hydrocarbon Receptor Antagonists Promote the Expansion of Humanhematopoietic Stem Cells" Science (2010) 329: pp. 1345-1348.
Nishino, T. et al., "Ex Vivo Expansion of Human Hematopoietic Stem Cells by Garcinol, A Potent Inhibitor of Histone Acetyltransferase" PLoS One, Sep. 2011 vol. 6 Issue 9: p. e24298.
Nishino, T. et al., "Ex Vivo Expansion of Human Hematopoietic Stem Cells by a Small-Molecule Agonist of c-MPL" Experimental Hematology, (2009) vol. 37, pp. 1364-1377.
Delaney, C. et al., "Notch-Mediated Expansion of Human Cord Blood Progenitor Cells Capable of Rapid Myeloid Reconstitution" Nature Medicine, Feb. 2010 vol. 16 No. 2: pp. 232-236.

(Continued)

Primary Examiner — Erich A Leeser
(74) Attorney, Agent, or Firm — Buchanan Ingersoll & Rooney P.C.

(57) ABSTRACT

Pyrimido[4,5-b]indole derivatives are provided. These compounds are useful to expand hematopoietic stem cell populations, particularly, human hematopoietic stem cell populations. The compounds are also useful in the medical treatment of diseases that involve hematopoietic stem cells.

49 Claims, 8 Drawing Sheets

(56) References Cited

FOREIGN PATENT DOCUMENTS

WO          2011/056739 A1      5/2011
WO          WO 2011/056739   *  5/2011   .............. A01N 43/54

OTHER PUBLICATIONS de Lima, M. et al., "Transplantation of Ex Vivo Expanded Cord Blood Cells Using the Copper Chelator Tetraethylenepentamine: A Phase I/II Clinical Trial" Bone Marrow Transplant (2008) vol. 41 No. 9: pp. 771-778.

Kishimoto, T., "Interleukin-6: From Basic Science to Medicine—40 Years in Immunology" Annu. Rev. Immunol 1 mm. (2005), vol. 23, pp. 1-21.

Smith, M.A. et al., "Stem Cell Factor: Biology and Relevance to Clinical Practice" ACT Haematologica; (2001) vol. 105 No. 3: pp. 143-150.

Hannum, C. et al., "Ligand for FLT/FLK2 Receptor Tyrosine Kinase Regulates Growth of Haematopoietic Stem Cells and is Encoded by Variant RNAs"; Nature; Apr. 14, 1994 vol. 368 (6472) pp. 643-648.

Kaushansky, K., "Lineage-Specific Hematopoietic Growth Factors" N. Engl. J. Med. May 11, 2006, vol. 354, No. 19: pp. 2034-2045.

Schwartz, R.M. et al., "Rapid Medium Perfusion Rate Significantly Increases the Productivity and Longevity of Human Bone Marrow Cultures" Proc. Natl. Acad. Sci. U.S.A. Aug. 1991; vol. 88, pp. 6760-6764.

Koller, M.R. et al., "Clinical-Scale Human Umbilical Cord Blood Cell Expansion in a Novel Automated Perfusion Culture System" Bone Marrow Transplant; (1998), vol. 21, pp. 653-663.

Koller, M.R. et al., "Large-Scale Expansion of Human Stem and Progenitor Cells From Bone Marrow Mononuclear Cells in Continuous Perfusion Cultures" Blood; Jul. 15, 1993; vol. 82, No. 2 pp. 378-384.

Astori, G. et al., Evaluation of ex vivo Expansion and Engraftment in NOD-SCID Mice of Umbilical Cord Blood CD34 + Cells Using the Dideco 'Pluricell System'; Bone Marrow Transplant; 2005; vol. 35; pp. 1101-1106.

Mosrin, M. et al., "Regio- and Chemoselective Metalation of Chloropyrimidine Derivatives With TMP2ZN.2Mgcl2.2LiCl**" Chemistry-A European; (2009), vol. 15, No. 6, pp. 1468-1477.

Zhang, Y. et al., "Synthesis of Pyrimido[4,5-b]Indoles and Benzo[4,5]Furo[2,3-d]Pyrimidines Via Palladium-Catalyzsed Intramolecular Arylation" Thtrahedron Letters.

Tully, W.R. et al., "2-(Oxadiazolyl)—and 2-(Thiazolyl)imidazo[1,2-a]pyrimidines as Agonists and Inverse Agonists at Benzodiazepine Receptors" Journal of Medicinal Chemistry, 1991, vol. 34, pp. 2060-2067.

* cited by examiner

PYRIMIDO[4,5-B]INDOLE DERIVATIVES AND USE THEREOF IN THE EXPANSION OF HEMATOPOIETIC STEM CELLS

CROSS-REFERENCED TO RELATED APPLICATION

This application claims the benefit of priority to U.S. Provisional Application No. 61/591,521, filed 27 Jan. 2012. The full disclosure of this application is incorporated herein by reference in its entirety.

FIELD OF THE INVENTION

The invention relates to pyrimido[4,5-b]indole derivatives. Also, the invention relates to use of pyrimido[4,5-b]indole derivatives for expanding hematopoietic stem cells. Moreover, the invention relates to medical treatments of diseases involving hematopoietic stem cells.

BACKGROUND OF THE INVENTION

The main sources of hematopoietic stem cells (HSCs) are the bone marrow and the umbilical cord blood (UCB). HSCs are used in the transplantation setting (autologous or allogeneic) which constitutes one of the most effective treatment strategies for achieving cures in patients with hematologic malignancies, bone marrow failure conditions, a variety of congenital diseases of global concern (e.g. sickle cell anemia and thalassemia) and autoimmune diseases such as lupus. However, this opportunity for life-saving or life-improving treatment is not available to many thousands of people worldwide due to an inability to amplify these cells ex vivo sufficiently to make the procedure safe and successful. More particularly, for every 3 patients, one will forego the opportunity for transplant because no human leucocyte antigen (HLA) identical donor can be found. Another proportion of patients will not have access to transplantation simply because too few HSCs are available in the graft (i.e. cord blood or autologous) for successful transplant. The safety and efficacy of marrow transplant is directly dependent on the number of HSCs and progenitor cells available for engrafting. The more that can be infused, the more rapidly is hematologic function restored, and the shorter is the window of risk for infection due to lack of granulocytes or of bleeding due to lack of platelets. The challenge in providing sufficient HSCs is further escalated where non-myeloablative conditioning is preferred such as in the context of gene therapy for major inherited blood disorders (the major genetic cause of morbidity and mortality worldwide).

In adults, HSCs mainly reside in the bone marrow and must be mobilized to enter the circulation prior to being collected by apheresis, either for autologous or allogeneic hematopoietic stem cell transplantation (HSCT). The collection of an adequate number of CD34+ cells, a surrogate marker of (HSCs), is paramount because the dose of CD34+ cells influences the success and rate of hematopoietic recovery. Several reports suggest that a higher infused CD34+ cell dose is independently predictive of improved survival.

The two most commonly used mobilizing regimens are granulocyte-colony stimulating factor (G-CSF) and G-CSF plus chemotherapy. Plerixafor, a CXCR4 antagonist approved by the United States Food and Drug Administration (FDA) in 2008 and in 2011 by Health Canada, enhances mobilization of HSCs when administered with G-CSF. However, Plerixafor is contraindicated in patients with leukemia because of mobilization of leukemic cells. Inability to obtain sufficient numbers of CD34+ cells/kg with currently used mobilization regimens is estimated to affect up to 15% of patients (varies between diseases). Use of autologous HSCT in hematological malignancies is often limited by the fact that both normal and cancer stem cells are present in the bone marrow and thus, likely to be mobilized.

Allogeneic HSCT with BM or mPBSC is another transplantation alternative. However, about one third to one fourth of the patients who are eligible for this type of transplant cannot find a suitable donor. For those who get transplanted, there is a high frequency of transplant related mortality due to graft-versus-host disease, relapse or graft rejection; and a risk of immunodeficiency for prolonged periods of time. Alternatively, umbilical cord blood has been shown as a valid option in allogeneic HSCT. However, a single CB unit typically provides insufficient HSCs for an adult patient for a rapid and efficient hematopoietic recovery.

In vitro conditions that support cytokine-mediated short-term maintenance or even modest increase in murine or human HSC numbers measured by mouse reconstitution assays are generally accompanied by much more robust increase in later types of progenitor cell populations. More marked increases in murine and human HSCs have more recently been described in cultures containing other factors such as fibroblast growth factor (FGF), insulin-like growth factor binding proteins, angiopoietin-like growth factors and pleiotrophin. However, these latter reports are thus far solitary and await independent confirmation. Short-term increases in HSCs obtained with standard cytokines in vitro are also inevitably followed by eventual HSC depletion.

Alternative strategies for human HSC expansion have involved their culture with stromal elements or soluble morphogenic ligands (e.g. stimulating the Notch, Wnt and Hedgehog pathways), targeted manipulation of specific intracellular signaling pathways (PGE2, ROS, p38 and MAPK inhibitors) or manipulation of specific transcription factors (e.g. Hox, Hlf). Other preclinical approaches for ex vivo expansion of HSCs include incubation with: i) StemRegenin1 (SR1), an aryl hydrocarbon receptor antagonist (Boitano, A E et al. "Aryl hydrocarbon receptor antagonists promote the expansion of human hematopoietic stem cells" *Science* 329: 1345-1348. 2010); ii) Garcinol, a histone acetyltransferase inhibitor (Nishino, T et al. "Ex vivo expansion of human hematopoietic stem cells by Garcinol, a potent inhibitor of histone acetyltransferase" *PLoS ONE* 6(9): e24298. 2011); and iii) NR-101, a non peptidyl small molecule c-MPL agonist (Nishino et al. "Ex vivo expansion of human hematopoietic stem cells by a small-molecule agonist of c-MPL" *Exp. Hem.* 2009; 37:1364-1377). Characterization of SR1 provided a proof of principle that low molecular weight (LMW) compounds have the ability to promote HSC expansion.

Clinical studies have stressed the requirement not only for permanence of the administered transplants, but also the importance of minimizing the time to appearance of useful granulocyte levels post-transplant which, in turn, depends on the number of short term repopulating cells infused. Transplantation of marrow or cord blood cells expanded in culture with cytokines has not so far demonstrated clinically useful acceleration of hematopoietic recovery compared to untreated cells. Early results of trials with cells expanded using immobilized Notch ligands have been the first to show potential clinical utility for any (even modest) progenitor cell expansion strategy (Delaney et al. "Notch-mediated expansion of human cord blood progenitor cells capable of rapid myeloid reconstitution" *Nat. Med.* 16(2): 232-236. 2010). This approach is however limited by the need to use an immobilized Delta-1 fusion protein during the ex vivo expansion step and by the lack of documented effect on stem cells (impact appears limited to more differentiated progenitors). Other approaches in clinical trial include: i) StemEx, a combination of UCB cells cultured with the copper chelator tetraethylenepentamine (TEPA) and cytokines, co-infused with non-treated UCB cells; phase I results show that time to neutrophil or platelet engraftment was not improved compared to previous reports (de Lima M et al. "Transplantation of ex vivo expanded cord blood cells using the copper chelator tetraethylenepentamine: a phase I/II clinical trial" *Bone Marrow Transplant.* 2008; 41(9): 771-778); and 16-16 dimethyl prostaglandin E2 (PGE2), used for improving homing of UCBT in a phase I trial.

There is thus a need for novel strategies for increasing the expansion of hematopoietic stem and progenitor cells. Certain pyrimido[4,5-b]indole derivatives are known in the art that are used in that regard; they are disclosed for example in: WO 2003/037898; WO 2004/058764; WO 1998/042708; WO 1997/002266; WO 2000/066585; WO 1993/020078; WO 2006/116733; WO 2008/055233; WO 2010/006032; WO 1995/019970; WO 2005/037825; and WO 2009/004329. However, these documents do not disclose the pyrimido[4,5-b]indole derivatives according to the invention or their use in the expansion of hematopoietic stem and progenitor cells.

SUMMARY OF THE INVENTION

Figure 1:
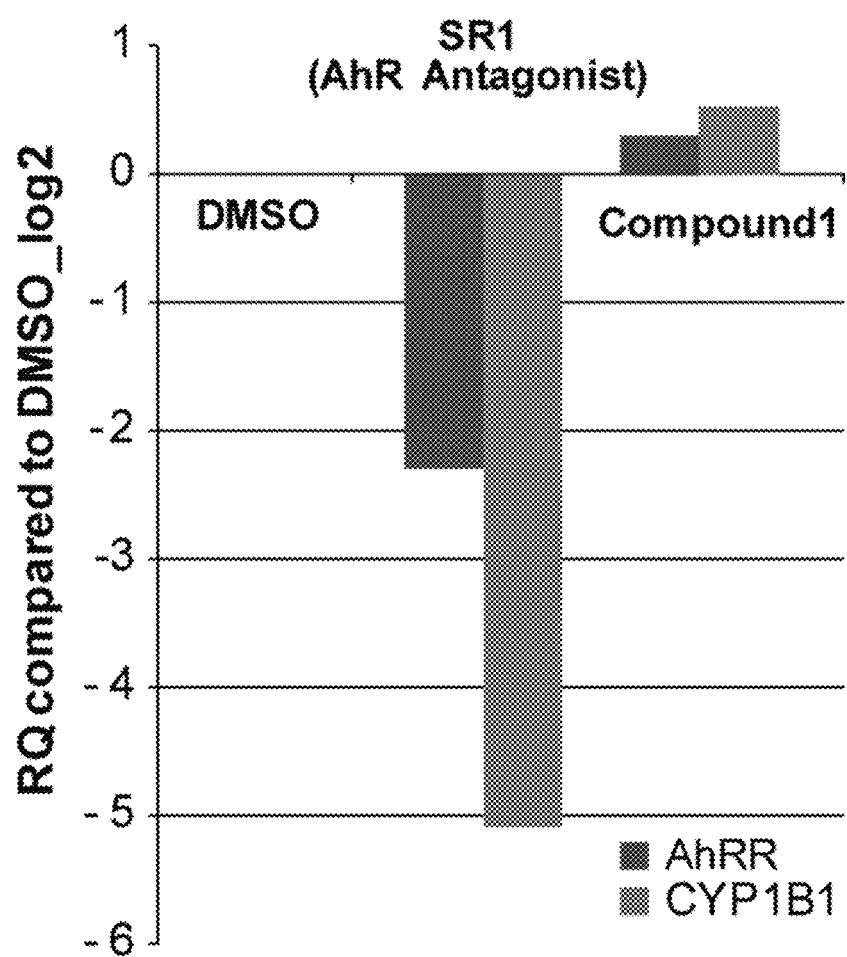
FIG. 1: Compound 1 does not act through aryl hydrocarbon (AhR) pathway. Mobilized peripheral blood CD34(+) cells were cultured for 12 hours with DMSO, SR1 [AhR antagonist 1000 nM], and Compound 1 [500 nM], cells were harvested and real-time quantitative RT-PCR for AhR-responsive genes (CYP1B1 and AhRR) was performed. Compound 1 unlike SR1, does not suppress AhR-downstream target genes suggesting that its function is independent on AhR pathway.

The inventors have discovered certain pyrimido[4,5-b]indole derivatives. These compounds are useful to expand hematopoietic stem cell populations, particularly, human hematopoietic stem cell populations. The compounds are also useful in the medical treatment of diseases that involve hematopoietic stem cells.

According to an aspect, the invention provides for compounds of the following general formulas I, II, III, IV, V and VI:

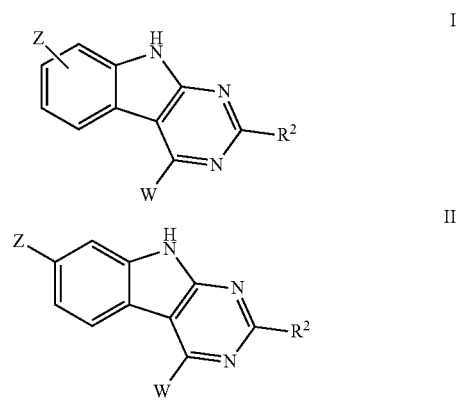

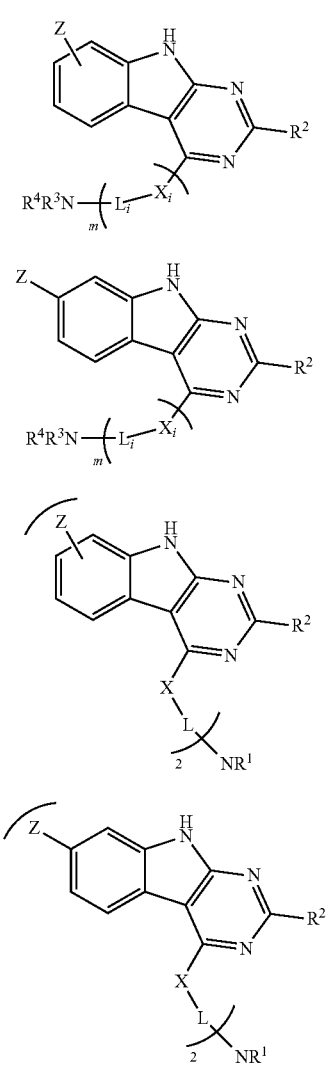

The substituents in the above general formulas I, II, III, IV, V and VI, namely, Z, W, L, Li, X, $X_i$, $R^1$, $R^2$, $R^3$, $R^4$ and m are as defined herein below.

According to an aspect, the invention provides for pharmaceutical compositions comprising a compound of general formula I, II, III, IV, V or VI.

According to an aspect, the invention provides for use of a compound of general formula I, II, III, IV, V or VI to expand hematopoietic stem cells. In embodiments of the invention, the hematopoietic stem cells are human cells.

According to an aspect, the invention provides for a method of increasing hematopoietic stem cells or progenitor cells, the method comprising culturing a starting cell population in the presence of a compound of general formula I, II, III, IV, V or VI. In embodiments of the invention, the starting cell population is in vivo, in vitro or ex vivo. Also, in embodiments of the invention, the starting cell population comprises CD34+ cells harvested from mobilized peripheral blood (mPB), bone marrow (BM) or umbilical cord blood (UCB). Moreover, in embodiments of the method according to the invention, optionally, culture of the starting cell population in the presence of a compound of general formula I, II, III, IV, V or VI in performed together with at least one cell expanding factor which is a biologic or another small molecule.

According to an aspect, the invention provides for a cell population expanded according to the method of the invention, more specifically, a cell population expanded using a compound according to the invention. In embodiments, the invention provides for hematopoietic stems cells expanded according to the method of the invention, more specifically, hematopoietic stems cells expanded using a compound according to the invention.

According to an aspect, the invention provides for a method of treating a hematopoietic disorder/malignancy, an autoimmune disease and/or an inherited immunodeficient disease in a subject, the method comprising administering to the subject in need of such treatment hematopoietic stem cells expanded using a compound of general formula I, II, III, IV, V or VI, or a compound of general formula I, II, III, IV, V or VI.

In embodiments of the invention, the hematopoietic disorder/malignancy, the autoimmune disease and/or the inherited immunodeficient disease comprise bone marrow failure conditions, a variety of congenital diseases of global concern (e.g. sickle cell anemia and thalassemia), lupus, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease among others).

According to an aspect, the invention provides for a kit for use in increasing stem or progenitor cells or in expanding hematopoietic stem cells, the kit comprising a compound of general formula I, II, III, IV, V or VI, and instructions for use. In embodiments of the invention, the kit comprises at least one cell expanding factor which is a biologic or another small molecule.

DETAILED DESCRIPTION OF THE INVENTION

The inventors have discovered certain pyrimido[4,5-b]indole derivatives. These compounds are useful to expand hematopoietic stem cell populations, particularly, human hematopoietic stem cell populations. The compounds are also useful in the medical treatment of diseases that involve hematopoietic stem cells.

The compounds according the invention have the general Formula I, II, III, IV, V or IV shown below. Salts or prodrugs of such compounds are also within the scope of the compounds according to the invention.

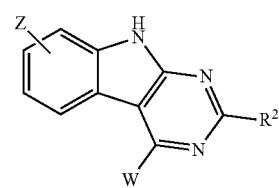

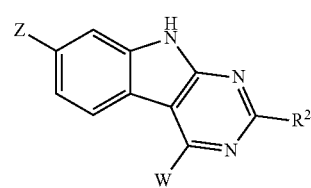

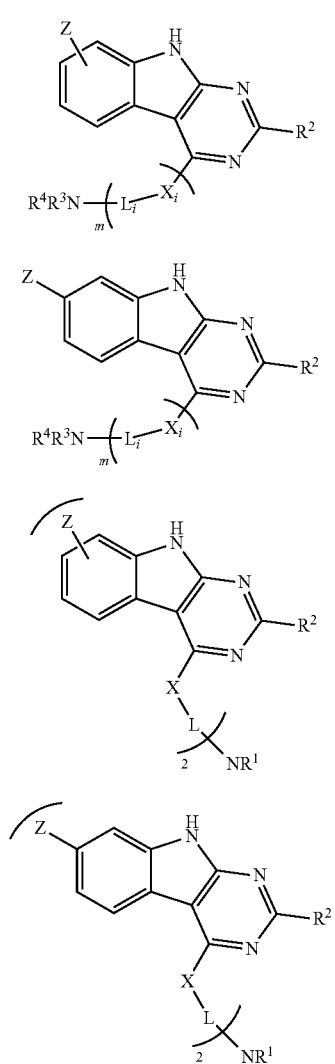

In formulas I, II, III, IV, V and VI, the substituents are defined as outlined below.

Z is: 1) —P(O)(OR$^1$)(OR$^1$), 2) —C(O)OR$^1$, 3) —C(O)NHR$^1$, 4) —C(O)N(R$^1$)R$^1$, 5) —C(O)R$^1$, 6) —CN, 7) —SR$^1$, 8) —S(O)$_2$NH$_2$, 9) —S(O)$_2$NHR$^1$, 10) —S(O)$_2$N(R$^1$)R$^1$, 11) —S(O)R$^1$, 12) —S(O)$_2$R$^1$, 13) -L, 14) -benzyl optionally substituted with 1, 2 or 3 R$^4$ or R$^1$ substituents, 15) -L-heteroaryl optionally substituted with one or more R$^4$ or R$^1$ substituents attached on either or both the L and the heteroaryl groups, 16) -L-heterocyclyl optionally substituted with one or more R$^4$ or R$^1$ substituents attached on either one or both the L and the heterocyclyl groups, 17) -L-aryl optionally substituted with one or more R$^4$ or R$^1$ substituents attached on either or both the L and the heteroaryl groups, 18) -heteroaryl optionally substituted with one or more R$^4$ or R$^1$ substituents, or 19) -aryl optionally substituted with one or more R$^4$ or R$^1$ substituents. In this list, each substituent is optionally attached to the L group if it is not already present; and, when (R$^1$) and R$^1$ are attached to a nitrogen atom, optionally they join together with the nitrogen atom to form a 3 to 7-membered ring which optionally includes one or more other heteroatom selected from N, O and S, optionally the ring is substituted with one or more R$^1$ or R$^4$.

W is H, a halogen or a group that is attached to the pyrimido indole core of the molecule through an atom which is N, O, S, or C. Optionally, W comprises at least one moiety which is saturated, unsaturated, linear, branched and/or cyclic alkyl and/or heteroalkyl having 1 to 20 carbon atoms. Also, optionally, the moiety comprises at least one other hetero atom which is N, O or S. As will be understood by a skilled person, W in the chemical structure of the compounds according to the invention can belong to various categories of chemical groups commonly used in the art.

More specifically, W is: 1) —H, 2) -halogen, 3) —OR$^1$, 4) -L-OH, 5) -L-OR$^1$, 6) —SR$^1$, 7) —CN, 8) —P(O)(OR$^1$)(OR$^1$), 9) —NHR$^1$, 10) —N(R$^1$)R$^1$, 11) -L-NH$_2$, 12) -L-NHR$^1$, 13) -L-N(R$^1$)R$^1$, 14) -L-SR$^1$, 15 -L-S(O)R$^1$, 16) -L-S(O)$_2$R$^1$, 17) -L-P(O)(OR$^1$)(OR$^1$), 18) —C(O)OR$^1$, 19) —C(O)NH$_2$, 20) —C(O)NHR$^1$, 21) —C(O)N(R$^1$)R$^1$, 22) —NHC(O)R$^1$, 23) —NR$^1$C(O)R$^1$, 24) —NHC(O)OR$^1$, 25) —NR$^1$C(O)OR$^1$, 26) —OC(O)NH$_2$, 27) —OC(O)NHR$^1$, 28) —OC(O)N(R$^1$)R$^1$, 29) —OC(O)R$^1$, 30) —C(O)R$^1$, 31) —NHC(O)NH$_2$, 32) —NHC(O)NHR$^1$, 33) —NHC(O)N(R$^1$)R$^1$, 34) —NR$^1$C(O)NH$_2$, 35) —NR$^1$C(O)NHR$^1$, 36) —NR$^1$C(O)N(R$^1$)R$^1$, 37) —NHS(O)$_2$R$^1$, 38) —NR$^1$S(O)$_2$R$^1$, 39) —S(O)$_2$NH$_2$, 40) —S(O)$_2$NHR$^1$, 41) —S(O)$_2$N(R$^1$)R$^1$, 42) —S(O)R$^1$, 43) —S(O)$_2$R$^1$, 44) —OS(O)$_2$R$^1$, 45) —S(O)$_2$OR$^1$, 46) -benzyl optionally substituted with 1, 2 or 3 R$^4$ or R$^1$ substituents, 47) -L-heteroaryl optionally substituted with one or more R$^4$ or R$^1$ substituents attached on either or both the L and the heteroaryl groups, 48) -L-heterocyclyl optionally substituted with one or more R$^4$ or R$^1$ substituents attached on either or both the L and the heterocyclyl groups, 49) -L-aryl optionally substituted with one or more R$^4$ or R$^1$ substituents attached on either or both the L and aryl optionally substituted with one or more R$^4$ or R$^1$ substituents attached on either or both the L and heteroaryl groups, 54) -L-(N(R$^1$)-L)$_n$-heterocyclyl optionally substituted with one or more R$^4$ or R$^1$ substituents attached on either or both the L and heterocyclyl groups, 55) -L-(N(R$^1$)-L)$_n$-aryl optionally substituted with one or more R$^4$ or R$^1$ substituents attached on either or both the L and aryl groups, 56) —O-L-N(R$^1$)R$^1$, 57) —O-L-heteroaryl optionally substituted with one or more R$^4$ or R$^1$ substituents attached on either or both the L and heteroaryl groups, 58) —O-L-heterocyclyl optionally substituted with one or more R$^4$ or R$^1$ substituents attached on either or both the L and heterocyclyl groups, 59) —O-L-aryl optionally substituted with one or more R$^4$ or R$^1$ substituents attached on either or both the L and aryl groups, 60) —O-L)$_2$-NR$^1$, 61) —O-L-(N(R$^1$)-L)$_n$-N(R$^1$)R$^1$, 62) —O-L-(N(R$^1$)-L)$_n$-heteroaryl optionally substituted with one or more R$^4$ or R$^1$ substituents attached on either or both the L and heteroaryl groups, 63) —O-L-(N(R$^1$)-L)$_n$-heterocyclyl optionally substituted with one or more R$^4$ or R$^1$ substituents attached on either or both the L and heterocyclyl groups, 64) —O-L-(N(R$^1$)-L)$_n$-aryl optionally substituted with one or more R$^4$ or R$^1$ substituents, 65) —S-L-heteroaryl optionally substituted with one or more R$^4$ or R$^1$ substituents, 66) —S-L-heterocyclyl optionally substituted with one or more R$^4$ or R$^1$ substituents, 67) —S-L-aryl optionally substituted with one or more R$^4$ or R$^1$ substituents attached on either or both the L and aryl groups, 68) —S-L)$_2$NR$^1$, 69) —S-L-(N(R$^1$)-L)$_n$-N(R$^1$)R$^1$, 70) —S-L-(N(R$^1$)-L)$_n$-heteroaryl optionally substituted with one or more R$^4$ substituents, 71) —S-L-(N(R$^1$)-L)$_n$-heterocyclyl optionally substituted with one or more R$^4$ substituents, 72) —S-L-(N(R$^1$)-L)$_n$-aryl optionally substituted with one or more R$^4$ substituents, 73) —NR$^1$(R$^1$), 74) —(N(R$^1$)-L)$_n$-N(R$^1$)R$^1$, 75) —N(R$^1$)L)$_2$-NR$^1$, 76) —(N(R$^1$)-L)$_n$-N(R$^1$)R$^4$, 77) —(N(R$^1$)-L)$_n$-heteroaryl optionally substituted with one or more R$^4$ or R$^1$ substituents, 78) —(N ($R^1$)-L)$_n$-heterocyclyl optionally substituted with one or more $R^4$ or $R^1$ substituents, 79) —(N($R^1$)-L)$_n$-aryl optionally substituted with one or more $R^4$ or $R^1$ substituents, 80) -heteroaryl optionally substituted with one or more $R^4$ substituents, or 81) -aryl optionally substituted with one or more $R^4$ substituents. In this list, each substituent is optionally attached to the L group if it is not already present; and when two $R^1$ substituents are present on the same nitrogen atom, then each $R^1$ substituent is independently selected from the list of $R^1$ values described thereafter; and n is an integer equal to either 0, 1, 2, 3, 4, or 5; and, when ($R^1$) and $R^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^4$.

L is: 1) —$C_{1-6}$ alkyl, 2) —$C_{2-6}$ alkenyl, 3) —$C_{2-6}$ alkynyl, 4) —$C_{3-7}$ cycloalkyl, 5) —$C_{3-7}$ cycloalkenyl, 6) heterocyclyl, 7) —$C_{1-6}$ alkyl-$C_{3-7}$ cycloalkyl, 8) —$C_{1-6}$ alkyl-heterocyclyl, 9) aryl, or 10) heteroaryl. In this list, the alkyl, the alkenyl, the alkynyl, the cycloalkyl, the cycloalkenyl, the heterocyclyl, the aryl and the heteroaryl groups are each independently optionally substituted with one or two $R^4$ substituent.

$R^1$ is: 1) —H, 2) —$C_{1-6}$ alkyl, 3) —$C_{2-6}$ alkenyl, 4) —$C_{2-6}$ alkynyl, 5) —$C_{3-7}$ cycloalkyl, 6) —$C_{3-7}$ cycloalkenyl, 7) —$C_{1-5}$ perfluorinated, 8) -heterocyclyl, 9) -aryl, 10) -heteroaryl, 11) -benzyl, or 12) 5-[(3aS,4S,6aR)-2-oxohexahydro-1H-thieno[3,4-d]imidazol-4-yl]pentanoyl. In this list, the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 $R^4$ or $R^1$ substituents.

$R^2$ is: 1) —H, 2) —$C_{1-6}$ alkyl, 3) —$SR^1$, 4) —C(O)$R^1$, 5) —S(O)$R^1$, 6) —S(O)$_2R^1$, 7) -benzyl optionally substituted with 1, 2 or 3 $R^4$ or $R^1$ substituents, 8) -L-heteroaryl optionally substituted with one or more $R^4$ or $R^1$ substituents attached on either one or both the L and the heteroaryl groups, 9) -L-heterocyclyl optionally substituted with one or more $R^4$ or $R^1$ substituents attached on either one or both the L and the heterocyclyl groups, 10) -L-aryl optionally substituted with one or more $R^4$ or $R^1$ substituents attached on either one or both the L and the aryl groups, 11) -heteroaryl optionally substituted with one or more $R^4$ or $R^1$ substituents, or 12) -aryl optionally substituted with one or more $R^4$ or $R^1$ substituents. In this list, each substituent is optionally attached to the L group if it is not already present.

$R^4$ is: 1) -halogen, 2) —$CF_3$, 3) —OH, 4) —$OR^1$, 5) -L-OH, 6) -L-$OR^1$, 7) —$OCF_3$, 8) —SH, 9) —$SR^1$, 10) —CN, 11) —$NO_2$, 12) —$NH_2$, 13) —$NHR^1$, 14) —$NR^1R^1$, 15) -L-$NH_2$, 16) -L-$NHR^1$, 17) -L-$NR^4R^1$, 18) -L-$SR^1$, 19) -L-S(O)$R^1$, 20) -L-S(O)$_2R^1$, 21) —C(O)OH, 22) —C(O)$OR^1$, 23) —C(O)$NH_2$, 24) —C(O)$NHR^1$, 25) —C(O)N($R^1$)$R^1$, 26) —NHC(O)$R^1$, 27) —$NR^1$C(O)$R^1$, 28) —NHC(O)$OR^1$, 29) —$NR^1$C(O)$OR^1$, 30) —OC(O)$NH_2$, 31) —OC(O)$NHR^1$, 32) —OC(O)N($R^1$)$R^1$, 33) —OC(O)$R^1$, 34) —C(O)$R^1$, 35) —NHC(O)$NH_2$, 36) —NHC(O)$NHR^1$, 37) —NHC(O)N($R^1$)$R^1$, 38) —$NR^1$C(O)$NH_2$, 39) —$NR^1$C(O)$NHR^1$, 40) —$NR^1$C(O)N($R^1$)$R^1$, 41) —NHS(O)$_2R^1$, 42) —$NR^1$S(O)$_2R^1$, 43) —S(O)$_2NH_2$, 44) —S(O)$_2NHR^1$, 45) —S(O)$_2$N($R^1$)$R^1$, 46) —S(O)$R^1$, 47) —S(O)$_2R^1$, 48) —OS(O)$_2R^1$, 49) —S(O)$_2OR^1$, 50) -benzyl, 51) —N3, or 52) —C(—N═N—)(CF$_3$). In this list, the benzyl group is optionally substituted with 1, 2 or 3 $R^4$ or $R^1$ substituents In embodiments of the invention, the compounds have the general Formula IIA, IIB, IIC, IVA or VIA shown below. Salts or prodrugs of such compounds are also within the scope of the compounds according to the invention.

IIA

IIB

IIC

IVA

VIA

In embodiments of the invention according to compounds of general formula IIA above, $R^1$, W and $R^2$ are each as defined herein above.

In embodiments of the invention according to compounds of general formula IIB above, W and $R^2$ are each as defined herein above, and Het is a 3 to 7-membered heterocycle, optionally substituted with one or more $R^1$ or $R^4$ as defined herein above.

In embodiments of the invention according to compounds of general formula IIC above, W and $R^2$ are each as herein above; $R^5$ and $R^6$ are the same or different and are each independently L as defined herein above, or they join together with C to form a 5 to 7-membered ring which optionally includes one or more heteroatom selected from N, O and S, and optionally the ring is substituted with one or more $R^1$ or $R^4$. In further embodiments, the ring is a 5-membered ring and the heteroatom is a nitrogen atom. Still in further embodiments, the ring includes four nitrogen atoms. Still in further embodiments, $R^2$ is benzyl.

In embodiments of the invention according to compounds of general formula IVA above, W, L, $R^1$ and $R^2$ are each as defined herein above. Also, m, Li, $R^3$ and $R^4$ are each as defined herein above.

In embodiments of the invention according to compounds of general formula VIA above, Z is $CO_2Me$ or 2-methyl-2H-tetrazol-5-yl; $R^2$ is benzyl, 3-thienylmethyl or 3-pyridinyl methyl; and W is NH-L-N($R^1$)$R^1$ wherein L is $C_{2-4}$ alkyl and $R^1$ is $C_{1-4}$ alkyl or ($R^1$) and $R^1$ join together with the nitrogen atom to which they are attached to form a 3 to 7-membered ring, which optionally includes one or more other heteroatom selected from N, O and S, optionally the ring is substituted with one or more $R^1$ or $R^4$.

In embodiments of the invention, the compounds of the invention are compounds No. 1 to 55 depicted in Table 1 herein below. Salts or prodrugs of such compounds are also within the scope of the compounds according to the invention.

In further embodiments of the invention, the compounds have the formulas depicted in Table 1 herein below. Salts or prodrugs of such compounds are also within the scope of the compounds according to the invention.

DEFINITIONS

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of." Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ in $C_1$-$C_6$ alkyl is defined as including groups having 1, 2, 3, 4, 5 or 6 carbons in a linear or branched saturated arrangement. Examples of $C_1$-$C_6$ alkyl as defined above include, but are not limited to, methyl, ethyl, n-propyl, i-propyl, n-butyl, t-butyl, i-butyl, pentyl, and hexyl.

As used herein, the term "cycloalkyl" is intended to mean a monocyclic saturated aliphatic hydrocarbon group having the specified number of carbon atoms therein, for example, $C_3$-$C_7$ in $C_3$-$C_7$ cycloalkyl is defined as including groups having 3, 4, 5, 6 or 7 carbons in a monocyclic saturated arrangement. Examples of $C_3$-$C_7$ cycloalkyl as defined above include, but are not limited to, cyclopropyl, cyclobutyl, cyclopentyl, cyclohexyl and cycloheptyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ in $C_2$-$C_6$ alkenyl is defined as including groups having 2, 3, 4, 5 or 6 carbons in a linear or branched arrangement, at least two of the carbon atoms being bonded together by a double bond.

Examples of $C_2$-$C_6$ alkenyl include, but are not limited to, ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ alkynyl is defined as including groups having 2, 3 or 4 carbon atoms in a chain, at least two of the carbon atoms being bonded together by a triple bond. Examples of such alkynyl include, but are not limited to, ethynyl, 1-propynyl, 2-propynyl and the like.

As used herein, the term "cycloalkenyl" is intended to mean a monocyclic saturated aliphatic hydrocarbon group having the specified number of carbon atoms therein, for example, $C_3$-$C_7$ in $C_3$-$C_7$ cycloalkenyl is defined as including groups having 3, 4, 5, 6 or 7 carbons in a monocyclic arrangement. Examples of $C_3$-$C_7$ cycloalkenyl as defined above include, but are not limited to, cyclopentenyl, cyclohexenyl and the like.

As used herein, the term "halo" or "halogen" is intended to mean fluorine, chlorine, bromine or iodine.

As used herein, the term "haloalkyl" is intended to mean an alkyl as defined above, in which each hydrogen atom may be successively replaced by a halogen atom. Examples of haloalkyl include, but are not limited to, $CH_2F$, $CHF_2$ and $CF_3$.

As used herein, the term "aryl," either alone or in combination with another radical, means a carbocyclic aromatic monocyclic group containing 6 carbon atoms which may be further fused to a second 5- or 6-membered carbocyclic group which may be aromatic, saturated or unsaturated. Examples of aryl include, but are not limited to, phenyl, indanyl, 1-naphthyl, 2-naphthyl, tetrahydronaphthyl and the like. The aryl may be connected to another group either at a suitable position on the cycloalkyl ring or the aromatic ring.

As used herein, the term "heteroaryl" is intended to mean a monocyclic or bicyclic ring system of up to 10 atoms, wherein at least one ring is aromatic, and contains from 1 to 4 hetero atoms selected from the group consisting of O, N, and S. The heteroaryl may be attached either via a ring carbon atom or one of the heteroatoms. Examples of heteroaryl include, but are not limited to, thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, tetrazolyl, oxadiazolyl, thiadiazolyl, thienyl and fluoroscein derivatives.

As used herein, the term "heterocycle," "heterocyclic" or "heterocyclyl" is intended to mean a 3, 4, 5, 6, or 7 membered non-aromatic ring system containing from 1 to 4 heteroatoms selected from the group consisting of O, N and S. Examples of heterocycles include, but are not limited to, pyrrolidinyl, tetrahydrofuranyl, piperidyl, 3,5-dimethylpiperidyl, pyrrolinyl, piperazinyl, imidazolidinyl, morpholinyl, imidazolinyl, pyrazolidinyl, pyrazolinyl, and the like, where the attachment to the ring can be on either the nitrogen atom or a carbon atom of the ring such as described hereafter:

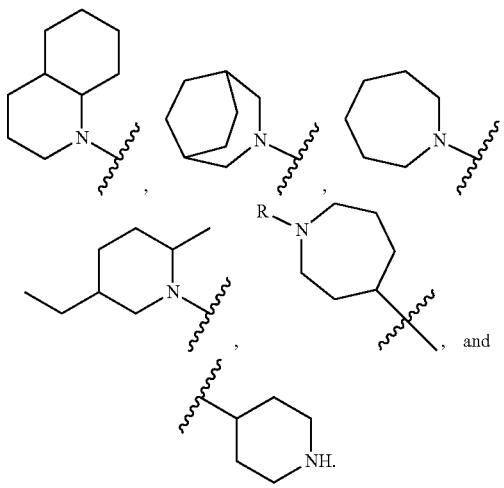

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

As used herein, the term "subject" or "patient" is intended to mean humans and non-human mammals such as primates, cats, dogs, swine, cattle, sheep, goats, horses, rabbits, rats, mice and the like.

If the substituents themselves are incompatible with the synthetic methods described herein, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, "Protecting Groups in Chemical Synthesis" (4th ed.), John Wiley & Sons, NY (2007), which is incorporated herein by reference in its entirety. Examples of protecting groups used throughout include, but are not limited to, Fmoc, Bn, Boc, CBz and $COCF_3$. In some instances, a substituent may be specifically selected to be reactive under the reaction conditions used in the methods described herein. Under these circumstances, the reaction conditions convert the selected substituent into another substituent that is either useful in an intermediate compound in the methods described herein or is a desired substituent in a target compound.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds according to the invention or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds according to the invention may exist as a mix of epimers. Epimers means diastereoisomers that have the opposite configuration at only one of two or more stereogenic centers present in the respective compound.

Compounds according to the invention may exist in Zwitterionic form and the present includes Zwitterionic forms of these compounds and mixtures thereof.

In addition, the compounds according to the invention also may exist in hydrated and anhydrous forms. Hydrates of the compound of any of the formulas described herein are included. In a further embodiment, the compound according to any of the formulas described herein is a monohydrate. In embodiments of the invention, the compounds described herein comprise about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In others embodiments, the compounds described herein comprise, about 0.1% or more, about 0.5% or more, about 1% or more, about 2% or more, about 3% or more, about 4% or more, about 5% or more, or about 6% or more by weight of water.

It may be convenient or desirable to prepare, purify, and/or handle the compound in the form of a prodrug. Thus, the term "prodrug", as used herein, pertains to a compound which, when metabolized (e.g., in vivo), yields the desired active compound. Typically, the prodrug is inactive, or less active than the desired active compound, but may provide advantageous handling, administration, or metabolic properties. Unless otherwise specified, a reference to a particular compound also includes prodrugs thereof.

As used herein, the term "$EC_{50}$" is intended to mean the concentration that results in a 50% increase in CD34+ CD45RA− cell count compared to vehicle cultures (DMSO).

As used herein, the term "hematopoietic stem cells" or "HSCs" is intended to mean cells having both pluripotency which allows them to differentiate into functional mature cells such as granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages), and the ability to regenerate while maintaining their pluripotency (self-renewal).

HSCs are part of the starting cell population. These cells are optionally obtained from the body or an organ of the body containing cells of hematopoietic origin. Such sources include un-fractionated bone marrow, umbilical cord, peripheral blood, liver, thymus, lymph and spleen. All of the aforementioned crude or un-fractionated blood products can be enriched for cells having hematopoietic stem cell characteristics in ways known to those of skill in the art.

As used herein, the term "starting cell population" is meant to identify a cell population comprising HSCs harvested from one of various sources mentioned above, as known in the art. The starting cell population can be enriched in CD34+ cells meaning a cell population selected based on the presence of the cell surface marker CD34+. CD34+ cells can be detected and counted using for example flow cytometry and fluorescently labeled anti-CD34 antibodies. Moreover, the starting cell population may be used directly for expansion or frozen and stored for use at a later point in time.

During hematopoiesis, HSCs first diverge into the progenitor stage into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-Eo), while lymphoid stem cells differentiate into T cells via T lymphoid progenitor cells and into B cells via B lymphoid progenitor cells. These myeloid stem cells and various hematopoietic progenitor cells derived from them are identified by the properties of colonies they form on soft agar, semisolid methylcellulose media or the like in the presence of various cytokines.

The present invention also includes use of a compound according to the invention and as defined herein, or a salt thereof, in the preparation of a medicament for the treatment of a subject (or patient) suffering from the following non-limiting list of disorders: autologous or allogeneic transplantation or treatment of a subject (or patient) suffering from the above-mentioned disorders or from auto-immune disorders. Examples of hematological malignancies/disorders and congenital diseases may include, without limitation, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease among others). Examples of immunological disorders that may benefit from transplantation are numerous and include multiple sclerosis, lupus, certain forms or arthritis, severe combined immunodeficiencies, and the like.

Thus, the present invention encompasses administration, to a patient suffering from any one of the above-mentioned disorders/malignancies, HSCs that are expanded using a compound according to the invention.

Furthermore, the compounds and compositions as described can be used in the following non-limiting settings: autologous or allogeneic transplantation or treatment of a subject (or patient) suffering from the above-mentioned disorders or from auto-immune disorders. Examples of hematological malignancies/disorders and congenital diseases may include, without limitation, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease among others). Examples of immunological disorders that may benefit from transplantation are numerous and include multiple sclerosis, lupus, certain forms or arthritis, severe combined immunodeficiencies, and the like.

Thus, the present invention encompasses administration, to a patient suffering from any one of the above-mentioned disorders/malignancies, HSCs that are expanded using a compound according to the invention.

Also encompassed within the present invention is a cell population obtained after expansion using the method according to the invention and as described herein. Both hematopoietic stem and progenitor cells can be harvested from adult, umbilical cord blood, fetal or embryonic sources. Cell expansion using the method of the present invention can lead to an increase in the number of progenitor cells which is useful in hastening the time to neutrophil or platelet engraftment, for example. Such method comprises: culturing a starting population comprising HSCs with an agent capable of increasing the number of HSCs. The starting population may be enriched in the cell surface marker of interest or a combination thereof (for e.g. CD34+, CD34+CD45RA+/−)

Methods for Expanding HSCs

The invention therefore relates to a method for expanding hematopoietic stem cells, comprising (a) providing a starting cell population comprising hematopoietic stem cells and (b) culturing said starting cell population ex vivo under suitable conditions for expanding hematopoietic stem cells.

The invention therefore relates to a method for expanding hematopoietic stem cells, comprising (a) providing a starting cell population comprising hematopoietic stem cells and (b) culturing said starting cell population ex vivo under suitable conditions for expanding hematopoietic stem cells.

In one specific embodiment, said method for expanding hematopoietic stem cells, comprises (a) providing a starting cell population comprising hematopoietic stem cells and (b)

culturing said starting cell population ex vivo in the presence of the compound or composition of the present invention.

The cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator.

In one embodiment, said starting cell population is enriched in CD34+ cells. Methods for enriching blood cell population in CD34+ cells include kits commercialized by Miltenyi Biotec (CD34+ direct isolation kit, Miltenyi Biotec, Bergisch, Gladbach, Germany) or by Baxter (Isolex 3000).

The amount of cord blood from a single birth is often inadequate to treat an adult or an older child. One advantage of the expansion method using the compound or composition of the invention is that it enables the production of a sufficient amount of hematopoietic stem cells from only one cord blood unit.

Accordingly, in one embodiment, the starting cell population is derived from neonatal umbilical cord blood cells which have been enriched in CD34+ cells. In one related embodiment, said starting cell population is derived from one or two umbilical cord blood units.

In another embodiment, the starting cell population is derived from human mobilized peripheral blood cells which have been enriched in CD34+ cells. In one related embodiment, said starting cell population is derived from human mobilized peripheral blood cells isolated from only one patient.

Said starting cell population may preferably contain at least 50% CD34+ cells, in some embodiments, more than 90% of CD34+ cells.

Culture conditions of the starting cell population for hematopoietic stem cell expansion will vary depending on the starting cell population, the desired final number of cells, and desired final proportion of HSCs.

In one specific embodiment, in particular, using a starting cell population from umbilical cord blood cells enriched in CD34+ cells, the culturing conditions comprises the use of other cell expanding factors like cytokines and growth factors, generally known in the art for HSC expansion. Such cytokines and growth factors can be biologics or small molecules and they include without limitation IL-1, IL-3, IL-6, IL-11, G-CSF, GM-CSF, SCF, FIT3-L, thrombopoietin (TPO), erythropoietin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to expand HSC and progenitor cells while limiting the production of terminally differentiated cells. In one specific embodiment, one or more cytokines and growth factors are selected from the group consisting of SCF, Flt3-L and TPO.

Human IL6 or interleukin-6, also known as B-cell stimulatory factor 2 has been described by (Kishimoto, Ann. review of 1 mm. 23:1 2005) and is commercially available. Human SCF or stem cell factor, also known as c-kit ligand, mast cell growth factor or Steel factor has been described (Smith, M A et al., ACTA Haematologica, 105, 3:143, 2001) and is commercially available. Flt3-L or FLT-3 Ligand, also referred as FL is a factor that binds to flt3-receptor. It has been described (Hannum C, Nature 368 (6472): 643-8) and is commercially available. TPO or thrombopoietin, also known as megakarayocyte growth factor (MGDF) or c-Mpl ligand has been described (Kaushansky K (2006). N. Engl. J. Med. 354 (19): 2034-45) and is commercially available.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

The expansion of HSC may be carried out in natural medium, a semi-synthetic medium or a synthetic medium in terms of composition, and may be a solid medium, a semi-solid medium or a liquid medium in terms of shape, and any nutrient medium used for hematopoietic stem cell and/or hematopoietic progenitor cell culture, which is supplemented with the mixtures of cell expanding factors described above. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transfferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. Examples of such basal medium appropriate for a method of expanding HSCs include, without limitation, StemSpan™ Serum-Free Expansion Medium (SFEM) (StemCell Technologies, Vancouver, Canada), StemSpan™ H3000-Defined Medium (StemCell Technologies, Vancouver, Canada), CellGro™, SCGM (CellGenix, Freiburg Germany), StemPro™-34 SFM (Invitrogen), Dulbecco's Modified Eagles's Medium (DMEM), Ham's Nutrient Mixture H12 Mixture F12, McCoy's 5A medium, Eagles's Minimum Essential Medium (EMEM), αMEM medium (alpha Modified Eagles's Minimum Essential Medium), RPMI1640 medium, Isocove's Modified Dulbecco's Medium (IMDM), StemPro34 (Invitrogen), X-VIVO 10 (Cambrex), X-VIVO 15 (Cambrex) and Stemline II (Sigma-Aldrich).

In one embodiment, the compound or the composition of the invention is administered during the expansion method of said starting cell population under a concentration appropriate for HSC expansion. In one specific embodiment, said compound or composition is administered at a concentration comprised between 1 and 3000 nmol or for example between 1 and 100 nmol.

In one specific embodiment where starting cell population essentially consists of CD34+ enriched cells from one or two cord blood units, or from mobilized PB cells or from harvested bone marrow, the cells are grown under conditions for HSC expansion, for example between 2 and 21 days and/or until the indicated fold expansion and the characteristic cell populations are obtained. In one specific embodiment, the cells are grown ex vivo under conditions for HSC expansion not more than 21 days, 12 days, 10 days or 7 days.

The cell population may then be washed to remove the compound or composition of invention and/or any other component of the cell culture and resuspended in an appropriate cell suspension medium for short term use or in a long-term storage medium, for example a medium suitable for cryopreservation.

The HSCs and/or hematopoietic progenitor cells can be cultured in a culture vessel generally used for animal cell culture such as a Petri dish, a flask, a plastic bag, a Teflon™ bag, optionally after preliminary coating with an extracellular matrix or a cell adhesion molecule. The material for such a coating may be collagens I to XIX, fibronectin, vitronectin, laminins 1 to 12, nitrogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005).

The invention further provides a cell population with expanded HSCs, obtainable or obtained by the expansion method described above. In one specific embodiment, such cell population is resuspended in a pharmaceutically acceptable medium suitable for administration to a mammalian host, thereby providing a therapeutic composition.

The invention further provides the cell population with expanded HSCs or its composition for use in allogeneic or autologous stem cell transplantation in a mammalian subject.

The subject referred to herein is, for example, a bone marrow donor or an individual with or at risk for depleted or limited blood cell levels. Optionally, the subject is a bone marrow donor prior to bone marrow harvesting or a bone marrow donor after bone marrow harvesting. The subject is optionally a recipient of a bone marrow transplant. The methods described herein are particularly useful in subjects that have limited bone marrow reserve such as elderly subjects or subjects previously exposed to an immune depleting treatment or myeloablative treatment such as chemotherapy, e.g., for treating leukemia or lymphomas. The subject, optionally, has a decreased blood cell level or is at risk for developing a decreased blood cell level as compared to a control blood cell level. As used herein the term control blood cell level refers to an average level of blood cells in a subject prior to or in the substantial absence of an event that changes blood cell levels in the subject. An event that changes blood cell levels in a subject includes, for example, anemia, trauma, chemotherapy, bone marrow transplant and radiation therapy. For example, the subject has anemia or blood loss due to, for example, trauma.

The transplant may be a composition containing a buffer solution, an antibiotic, a pharmaceutical in addition to hematopoietic stem cells and/or hematopoietic progenitor cells expanded by the method of the present invention.

The expanded HSC population or the composition comprising the cell population with expanded HSCs is administered to the subject, for example, before, at the same time, or after chemotherapy, radiation therapy or a bone marrow transplant. The subject optionally has depleted bone marrow related to, for example, congenital, genetic or acquired syndrome characterized by bone marrow loss or depleted bone marrow. Thus, the subject is optionally a subject in need of hematopoiesis. Optionally, the subject is a bone marrow donor or is a subject with or at risk for depleted bone marrow.

Hematopoietic stem cell manipulation is useful as a supplemental treatment to chemotherapy or radiation therapy. For example, HSCs are localized into the peripheral blood and then isolated from a subject that will undergo chemotherapy, and after the therapy the cells are returned. Thus, the subject is a subject undergoing or expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy. Therefore, as described herein, HSCs or blood cells made by the methods described herein are optionally administered to such subjects in need of additional blood cells.

Provided are HSCs expanded by a compound or a composition of the invention as described above in combination with a therapeutic capable of enhancing the proliferation of HSCs in vivo, in vitro, or ex vivo (for example, a small molecule, an antibody, or the like) and optionally at least one pharmaceutically acceptable excipient or carrier. By a therapeutic capable of enhancing HSC proliferation is meant: an agonist antibody against the TPO receptor (for example, VB22B sc(Fv)2 as detailed in patent publication WO 2007/145227, and the like); a cytokine such as SCF, IL-6, Flt-3 ligand, TPO or a TPO mimetic (for example, such as described in WO/2007/022269; WO/2007/009120; WO/2004/054515; WO/2003/103686; WO/2002/085343; WO/2002/049413; WO/2001/089457; WO/2001/039773; WO/2001/034585; WO/2001/021180; WO/2001/021180; WO/2001/017349; WO/2000/066112; WO/2000/035446; WO/2000/028987; WO/2008/028645; and the like); granulocyte colony stimulating factor (G-CSF); granulyte macrophage colony stimulating factor (GM-CSF); a prostaglandin or a prostaglandin receptor agonist (for example, prostaglandin E2 receptor-1 (EP-I) agonist, prostaglandin E2 receptor-2 (EP-2) agonist, prostaglandin E2 receptor-3 (EP-3) agonist and prostaglandin E2 receptor-4 (EP-4) agonists, as detailed in patent publication WO/2008/073748); tetraethylenepentamine (TEPA); Notch-ligands (Delta-1); and/or a WNT agonist. In addition, culturing stem cells with mesenchymal stem cells (MSCs) prevents graft-versus-host disease (GVHD) and may help stem cell expansion.

By pharmaceutically acceptable is meant a material that is not biologically or otherwise undesirable, i.e., the material may be administered to a subject or cell, without causing undesirable biological effects or interacting in a deleterious manner with the other components of the pharmaceutical composition in which it is contained. The carrier or excipient is selected to minimize degradation of the active ingredient and to minimize adverse side effects in the subject or cell.

The compositions are formulated in any conventional manner for use in the methods described herein. Administration is via any route known to be effective by one of ordinary skill. For example, the composition is administered orally, parenterally (e.g., intravenously), by intramuscular injection, by intraperitoneal injection, transdermally, extracorporeally, intranasally or topically.

The preferred method of administration is intravenous infusion. The number of cells transfused will take into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least $\geq 0.3 \times 10^5$ CD34$^+$/kg or $>2 \times 10^6$ CD34$^+$ for cord blood and $2.5 \times 10^5$ CD34$^+$/kg or more for bone marrow or mobilized peripheral blood cells. In one specific embodiment, the infused cells are all deriving from expanded cord blood cells from a single birth.

Expanded hematopoietic stem cells and/or hematopoietic progenitor cells may be infused by drip, for example, in the case of treatment of leukemia, into patients pretreated with an anticancer drug, total body irradiation or an immunosuppressive drug for eradication of cancer cells or for facilitation of donor cell engraftment. The disease to be treated, the pretreatment and the cell transplantation method are selected appropriately by the person in charge. The engraftment of so transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

As described above, the present invention makes it possible to expand hematopoietic stem cells and/or hematopoietic progenitor cells and to carryout transplantation therapy safely and easily in a short term by using the expanded HSCs.

Also provided herein is a kit comprising one or more containers filled with one or more of the ingredients described herein. Such kits optionally comprise solutions and buffers as needed or desired. The kit optionally includes an expanded population of stem cells made by the methods described above or can contain containers or compositions for making an expanded population of HSCs. In particular, the invention provides a kit for expanding ex vivo hematopoietic stem cells, comprising a compound as defined in the Summary of Invention and instructions for use of such compound in a method for HSC expansion and, optionally, one or more cell expanding factors, or media for cell growth, in particular media for HSC growth as described above. The kit may further comprise antibodies for monitoring production of the cells, such as anti-CD34, anti-CD38 and/or anti-CD45RA antibodies. In one specific embodiment, such kit further includes one or more cell expanding factor selected from the group consisting of IL6, FLT3-L, SCF and TPO. Optionally associated with such pack(s) or kit(s) are instructions for use.

In vivo application: Also provided is a kit for providing an effective amount of a compound of the invention to increase HSCs in a subject comprising one or more doses of the compound for use over a period of time, wherein the total number of doses of the compound of the invention in the kit equals the effective amount sufficient to increase HSCs in a subject. The period of time is from about one to several days or weeks or months. Thus, the period of time is from at least about 5, 6, 7, 8, 10, 12, 14, 20, 21, 30 or 60 days or more or any number of days between one and 180.

Biological Assays
Screening Assay:

To identify novel putative agonists of HSC self-renewal, we have adapted a high throughput based-screening assay to test a library of small molecule compounds (5,280 low molecular weight compounds) on primary human mobilized CD34+ cells. It is to be understood that the same approach applies to CD34+ cells from the various sources known by a person skilled in the art to isolate CD34+ cells. Mononuclear cells were stained with Mouse antihuman CD34+APC (from BD Pharmingen) and subsequently magnetically labeled with Anti-APC magnetic MicroBeads (from MACS, Miltenyi Biotec). The magnetically labeled cells were retained using AutoMACS column. Our study was based on the fact that mobilized peripheral blood-derived CD34+CD45RA− cells cultured in media supplemented with interleukin-6, thrombopoietin, Flt-3 ligand, and stem cell factor, would promote the expansion of mononuclear cells (MNC) concomitant with a decrease in CD34+CD45RA− population and HSC depletion. Low molecular weight compounds preventing this loss could therefore act as agonists of HSC expansion.

In a 384-well plate, 2000 CD34$^+$ cells/well were cultured in 50 μl medium containing 1 μM of test compounds or 0.1% DMSO (vehicle). The proportion of CD34$^+$CD45RA$^−$ cells was determined at the start of the experiment and after a 7-day incubation. Six out of the 5,280 compounds of different chemical backgrounds initially tested promoted CD34+CD45RA− cell expansion, and seventeen (17) enhanced differentiation as determined by the increase in proportions of CD34−CD45RA+ cells compared to control (DMSO). The six compounds promoting expansion of the CD34+CD45RA− cell population were re-analyzed in a secondary screen. Four out of these six compounds act as aryl hydrocarbon receptor (AhR) antagonists, a mechanism of action (same as the SR1's) shown to promote the ex vivo expansion of huCD34+ cells. The remaining two compounds, determined as not being aryl hydrocarbon receptor (AhR) antagonists, were shown to promote the expansion of MNCs including CD34+ cells during 7-day incubation. One of those two remaining compounds identified is Compound 1 (Table 1).

The following biological assays were used to assess the effect of the compounds of the invention on hematopoietic stem cell expansion. Culture medium: The culture medium used consisted of serum-free medium supplemented with the following recombinant cytokines: interleukin-6, thrombopoietin, Flt-3 ligand, and stem cell factor, each at a final concentration of 100 ng/ml, in the presence of vehicle (DMSO), positive control (SR1), or compound of the invention or a combination of compounds. Cell Culture: CD34+ cell purity of initial harvests was higher than 90%, as determined by flow cytometry. The CD34+CD45RA− subpopulation reached purity levels higher than 70%. Cells were plated at 40,000 cells/ml and incubated for 7 to 12-days at 37° C. in 5% CO$_2$. For long term cultures, 200,000 CD34+ cells/ml from mobilized PB were plated with serum free media supplemented with interleukin-6, thrombopoietin, Flt3 ligand, and stem cell factor, each at a final concentration of 100 ng/ml, in the presence of vehicle (DMSO), positive control, or a compound of the invention at 500 nM. After a 10-day ex vivo culture Compound 1 (Table 1) promoted more than 7-fold expansion of MNCs, more than 5-fold increase in CD34+ cells over input values (day 0), and almost 4-fold increase over the values determined for vehicle. After 10 days of ex vivo culture, Compound 1-treated cells retained a high level of CD34 expression (65.8±5.5%) compared to cells cultured with vehicle (DMSO) (22.8±0.9%). Moreover, only Compound 1-treated cells retained the highest expression of CD34+

CD45RA− population (24.8±0.9%) compared to that of vehicle (4.7±0.4%). The numbers of CD34+CD45RA− cultured with Compound 1 increased by almost 3-fold compared to that of vehicle and 7-fold more than that of input. Finally, the compounds of the invention were assayed in a dose-response format (concentrations ranging from 1 nM to 5000 nM) to determine the effective concentration that produced a 50% increase in the number of CD34+CD45RA− cells compared to vehicle condition. The results are shown in Table 1.

Compound 1 does not Act Through Aryl Hydrocarbon (AhR) Pathway (FIG. 1)

Figure 2:
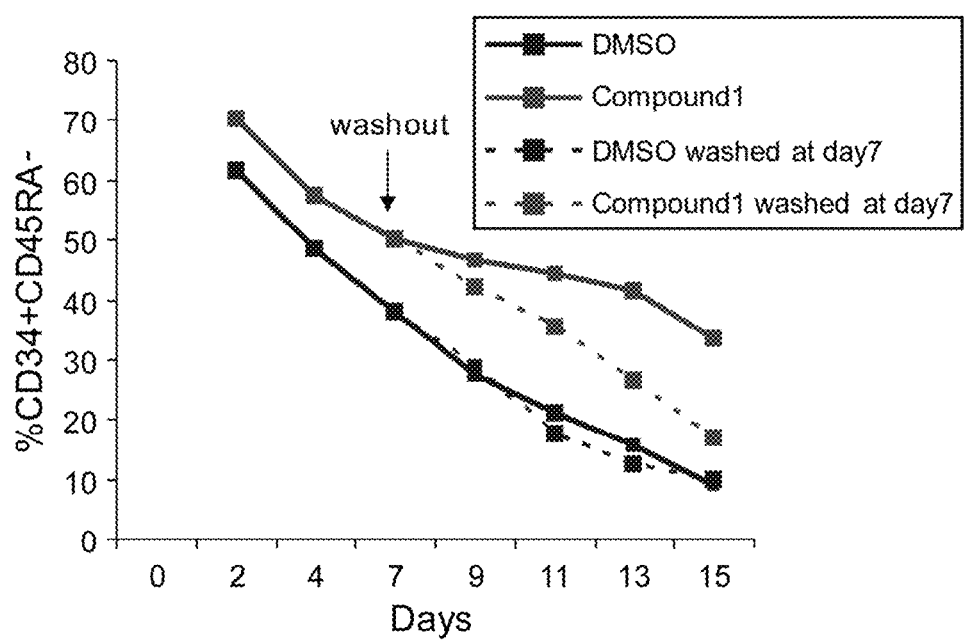
FIG. 2: Effect of compound 1 is reversible. Mobilized peripheral blood CD34(+) cells cultured for 7 days with compound 1 (shown in green) or vehicle (DMSO, shown in blue) were washed and re-plated in fresh media with or without Compound addition (solid vs dashed line respectively). Cells were cultured for 8 additional days and the percentage of CD34+CD45RA− was monitored. A rapid decrease in CD34+CD45RA− percentage was observed when compound 1 was washed out indicating that its effect is reversible.

We next documented that the impact of Compound 1 on primitive CD34+CD45RA− primitive hematopoietic cell is rapidly reversible in culture. This effect is best shown in FIG. 2 where CD34+ mobilized peripheral blood cells are cultured in the presence of Compound 1 for up to 7 days, at which time the Compound 1 is removed by washing the cells. The green dotted line shows that the reduction in the proportion of CD34+CD45RA− cells rapidly follows that of controlled cultures (DMSO: solid blue and dotted lines) whereas cells maintained in the presence of Compound 1 retain a more primitive phenotype throughout the 2 week culture (solid green line). These results clearly indicate that within 2 days of compound-free exposure, cells have already acquired differentiation markers as seen in control cultures. Thus, the impact of Compound 1 is rapidly reversible on primitive human cells.

Figure 3:
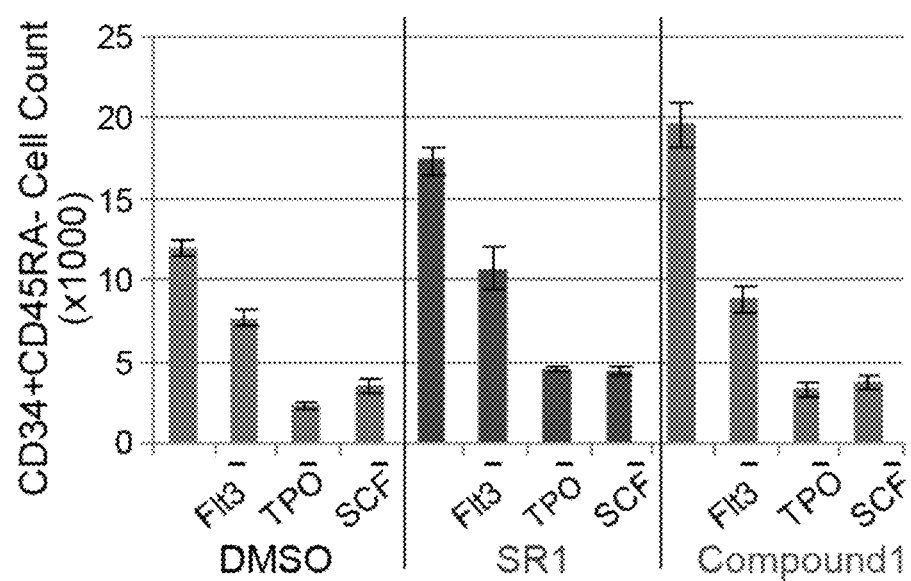
FIG. 3: Flt3, SCF, and TPO are required for compound 1 mediated stem cell expansion. Mobilized peripheral blood CD34(+) cells were cultured for 7 days in the presence or absence of the growth factors (Flt3+SCF+TPO). CD34+CD45RA− cell count was lower in the absence of any of the growth factors suggesting their requirement for the observed effect.

Compound 1 is not a Mitogen (FIG. 3)

We also showed that Compound 1 does not independently trigger cell proliferation in the absence of growth factor. These results, shown in FIG. 3, indicate that similar to what was observed with an antagonist of Aryl Hydrocarbon receptor (SR1), Compound 1 was not able to induce cell proliferation in the absence of any of the 3 listed growth factors, namely Flt3, TPO and SCF. This indicate that akin to SR1, Compound 1's effect on maintenance of primitive HSC phenotype ex vivo is not due to a mitogenic effect on this population but rather on the prevention of cell differentiation.

Figure 4:
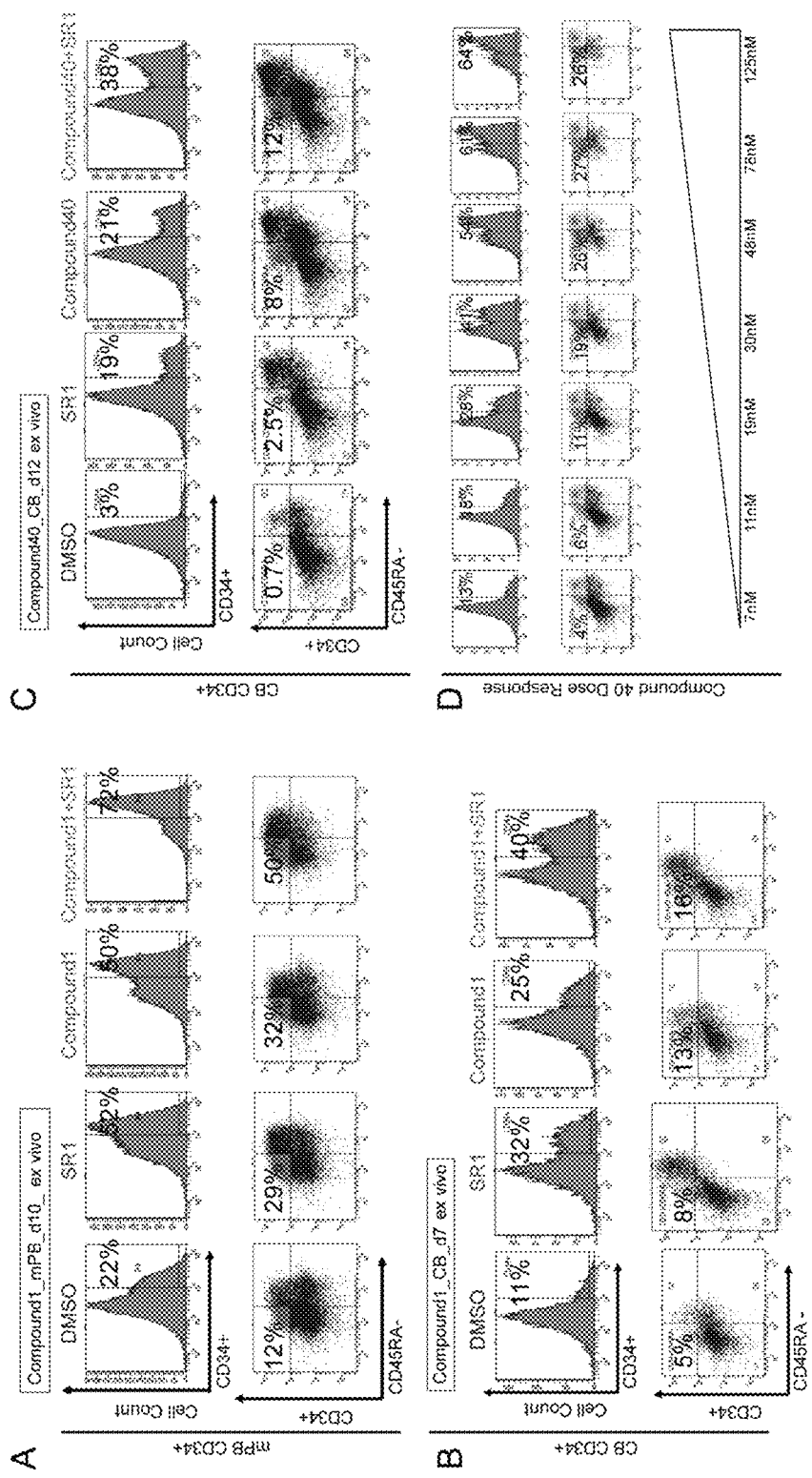
FIG. 4: A) Compound 1 reduces differentiation of CD34+ mobilized peripheral blood cells. As determined by FACS analysis, compound 1 was able to expand CD34+ cell population compared to DMSO treated control cells. SR1 synergizes with compound 1 to keep the expanded culture cell CD34+ suggesting that the inhibition of differentiation is even more prominent with the combination. B) Compound 1 reduces differentiation of CD34+ cord blood cells. C) Compound 40 reduces differentiation of CD34+ cord blood cells. D) Compound 40 exhibits a dose-dependent effect on suppression of CD34+ cell differentiation.

Compound 1 and Compound 40 Both Prevent Cell Differentiation and Synergizes with AhR Antagonist (FIG. 4)

We also assessed the impact of Compound 1 and also one of its potent derivative Compound 40 on cell differentiation using both cytological analysis and flow cytometry. Both types of studies showed that Compound 1 and its derivative Compound 40 prevent cell differentiation. FACS results are shown in FIG. 4. FIG. 4A illustrates the impact of Compound 1 on mobilized peripheral blood cell differentiation. Following a 7 day expansion, a relatively pure (>85% CD34$^+$) population of mobilized peripheral blood was exposed to control the (DMSO) or Compound 1 or SR1 or Compound 1+SR1. Results strongly indicate that cells rapidly loose CD34 cell surface expression in control cultures whereas this effect is partly abrogated by introducing optimal levels of SR1 and Compound 1. Interestingly both SR1 and Compound 1 synergize in maintaining CD34 expression on the cell surface. These observations have been repeated for cord blood specimens in FIG. 4B and also with Compound 40 in FIG. 4C.

In addition to this, we showed that the impact of Compound 1 or Compound 40 is most impressive on cells which have a more primitive phenotype. For example, CD34$^+$CD45RA$^-$ cells (upper left quadrant in bottom panels of FIG. 4A to 4C) are more numerous in cultures supplemented with Compound 1 or 40 than they are in SR1 or in control cultures. Again additive effects of Compound 1 or compound 40 plus SR1 is observed in these cultures.

FIG. 4D provides a dose-response curve which indicates the potency of Compound 40 in preventing the disappearance of the CD34 marker on the surface of primitive human HSC enriched population. Note expression of CD34 varying with different dose of the compound.

Figure 5:
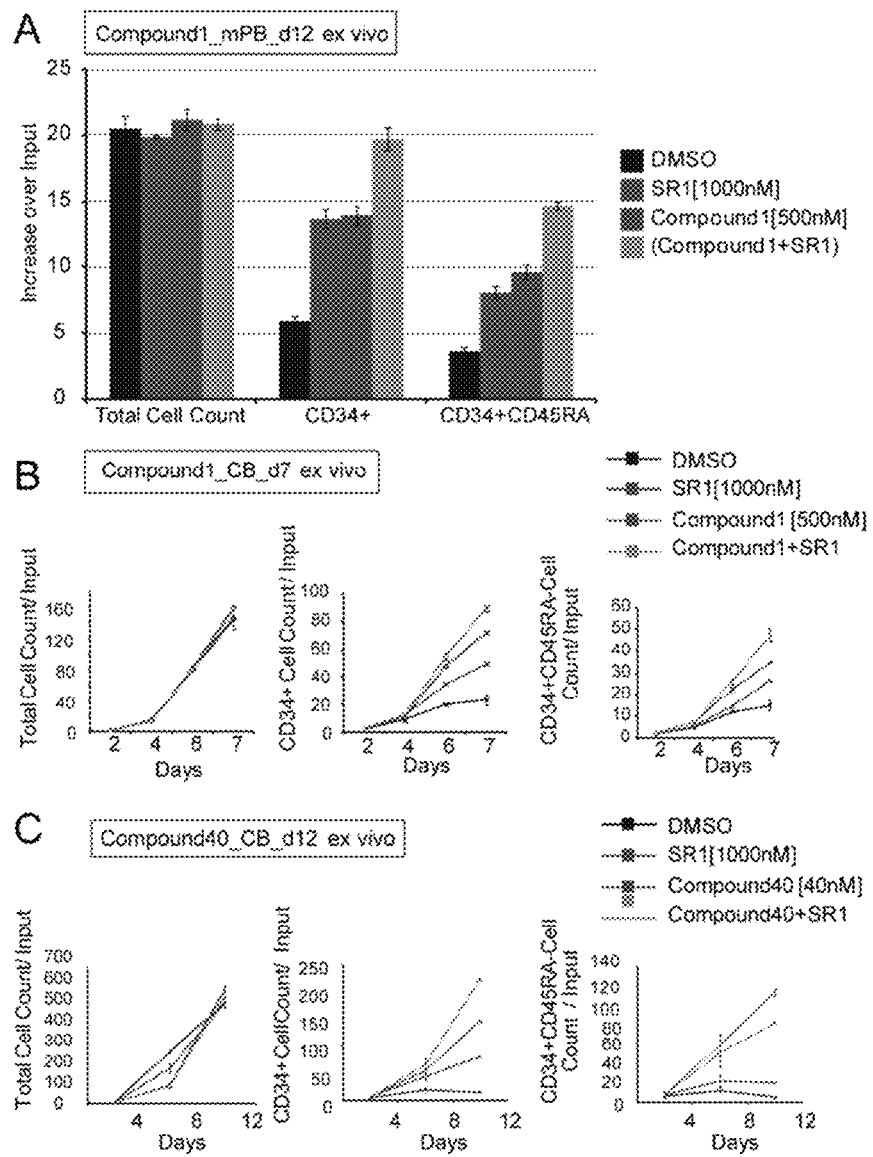
FIG. 5: A) Compound 1 expands mobilized peripheral blood-derived CD34+ and CD34+CD45RA− cell populations ex vivo. Although the total cell count was the same in DMSO and compound 1 treated cells, CD34+ population was more than twice that of DMSO. Similarly, CD34+CD45RA− population was more than three times in the compound 1 treated group vs. DMSO. This observation was enhanced with the co-treatment with SR1. B) Compound 1 enhances expansion of the cord blood-derived CD34+ and CD34+CD45RA− cells during 7-day incubation. C) Compound 1 exerts the positive effect on the in vitro expansion of the cord blood-derived CD34+ and CD34+CD45RA− cells during 12-day incubation.

Compounds 1 and 40 Expand Human HSC Phenotype Ex Vivo (FIG. 5)

FIG. 5 shows that Compound 1 but also Compound 40 expand human HSC phenotype ex vivo in both short term and long term cultures. FIG. 5A shows that total cell count is increased by about 20 fold above the input in cultures initiated with CD34+ mobilized peripheral blood (mPB) and maintained for 12-days. The level of expansion is the same whether cultures are initiated with Compound 1, SR1, Compound 1+SR1, or control DMSO. Most strikingly the impact of Compound 1 is observed on more primitive CD34$^+$CD45RA$^-$ cell subpopulation which expands by about ten fold in the presence of Compound 1 and by about fifteen fold in the presence of Compound 1+SR1. This observation together with the results presented in FIG. 4 strongly suggest that Compound 1 has no impact on cell proliferation but rather on preventing differentiation of CD34$^+$CD45RA$^-$ cells leading to their net expansion at the expense of more mature cells. Results in FIG. 5B indicate that Compound 1 will lead to a 30-40-fold expansion of CD34$^+$CD45RA− cord blood cells over a seven day period whereas these cells are expanded by about fifteen fold in the presence of DMSO (control). FIG. 5C shows similar results but this time with cultures extended to twelve days and Compound 1 is replaced by Compound 40. Again, as indicated in the left panel, total cell expansion is the same whether cells are exposed to DMSO (control), SR1, Compound 40 or both Compound 40 plus SR1. Most impressively, the more primitive CD34$^+$CD45RA− cells expand by 80-fold over 12-days in cultures supplemented with Compound 40, whereas these cells expand a little less than 20-fold in cultures initiated with SR1, showing the superiority of this compound over Aryl Hydrocarbon Repressor antagonist.

In summary, these results show that Compound 1 and Compound 40 have major effects on expansion of CD34$^+$ and the more primitive CD34$^+$CD45RA− population, both with CD34+ derived from mobilized peripheral blood or cord blood cells.

The ex vivo functionality of expanded cells was tested using the conventional colony-forming units in culture (CFU-C) assay. Untreated cells or cells incubated with DMSO, positive control or a compound of the invention were plated in methylcellulose medium in conventional conditions. As an example, Compound 1 (Table 1, Example 1) expands the number of multipotent hematopoietic progenitors. Methylcellulose culture of 1000 CD34+ mPB cells treated with Compound 1 for 10 days resulted in a 5-fold increase in multilineage granulocyte erythrocyte, macrophage and megakaryocyte (GEMM colonies) over input cells and a 10-fold increase compared to control cells. This suggests that Compound 1 described herein also promotes expansion of multipotent progenitor cells.

Figure 6:
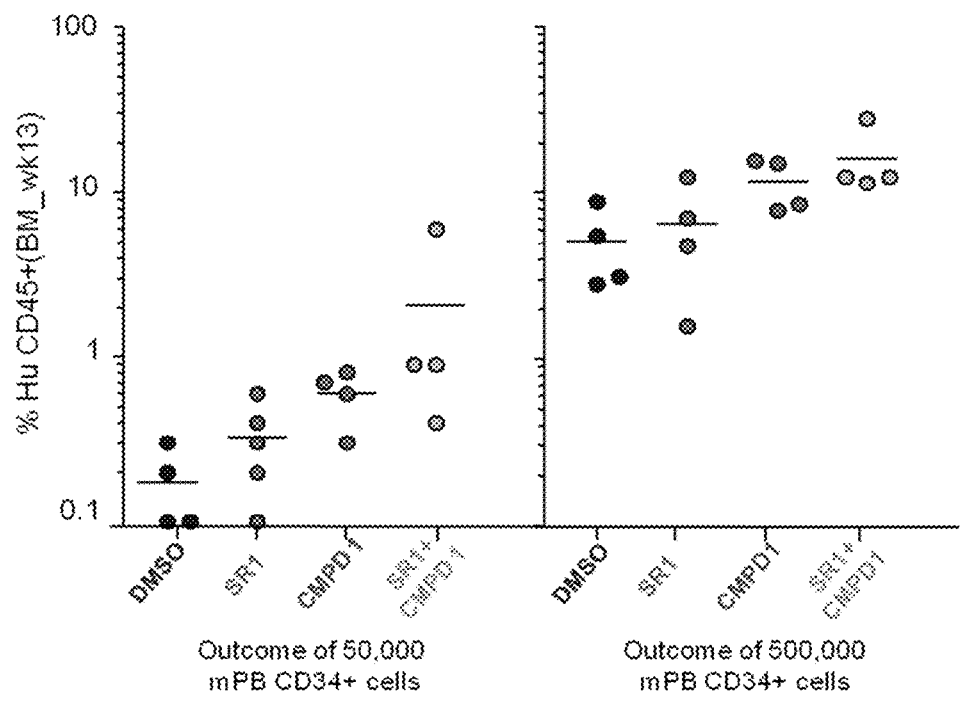
FIG. 6: CD34+ mPB cells were cultured for ten days in the presence of the vehicle (DMSO), SR1, compound 1, and a combination of compound 1 and SR1. The outcome of 50,000 and 500,000 treated cells were transplanted in NSG mice and the bone marrow analysis was performed after 13 week post-transplantation to evaluate the human hematopoietic engraftment. At any give cell dose, CD34+ mPB cells treated with Compound 1 engrafted better than that of DMSO. Interestingly, the percentage of the human CD45+ cells in the BM was highest in NSG mice which received cells treated with the combination (compound 1+SR1) compared to the individual compounds.

Impact of Compound 1 on Cultured mPB HSC Assessed Using NSG Mouse Model (FIG. 6)

We next assessed the impact of Compound 1 and Compound 40 on cord blood and mobilized peripheral blood human HSC expanded in vitro for ten to twelve days and introduced in vivo in NSG mouse model. The goal of these experiments is to verify that the impact of our compound on primitive HSC phenotype shown in FIGS. 4 and 5 is also observed on the long term repopulating bone marrow stem/progenitor cells. FIG. 6 shows reconstitution of mouse bone marrow by human cells assessed thirteen weeks after transplantation. For mobilized blood, the outcome of 50,000 and 500,000 cells is presented in 6A. As shown there, HSC agonist SR1 was consistently better than DMSO (control) in expanding human stem cells as assessed in the NSG mouse model. Again Compound 1 appears to be superior to SR1 in these experiments. As seen in the in vitro cultures, Compound 1 and SR1 showed a synergistic effect in these experiments (FIG. 6).

Figure 7:
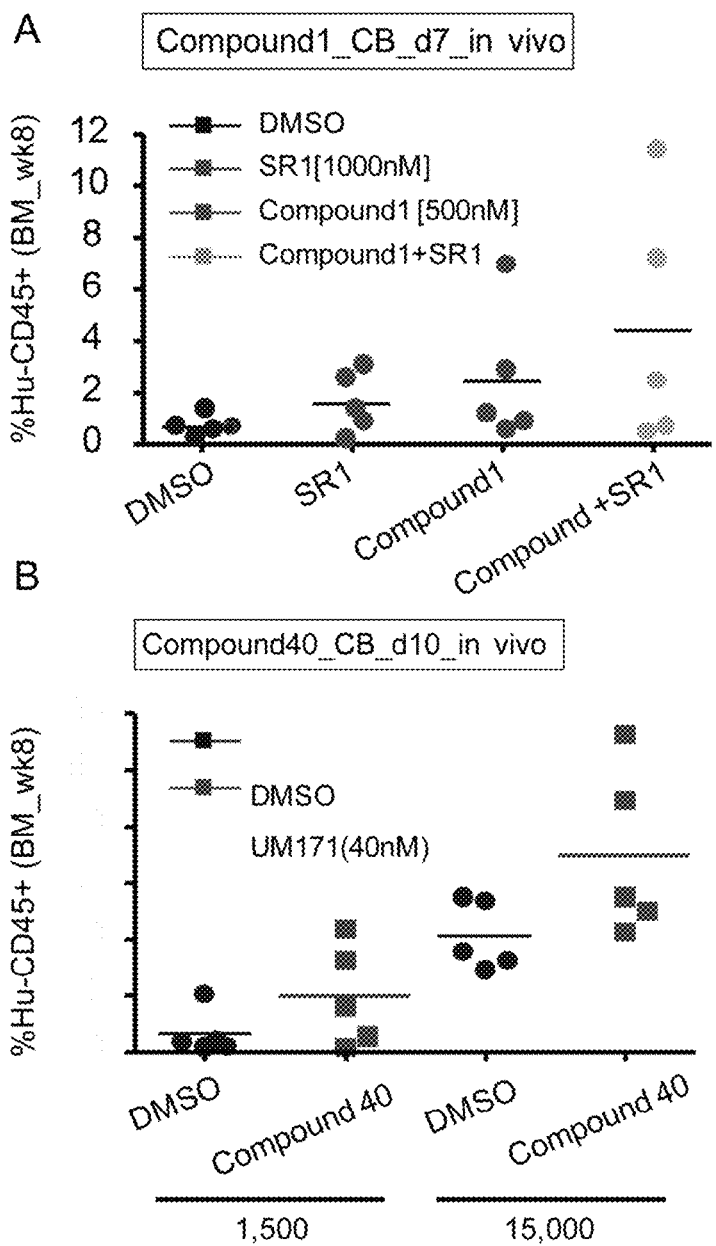
FIG. 7: A) Compound 1 expanded cells are capable of reconstituting human hematopoietic cells in NSG mice. The outcome of 5,000 CD34+ CB Cells treated with vehicle (DMSO), SR1, compound 1 and combination were transplanted in immunocompromised NSG mice. After 8-weeks post transplantation, the bone marrow analysis showed a human CD45+ engraftment in all treatment groups except DMSO. The cells treated with the combination (compound 1+SR1) showed the highest engraftment levels. B) During 12-day in vitro incubation Compound 40 prevents the loss of human hemopoietic cells with ability to engraft NSG mouse bone marrow.

Impact of Compound 1 and 40 on Cultured Cord Blood (CB) HSC Assessed Using NSG Mouse Model (FIG. 7)

FIG. 7 shows the impact of Compound 1 and Compound 40 on cultured cord blood human HSC assessed in vivo in NSG mouse model. Results in FIG. 7A indicate that Compound 1 has a clear effect on reconstitution activity of human cells when compared to control cultures. These experiments were done in short term cultures i.e. 7 days. Most importantly, FIG. 7B indicates that Compound 40 has quite an important effect with average levels of reconstitution at 10% compared to 2% for DMSO control when using 1500 CD34$^+$ cells. The greater impact of Compound 40 in this experiment over Compound 1 (FIG. 7A) is potentially due to the longer culture period used in experiments described in FIG. 7B. More definitive in vivo experiments are provided in the next section using longer culture periods (12 to 16 days).

Figure 8:
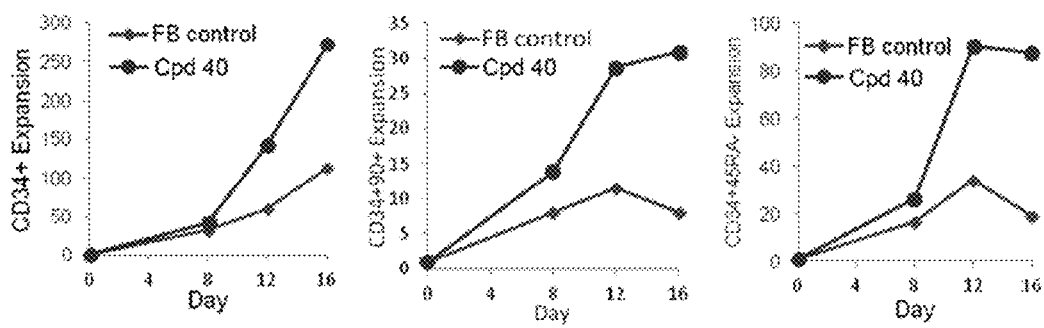
FIG. 8: Expansion of primitive cell phenotypes (CD34$^+$, CD34$^+$CD90$^+$, and CD34$^+$CD45RA$^+$) in bioreactor using the fed-batch approach as measured by flow cytometry. FB control=fed-batch without Compound 40, Cpd 40=fed-batch with Compound 40.

Impact of Compound 1 and 40 on Cultured Cord Blood (CB) HSC Assessed Using NSG Mouse Model (FIG. 8)

Zandstra et al. recently documented that a new method called fed-batch optimizes in vitro conditions leading to human HSC expansion (U.S. Pat. No. 7,795,024). We wanted to verify whether compounds of the invention are active in these previously optimized fed-batch conditions. For these studies, we assessed the expansion of cord blood-derived hematopoietic stem cells (HSCs) following in vitro culture with the fed-batch+Compound 40 for 12 or 16 days. HSC numbers were assessed based on engraftment of human cells into immune-deficient mice.

As shown in FIG. 8 the addition of Compound 40 (Cpd 40) provided a major effect on expansion of all populations tested including CD34+CD45RA− cells up to at least 16 days. This effect was most impressive in the 12-16 day time points clearly demonstrating the synergy between fed-batch (FB in FIG. 8) and Compound 40.

Moreover, freshly enriched CD34+ cells and cells expanded for 12 or 16 days were transplanted into female NOD/SCID/IL-2Rγc-null (NSG) mice, which had been sub-lethally (250 rad) irradiated 24 h prior to transplantation. Cells were injected intravenously through the tail vein. At defined time-points (week 3, week 9, and week 16), the animals were sacrificed and bone marrow was harvested from two tibias and two femurs. The bone marrow was depleted of red blood cells and assessed by flow cytometry to quantify the engraftment of human cells. Cells were scored positive for engraftment if ≥0.5% of the cells were positive for human CD45 and human HLA-ABC. At each time-point of assessment, some animals were sent for independent histology analysis.

As shown in Table 2 below, at the late 16-week time-point, there is a dose response of engraftment for each condition. Limiting dilution analysis revealed that the highest HSC expansion was produced by the fed-batch+Compound 40 12-day culture (18.4-fold). This was significantly higher than the expansion produced by the fed-batch control 12-day culture (8.1-fold). Higher expansion was produced by both conditions with the 12-day culture as compared to the 16-day culture. These results provide unequivocal demonstration of net human HSC expansion in vitro in the presence of Compound 40 and its activity in fed-batch conditions (FIG. 8+Table 2).

TABLE 2

Summary of Week 16 limiting dilution engraftment data

| Condition | frequency of HSCs | TNC expansion | day 0 HSC equivalent | Net HSC expansion* |
|---|---|---|---|---|
| Day 0 fresh | 1/6115 | NA | 1/6115 | NA |
| Day 12 Fed-batch | 1/117676 | 156 | 1/754.3 | 8.1 |
| Day 12 Fed-batch + Cpd 40 | 1/54548 | 164 | 1/332.6 | 18.4 |
| Day 16 Fed-batch | 1/635952 | 413 | 1/1539.8 | 4 |
| Day 16 Fed-batch + Cpd 40 | 1/323585 | 495 | 1/653.7 | 9.4 |

*Net HSC Expansion = (# HSC Day 0)/(# HSC Day 12 or Day 16); measured using limiting dilution analysis (LDA) in NSG mice at week 16

SYNTHETIC METHODOLOGY

The synthetic methodology outlined below relates to embodiments of the invention wherein substituent Z is at the 7-position of the pyrimido indole nucleus. As will be understood by a skilled person, a similar synthetic methodology can be performed, with variations that are apparent to such person, for embodiments of the invention wherein substituent Z is at a different position, such as for example at the 5, 8 or 6-position, particularly at the 6-position.

Scheme 1 describes the synthesis of the common precursor (1-VI) to the compounds of the present invention. In the first step an aryl fluoride 1-I is treated with an alkyl cyanoacetate 1-II in the presence of a base such as, but not limited to, sodium hydride. The resulting product 1-III is then treated with a reducing agent such as, but not limited to, zinc dust in acetic acid to provide amino indoles 1-IV which are converted to the pyrimidines 1-V upon treatment with formamide and ammonium formate. Compounds 1-V are treated with reagents such as phosphoryl chloride or phosphoryl bromide to provide the reactive intermediates 1-VI which are treated with amines 1-VII to provide the compounds 1-VIII of the present invention.

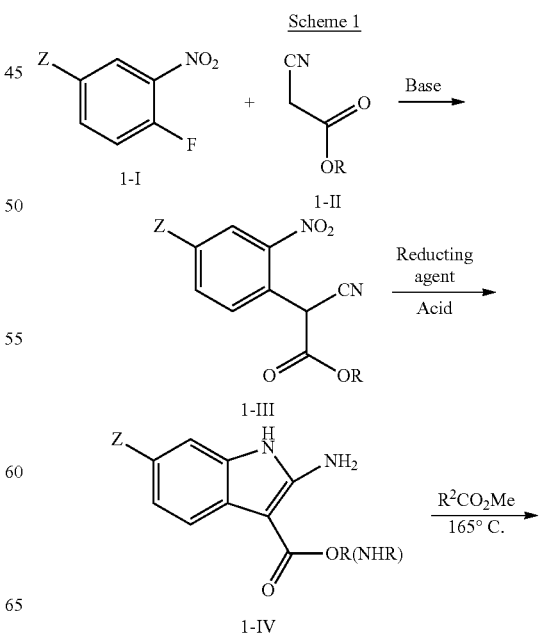

Scheme 1

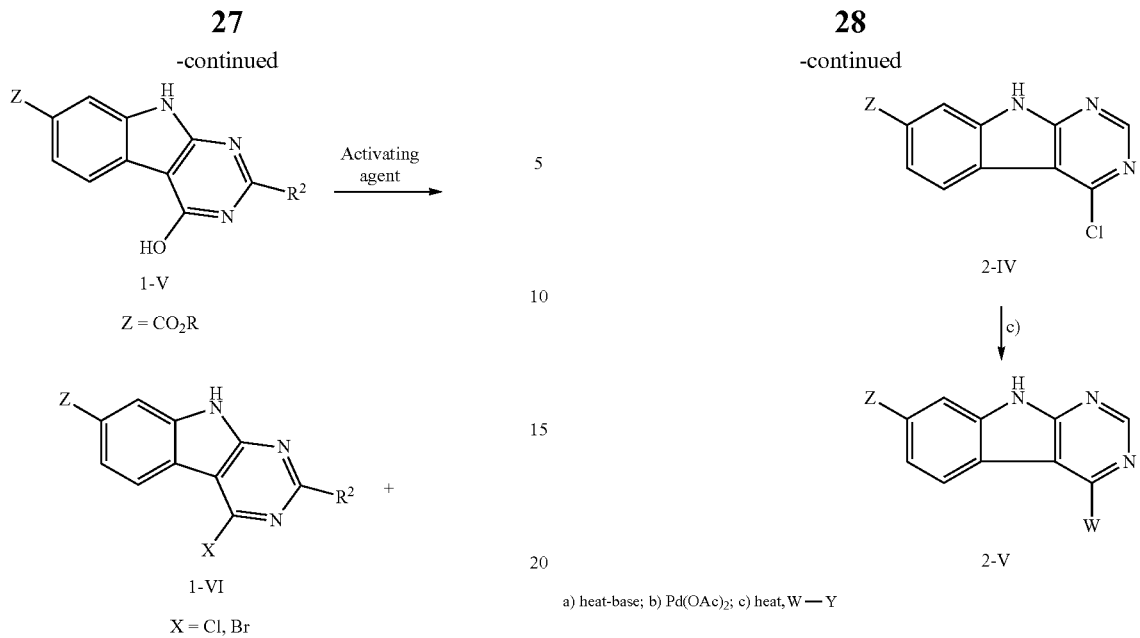

Scheme 2 describes the preparation of compounds 2-V. The reaction of 4,6-dichloro-5-iodopyrimidine 2-II and the corresponding phenol, aniline or thiophenol 2-I with or without a base (Morsin M. et al. *Chemistiy-A European Journal*, 2009, vol. 15, #6, pp. 1468-1477) or a palladium catalyst to give intermediates 2-III. The resulting intermediates 2-III are converted to the tricyclic adduct 2-IV with Pd(OAc)$_2$ (Zhang M. et al. *Tetrahedron Letters*, 2002, vol. 43, p. 8235). Finally, according to Example 1 outlined herein below, the compounds of the present invention 2-V are obtained.

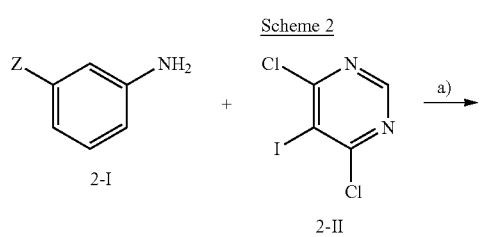

a) heat-base; b) Pd(OAc)$_2$; c) heat, W—Y

Scheme 3: Compounds 4-II are treated with hydroxyl amine followed by dimethylacetamide dimethylacetal (Tully W. R. et al. *Journal of Medicinal Chemistry*, 1991, vol. 34, p. 2060. This gives the compounds 5-I.

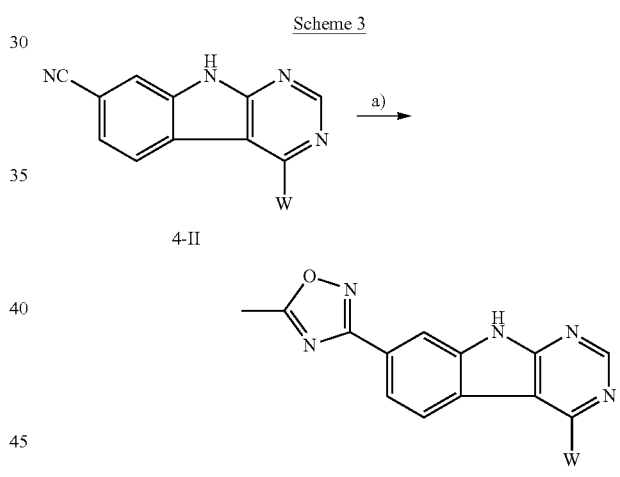

a) 1-NH$_2$OH, 2-DMA acetal

Scheme 4: Intermediate 1B (Example 1 herein below) is treated with propionitrile in HCl/dioxane followed by a basic treatment to furnish methyl 2-ethyl-4-hydroxy-9H-pyrimido [4,5-b]indole-7-carboxylate (6-I). Then according to the procedures described for Example 1 compounds 6-II are obtained.

Scheme 4

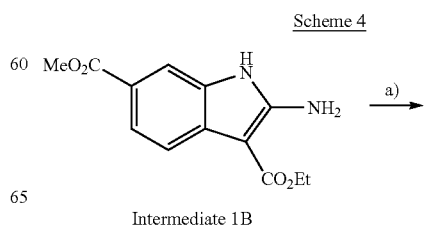

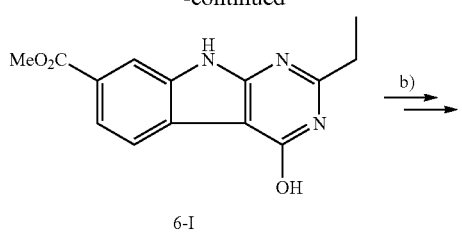

6-I

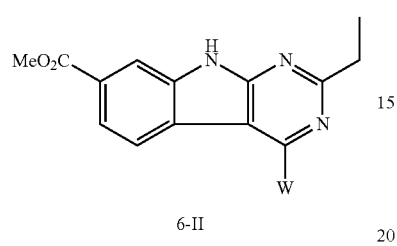

6-II a) HCl, propionitrile; b) see Example 1

Scheme 5: Starting from methyl 3-fluoro-4-nitrobenzoate 7-I and according to the procedure of Example 1, compounds 7-II are obtained.

Scheme 5

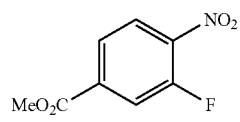

7-I

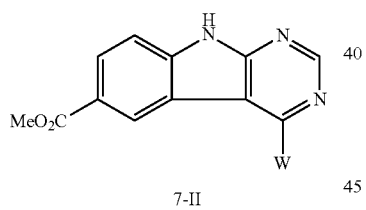

7-II a) see Example 1

EXAMPLES

General

Reported HPLC retention time are for reverse-phase HPLC (Agilent, 1200 series) using the following conditions Solvent A: MeOH:H$_2$O:TFA (5:95:0.05); Solvent B: MeOH:H$_2$O:TFA (95:5:0.05); flow: 3.0 mL/min; gradient 0 to 100% B in 2.0 minutes; column: ZorbaxC18, 3.5 microns, 4.6×30 mm: wavelength 220 nm.

Mass spectra were recorded on a 6210 G1969A LC/MSD TOF spectrometer from Agilent Technologies or on a Quadrupole LC/MS Model G6120B from Agilent Technologies using the following LC conditions: Solvent A: AcCN:H$_2$O:HCOOH (5:95:0.05); Solvent B: AcCN:H$_2$O:HCOOH (95:5: 0.05); gradient 0 to 100% B in 2.0 minutes; flow: 0.3 mL/min; column: ZorbaxC18, 3.5 microns, 2.1×30 mm; wavelength 220 nm.

Experimental Procedures

Example 1

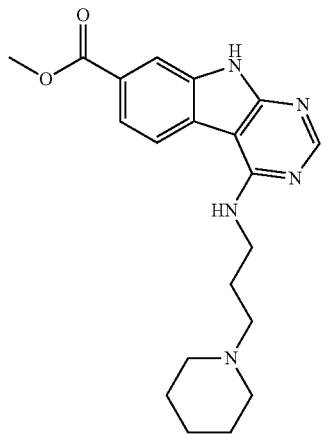 [SMILES: COC(=O)c1ccc2c(c1)[nH]c1ncnc(NCCCN3CCCCC3)c12]

Methyl 4-((3-(piperidin-1-yl)propyl)amino)-9H-pyrimido[4,5-b]indole-7-carboxylate Intermediate 1A

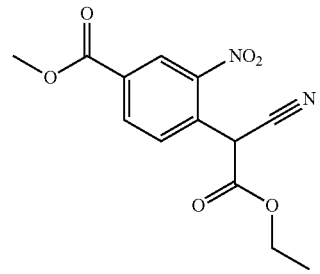 [SMILES: CCOC(=O)C(C#N)c1ccc(C(=O)OC)cc1[N+](=O)[O-]]

methyl 4-(1-cyano-2-ethoxy-2-oxoethyl)-3-nitrobenzoate

Ethyl 2-cyanoacetate (10.9 mL, 102 mmol) was slowly added to a 60% suspension of sodium hydride (4.10 g, 102 mmol) in N,N-dimethylformamide (125 mL) at 0° C. to give a gray suspension. The mixture was stirred at 0° C. for 15 minutes and methyl 4-fluoro-3-nitrobenzoate (10.2 g, 51 mmol) in N,N-dimethylformamide (125 mL) was added. The resulting deep red mixture was stirred at 0° C. for 30 minutes and at room temperature for 3 hours. The reaction mixture was diluted with 1N HCl (40 mL) and ethyl acetate (40 mL). The separated aqueous layer was extracted with ethyl acetate (3×50 mL). The organic layers were combined and dried over anhydrous sodium sulfate, filtered and concentrated to afford a residue (26 g) which was purified by flash-chromatography (started with 100% hexanes and gradually added ethyl acetate increments to complete with 100% ethyl acetate) to afford 14.9 g of the title compound. LCMS m/z 291.0 (M−H)⁻, retention time (on analytical HPLC)=1.76 minutes.

Intermediate 1B

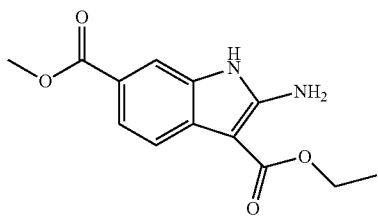 [SMILES: CCOC(=O)c1c(N)[nH]c2cc(C(=O)OC)ccc12]

3-ethyl 6-methyl 2-amino-1H-indole-3,6-dicarboxylate

In a 500 mL round-bottom flask were added methyl 4-(1-cyano-2-ethoxy-2-oxoethyl)-3-nitrobenzoate (14.9 g, 51.0 mmol) and zinc dust (16.7 g, 255 mmol) in acetic acid (255 mL) to give a gray suspension. The addition of zinc was done over 35 minutes at room temperature over an atmosphere of nitrogen and was fairly exothermic. The mixture was heated at 100° C. for 15 hours. The mixture was allowed to cool down, filtered through Celite and rinsed with ethyl acetate. Evaporation afforded a residue which was triturated in dichloromethane-hexanes and afforded, after filtration 6.3 g of the title compound. LCMS m/z 263.2 (M+H)⁺, retention time (on analytical HPLC)=1.90 minutes.

Intermediate 1C

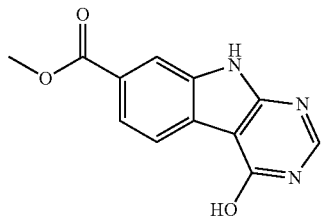 [SMILES: COC(=O)c1ccc2c(c1)[nH]c1ncnc(O)c12]

methyl 4-hydroxy-9H-pyrimido[4,5-b]indole-7-carboxylate

In a 100 mL round-bottom flask were added 3-ethyl 6-methyl 2-amino-1H-indole-3,6-dicarboxylate (1.1 g, 4.19 mmol), ammonium formate (0.53 g, 8.39 mmol), and formamide (16.7 mL, 419 mmol) to give a tan suspension which was heated to 165° C. for 12 hours. The mixture was allowed to cool to room temperature and water was added. The resulting precipitate was filtered, air-dried and dried under high vacuum overnight to afford 1.1 g of the title compound. LCMS m/z 244.2 (M+H)⁺, retention time (on analytical HPLC)=1.51 minutes.

Intermediate 1D

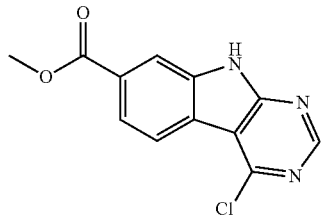 [SMILES: COC(=O)c1ccc2c(c1)[nH]c1ncnc(Cl)c12]

methyl 4-chloro-9H-pyrimido[4,5-b]indole-7-carboxylate

In a 100 mL round-bottom flask a mixture of methyl 4-hydroxy-9H-pyrimido[4,5-b]indole-7-carboxylate (1.1 g, 4.5 mmol) and phosphorous oxychloride (15 mL, 161 mmol) was heated to 90° C. for 16 hours, cooled down to room temperature and evaporated under reduced pressure. The residue was suspended in dichloromethane (20 mL) and filtered through Celite. Evaporation afforded the title compound as an orange solid (360 mg). LCMS m/z 262.0 (M+H)⁺, retention time (on analytical HPLC)=2.02 minutes.

Example 1

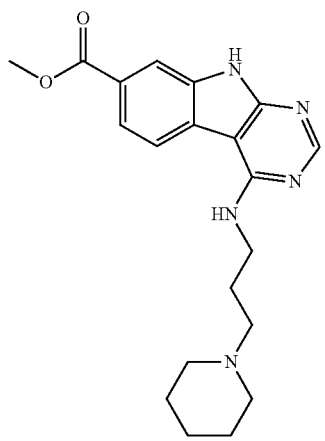 [SMILES: COC(=O)c1ccc2c(c1)[nH]c1ncnc(NCCCN3CCCCC3)c12]

methyl 4-((3-(piperidin-1-yl)propyl)amino)-9H-pyrimido[4,5-b]indole-7-carboxylate In a 2-5 mL microwave vial was added methyl 4-chloro-9H-pyrimido[4,5-b]indole-7-carboxylate (86 mg, 0.33 mmol), triethylamine (0.09 mL, 0.66 mmol) and 3-(piperidin-1-yl)propan-1-amine (0.078 mL, 0.49 mmol) in methanol (2 mL) and the mixture was heated to 140° C. for 15 minutes in a microwave reactor. The mixture was allowed to cool to room temperature and evaporated under reduced pressure. The crude material was dissolved in N,N-dimethylformamide and purified on a reverse-phase Zorbax SB-C18 column 21.2×100 mm and was eluted with MeOH-Water-0.1% TFA. Gradient: Isocratic 20% for 4 minute(s) then gradient to 100% MeOH over 15 minutes. The title compound was obtained as the trifluoroacetic acid salt (the corresponding free base and HCl salt were prepared according to standard procedures known by those skilled in the art). LCMS m/z 368.2 (M+H)$^+$, retention time (on analytical HPLC)=1.38 minutes.

Example 14

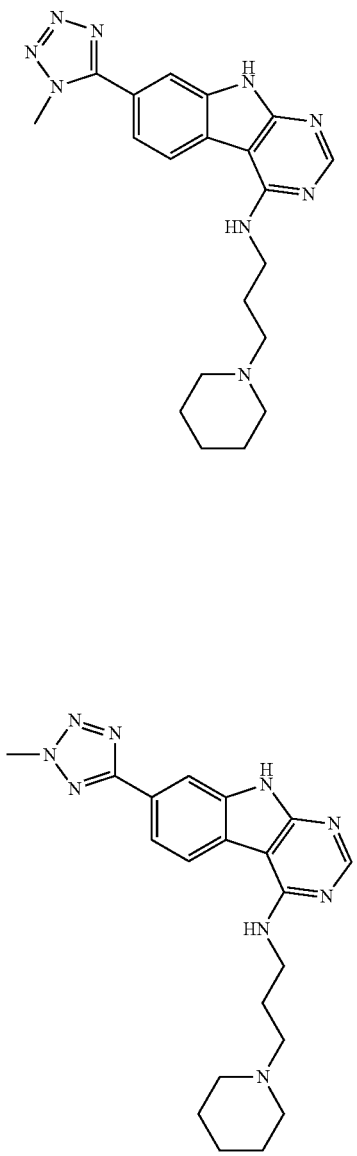

7-(1-methyl-1H-tetrazol-5-yl)-N-(3-(piperidin-1-yl) propyl)-9H-pyrimido[4,5-b]indol-4-amine and 7-(2-methyl-2H-tetrazol-5-yl)-N-(3-(piperidin-1-yl)propyl)-9H-pyrimido[4,5-b]indol-4-amine Intermediate 14A

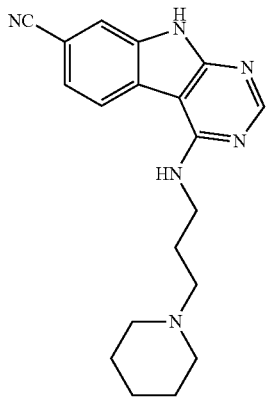 [SMILES: N#Cc1ccc2c(c1)[nH]c1ncnc(NCCCN3CCCCC3)c12]

4-((3-(piperidin-1-yl)propyl)amino)-9H-pyrimido[4,5-b]indole-7-carbonitrile

Starting from 4-fluoro-3-nitrobenzonitrile, Intermediate 2A was prepared according to the procedure described in Example 1.

Intermediate 14B

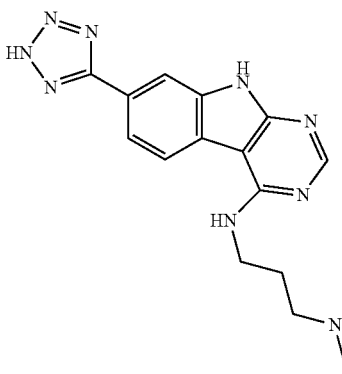

N-(3-(piperidin-1-yl)propyl)-7-(2H-tetrazol-5-yl)-9H-pyrimido[4,5-b]indol-4-amine In a 2-5 mL microwave vial was added 4-((3-(piperidin-1-yl)propyl)amino)-9H-pyrimido[4,5-b]indole-7-carbonitrile (47.5 mg, 0.142 mmol) and azidotributyltin (409 µl, 1.491 mmol) in (trifluoromethyl)benzene (2 mL) to give a tan suspension. The vial was placed in the microwave and heated to 180° C. for 30 minutes. The mixture was concentrated to dryness and MeOH (3 mL) followed by HCl 4M in Dioxane (1.07 mL, 4.26 mmol) was added to get a yellow solution. To the resulting solution was added diethyl ether (3 mL) Stirred at 20° C. for 16 hours. The solid obtained was collected on a Buchner. The cake was washed with diethyl ether (3×1 mL) and with Hexane (3×1 mL) and the solid dried at 30° C. under high vacuum until constant weight to afford 56 mg of the title compound as the HCl salt. LCMS m/z 378.2 (M+H)+, retention time (on analytical HPLC)=1.30 minutes.

Example 14

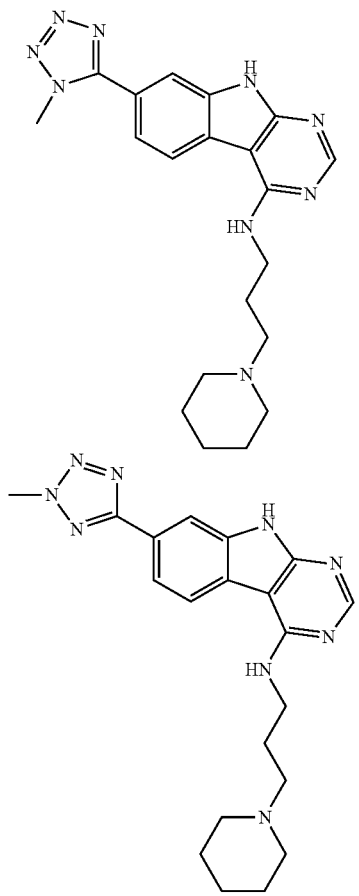

7-(1-methyl-1H-tetrazol-5-yl)-N-(3-(piperidin-1-yl)propyl)-9H-pyrimido[4,5-b]indol-4-amine and 7-(2-methyl-2H-tetrazol-5-yl)-N-(3-(piperidin-1-yl)propyl)-9H-pyrimido[4,5-b]indol-4-amine In a 25 mL round-bottomed flask were added N-(3-(piperidin-1-yl)propyl)-7-(2H-tetrazol-5-yl)-9H-pyrimido[4,5-b]indol-4-amine hydrochloride (43 mg, 0.10 mmol) and N,N-diisopropylethylamine (36 μl, 0.21 mmol) in tetrahydrofuran (2 mL) and methanol (0.5 ml) to give a tan suspension. Trimethylsilyldiazomethane 2M in hexane (260 μl, 0.52 mmol) was then added. The resulting thin yellow suspension was stirred at 20° C. for 3 hours and acetic acid (59 μl, 1.04 mmol) was added. Stirring continued for 30 minutes and the solvents were removed under vacuum to afford a residue which was purified by flash-chromatography (started with 100% dichloromethane and gradually added a mixture of dichloromethane:methanol:28% wt. aqueous ammonium hydroxide (90:10:1) increments to complete with 100% dichloromethane:methanol:28% wt. aqueous ammonium hydroxide (90:10:1). The first eluting product obtained was of 7-(2-methyl-2H-tetrazol-5-yl)-N-(3-(piperidin-1-yl)propyl)-9H-pyrimido[4,5-b]indol-4-amine (19 mg). LCMS m/z 392.2 (M+H)+, retention time (on analytical HPLC)=1.44 minute. The second eluting product was of 7-(1-methyl-1H-tetrazol-5-yl)-N-(3-(piperidin-1-yl)propyl)-9H-pyrimido[4,5-b]indol-4-amine (5 mg). LCMS m/z 392.2 (M+H)+, retention time (on analytical HPLC)=1.27 minutes.

Example 15

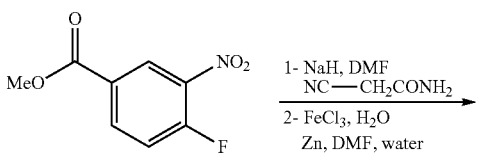

Intermediate 15A

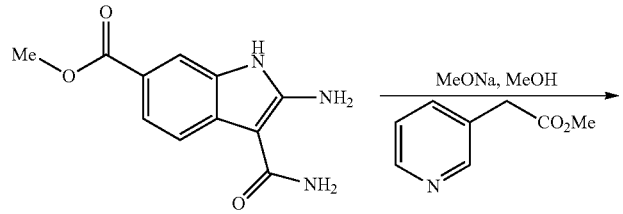

Intermediate 15B

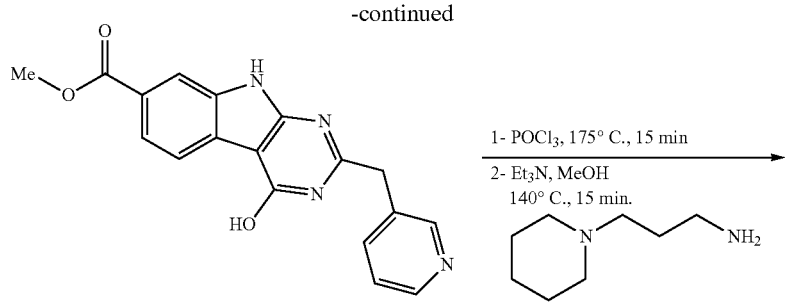

Intermediate 15C

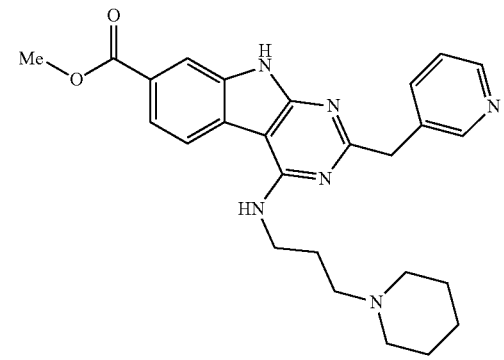

Example 15

NaH (3.41 g, 85 mmol) was added portionwise to a cold solution of 2-cyanoacetamide (7.18 g, 85 mmol) in DMF (53 mL). After 30 minutes at room temperature, a solution of methyl 4-fluoro-3-nitrobenzoate (8.5 g, 42.7 mmol) in 15 mL of DMF was added dropwise. After 3 hours a mixture of ice, water and 12 mL HCl (10%) were added. The resulting solid was filtered, rinsed with water and dried under high vacuum overnight to give 9.1 g of methyl 4-(2-amino-1-cyano-2-oxo-ethyl)-3-nitrobenzoate: $^1$H NMR (400 MHz, DMSO-d$_6$) δ ppm 3.93 (s, 3H) 5.78 (s, 1H) 7.77 (s, 1H) 7.91 (d, J=7.83 Hz, 1H) 8.04 (s, 1H) 8.39 (dd, J=8.02, 1.76 Hz, 1H) 8.56 (d, J=1.56 Hz, 1H).

Ferric chloride hexahydrate (1.540 g, 5.70 mmol) and zinc (1.242 g, 19.00 mmol) were added to a solution of the crude cyano-amide prepared above (0.5 g, 1.900 mmol) in DMF (4.75 mL) and water (4.75 mL) to give a yellow suspension. After the exotherm, the mixture was heated to 100° C. for 45 minutes and then slowly cooled to 20° C. and stirred for 22 hours. The solid was filtered, washed with DMF (3×3 mL) and the filtrate was diluted with water (40 mL) while stirring at 0° C. The solid was filtered and the cake washed with water (2×5 mL). The solid contains mostly impurities. The aqueous layer was extracted with EtOAc (3×50 mL) and the combined organic layers were washed with water (50 mL) and then with brine (30 mL). The organic layer was dried over anh. MgSO$_4$, filtered and concentrated to give 287 mg as a brown solid which was treated with acetone (6 mL) to give a solid suspension which was diluted with hexane (5 mL). Then the solid was collected and dried at 40° C. under high vacuum until constant weight to give Intermediate 15B methyl 2-amino-3-carbamoyl-1H-indole-6-carboxylate (162 mg, 36.6% yield) as an off-white solid: $^1$H NMR (400 MHz, DMSO-d$_6$) δ ppm 3.80 (s, 3H) 6.62 (br. s., 2H) 7.04-7.18 (m, 2H) 7.53-7.63 (m, 2H) 7.72 (s, 1H) 10.80 (s, 1H); MS m/z 232.2 (M+H)$^+$; HPLC ca. 96%, RT=1.37 minutes.

A mixture of Intermediate 15B (0.100 g, 0.429 mmol), methyl 2-(pyridin-3-yl)acetate (0.130 g, 0.858 mmol) and sodium methoxide 25% wt in MeOH (0.196 mL) in methanol (0.954 mL) was placed in the microwave oven and heated to 140° C. for 45 minutes. After cooling, AcOH (0.050 mL, 0.879 mmol) was added and the resulting slurry was stirred at 20° C. for 1 hour. The solids were filtered, washed with MeOH (3×0.5 mL), dried at 20° C. under high vacuum until constant weight to give Intermediate 15C: methyl 4-hydroxy-2-(pyridin-3-ylmethyl)-9H-pyrimido[4,5-b]indole-7-carboxylate (82 mg, 57.2% yield) as a brown solid: $^1$H NMR (400 MHz, DMSO-d$_6$) δ ppm 3.87 (s, 3H) 4.09 (s, 2H) 7.34-7.40 (m, 1H) 7.79 (dt, J=8.1, 1.8 Hz, 1H) 7.83 (dd, J=8.2, 1.2 Hz, 1H) 7.99 (d, J=0.8 Hz, 1H) 8.02 (d, J=8.2 Hz, 1H) 8.48 (dd, J=4.9, 1.4 Hz, 1H) 8.60 (d, J=2.0 Hz, 1H) 12.49 (br. s., 2H): MS m/z 335.2 (M+H)$^+$; HPLC 95.2% @ 220 nm and 92.8% @ 254 nm, RT=1.42 minutes.

A mixture of methyl 4-hydroxy-2-(pyridin-3-ylmethyl)-9H-pyrimido[4,5-b]indole-7-carboxylate (0.050 g, 0.150 mmol) in POCl$_3$ (0.948 mL, 10.17 mmol) was placed in a vial and heated to 175° C. for 15 minutes in a microwave oven. After cooling, the reaction mixture was poured into ice-water (19 mL) then basified to pH 8 by the slow addition of 50% aq. NaOH (2.7 mL) and finally diluted with EtOAc (20 mL), the solids were filtered (first crop of chloride) and the aqueous layer was extracted with EtOAc (20 mL) and the combined organic layers were dried over anh. MgSO$_4$, filtered and concentrated to dryness to afford an additional 35 mg crop of the desired chloride derivative. The combined isolated crops of methyl 4-chloro-2-(pyridin-3-ylmethyl)-9H-pyrimido[4,5-b]indole-7-carboxylate (53 mg, 100% yield) were used directly in the next step.

A mixture of methyl 4-chloro-2-(pyridin-3-ylmethyl)-9H-pyrimido[4,5-b]indole-7-carboxylate (0.053 g, 0.150 mmol), 3-(piperidin-1-yl)propan-1-amine (0.072 mL, 0.451 mmol) and triethylamine (0.063 mL, 0.451 mmol) in MeOH (2.5 mL) was placed in a vial and heated to 140° C. for 15 minutes in a microwave oven for 15 minutes. After cooling and evaporation of the solvent, the residue was purified by flash chromatography to give 23 mg of a yellow oil+solid which was diluted with CH$_3$CN (3 mL) and stirred for 30 minutes. The solids were filtered and washed with CH$_3$CN (2×0.5 mL), then dried at 30° C. under high vacuum until constant weight to afford the compound of Example 15: methyl 4-((3-(piperidin-1-yl)propyl)amino)-2-(pyridin-3-ylmethyl)-9H-pyrimido[4,5-b]indole-7-carboxylate (11 mg, 16% yield) as a tan solid: $^1$H NMR (400 MHz, DMSO-d$_6$) δ ppm 1.31-1.44 (m, 2H) 1.44-1.56 (m, 4H) 1.71-1.86 (m, 2H) 2.17-2.47 (m, 6H) 3.56-3.66 (m, 2H) 3.88 (s, 3H) 4.08 (s, 2H) 7.28-7.34 (m, 1H) 7.43 (t, J=5.5 Hz, 1H) 7.76 (dt, J=7.8, 2.0 Hz, 1H) 7.81 (dd, J=8.2, 1.4 Hz, 1H) 7.99 (d, J=1.4 Hz, 1H) 8.35 (d, J=8.2 Hz, 1H) 8.41 (dd, J=4.7, 1.6 Hz, 1H) 8.59 (d, J=2.0 Hz, 1H) 12.08 (s, 1H); MS m/z 459.2 (M+H)$^+$; HPLC >99.5%, RT=1.43 minutes.

Example 22

Hydrogenolysis of the benzyl group was performed on derivative methyl 2-((benzyloxy)(phenyl)methyl)-4-((3-(piperidin-1-yl)propyl)amino)-9H-pyrimido[4,5-b]indole-7-carboxylate (0.042 g, 0.075 mmol) in the presence of Pd—C 10% wt. (50% wet) (0.159 g, 0.075 mmol) and ammonium formate (0.235 g, 3.73 mmol) under hydrogen in methanol. After 26 hours of stirring at 55° C., the reaction mixture was filtered over Celite, rinsed with MeOH, and concentrated to dryness on a rotovap to give 133 mg of a residue which was purified by RP HPLC using a Zorbax SB-C18 column 21.2× 150 mm eluted with MeOH-water-0.1% TFA to afford 21.9 mg (50% yield) of Example 22: methyl 2-(hydroxy(phenyl)methyl)-4-((3-(piperidin-1-yl)propyl)amino)-9H-pyrimido[4,5-b]indole-7-carboxylate, TFA salt as a white solid: $^1$H NMR (400 MHz, DMSO-d$_6$) δ ppm 1.30-1.43 (m, 1H) 1.52-1.73 (m, 3H) 1.79 (br. d, J=14.5 Hz, 2H) 1.96-2.09 (m, 2H) 2.54 (s, 1H) 2.74-2.89 (m, 2H) 3.11 (dt, J=10.4, 5.4 Hz, 2H) 3.38 (d, J=12.1 Hz, 2H) 3.71-3.77 (m, 2H) 3.88 (s, 3H) 5.63 (s, 1H) 7.19-7.26 (m, 1H) 7.27-7.35 (m, 2H) 7.48-7.56 (m, 2H) 7.62 (t, J=5.9 Hz, 1H) 7.85 (dd, J=8.2, 1.4 Hz, 1H) 8.03

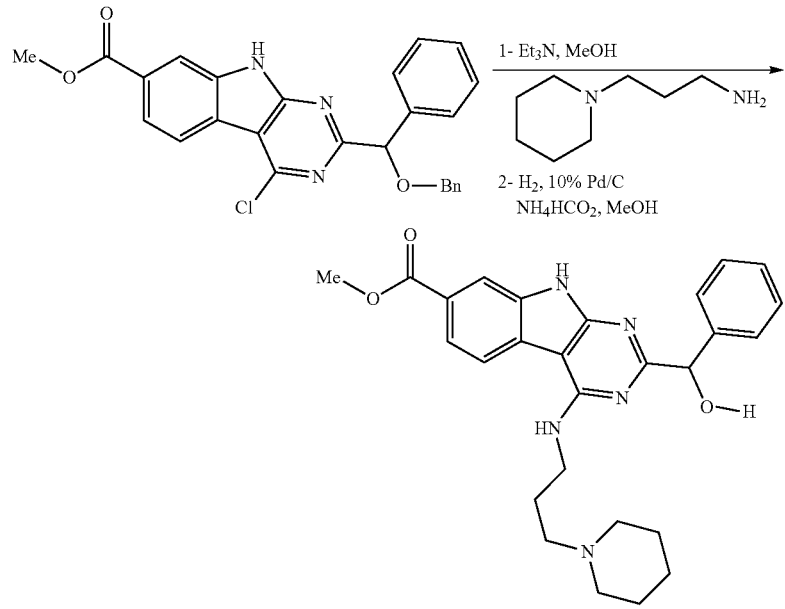

Example 22

A mixture of methyl 2-((benzyloxy)(phenyl)methyl)-4-chloro-9H-pyrimido[4,5-b]indole-7-carboxylate (prepared as described for Example 15, 0.228 g, 0.498 mmol), 3-(piperidin-1-yl)propan-1-amine (0.158 mL, 0.996 mmol) and triethylamine (0.173 mL, 1.245 mmol) in MeOH (3.8 mL) was placed in the microwave oven and heated to 140° C. for 30 minutes. After cooling to room temperature, the mixture was concentrated to dryness and the residue was purified by flash chromatography to afford methyl 2-((benzyloxy)(phenyl)methyl)-4-((3-(piperidin-1-yl)propyl)amino)-9H-pyrimido[4,5-b]indole-7-carboxylate (172 mg, 61.3% yield) as a light yellow solid: $^1$H NMR (400 MHz, DMSO-d$_6$) δ ppm 1.29-1.42 (m, 2H) 1.42-1.56 (m, 4H) 1.72-1.91 (m, 2H) 2.18-2.47 (m, 6H) 3.66 (tt, J=13.2, 6.6 Hz, 2H) 3.88 (s, 3H) 4.54 (d, J=11.7 Hz, 1H) 4.64 (d, J=12.1 Hz, 1H) 5.50 (s, 1H) 7.21-7.43 (m, 8H) 7.51 (t, J=5.9 Hz, 1H) 7.57 (d, J=7.0 Hz, 2H) 7.82 (dd, J=8.2, 1.2 Hz, 1H) 8.00 (d, J=1.2 Hz, 1H) 8.38 (d, J=8.2 Hz, 1H) 12.22 (s, 1H); HRMS m/z 564.2979 (M+H)$^+$; HPLC 99.6%, RT=2.02 minutes.

(d, J=1.4 Hz, 1H) 8.38 (d, J=8.2 Hz, 1H) 8.92 (br. s., 1H) 12.21 (s, 1H); HRMS m/z 474.2511 (M+H)$^+$; HPLC >99%, RT=1.68 minutes.

Dess-Martin periodinane reagent (22.67 mg, 0.053 mmol) was added to a mixture of methyl 2-(hydroxy(phenyl)methyl)-4-((3-(piperidin-1-yl)propyl)amino)-9H-pyrimido[4,5-b]indole-7-carboxylate (compound of Example 22) and TFA (15.7 mg, 0.027 mmol) in DCM (1000 μL, 15.54 mmol) to give a light orange solution. After 1 h, the solvent was evaporated and the residue was purified by flash chromatography to afford Example 23: methyl 2-benzoyl-4-((3-(piperidin-1-yl)propyl)amino)-9H-pyrimido[4,5-b]indole-7-carboxylate (10 mg, 79% yield) as a bright yellow solid: $^1$H NMR (400 MHz, DMSO-d$_6$) δ ppm 1.27-1.36 (m, 2H) 1.36-1.48 (m, 4H) 1.74-1.88 (m, 2H) 2.14-2.44 (m, 6H) 3.52-3.68 (m, 2H) 3.91 (s, 3H) 7.54 (t, J=7.8 Hz, 2H) 7.69 (t, J=7.4 Hz, 1H) 7.76 (t, J=5.1 Hz, 1H) 7.90 (dd, J=8.2, 1.4 Hz, 1H) 7.94 (d, J=7.0 Hz, 2H) 8.10 (d, J=1.4 Hz, 1H) 8.52 (d, J=8.2 Hz, 1H) 12.43 (s, 1H);

HRMS m/z 472.2342 (M+H)+; HPLC 97.1% @ 220 nm and 98.9% @ 254 nm, RT=1.86 minutes.

Example 25

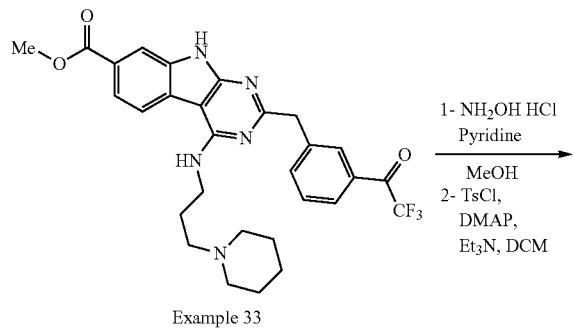

Example 33

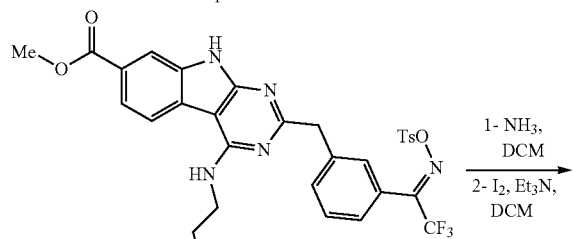

Intermediate 33A

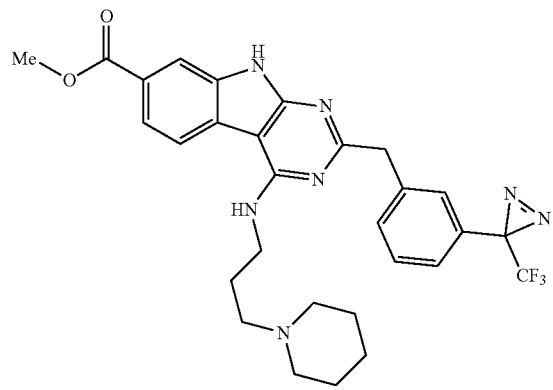

Example 25

Hydroxylamine hydrochloride (0.08 g, 1.2 mmol) was added to methyl 4-((3-(piperidin-1-yl)propyl)amino)-2-(3-(2,2,2-trifluoroacetyl)benzyl)-9H-pyrimido[4,5-b]indole-7-carboxylate (compound of Example 33) (0.285 g, 0.515 mmol) in MeOH (4.00 mL) and pyridine (0.666 mL) to give a yellow solution. After heating at 60° C. 5 days, the mixture was concentrated to dryness and the residue was dissolved into DCM (75 mL) and MeOH (15 mL) and this solution was washed with sat. NaHCO$_3$ (20 mL). The aqueous layer was extracted two time with a mixture of CH$_2$Cl$_2$ (50 mL) and MeOH (10 mL) and the combined organic layers were dried over anh. MgSO$_4$, filtered and concentrated to dryness to give methyl 4-((3-(piperidin-1-yl)propyl)amino)-2-(3-(2,2,2-trifluoro-1-(hydroxyimino)ethyl)benzyl)-9H-pyrimido[4,5-b]indole-7-carboxylate (293 mg, 100% yield) as an off-white solid: $^1$H NMR (400 MHz, DMSO-d$_6$) δ ppm 1.32-1.43 (m, 2H) 1.44-1.56 (m, 4H) 1.76-1.87 (m, 2H) 2.23-2.44 (m, 6H) 3.57-3.67 (m, 2H) 3.88 (s, 3H) 4.04-4.12 (m, 2H) 7.25-7.33 (m, 1H) 7.34-7.46 (m, 2H) 7.50 (m, J=7.6, 4.1 Hz, 1H) 7.55 (d, J=7.4 Hz, 1H) 7.81 (dd, J=8.2, 1.2 Hz, 1H) 7.99 (d, J=1.2 Hz, 1H) 8.36 (d, J=8.2 Hz, 1H) 12.07 (d, J=3.5 Hz, 1H); MS m/z 569.2 (M+H)+; HPLC >95%, RT=1.88 minutes.

Tosyl chloride (0.048 g, 0.251 mmol) was added portionwise to a cold mixture of methyl 4-((3-(piperidin-1-yl)propyl)amino)-2-(3-(2,2,2-trifluoro-1-(hydroxyimino)ethyl)benzyl)-9H-pyrimido[4,5-b]indole-7-carboxylate (0.130 g, 0.229 mmol), 4-dimethylaminopyridine (2.79 mg, 0.023 mmol) and triethylamine (0.038 mL, 0.274 mmol) in DCM (10.00 mL) to give a white suspension. After one hour at room temperature, the amber solution was diluted with DCM (10 mL) and washed with water (3×10 mL). The organic layer was dried over anh. MgSO4, filtered and concentrated to dryness to give methyl 4-((3-(piperidin-1-yl)propyl)amino)-2-(3-(2,2,2-trifluoro-1-((tosyloxy)imino)ethyl)benzyl)-9H-pyrimido[4,5-b]indole-7-carboxylate (188 mg, 99% yield) as a tan foam: MS m/z 723.2 (M+H)+; HPLC >89%, RT=2.09 minutes.

To a solution of methyl 4-((3-(piperidin-1-yl)propyl)amino)-2-(3-(2,2,2-trifluoro-1-((tosyloxy)imino)ethyl)benzyl)-9H-pyrimido[4,5-b]indole-7-carboxylate (0.188 g, 0.260 mmol) in DCM (5.00 mL) cooled to −78° C., ammonia (1.689 mL, 78 mmol) was added and the tube was sealed and warmed to 20° C. The reaction mixture turned blue over time and after 3.5 hours it was cooled again to −78° C. and then slowly warmed to 20° C. with septa+nitrogen outlet to evaporate most of the ammonia. After 3.5 hours, the reaction mixture was filtered over Buchner to remove most of the ammonium p-toluenesulfonate), the solids were washed with DCM (3×1.5 mL) and the filtrate was concentrated to dryness to give a yellow foam which was purified by flash chromatography to afford methyl 4-((3-(piperidin-1-yl)propyl)amino)-2-(3-(3-(trifluoromethyl)diaziridin-3-yl)benzyl)-9H-pyrimido[4,5-b]indole-7-carboxylate (115 mg, 78% yield) as a white foam: $^1$H NMR (400 MHz, DMSO-d$_6$) δ ppm 1.31-1.43 (m, 2H) 1.50 (quin, J=5.3 Hz, 4H) 1.80 (dt, J=14.1, 7.0 Hz, 2H) 2.32 (m, J=6.7, 6.7 Hz, 6H) 3.58-3.67 (m, 2H) 3.88 (s, 3H) 3.93 (br. d, J=7.4 Hz, 1H) 4.05 (br. d, J=8.6 Hz, 1H) 4.07 (s, 2H) 7.32-7.43 (m, 3H) 7.47 (m, J=6.3 Hz, 1H) 7.59 (s, 1H) 7.81 (dd, J=8.4, 1.2 Hz, 1H) 7.99 (d, J=1.2 Hz, 1H) 8.35 (d, J=8.4 Hz, 1H) 12.07 (s, 1H); MS m/z 568.2 (M+H)+; HPLC >94%, RT=1.72 minutes.

Iodine (0.028 g, 0.111 mmol) was added to a mixture of methyl 4-((3-(piperidin-1-yl)propyl)amino)-2-(3-(3-(trifluoromethyl)diaziridin-3-yl)benzyl)-9H-pyrimido[4,5-b]indole-7-carboxylate (0.060 g, 0.106 mmol) and triethylamine (0.044 mL, 0.317 mmol) in DCM (2 mL) to give a yellow solution. After 15 minutes, the solvent was evaporated under reduced pressure to give a residue which was purified by flash chromatography to afford 95 mg as a yellow foam. The foam was dissolved in DCM (15 mL) and washed with sat. NaHCO3 (10 mL). The organic layer was dried over anh. MgSO4, filtered and concentrated to dryness to afford the compound of Example 25: methyl 4-((3-(piperidin-1-yl)propyl)amino)-2-(3-(3-(trifluoromethyl)-3H-diazirin-3-yl)benzyl)-9H-pyrimido[4,5-b]indole-7-carboxylate (50 mg, 84% yield) as a light yellow solid: $^1$H NMR (400 MHz, DMSO-d$_6$) δ ppm 1.36 (m, J=5.1 Hz, 2H) 1.48 (quin, J=5.5 Hz, 4H) 1.76 (quin, J=7.0 Hz, 2H) 2.30 (br. t, J=6.5, 6.5 Hz, 6H) 3.54-3.67 (m, 2H) 3.88 (s, 3H) 4.09 (s, 2H) 7.14 (d, J=7.8 Hz, 1H) 7.26 (s, 1H) 7.38-7.47 (m, 2H) 7.52 (d, J=7.4 Hz, 1H) 7.81 (d, J=8.2 Hz, 1H) 7.99 (s, 1H) 8.35 (d, J=8.2 Hz, 1H) 12.06 (s, 1H); HRMS m/z 566.2497 (M+H)+; HPLC 94.5% @ 220 nm and 92.9% @ 254 nm, RT=2.05 minutes.

Examples 33 and 34

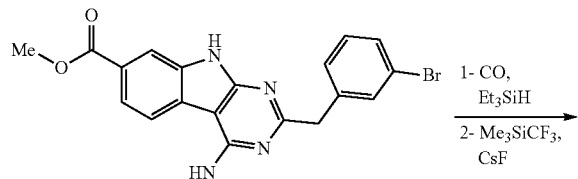

Example 28

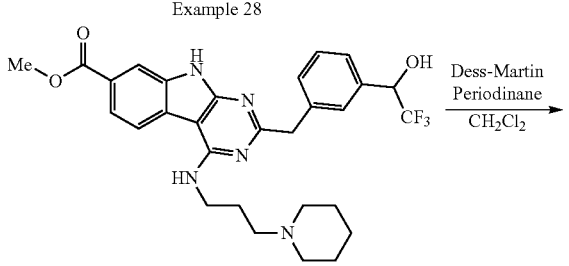

Example 34

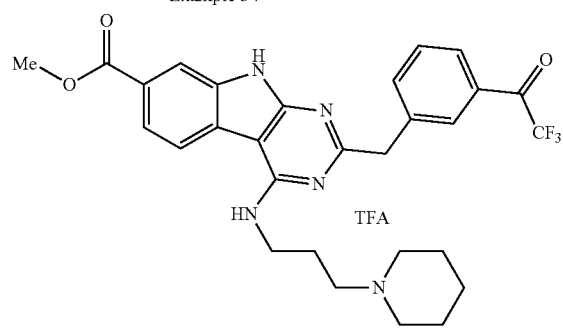

Example 33

CO was bubbled into a solution of methyl 2-(3-bromobenzyl)-4-((3-(piperidin-1-yl)propyl)amino)-9H-pyrimido[4,5-b]indole-7-carboxylate (prepared as for Example 15, 0.090 g, 0.168 mmol), triethylsilane (0.054 mL, 0.336 mmol) and PdCl$_2$ (dppf) (6.14 mg, 8.39 µmol) and the mixture was heated overnight at 95° C. The crude mixture was purified by preparative HPLC to give 44 mg of carbonylated product as a solid: $^1$H NMR (400 MHz, DMSO-d6) δ ppm 1.28-1.40 (m, 1H) 1.50-1.72 (m, 3H) 1.73-1.84 (m, 2H) 1.95-2.06 (m, 2H) 2.74-2.87 (m, 2H) 3.03-3.12 (m, 2H) 3.33-3.41 (m, 2H) 3.88 (s, 3H) 4.20 (s, 2H) 7.46-7.60 (m, 2H) 7.73 (d, J=7.83 Hz, 1H) 7.79 (d, J=7.43 Hz, 1H) 7.84 (dd, J=8.22, 1.57 Hz, 1H) 7.91 (s, 1H) 8.01 (d, J=1.17 Hz, 1H) 8.37 (d, J=8.61 Hz, 1H) 8.92 (br. s., 1H) 10.00 (s, 1H) 12.16 (s, 1H).

Trimethyl(trifluoromethyl)silane (0.7 mL, 3.5 mmol) was added to a mixture of methyl 2-(3-formylbenzyl)-4-((3-(piperidin-1-yl)propyl)amino)-9H-pyrimido[4,5-b]indole-7-carboxylate (0.260 g, 0.535 mmol) and cesium fluoride (5.69 mg, 0.037 mmol) cooled to 0° C. After stirring for 2 days at room temperature, HCl conc. (0.5 mL) in 2 mL of water was added and stirred 15 min. The mixture was diluted with ethyl acetate, neutralized with solid Na2CO3, the phases were separated and the aqueous layer was extracted 2 times with EA. The combined organic layers were washed with water, dried over anh. MgSO4, filtered and the solvent removed to give a residue which was purified by preparative HPLC to give 126 mg of corresponding TFA salt: $^1$H NMR (400 MHz, DMSO-d6) δ ppm 1.24-1.43 (m, 1H) 1.49-1.73 (m, 4H) 1.73-1.82 (m, 2H) 1.97-2.07 (m, 2H) 2.80 (q, J=11.70 Hz, 2H) 3.02-3.12 (m, 2H) 3.36-3.42 (m, 2H) 3.88 (s, 3H) 4.10 (s, 2H) 5.12 (q, J=7.17 Hz, 1H) 6.81 (br. s., 1H) 7.30-7.35 (m, 2H) 7.36-7.42 (m, 1H) 7.48-7.58 (m, 2H) 7.84 (dd, J=8.41, 1.37 Hz, 1H) 8.01 (s, 1H) 8.37 (d, J=8.61 Hz, 1H) 8.95 (br. s., 1H) 12.17 (s, 1H); MS m/z 554.2 (M+H)+; HPLC RT 2.142 minutes.

Dess-Martin periodinane (56.5 mg, 0.133 mmol) was added to methyl 4-((3-(piperidin-1-yl)propyl)amino)-2-(3-(2,2,2-trifluoro-1-hydroxyethyl)benzyl)-9H-pyrimido[4,5-b]indole-7-carboxylate (20 mg, 0.036 mmol) in DCM (753 µL) to give a white suspension. After stirring at 20° C. for 1 hour the mixture was purified by flash chromatography to give methyl 4-((3-(piperidin-1-yl)propyl)amino)-2-(3-(2,2,2-trifluoroacetyl)benzyl)-9H-pyrimido[4,5-b]indole-7-carboxylate as Example 33 (18.4 mg, 92% yield) as a yellow solid: $^1$H NMR in DMSO-d$_6$ was consistent with the desired product but complicated because of the presence of hydrate forms; HRMS m/z 554.2384 (M+H)+; HPLC >95%, RT=1.76 and 1.87 minutes (ketone+hydrate).

Example 35

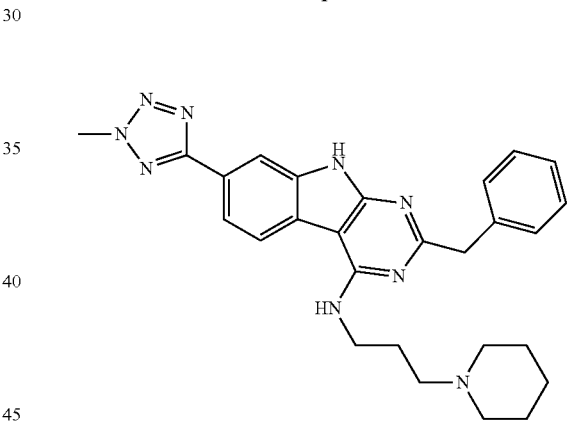

Intermediate 35B

N2 Isomer Precursor

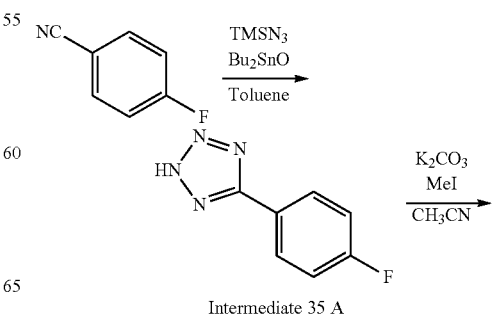

Intermediate 35 A

Intermediates 35 C et D

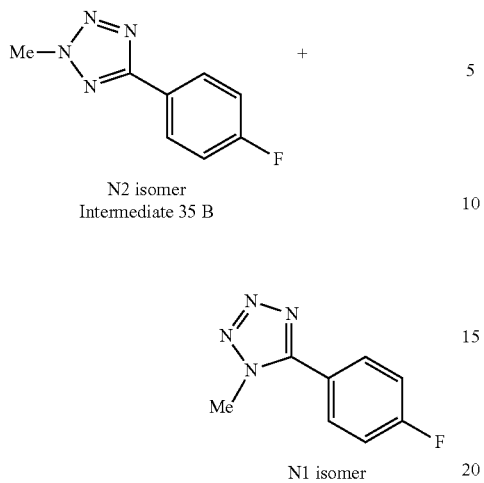

N2 isomer
Intermediate 35 B

N1 isomer

A mixture of 4-fluorobenzonitrile (5 g, 41.3 mmol), dibutyltin oxide (2.055 g, 8.26 mmol), and trimethylsilyl azide (8.22 mL, 61.9 mmol) in toluene (165 mL) was heated to 100° C. and stirred for 16.5 hours. After cooling to room temperature, the organic layer was extracted with NaOH 1M (83 mL) and the aqueous layer was washed with EtOAc (2×85 mL). The aqueous layer was acidified with HCl 2M (41.3 mL) to pH 2. The aqueous mixture was extracted twice with EtOAc (200 mL then 100 mL) and the combined organic layers were washed with brine (60 mL), dried over anh. MgSO$_4$, filtered and concentrated to dryness to afford Intermediate 35A (5-(4-fluorophenyl)-2H-tetrazole, 6.61 g, 98% yield) as a white solid: $^1$H NMR (400 MHz, DMSO-d$_6$) δ ppm 7.42-7.53 (m, 2H) 8.04-8.14 (m, 2H); MS m/z 165.2 (M+H)$^+$; HPLC >99.5%, RT=1.96 minutes.

A mixture of 5-(4-fluorophenyl)-2H-tetrazole (6.61 g, 40.3 mmol), K$_2$CO$_3$ (6.68 g, 48.3 mmol), and iodomethane (3.02 mL, 48.3 mmol) in acetonitrile (115 mL) was heated to reflux (ca. 82° C.) for one hour. After cooling, the mixture was concentrated to dryness and the residue was partitioned between water (75 mL) and EtOAc (100 mL). The layers were separated, the aqueous layer was back-extracted with EtOAc (50 mL) and the combined organic layers were washed with water (50 mL) and brine (50 mL). The organic layer was dried over anh. MgSO4, filtered and concentrated to give 9.5 g as a colorless oil that solidified upon standing. The residue was purified by flash chromatography to give 2 main products: Intermediate 35B as the N2 isomer: 5-(4-fluorophenyl)-2-methyl-2H-tetrazole (5.09 g, 70.9% yield) as a white solid: No NOE observed between the methyl group at 4.42 ppm and the aromatic protons; $^1$H NMR (400 MHz, DMSO-d$_6$) δ ppm 4.42 (s, 3H) 7.33-7.45 (m, 2H) 8.03-8.14 (m, 2H); MS m/z 179.2 (M+H)$^+$; HPLC >99.5%, RT=1.75 minutes.

The N1 isomer: 5-(4-fluorophenyl)-1-methyl-1H-tetrazole (1.87 g, 26.1% yield) as a white solid: the NOE observed between the methyl group at 4.16 ppm and the two aromatic protons at 7.89-7.97 ppm confirms the structure; $^1$H NMR (400 MHz, DMSO-d$_6$) δ ppm 4.16 (s, 3H) 7.43-7.53 (m, 2H) 7.89-7.97 (m, 2H); MS m/z 179.2 (M+H)$^+$; HPLC >99.5%, RT=1.29 minutes.

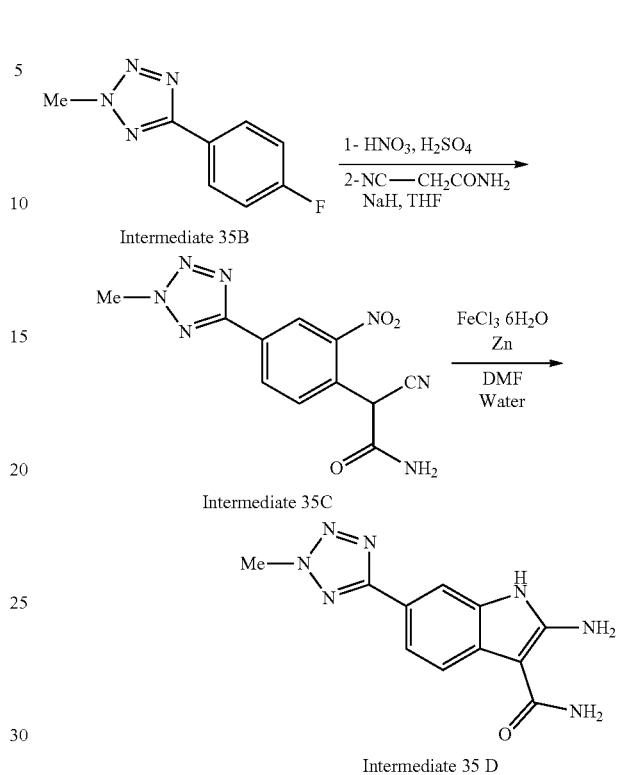

Intermediate 35C

Intermediate 35 D

A solution of Intermediate 35B (5-(4-fluorophenyl)-2-methyl-2H-tetrazole, 1 g, 5.61 mmol) in sulfuric acid (16.45 mL, 309 mmol) was cooled to 0° C. and then fuming nitric acid (0.288 mL, 6.17 mmol) was added dropwise. After 2.5 hours, more fumic nitric acid was added (0.065 mL, 1.403 mmol) was added and the mixture allowed to warm to 20° C. After 5 hours, the mixture was poured into a 2:1 ice-water mixture (150 mL) leading to the formation of a white suspension. After 30 minutes, the solid was filtered, washed with water (4×10 mL, until neutral pH of the washes), dried at 25° C. under high vacuum until constant weight: 5-(4-fluoro-3-nitrophenyl)-2-methyl-2H-tetrazole (1.16 g, 93% yield) as an off-white solid: $^1$H NMR (400 MHz, DMSO-d$_6$) δ ppm 4.47 (s, 3H) 7.81 (dd, J=11.2, 8.8 Hz, 1H) 8.44 (ddd, J=8.7, 4.2, 2.3 Hz, 1H) 8.68 (dd, J=7.2, 2.2 Hz, 1H); MS m/z 224.2 (M+H)$^+$; HPLC 98.3%, RT=1.72 minutes.

A solution of 2-cyanoacetamide (0.888 g, 10.56 mmol) in DMF (2.268 mL) was added to a suspension of sodium hydride 60% wt. in mineral oil (0.443 g, 11.08 mmol) in DMF (5.67 mL) to give a grey suspension. After cooling to 0° C. (Note: Hydrogen Gas evolution) the resulting mixture was stirred at 0° C. for 30 minutes. Then a solution of 5-(4-fluoro-3-nitrophenyl)-2-methyl-2H-tetrazole (1.15 g, 5.15 mmol) in DMF (2.3 mL) was added to give a deep purple solution. After 3 hours, the reaction mixture was slowly poured into an ice-water mixture (33.0 mL) and conc.HCl (0.952 mL). The resulting yellow slurry was stirred for 30 minutes, the solid was filtered, washed with water (3×5 mL) and then with Hexane (2×5 mL), dried at 40° C. under high vacuum until constant weight to give 2-cyano-2-(4-(2-methyl-2H-tetrazol-5-yl)-2-nitrophenyl)acetamide (1.41 g, 95% yield) as a yellow solid: $^1$H NMR (400 MHz, DMSO-d$_6$) δ ppm 4.49 (s, 3H) 5.77 (s, 1H) 7.77 (s, 1H) 7.95 (d, J=8.2 Hz, 1H) 8.03 (s, 1H)

8.51 (dd, J=8.2, 1.8 Hz, 1H) 8.70 (d, J=1.8 Hz, 1H); MS m/z 288.1 (M+H)+; HPLC 96.4% @ 220 nm, RT=1.31 minutes.

Ferric chloride hexahydrate (2.82 g, 10.44 mmol) and zinc (2.276 g, 34.8 mmol) were added portionwise to a mixture of 2-cyano-2-(4-(2-methyl-2H-tetrazol-5-yl)-2-nitrophenyl)acetamide (1 g, 3.48 mmol) in DMF (8.71 mL) and water (8.71 mL) to give a yellow suspension which was heated to 100° C. for 1.25 hour. The mixture was then cooled to 20° C., diluted with MeOH (50.0 mL), filtered over Celite and concentrated under reduced pressure to ca. 20 mL (to remove most of the MeOH). Then the mixture was diluted with water (50 mL) and EtOAc (100 mL), stirred vigorously and filtered. The aqueous layer was extracted with EtOAc (2×50 mL) and the combined organic layers were washed with sat. NaHCO$_3$ (50 mL) and brine (50 mL). The organic layer was dried over anh. MgSO$_4$, filtered and concentrated to give 489 mg as a purple solid which was purified by flash chromatography to give 2-amino-6-(2-methyl-2H-tetrazol-5-yl)-1H-indole-3-carboxamide (356 mg, 39.7% yield) as a purple solid: $^1$H NMR (400 MHz, DMSO-d$_6$) δ ppm 4.38 (s, 3H) 6.57 (s, 2H) 7.01 (s, 2H) 7.61-7.69 (m, 2H) 7.81 (s, 1H) 10.77 (s, 1H); MS m/z 258.2 (M+H)+; HPLC ca. 78%, RT=1.34 minutes.

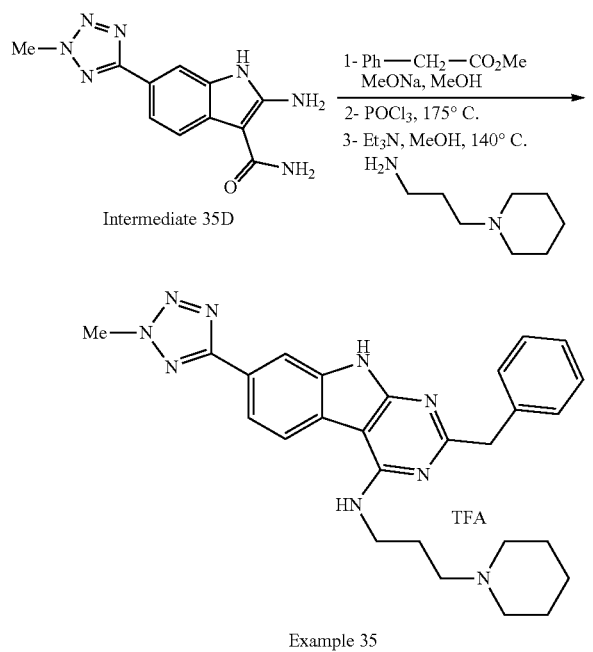

Example 35

A mixture of Intermediate 35D (2-amino-6-(2-methyl-2H-tetrazol-5-yl)-1H-indole-3-carboxamide, 0.35 g, 1.361 mmol), methyl 2-phenylacetate (0.288 mL, 2.041 mmol) and sodium methoxide 25% wt. in MeOH (0.467 mL) and methanol (3.03 mL) in a microwave tube was placed in the microwave oven and heated to 140° C. for one hour. After cooling to room temperature and dilution with water (1 mL) and AcOH (4 mL) the mixture was stirred for 30 minutes to allow crystallization. The solid was filtered, washed with MeOH (5×1 mL), dried at 40° C. under high vacuum until constant weight to afford 2-benzyl-7-(2-methyl-2H-tetrazol-5-yl)-9H-pyrimido[4,5-b]indol-4-ol (220 mg, 45.2% yield) as a brown solid. $^1$H NMR (400 MHz, DMSO-d$_6$) δ ppm 4.03 (s, 2H) 4.43 (s, 3H) 7.24-7.29 (m, 1H) 7.34 (t, J=7.8 Hz, 2H) 7.37-7.43 (m, 2H) 7.92 (dd, J=8.0, 1.4 Hz, 1H) 8.04-8.10 (m, 2H) 12.38 (s, 1H) 12.47 (s, 1H); MS m/z 358.2 (M+H)+; HPLC 82.9%, RT=1.89 minutes.

In a 2-5 mL microwave vial was added the crude product 2-benzyl-7-(2-methyl-2H-tetrazol-5-yl)-9H-pyrimido[4,5-b]indol-4-ol (0.220 g, 0.616 mmol) and POCl$_3$ (3.90 mL, 41.9 mmol) to give a brown suspension. The vial was placed in the microwave oven and heated to 175° C. for 15 min., then allowed to cool. The reaction mixture was then poured into water and ice mixture (80 ml), basified to pH 8 by slow addition of NaOH 50% wt (11 mL) and then EtOAc (80 mL). Some solids were filtered and the layers separated. The aqueous layer was extracted with EtOAc (80 mL) and the organic layer was dried over anh. MgSO$_4$, filtered and concentrated to dryness to give the corresponding chloro derivative: 2-benzyl-4-chloro-7-(2-methyl-2H-tetrazol-5-yl)-9H-pyrimido[4,5-b]indole (189 mg, 82% yield) as a brown solid $^1$H NMR (400 MHz, DMSO-d$_6$) δ ppm 4.31 (s, 2H) 4.46 (s, 3H) 7.20-7.26 (m, 1H) 7.28-7.39 (m, 4H) 8.09 (dd, J=8.2, 1.2 Hz, 1H) 8.21-8.25 (m, 1H) 8.39 (d, J=8.2 Hz, 1H) 12.93 (s, 1H); MS m/z 376.2 (M+H)+; HPLC 95.6%, RT=2.30 minutes.

A mixture of 2-benzyl-4-chloro-7-(2-methyl-2H-tetrazol-5-yl)-9H-pyrimido[4,5-b]indole prepared as described above (0.050 mg, 0.133 mmol) and Et$_3$N (0.037 mL, 0.266 mmol) and 3-(piperidin-1-yl)propan-1-amine (0.033 mL, 0.200 mmol) in MeOH (0.6 mL) was heated 25 minutes at 140° C. in a microwave oven. After cooling and evaporation of the solvent, the residue was purified by RP-HPLC (MeOH-water (0.5% TFA) 20% to 100% MeOH to afford 55 mg of Example 35: 2-benzyl-7-(2-methyl-2H-tetrazol-5-yl)-N-(3-(piperidin-1-yl)propyl)-9H-pyrimido[4,5-b]indol-4-amine 2,2,2-trifluoroacetate; $^1$H NMR (400 MHz, DMSO-d$_6$) δ ppm 1.27-1.41 (m, 1H) 1.53-1.72 (m, 3H) 1.79 (d, J=13.69 Hz, 2H) 1.98-2.09 (m, 2H) 2.75-2.87 (m, 2H) 3.09 (dt, J=10.27, 5.23 Hz, 2H) 3.39 (d, J=11.35 Hz, 2H) 3.69 (q, J=5.87 Hz, 2H) 4.09 (s, 2H) 4.44 (s, 3H) 7.18-7.24 (m, 1H) 7.31 (t, J=7.63 Hz, 2H) 7.35-7.42 (m, 2H) 7.51 (br. s., 1H) 7.93 (dd, J=8.22, 1.17 Hz, 1H) 8.11 (d, J=1.17 Hz, 1H) 8.43 (d, J=8.22 Hz, 1H) 9.04 (br. s., 1H) 12.15 (s, 1H); HPLC 99% at 254 nm, Rt 2.063 minutes; HRMS m/z 482.2817 (M+H)+.

Example 36

Methyl Oxadiazole from Cyanide

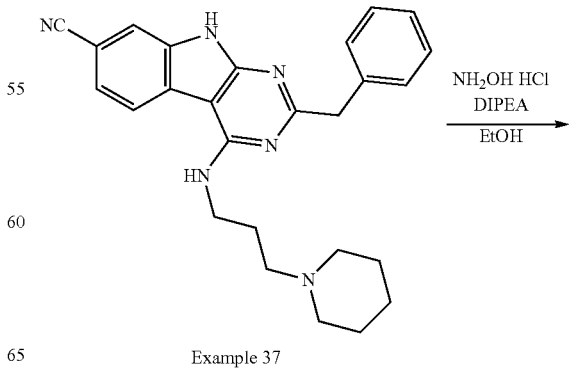

Example 37

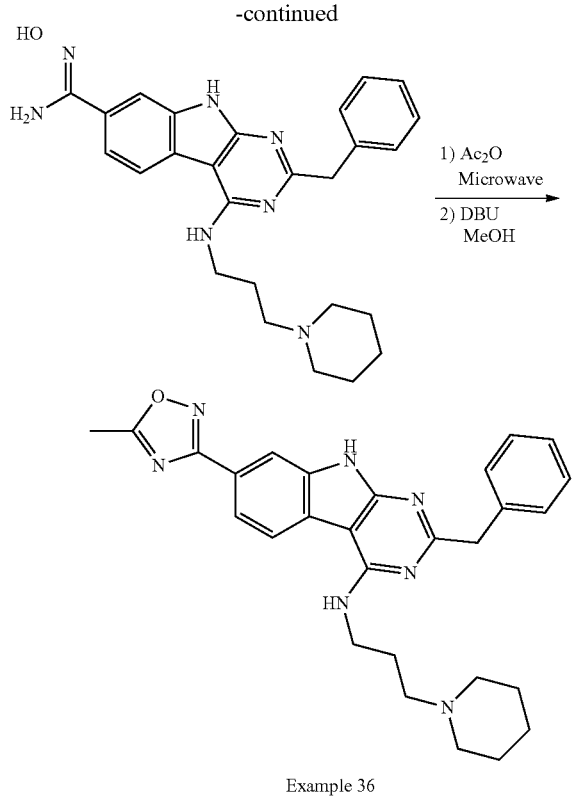

Example 36

Hydroxylamine hydrochloride (32.7 mg, 0.471 mmol) was added to a solution of Example 37 (2-benzyl-4-((3-(piperidin-1-yl)propyl)amino)-9H-pyrimido[4,5-b]indole-7-carbonitrile, 50 mg, 0.118 mmol) in EtOH (1.5 mL) followed by DIPEA (84 μL, 0.483 mmol) to give a light yellow suspension. After stirring for 2.5 days at room temperature and 6 hours at 75° C., the solvent was evaporated and water (3 mL) was added and after stirring for 30 min., the solid was collected, washed with water (3×1 mL) and the solid material was dried at 35° C. under high vacuum until constant weight to give (Z)-2-benzyl-N'-hydroxy-4-((3-(piperidin-1-yl)propyl)amino)-9H-pyrimido[4,5-b]indole-7-carboximidamide·HCl (53 mg, 0.107 mmol, 91% yield) as a tan solid; $^1$H NMR (400 MHz, DMSO-$d_6$) δ ppm 1.58-1.85 (m, 6H) 1.98-2.10 (m, 2H) 2.69-2.90 (m, 2H) 2.94-3.15 (m, 2H) 3.34-3.46 (m, 2H) 3.59-3.74 (m, 2H) 4.05 (s, 2H) 5.84 (br. s., 2H) 7.15-7.24 (m, 1H) 7.29 (t, J=7.4 Hz, 3H) 7.37 (d, J=7.4 Hz, 2H) 7.55 (dd, J=8.2, 1.2 Hz, 1H) 7.72 (d, J=1.2 Hz, 1H) 8.25 (d, J=8.6 Hz, 1H) 9.47 (d, J=7.4 Hz, 1H) 9.56 (s, 1H) 11.88 (s, 1H); HRMS m/z 458.2662 (M+H)$^+$. HPLC 95.4% @ 220 nm and 97.4% @ 254 nm, RT=1.40 minutes.

Acetic anhydride (0.917 mL, 9.72 mmol) was added to (Z)-2-benzyl-N'-hydroxy-4-((3-(piperidin-1-yl)propyl)amino)-9H-pyrimido[4,5-b]indole-7-carboximidamide, HCl (0.040 g, 0.081 mmol) to give a tan suspension and the mixture was heated by microwaves to 140° C. for 30 minutes. The solvent was then evaporated and the residue purified by flash chromatography to give 36 mg (85% yield) of 1-(2-benzyl-7-(5-methyl-1,2,4-oxadiazol-3-yl)-4-((3-(piperidin-1-yl)propyl)amino)-9H-pyrimido[4,5-b]indol-9-yl)ethanone as a tan solid which was dissolved immediately in methanol (2.3 mL) and treated with DBU (0.021 mL, 0.138 mmol). The resulting yellow solution was heated to reflux for 30 minutes, then cool to 0° C. while stirring for 1 hour. The solids were filtered and washed with cold MeOH (2×0.5 mL), dried at 40° C. under high vacuum until constant weight to afford Example 36: 2-benzyl-7-(5-methyl-1,2,4-oxadiazol-3-yl)-N-(3-(piperidin-1-yl)propyl)-9H-pyrimido[4,5-b]indol-4-amine (20 mg, 51.3% yield) as a tan solid: $^1$H NMR (400 MHz, DMSO-$d_6$) δ ppm 1.38 (m, J=4.7 Hz, 2H) 1.50 (quin, J=5.5 Hz, 4H) 1.80 (quin, J=6.9 Hz, 2H) 2.18-2.45 (m, 6H) 2.67 (s, 3H) 3.57-3.70 (m, 2H) 4.04 (s, 2H) 7.15-7.22 (m, 1H) 7.27 (m, J=7.6, 7.6 Hz, 2H) 7.34 (t, J=5.9 Hz, 1H) 7.36-7.40 (m, 2H) 7.83 (dd, J=8.2, 1.4 Hz, 1H) 8.01 (d, J=1.4 Hz, 1H) 8.39 (d, J=8.2 Hz, 1H) 12.02 (br. s., 1H); HRMS m/z 482.2663 (M+H)$^+$. HPLC 99.3%, RT=1.79 minutes.

Example 37

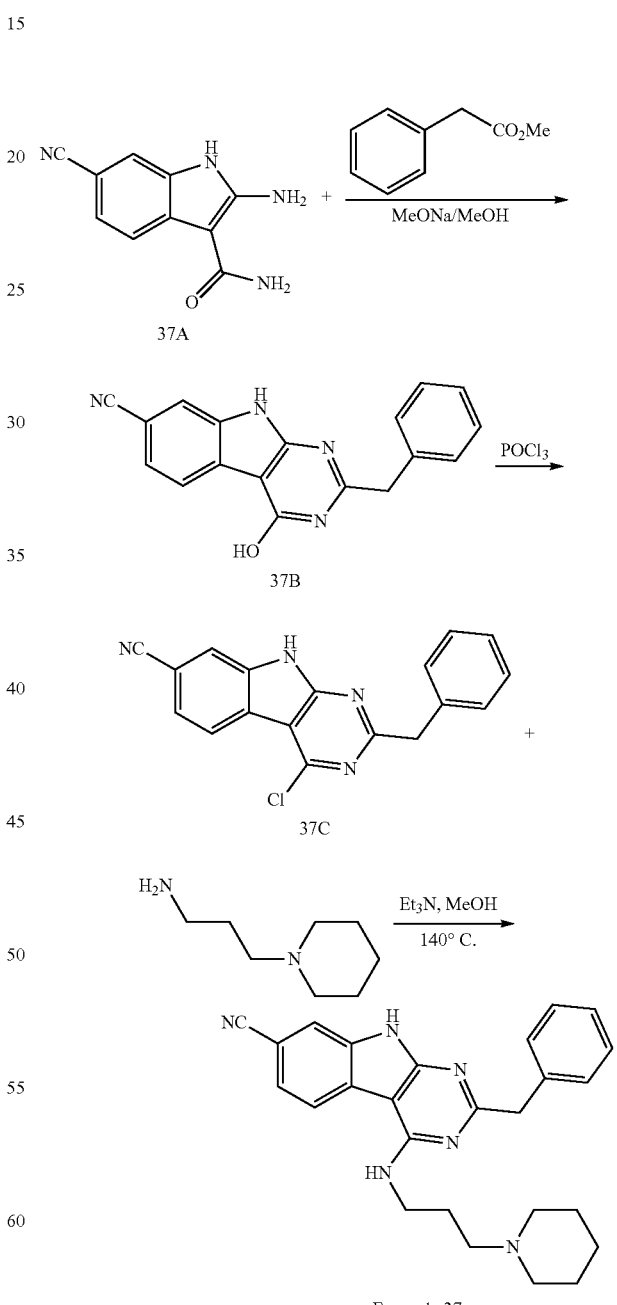

Example 37

An orange mixture of 2-amino-6-cyano-1H-indole-3-carboxamide (0.172 g, 0.859 mmol), methyl 2-phenylacetate (0.303 mL, 2.148 mmol) and sodium methoxide 30% wt in MeOH (0.403 mL, 2.148 mmol) in methanol (2.82 mL) was heated in a microwave tube at 140° C. for 45 minutes. Then, a new load of methyl 2-phenylacetate (0.151 mL, 1.074 mmol) and sodium methoxide 30% wt in MeOH (0.201 mL, 1.074 mmol) were added and the vial was placed in the microwave and heated again at 140° C. for 45 minutes. Then, after cooling to room temperature, AcOH (0.197 mL, 3.44 mmol) was added and the resulting slurry was stirred at 20° C. for 1 hour. The solids were filtered, washed with MeOH (3×1 mL) and dried at 20° C. under high vacuum until constant weight to give Intermediate 37B: 2-benzyl-4-hydroxy-9H-pyrimido[4,5-b]indole-7-carbonitrile (182 mg, 70.5% yield) as a tan solid: $^1$H NMR (400 MHz, DMSO-d$_6$) δ ppm 4.03 (s, 2H) 7.22-7.29 (m, 1H) 7.30-7.36 (m, 2H) 7.36-7.43 (m, 2H) 7.58 (dd, J=8.2, 1.4 Hz, 1H) 7.82-7.87 (m, 1H) 8.05 (d, J=8.2 Hz, 1H) 12.59 (br. s., 2H); MS m/z 301.2 (M+H)$^+$; HPLC 94.2% @ 220 nm and 91.3% @ 254 nm; RT=1.90 minutes.

A red mixture of 2-benzyl-4-hydroxy-9H-pyrimido[4,5-b]indole-7-carbonitrile (Intermediate 37B, 0.180 g, 0.599 mmol) and phosphorus oxychloride (3.63 mL, 39.0 mmol) was heated to 95° C. and stirred for 16 hours. After concentration to dryness on a rotovap, the resulting dark red foam was suspended in sat. NaHCO$_3$ (10 mL) and stirred for 30 minutes. The solids were collected and washed with water (3×1 mL), dried at 40° C. under high vacuum until constant weight to give Intermediate 37C: 2-benzyl-4-chloro-9H-pyrimido[4,5-b]indole-7-carbonitrile (190 mg, 99% yield) as a tan solid which was used directly in the next step: MS m/z 319.2 (M+H)$^+$; HPLC 95.0% @ 220 nm and 92.3% @ 254 nm, RT=2.28 minutes.

A mixture of 2-benzyl-4-chloro-9H-pyrimido[4,5-b]indole-7-carbonitrile (Intermediate 37C, 0.190 g, 0.596 mmol), 3-(piperidin-1-yl)propan-1-amine (0.142 mL, 0.894 mmol) and triethylamine (0.208 mL, 1.490 mmol) in MeOH (4.50 mL) was heated by microwaves to 140° C. for 30 minutes. Then it was concentrated to dryness to give 346 mg of an orange solid which was purified by flash chromatography to give 176 mg of a yellow solid which was suspended in ether (7 mL) and stirred at 20° C. for 1 hour. The solids were filtered, washed with ether (3×1 mL) and dried at 30° C. under high vacuum until constant weight to afford 2-benzyl-4-((3-(piperidin-1-yl)propyl)amino)-9H-pyrimido[4,5-b]indole-7-carbonitrile as Example 37 (172 mg, 68.0% yield) as a light yellow solid: $^1$H NMR (400 MHz, DMSO-d$_6$) δ ppm 1.30-1.43 (m, 2H) 1.43-1.57 (m, 4H) 1.80 (m, J=5.5 Hz, 2H) 2.18-2.47 (m, 6H) 3.62 (q, J=6.4 Hz, 2H) 4.04 (s, 2H) 7.15-7.22 (m, 1H) 7.27 (m, J=7.4, 7.4 Hz, 2H) 7.33-7.39 (m, 2H) 7.47 (t, J=5.7 Hz, 1H) 7.62 (dd, J=8.2, 1.2 Hz, 1H) 7.79 (d, J=1.2 Hz, 1H) 8.43 (d, J=8.2 Hz, 1H) 12.19 (s, 1H); HRMS m/z 425.2448 (M+H)$^+$; HPLC >99%, RT=1.68 minutes.

Example 43

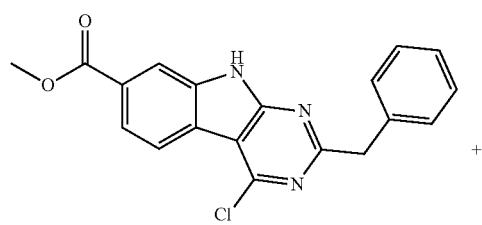

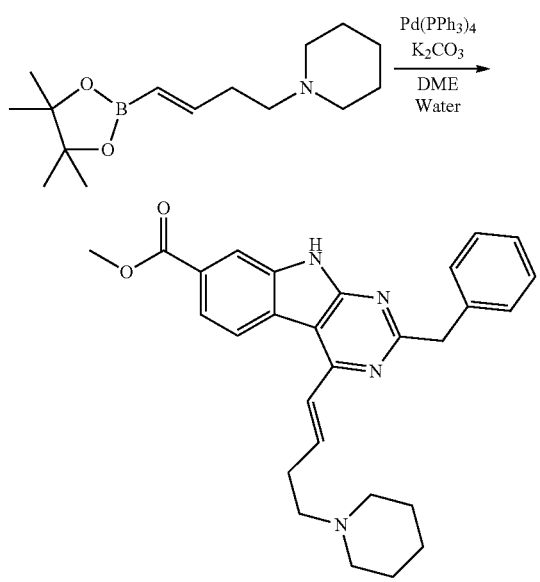

In a 2-5 mL microwave vial was added methyl 2-benzyl-4-chloro-9H-pyrimido[4,5-b]indole-7-carboxylate (0.100 g, 0.284 mmol), (E)-1-(4-(4,4,5,5-tetramethyl-1,3,2-dioxaborolan-2-yl)but-3-en-1-yl)piperidine (0.113 g, 0.426 mmol), potassium carbonate (0.106 g, 0.768 mmol) and Pd(Ph$_3$P)$_4$ (0.05 g, 0.044 mmol). The vial was purged with N2 (3 vacuum+refill cycles). DME (2.84 mL) and water (0.398 mL) were added and the vial was flushed with N2 (one vacuum+refill) and then heated to 110° C. while stirred for 24 hours. After cooling, the mixture was concentrated to dryness under reduced pressure and the residue was purified by flash chromatography to give (E)-methyl 2-benzyl-4-(4-(piperidin-1-yl)but-1-en-1-yl)-9H-pyrimido[4,5-b]indole-7-carboxylate (55 mg, 0.121 mmol, 42.6% yield) as a light yellow solid: $^1$H NMR (400 MHz, DMSO-d$_6$) δ ppm 1.41 (s, 2H) 1.50-1.61 (m, 4H) 2.30-2.47 (m, 4H) 2.53-2.59 (m, 2H) 2.59-2.70 (m, 2H) 3.91 (s, 3H) 4.27 (s, 2H) 7.16-7.24 (m, 1H) 7.29 (t, J=7.6 Hz, 2H) 7.34-7.43 (m, 4H) 7.88 (dd, J=8.2, 1.4 Hz, 1H) 8.07 (d, J=1.4 Hz, 1H) 8.41 (d, J=8.2 Hz, 1H) 12.48 (s, 1H); HRMS m/z 455.2442 (M+H)$^+$; HPLC 100% @ 220 nm and 99.4% @ 254 nm, RT=1.84 minutes.

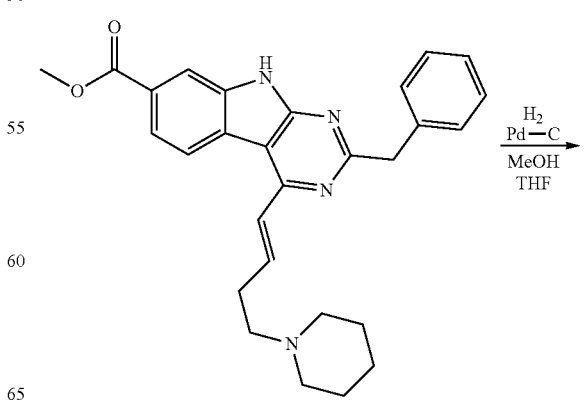

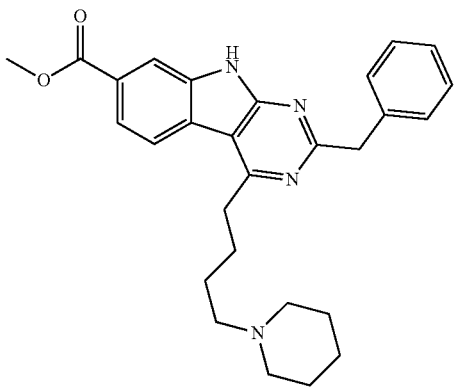

Example 43

A mixture of (E)-methyl 2-benzyl-4-(4-(piperidin-1-yl)but-1-en-1-yl)-9H-pyrimido[4,5-b]indole-7-carboxylate (20 mg, 0.044 mmol) and Pd—C 10% wt. (50% wet) (23.41 mg) in MeOH (2 mL) and THF (2 mL) was treated with hydrogen for 17 hours. The reaction mixture was diluted with DCM (3 mL), filtered, rinsed with MeOH (2×2 mL) and then with DCM (2×2 mL) and concentrated to dryness to give 19 mg as a light yellow solid which was purified by flash chromatography to give a white solid (14 mg) which was treated with $CH_3CN$ (2 mL). After stirring the white suspension at 20° C. for 1 hour, the solid was filtered, washed with $CH_3CN$ (1×1 mL) and dried at 40° C. under high vacuum until constant weight to afford the compound of Example 43 as methyl 2-benzyl-4-(4-(piperidin-1-yl)butyl)-9H-pyrimido[4,5-b]indole-7-carboxylate (14.4 mg, 71.7% yield) as a white solid: $^1$H NMR (400 MHz, DMSO-$d_6$) δ ppm 1.36 (m, J=5.5 Hz, 2H) 1.45 (quin, J=5.5 Hz, 4H) 1.57 (quin, J=7.3 Hz, 2H) 1.83 (dt, J=14.9, 7.4 Hz, 2H) 2.18-2.31 (m, 6H) 3.20-3.28 (m, 2H) 3.91 (s, 3H) 4.26 (s, 2H) 7.16-7.22 (m, 1H) 7.28 (t, J=7.4 Hz, 2H) 7.32-7.38 (m, 2H) 7.90 (dd, J=8.2, 1.2 Hz, 1H) 8.09 (d, J=1.2 Hz, 1H) 8.25 (d, J=8.2 Hz, 1H) 12.48 (br. s., 1H); HRMS m/z 457.2598 (M+H)$^+$; HPLC >99.5%, RT=1.75 minutes.

Example 44

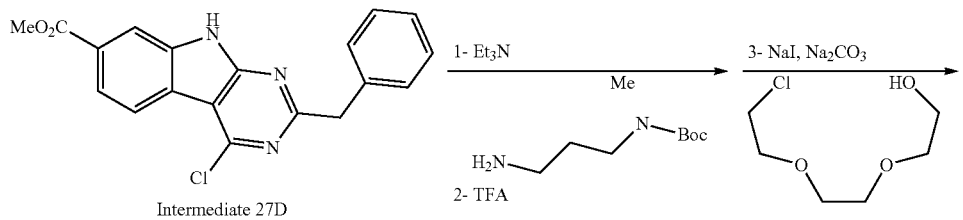

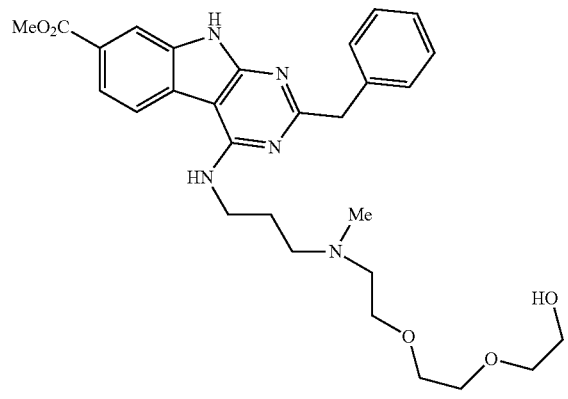

Example 44

A mixture of methyl 2-benzyl-4-chloro-9H-pyrimido[4,5-b]indole-7-carboxylate (0.100 g, 0.284 mmol), Et₃N (0.079 mL, 0.569 mmol) and tert-butyl (3-aminopropyl)(methyl)carbamate (0.080 g, 0.426 mmol) in MeOH (1 mL) was heated in a microwave oven at 140° C. for 40 minutes. The solvent was removed under reduced pressure and the residue was purified by flash chromatography to give 0.092 mg of crude Boc derivative which was used directly in the next step. TFA (1.0 ml, 12.98 mmol) was added dropwise to a cold suspension of methyl 2-benzyl-4-((3-((tert-butoxycarbonyl)(methyl)amino)propyl)amino)-9H-pyrimido[4,5-b]indole-7-carboxylate (0.092 g, 0.183 mmol) and the mixture was allowed to warm to room temperature over 30 minutes. After dilution with toluene, the solvent was removed under reduced pressure and then the residue was diluted with EtOAc to produce 85 mg of a solid used directly in the next step: HRMS m/z 404.2091 (M+H)⁺.

A mixture of methyl 2-benzyl-4-((3-(methylamino)propyl)amino)-9H-pyrimido[4,5-b]indole-7-carboxylate 2,2,2-trifluoroacetate (0.020 g, 0.039 mmol), sodium carbonate (8.81 mg, 0.083 mmol), sodium iodide (1.448 mg, 9.66 μmol) and 2-(2-(2-chloroethoxy)ethoxy)ethanol (6.46 μl, 0.044 mmol) was heated at 70° C. in acetone (0.2 mL). After 15 hours, a second portion of 2-(2-(2-chloroethoxy)ethoxy)ethanol reagent (6.46 μl, 0.044 mmol) was added and the mixture was heated again at 70° C. for 15 hours. After cooling to room temperature, the mixture was diluted with EtOAc, washed with water, dried over anh. MgSO₄, filtered and the solvent evaporated to give a residue which was purified by flash chromatography to afford 9 mg of Example 44: ¹H NMR (400 MHz, DMSO-d₆) δ ppm 1.74-1.85 (m, 2H) 2.25 (br. s., 3H) 2.55 (br. s., 2H) 3.32-3.36 (m, 4H) 3.39-3.46 (m, 6H) 3.51 (t, J=5.87 Hz, 2H) 3.64 (q, J=6.52 Hz, 2H) 3.88 (s, 3H) 4.04 (s, 2H) 4.53 (br. s., 1H) 7.18 (t, J=7.40 Hz, 1H) 7.28 (t, J=7.63 Hz, 2H) 7.37 (d, J=7.04 Hz, 2H) 7.55 (t, J=5.28 Hz, 1H) 7.82 (dd, J=8.22, 1.17 Hz, 1H) 7.99 (s, 1H) 8.27 (d, J=8.22 Hz, 1H) 12.05 (s, 1H); HRMS m/z 536.2855 (M+H)⁺; HPLC RT 2.035 minutes.

Examples 45 and 51

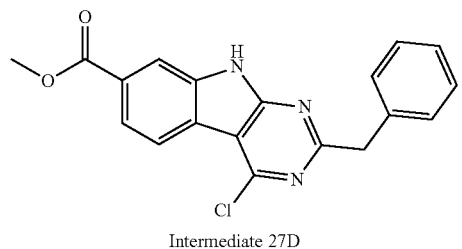

Intermediate 27D

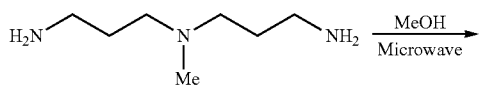

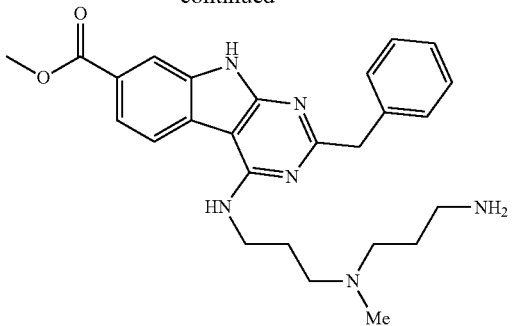

Example 45

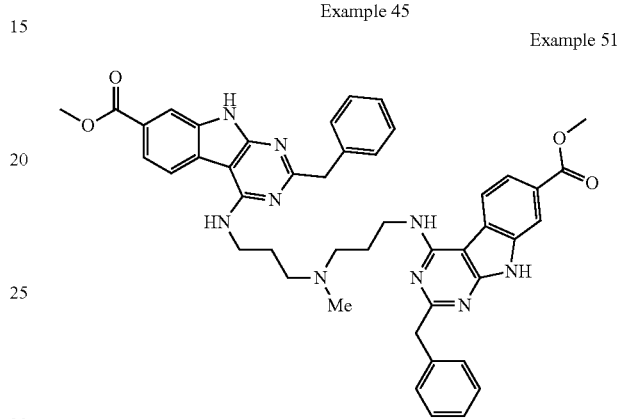

Example 51

In a 2-5 mL microwave vial was added methyl 2-benzyl-4-chloro-9H-pyrimido[4,5-b]indole-7-carboxylate (0.050 g, 0.142 mmol) and N1-(3-aminopropyl)-N1-methylpropane-1,3-diamine (0.115 mL, 0.711 mmol) in MeOH (2.000 mL, 49.4 mmol) to give a tan suspension. The vial was placed in the microwave and heated to 140° C. for 30 min. After 30 minutes, the mixture was concentrated to dryness on a rotavap. and the residue was purified by flash chromatography and lyophilized from CH₃CN to afford two distinct products: Example 45 as the mono-N-alkylated product: methyl 4-((3-((3-aminopropyl)(methyl)amino)propyl)amino)-2-benzyl-9H-pyrimido[4,5-b]indole-7-carboxylate (44 mg, 67.2% yield) as a white solid; ¹H NMR (400 MHz, DMSO-d₆) δ ppm 1.44 (dt, J=13.8, 6.6 Hz, 2H) 1.72 (dt, J=13.7, 6.8 Hz, 2H) 2.11 (s, 3H) 2.24-2.30 (m, 2H) 2.33 (t, J=6.7 Hz, 2H) 2.47 (br. s., 2H) 3.51-3.61 (m, 2H) 3.76-3.85 (m, 3H) 3.97 (s, 2H) 7.08-7.15 (m, 1H) 7.17-7.24 (m, 2H) 7.27-7.34 (m, 2H) 7.50 (t, J=5.3 Hz, 1H) 7.76 (dd, J=8.2, 1.6 Hz, 1H) 7.92 (d, J=1.6 Hz, 1H) 8.20 (d, J=8.2 Hz, 1H); MS m/z 461.2 (M+H)⁺; HPLC >99%, RT=1.63 minutes.

Example 51 as a bis-alkylated product: dimethyl 4,4'-(((methylazanediyl)bis(propane-3,1-diyl))bis(azanediyl))bis(2-benzyl-9H-pyrimido[4,5-b]indole-7-carboxylate) (3.7 mg, 6.71% yield) as a light yellow solid: ¹H NMR (400 MHz, DMSO-d₆) δ ppm 1.18-1.29 (m, 4H) 1.79-1.91 (m, 4H) 2.25 (s, 3H) 3.58-3.71 (m, 4H) 3.84 (s, 6H) 3.97 (s, 4H) 7.07-7.16 (m, 2H) 7.22 (t, J=7.4 Hz, 4H) 7.29-7.34 (m, 4H) 7.53 (t, J=5.3 Hz, 2H) 7.77 (dd, J=8.2, 1.4 Hz, 2H) 7.96 (d, J=1.4 Hz, 2H) 8.22 (d, J=8.2 Hz, 2H) 12.01 (s, 2H); MS m/z 776.3 (M+H)⁺; HPLC 94.6% @ 220 nm and 93.8% @ 254 nm, RT=2.01 minutes.

Example 52

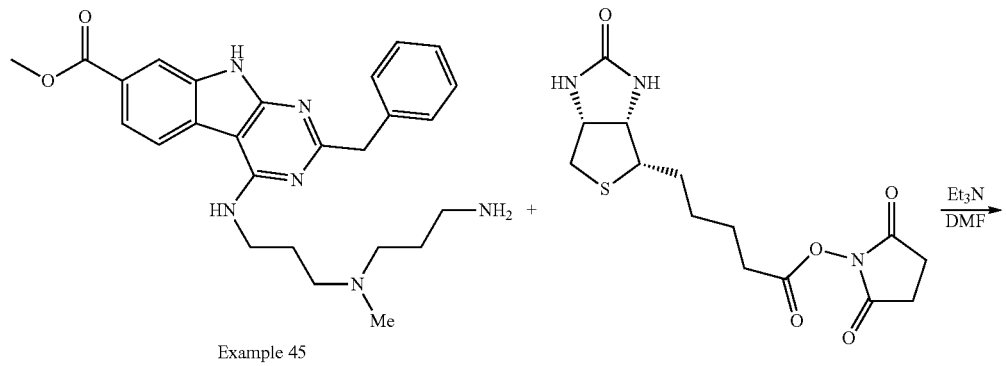

Example 45

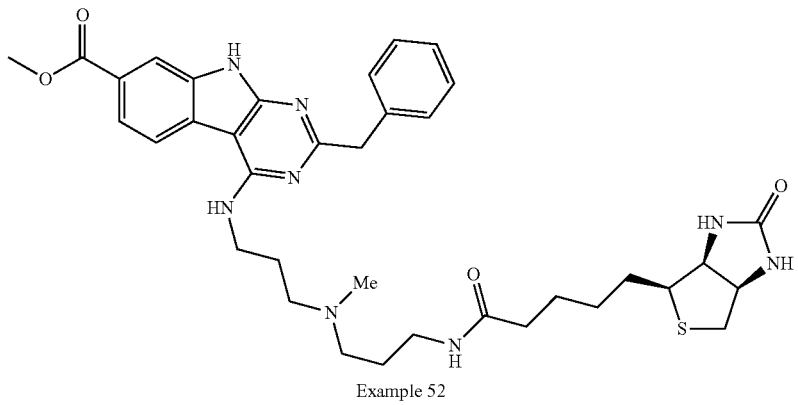

Example 52

2,5-Dioxopyrrolidin-1-yl-5-((3aS,4S,6aR)-2-oxohexahydro-1H-thieno[3,4-d]imidazol-4-yl)pentanoate (12.01 mg, 0.035 mmol) was added to a solution of methyl 4-((3-((3-aminopropyl)(methyl)amino)propyl)amino)-2-benzyl-9H-pyrimido[4,5-b]indole-7-carboxylate (Example 45, 15 mg, 0.033 mmol) and triethylamine (6.81 μL, 0.049 mmol) in DMF (750 μL, 9.69 mmol) to give a light yellow solution. After stirring at 20° C. for 1 hour the mixture was concentrated to dryness and the residue was purified by flash chromatography to give a light yellow foam. The foam was suspended in Et$_2$O (1 mL) and stirred for 30 minutes and the solid was collected, washed with Et$_2$O (2×0.5 mL) and dried at 20° C. under high vacuum until constant weight to give the compound of Example 52: methyl 2-benzyl-4-((3-(methyl(3-(5-((3aS,4S,6aR)-2-oxohexahydro-1H-thieno[3,4-d]imidazol-4-yl)pentanamido)propyl)amino)propyl)amino)-9H-pyrimido[4,5-b]indole-7-carboxylate (17 mg, 76% yield) as a light yellow solid: $^1$H NMR (400 MHz, DMSO-d$_6$) δ ppm 1.17-1.34 (m, 3H) 1.36-1.51 (m, 2H) 1.51-1.64 (m, 3H) 1.78 (dt, J=13.5, 6.6 Hz, 2H) 2.02 (t, J=7.4 Hz, 2H) 2.17 (s, 3H) 2.32 (t, J=7.0 Hz, 2H) 2.40 (t, J=6.7 Hz, 2H) 2.55 (d, J=12.3 Hz, 1H) 2.77 (dd, J=12.3, 5.1 Hz, 1H) 2.99-3.11 (m, 3H) 3.58-3.68 (m, 2H) 3.88 (s, 3H) 4.04 (s, 2H) 4.08 (m, J=4.9, 4.9, 2.3 Hz, 1H) 4.26 (dd, J=7.6, 5.3 Hz, 1H) 6.34 (s, 1H) 6.40 (s, 1H) 7.14-7.22 (m, 1H) 7.27 (t, J=7.4 Hz, 2H) 7.37 (d, J=7.0 Hz, 2H) 7.54 (t, J=5.5 Hz, 1H) 7.74 (t, J=5.5 Hz, 1H) 7.82 (dd, J=8.2, 1.6 Hz, 1H) 7.99 (d, J=1.6 Hz, 1H) 8.27 (d, J=8.2 Hz, 1H) 12.05 (s, 1H); MS m/z 687.3 (M+H)$^+$; HPLC >99.5%, RT=1.70 minutes.

Example 53

Intermediate 53A was prepared from commercial ethyl 2(3-tolyl)acetate. It was then converted to Intermediate 53B as described for Examples 15, 45 and 47. Then, the azirine portion was developed according to the description provided for Example 25. The last step was based on Example 52.

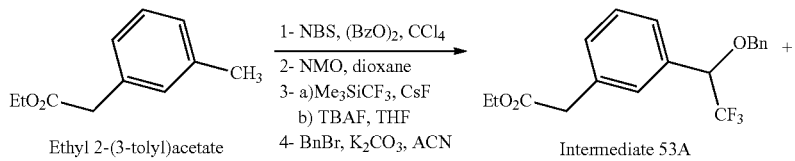

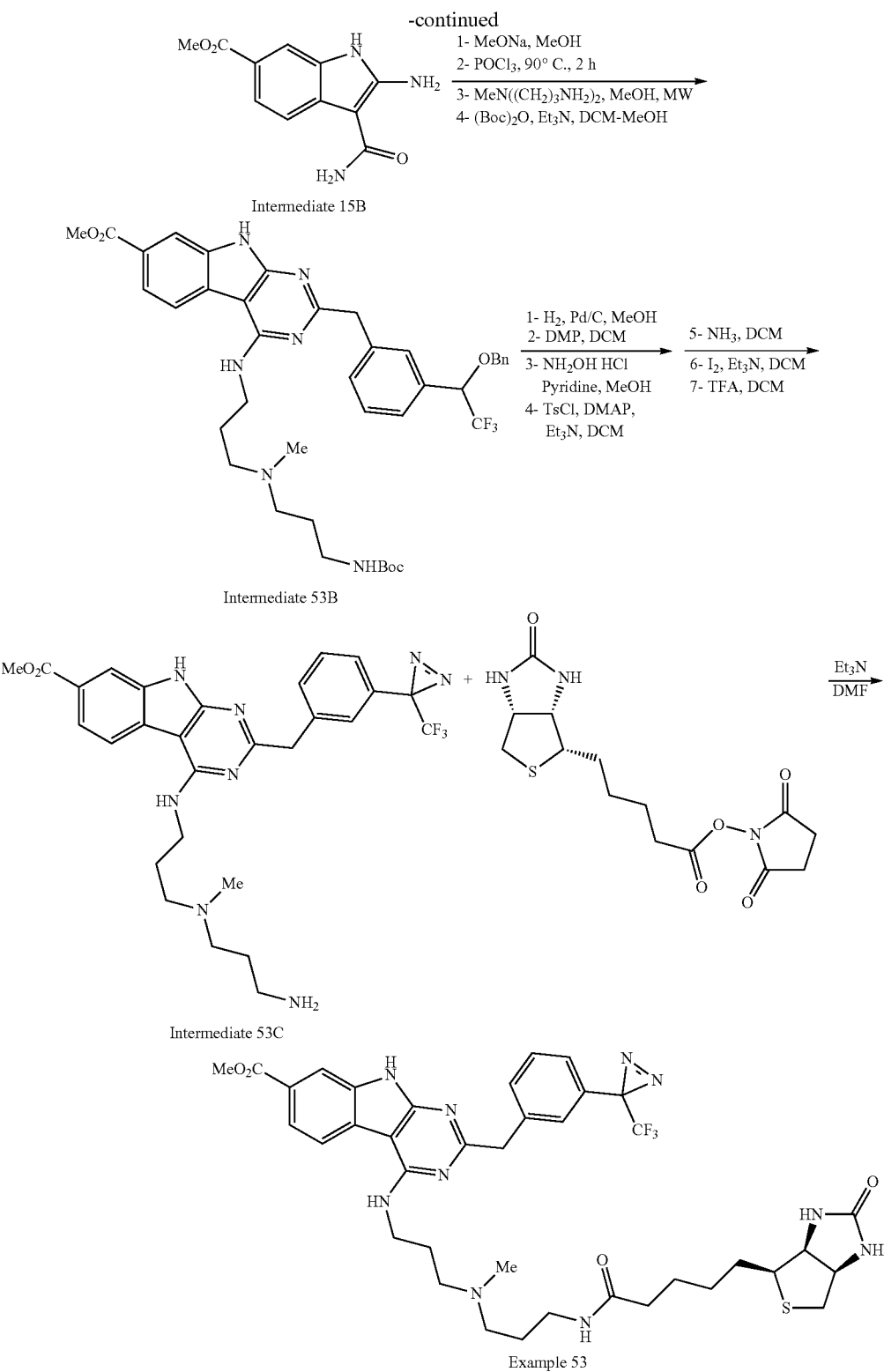

Intermediate 15B

Intermediate 53B

Intermediate 53C

Example 53

A mixture of ethyl 2-(m-tolyl)acetate (4.8 g, 26.9 mmol), NBS (5.27 g, 29.6 mmol) and benzoyl peroxide (0.110 g, 0.454 mmol) was brought to reflux in CCl$_4$ (28 mL). After 5 hours, the reaction was cooled to 5° C., filtered and the solvent removed. Purification by flash chromatography using ethylacetate-hexane gave 3.8 g of the corresponding bromobenzyl derivative: $^1$H NMR (400 MHz, DMSO-d6) δ ppm 1.19 (t, J=6.70 Hz, 3H) 3.67 (s, 2H) 4.09 (q, J=6.70 Hz, 2H) 4.69 (s, 2H) 7.15-7.25 (m, 1H) 7.27-7.42 (m, 3H); this material was used directly in the next step.

A mixture of ethyl 2-(3-(bromomethyl)phenyl)acetate (8.11 g, 31.5 mmol) and 4-methylmorpholine 4-oxide hydrate (5.54 g, 47.3 mmol) in 1,4-dioxane (110 mL) was heated to 100° C. for 1.5 hour. After cooling to room temperature, the volume of solvent was reduced to half and then diluted with Et$_2$O:EtOAc (1:1, 120 mL), washed with water (50 mL) and the aqueous layer extracted with EtOAc (60 mL). The combined organic layers were washed with water (2×50 mL) and then with brine (50 mL). The organic layer was dried over anh. MgSO$_4$, filtered and concentrated to give 4.72 g of a light yellow oil which was purified by flash chromatography to afford 2-(3-formylphenyl)acetate (2.91 g, 48% yield) as a light yellow oil: $^1$H NMR (400 MHz, DMSO-d6) δ ppm 1.19 (t, J=7.0 Hz, 3H) 3.81 (s, 2H) 4.09 (q, J=7.0 Hz, 2H) 7.52-7.65 (m, 2H) 7.79-7.85 (m, 2H) 10.00 (s, 1H); MS m/z 207.2 (M+H)$^+$; HPLC 99%, RT=1.67 minutes.

Trimethyl(trifluoromethyl)silane (3.13 mL, 21.20 mmol) was added to a mixture of ethyl 2-(3-formylphenyl)acetate (2.91 g, 15.14 mmol) and cesium fluoride (0.161 g, 1.060 mmol) in DMF (20.19 mL) cooled to 0-5° C. After stirring for 1.5 hour, a solution of TBAF 1M in THF (15.14 mL) was added. The resulting yellow solution was stirred at 0-5° C. and after 30 minutes, the mixture was poured into water (150 mL) and extracted with MTBE (1×150 mL, then 2×100 mL). The combined organic layers were washed with water (1×150 mL then 1×100 mL) and with brine (100 mL) and then the organic layer was dried over anh. MgSO$_4$, filtered and concentrated to give 3.84 g as a light orange oil which was purified by flash chromatography to give ethyl 2-(3-(2,2,2-trifluoro-1-hydroxyethyl)phenyl)acetate (663 mg, 16% yield) as a colorless oil: $^1$H NMR (400 MHz, DMSO-d6) δ ppm 1.17 (t, J=7.0 Hz, 3H) 3.68 (s, 2H) 4.08 (q, J=7.0 Hz, 2H) 5.13 (q, J=7.4 Hz, 1H) 6.82 (s, 1H) 7.24-7.31 (m, 1H) 7.37 (t, J=7.2 Hz, 3H); MS m/z 263.1 (M+H)$^+$; HPLC 93.7% @ 220 nm, RT=1.82 minutes.

Benzyl bromide (0.330 mL, 2.78 mmol) was added to a mixture of ethyl 2-(3-(2,2,2-trifluoro-1-hydroxyethyl)phenyl)acetate (0.648 g, 2.471 mmol) and K$_2$CO$_3$ (1.059 g, 7.66 mmol) in acetonitrile (17.00 mL) and the mixture was stirred while heated to reflux (75-80° C.) for 24 hours. After cooling and concentration to dryness, the residue was purified by flash chromatography to give Intermediate 53A: ethyl 2-(3-(1-(benzyloxy)-2,2,2-trifluoroethyl)phenyl)acetate (686 mg, 79% yield) as a colorless oil: MS m/z 353.2 (M+H)$^+$; HPLC 99.7%, RT=2.19 minutes.

A mixture of Intermediate 15B (0.310 g, 1.329 mmol), ethyl 2-(3-(1-(benzyloxy)-2,2,2-trifluoroethyl)phenyl)acetate (0.679 g, 1.927 mmol) and Intermediate 53A and sodium methoxide 30% wt. in MeOH (0.524 mL) in methanoL (3.23 mL) to give a thin brown suspension which was heated in a microwave apparatus to 140° C. for 1 hour. After cooling and dilution with MeOH (0.75 mL) and AcOH (0.167 mL, 2.92 mmol), the resulting suspension was stirred at 20° C. for 2 hours. The solid was then collected and washed with MeOH (4×0.5 mL), then dried at 40° C. under high vacuum until constant weight to afford methyl 2-(3-(1-(benzyloxy)-2,2,2-trifluoroethyl)benzyl)-4-hydroxy-9H-pyrimido[4,5-b]indole-7-carboxylate (399 mg, 57.6% yield) as a tan solid: $^1$H NMR (400 MHz, DMSO-d6) δ ppm 3.87 (s, 3H) 4.09 (s, 2H) 4.45-4.57 (m, 2H) 5.23 (q, J=7.2 Hz, 1H) 7.20-7.29 (m, 5H) 7.36-7.51 (m, 3H) 7.52 (s, 1H) 7.84 (dd, J=8.2, 1.4 Hz, 1H) 8.01 (d, J=1.4 Hz, 1H) 8.03 (d, J=8.2 Hz, 1H) 12.46 (br. s., 1H) 12.56 (br. s., 1H); MS m/z 522.2 (M+H)$^+$; HPLC 92.7% @ 220 nm and 91.7% @ 254 nm, RT=2.20 minutes.

A mixture of methyl 2-(3-(1-(benzyloxy)-2,2,2-trifluoroethyl)benzyl)-4-hydroxy-9H-pyrimido[4,5-b]indole-7-carboxylate (0.395 g, 0.757 mmol) in phosphorus oxychloride (6 mL, 64.4 mmol) was heated to 90° C. for 2 hours then after cooling, it was concentrated to dryness to give 650 mg as a brown foam which was suspended in sat. NaHCO$_3$ (15 mL) and stirred for 1 hour. The solid was filtered, washed with water (3×2 mL) and dried at 40° C. under high vacuum until constant weight to afford methyl 2-(3-(1-(benzyloxy)-2,2,2-trifluoroethyl)benzyl)-4-chloro-9H-pyrimido[4,5-b]indole-7-carboxylate (375 mg, 92% yield) as a tan solid and used as such in the next step: MS m/z 540.2 (M+H)$^+$; HPLC 92%, RT 2.51 minutes.

A mixture of methyl 2-(3-(1-(benzyloxy)-2,2,2-trifluoroethyl)benzyl)-4-chloro-9H-pyrimido[4,5-b]indole-7-carboxylate (0.375 g, 0.695 mmol) and N1-(3-aminopropyl)-N1-methylpropane-1,3-diamine (0.784 mL, 4.86 mmol) in MeOH (9.83 mL, 243 mmol) was heated in a microwave oven to 140° C. for 30 minutes. Then, after concentration to dryness under reduced pressure the resulting brown oil was purified by flash chromatography to afford methyl 4-((3-((3-aminopropyl)(methyl)amino)propyl)amino)-2-(3-(1-(benzyloxy)-2,2,2-trifluoroethyl)benzyl)-9H-pyrimido[4,5-b]indole-7-carboxylate (288 mg, 63.9% yield) as a yellow foam: $^1$H NMR (400 MHz, DMSO-d6) δ ppm 1.48 (dt, J=14.0, 6.9 Hz, 2H) 1.75 (quin, J=6.7 Hz, 2H) 2.14 (s, 3H) 2.24-2.42 (m, 4H) 2.52-2.60 (m, 2H) 3.61 (q, J=6.3 Hz, 2H) 3.88 (s, 3H) 4.10 (s, 2H) 4.49 (s, 2H) 5.17 (q, J=7.0 Hz, 1H) 7.18-7.30 (m, 5H) 7.31-7.36 (m, 1H) 7.39 (t, J=7.6 Hz, 1H) 7.44-7.53 (m, 2H) 7.58 (t, J=5.3 Hz, 1H) 7.84 (dd, J=8.2, 1.4 Hz, 1H) 8.00 (d, J=1.4 Hz, 1H) 8.28 (d, J=8.2 Hz, 1H); MS m/z 649.3 (M+H)$^+$; HPLC 97.6% @ 220 nm and 95.5% @ 254 nm, RT=1.96 minutes.

A solution of di-tert-butyl dicarbonate (0.124 mL, 0.533 mmol) in DCM (1 mL) was added slowly to a mixture of methyl 4-((3-((3-aminopropyl)(methyl)amino)propyl)amino)-2-(3-(1-(benzyloxy)-2,2,2-trifluoroethyl)benzyl)-9H-pyrimido[4,5-b]indole-7-carboxylate (0.288 g, 0.444 mmol) and triethylamine (0.074 mL, 0.533 mmol) in DCM (3 mL) and MeOH (2 mL) to give a yellow solution. After stirring at 20° C. for 45 minutes, the solution was concentrated to dryness to give 373 mg as a yellow foam which was purified by flash chromatography to afford Intermediate 53B as methyl 2-(3-(1-(benzyloxy)-2,2,2-trifluoroethyl)benzyl)-4-((3-((3-((tert-butoxycarbonyl)amino)propyl)(methyl)amino)propyl)amino)-9H-pyrimido[4,5-b]indole-7-carboxylate (306 mg, 92% yield) as a yellow foam: $^1$H NMR (400 MHz, DMSO-d6) δ ppm 1.33 (s, 9H) 1.52 (dt, J=14.1, 7.0 Hz, 2H) 1.67-1.81 (m, 2H) 2.12 (s, 3H) 2.28 (t, J=7.2 Hz, 2H) 2.34 (t, J=6.8 Hz, 2H) 2.92 (q, J=6.7 Hz, 2H) 3.54-3.67 (m, 2H) 3.88 (s, 3H) 4.10 (s, 2H) 4.49 (s, 2H) 5.17 (q, J=6.8 Hz, 1H) 6.76 (t, J=5.5 Hz, 1H) 7.16-7.30 (m, 5H) 7.31-7.36 (m, 1H) 7.39 (t, J=7.6 Hz, 1H) 7.43-7.51 (m, 2H) 7.53 (t, J=5.3 Hz, 1H) 7.83 (dd, J=8.4, 1.4 Hz, 1H) 8.00 (d, J=1.4 Hz, 1H) 8.27 (d, J=8.2 Hz, 1H) 12.06 (s, 1H); MS m/z 749.3 (M+H)$^+$; HPLC 97.7%, RT=2.06 minutes.

A mixture of methyl 2-(3-(1-(benzyloxy)-2,2,2-trifluoroethyl)benzyl)-4-((3-((3-((tert-butoxycarbonyl)amino)propyl)(methyl)amino)propyl)amino)-9H-pyrimido[4,5-b]indole-7-carboxylate (0.306 g, 0.409 mmol) and Pd—C 10% wt (50% wet) (0.304 g, 0.143 mmol) in MeOH (9.92 mL) was treated with hydrogen at 20° C. for 22 hours. Then, the reaction mixture was filtered over Celite, the cake was rinsed with MeOH (2×10 mL) and with DCM:MeOH (1:1, 2×10 mL) then concentrated to dryness on rotovap to give 226 mg of an oil was purified by flash chromatography to afford methyl 4-((3-((3-((tert-butoxycarbonyl)amino)propyl)(methyl)amino)propyl)amino)-2-(3-(2,2,2-trifluoro-1-hydroxyethyl)benzyl)-9H-pyrimido[4,5-b]indole-7-carboxylate (202 mg, 75% yield) as a white foam: $^1$H NMR (400 MHz, DMSO-d6) δ ppm 1.33 (s, 9H) 1.48-1.62 (m, 2H) 1.71-1.85 (m, 2H) 2.16 (s, 3H) 2.25-2.35 (m, 2H) 2.39 (t, J=6.8 Hz, 2H) 2.86-3.00 (m, 2H) 3.56-3.70 (m, 2H) 3.88 (s, 3H) 4.06 (s, 2H) 5.01-5.14 (m, 1H) 6.77 (m, J=6.3 Hz, 2H) 7.30 (d, J=4.7 Hz, 2H) 7.36-7.42 (m, 1H) 7.49 (s, 1H) 7.51-7.57 (m, 1H) 7.82 (dd, J=8.2, 1.2

Hz, 1H) 7.99 (d, J=1.2 Hz, 1H) 8.26 (d, J=8.2 Hz, 1H) 12.06 (br. s., 1H); MS m/z 659.2 (M+H)+; HPLC >97%, RT=1.90 minutes.

A mixture of methyl 4-((3-((3-((tert-butoxycarbonyl) amino)propyl)(methyl)amino)propyl)amino)-2-(3-(2,2,2-trifluoro-1-hydroxyethyl)benzyl)-9H-pyrimido[4,5-b]indole-7-carboxylate (0.200 g, 0.304 mmol) and Dess-Martin periodinane reagent (0.567 g, 1.336 mmol) in DCM (7.50 mL) were stirred at 20° C. for one hour. After evaporation to dryness, the residue was purified by flash chromatography to afford methyl 4-((3-((3-((tert-butoxycarbonyl)amino)propyl) (methyl)amino)propyl)amino)-2-(3-(2,2,2-trifluoroacetyl) benzyl)-9H-pyrimido[4,5-b]indole-7-carboxylate (181 mg, 91% yield) as a yellow foam: $^1$H NMR in DMSO-d6 is consistent with the desired product but complicated due to presence of hydrate form: MS m/z 657.3 (M+H)+; HPLC 96.0% @ 220 nm and 95.3% @ 254 nm, RT 1.87 and 1.96 (ketone+hydrate) minutes.

A mixture of methyl 4-((3-((3-((tert-butoxycarbonyl) amino)propyl)(methyl)amino)propyl)amino)-2-(3-(2,2,2-trifluoroacetyl)benzyl)-9H-pyrimido[4,5-b]indole-7-carboxylate (0.180 g, 0.274 mmol), hydroxylamine hydrochloride (0.023 g, 0.329 mmol) and pyridine (0.355 mL) in MeOH (1.9 mL) was heated in a microwave oven to 65° C. for 48 hours. After concentration of the reaction mixture to dryness, a solution of the residue was washed with sat. NaHCO$_3$ (15 mL), the organic layer was dried over anh. MgSO$_4$, filtered and concentrated to dryness to afford methyl 4-((3-((3-((tert-butoxycarbonyl)amino)propyl)(methyl) amino)propyl)amino)-2-(3-(2,2,2-trifluoro-1-(hydroxyimino)ethyl)benzyl)-9H-pyrimido[4,5-b]indole-7-carboxylate (184 mg, 100% yield) as a light yellow foam: MS m/z 672.3 (M+H)+; HPLC 96.0% @ 220 nm and 91.4% @ 254 nm, RT=2.01 minutes.

Ts-Cl (0.060 g, 0.315 mmol) was added portion-wise to a mixture of methyl 4-((3-((3-((tert-butoxycarbonyl)amino) propyl)(methyl)amino)propyl)amino)-2-(3-(2,2,2-trifluoro-1-(hydroxyimino)ethyl)benzyl)-9H-pyrimido[4,5-b]indole-7-carboxylate (0.184 g, 0.274 mmol), DMAP (3.35 mg, 0.027 mmol) and triethylamine (0.048 mL, 0.342 mmol) in DCM (12 mL) to give a tan solution. After 1 hour, the reaction mixture was diluted with DCM (12 mL), washed with water (3×12 mL) and the organic layer was dried over anh. MgSO$_4$, filtered and concentrated to dryness to afford methyl 4-((3-((3-((tert-butoxycarbonyl)amino)propyl)(methyl)amino) propyl)amino)-2-(3-(2,2,2-trifluoro-1-((tosyloxy)imino) ethyl)benzyl)-9H-pyrimido[4,5-b]indole-7-carboxylate (217 mg, 96% yield) as a tan foam: MS m/z 826.2 (M+H)+; HPLC 93.2% @ 220 nm and 91.3% @ 254 nm, RT=2.20 minutes.

A solution of methyl 4-((3-((3-((tert-butoxycarbonyl) amino)propyl)(methyl)amino)propyl)amino)-2-(3-(2,2,2-trifluoro-1-((tosyloxy)imino)ethyl)benzyl)-9H-pyrimido[4, 5-b]indole-7-carboxylate (0.217 g, 0.263 mmol) in DCM (5.07 mL) was cooled to −78° C. and ammonia (1.7 mL, 79 mmol) was condensed into the sealed tube. The mixture was allowed to slowly warm to 20° C. and stirred for 3 hours. After cooling again to −78° C., the sealed tube was fitted with a septa with gas outlet and slowly warmed to 20° C. to evaporate ammonia. After 3 hours, the mixture was concentrated to dryness and then purified by flash chromatography to afford methyl 4-((3-((3-((tert-butoxycarbonyl)amino)propyl)(methyl)amino)propyl)amino)-2-(3-(3-(trifluoromethyl)diaziridin-3-yl)benzyl)-9H-pyrimido[4,5-b]indole-7-carboxylate (139 mg, 79% yield) as a white foam: $^1$H NMR (400 MHz, DMSO-d6) δ ppm 1.34 (s, 9H) 1.52-1.62 (m, 2H) 1.72-1.89 (m, 2H) 2.08-2.25 (m, 3H) 2.30-2.44 (m, 4H) 2.94 (q, J=6.4 Hz, 2H) 3.64 (q, J=6.5 Hz, 2H) 3.88 (s, 3H) 3.93 (d, J=8.4 Hz, 1H) 4.04 (d, J=8.4 Hz, 1H) 4.08 (s, 2H) 6.78 (br. s., 1H) 7.31-7.41 (m, 2H) 7.44-7.50 (m, 1H) 7.54 (t, J=5.5 Hz, 1H) 7.59 (s, 1H) 7.83 (dd, J=8.4, 1.4 Hz, 1H) 7.99 (d, J=1.4 Hz, 1H) 8.27 (d, J=8.4 Hz, 1H) 12.07 (s, 1H); MS m/z 671.4 (M+H)+; HPLC 98.6% @ 220 nm and 96.4% @ 254 nm, RT=1.91 minutes.

Iodine (27.8 mg, 0.110 mmol) was added to a 5 mL round-bottomed flask protected from light and pre-charged with methyl 4-((3-((3-((tert-butoxycarbonyl)amino)propyl)(methyl)amino)propyl)amino)-2-(3-(3-(trifluoromethyl)diaziridin-3-yl)benzyl)-9H-pyrimido[4,5-b]indole-7-carboxylate (70 mg, 0.104 mmol) and triethylamine (43.6 µL, 0.313 mmol) in DCM (2 mL) to give a light yellow solution. After stirring at 20° C. for 15 minutes, the solvent was evaporated and the residue purified by flash chromatography to give methyl 4-((3-((3-((tert-butoxycarbonyl)amino)propyl)(methyl)amino)propyl)amino)-2-(3-(3-(trifluoromethyl)-3H-diazirin-3-yl)benzyl)-9H-pyrimido[4,5-b]indole-7-carboxylate (65 mg, 0.097 mmol, 93% yield) as a light yellow foam: $^1$H NMR (400 MHz, DMSO-d6) δ ppm 1.33 (s, 9H) 1.53 (dt, J=13.8, 7.0 Hz, 2H) 1.70-1.82 (m, 2H) 2.15 (br. s., 3H) 2.24-2.34 (m, 2H) 2.34-2.42 (m, 2H) 2.87-2.98 (m, 2H) 3.55-3.66 (m, 2H) 3.88 (s, 3H) 4.10 (s, 2H) 6.76 (br. s., 1H) 7.14 (d, J=8.2 Hz, 1H) 7.27 (s, 1H) 7.43 (t, J=7.8 Hz, 1H) 7.49-7.58 (m, 2H) 7.83 (dd, J=8.2, 1.4 Hz, 1H) 7.99 (d, J=1.4 Hz, 1H) 8.27 (d, J=8.2 Hz, 1H) 12.06 (s, 1H); MS m/z 669.2 (M+H)+; HPLC 97.6% @ 220 nm and 97.3% @ 254 nm, RT=2.18 minutes.

Trifluoroacetic acid (0.400 mL, 5.19 mmol) was added to a solution of methyl 4-((3-((3-((tert-butoxycarbonyl)amino) propyl)(methyl)amino)propyl)amino)-2-(3-(3-(trifluoromethyl)-3H-diazirin-3-yl)benzyl)-9H-pyrimido[4,5-b]indole-7-carboxylate (0.064 g, 0.096 mmol) in DCM (4 mL) to give a light yellow solution. After stirring at 20° C. for 30 minutes, the reaction mixture was diluted with DCM (15 mL), washed with sat. NaHCO$_3$ (10 mL) and the aqueous layer was back-extracted with DCM (10 mL). The combined organic layers were dried over anh. MgSO$_4$, filtered and concentrated to dryness to afford Intermediate 53C: methyl 4-((3-((3-aminopropyl)(methyl)amino)propyl)amino)-2-(3-(3-(trifluoromethyl)-3H-diazirin-3-yl)benzyl)-9H-pyrimido[4,5-b]indole-7-carboxylate (45 mg, 83% yield) as a light yellow foam: HRMS m/z 569.2601 (M+H)+; HPLC 97.1% @ 220 nm and 96.9% @ 254 nm, RT=1.96 minutes.

2,5-Dioxopyrrolidin-1-yl-5-((3aS,4S,6aR)-2-oxohexahydro-1H-thieno[3,4-d]imidazol-4-yl)pentanoate (29.2 mg, 0.085 mmol) was added to a mixture of methyl 4-((3-((3-aminopropyl)(methyl)amino)propyl)amino)-2-(3-(3-(trifluoromethyl)-3H-diazirin-3-yl)benzyl)-9H-pyrimido[4,5-b] indole-7-carboxylate (45 mg, 0.079 mmol) and triethylamine (16.55 µL, 0.119 mmol) in DMF (750 µL) to give a yellow solution. After stirring at 20° C. for 30 minutes, the reaction mixture was concentrated to a light orange oil under high vacuum and the residue was purified by flash chromatography to give 56 mg as a white solid which was lyophilized from CH$_3$CN to afford the compound of Example 53: methyl 4-((3-(methyl(3-(5-((3aS,4S,6aR)-2-oxohexahydro-1H-thieno[3, 4-d]imidazol-4-yl)pentanamido)propyl)amino)propyl) amino)-2-(3-(3-(trifluoromethyl)-3H-diazirin-3-yl)benzyl)-9H-pyrimido[4,5-b]indole-7-carboxylate (51 mg, 0.064 mmol, 81% yield) as a white solid: $^1$H NMR (400 MHz, DMSO-d$_6$) δ ppm 1.18-1.34 (m, 3H) 1.35-1.50 (m, 3H) 1.50-1.64 (m, 3H) 1.70-1.82 (m, 2H) 2.02 (t, J=7.4 Hz, 2H) 2.15 (s, 3H) 2.26-2.34 (m, 2H) 2.37 (t, J=6.7 Hz, 2H) 2.55 (d, J=12.5 Hz, 1H) 2.77 (dd, J=12.1, 5.1 Hz, 1H) 2.99-3.10 (m, 3H) 3.56-3.66 (m, 2H) 3.88 (s, 3H) 4.03-4.14 (m, 1H) 4.10 (s, 2H) 4.26 (dd, J=7.6, 5.3 Hz, 1H) 6.34 (s, 1H) 6.39 (s, 1H) 7.14 (d, J=7.4 Hz, 1H) 7.28 (s, 1H) 7.44 (t, J=7.8 Hz, 1H) 7.52 (t, J=7.8 Hz, 1H) 7.56 (t, J=5.3 Hz, 1H) 7.73 (t, J=5.5 Hz, 1H) 7.83 (dd, J=8.2, 1.4 Hz, 1H) 8.00 (d, J=1.4 Hz, 1H) 8.28 (d, J=8.2 Hz, 1H) 12.07 (s, 1H); HRMS m/z 795.3368 (M+H)+; HPLC 95.4% @ 220 nm and 96.2% @ 254 nm, RT=2.06 minutes.

Example 55

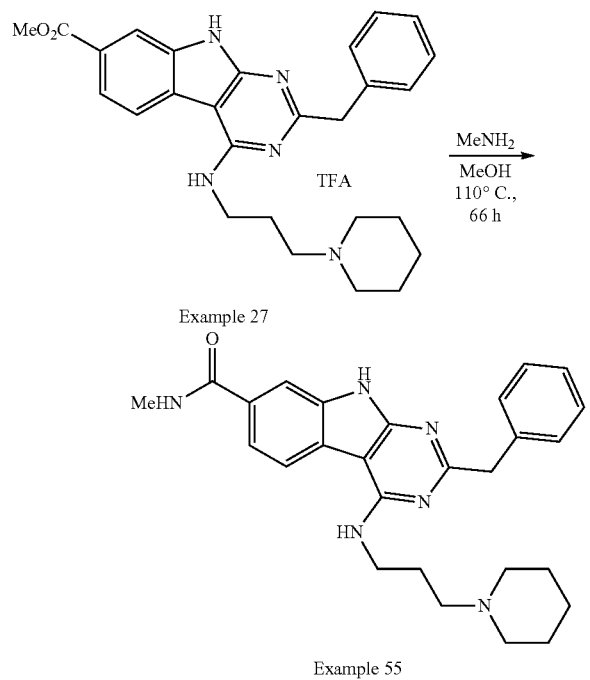

A solution of methyl 2-benzyl-4-((3-(piperidin-1-yl)propyl)amino)-9H-pyrimido[4,5-b]indole-7 carboxylate (Example 27, 0.030 g, 0.066 mmol) in methylamine 2M in MeOH (10.00 mL) was placed in a sealed the tube and heated to 110° C. for 66 hours, then the mixture was cooled to 20° C., concentrated to dryness and purified by flash chromatography to afford 28 mg of a colorless oil which was suspended in ether (2 mL). After stirring the resulting suspension for 2 hours, the solids were collected on a Buchner, the cake was washed with ether (2×0.5 mL) and the product was dried at 40° C. under high vacuum until constant weight to afford Example 55: 2-benzyl-N-methyl-4-((3-(piperidin-1-yl)propyl)amino)-9H-pyrimido[4,5-b]indole-7-carboxamide (23 mg, 77% yield) as a white solid: $^1$H NMR (400 MHz, DMSO-$d_6$) δ ppm 1.38 (m, J=5.1 Hz, 2H) 1.50 (quin, J=5.5 Hz, 4H) 1.80 (quin, J=7.0 Hz, 2H) 2.22-2.41 (m, 6H) 2.81 (d, J=4.3 Hz, 3H) 3.58-3.68 (m, 2H) 4.03 (s, 2H) 7.15-7.21 (m, 1H) 7.27 (m, J=7.4, 7.4 Hz, 3H) 7.34-7.40 (m, 2H) 7.70 (dd, J=8.2, 1.4 Hz, 1H) 7.90 (d, J=1.4 Hz, 1H) 8.27 (d, J=8.2 Hz, 1H) 8.46 (q, J=4.3 Hz, 1H) 11.96 (s, 1H); HRMS m/z 457.2708 (M+H)+; HPLC >99.5% @ 220 nm and 98.9% @ 254 nm, RT=1.53 minutes.

Reported HPLC retention time are for reverse-phase HPLC (Agilent, 1200 series) using the following conditions Solvent A: MeOH:H$_2$O:TFA (5:95:0.05); Solvent B: MeOH:H$_2$O:TFA (95:5:0.05); flow: 3.0 mL/min.; gradient 0 to 100% B in 2.0 min; column: ZorbaxC18, 3.5 microns, 4.6×30 mm; wavelength 220 nm.

TABLE 1

Structure, analytical HPLC retention time, LCMS data and biological data of Examples.

| Compound number | Structure | HPLC R$_T$ (min) analytical | MS m/z (M + H)+ | Biological data (EC$_{50}$)* |
|---|---|---|---|---|
| 1 | 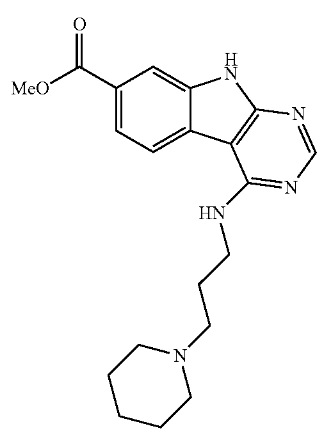 [SMILES: COC(=O)c1ccc2c(c1)[nH]c1ncnc(NCCCN3CCCCC3)c12] | 1.38 | 368.2 | C |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 2 | 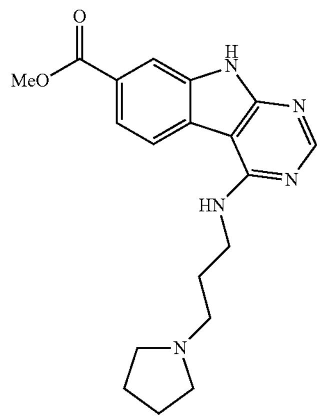 [SMILES: COC(=O)c1ccc2c(c1)[nH]c1ncnc(NCCCN3CCCC3)c12] | 1.35 | 354.2 | D |
| 3 | 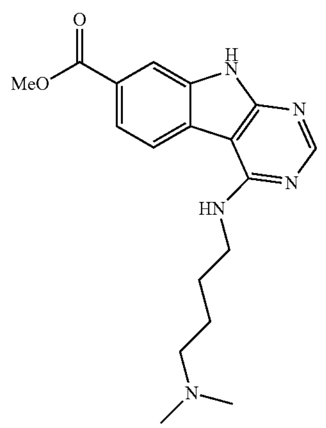 [SMILES: COC(=O)c1ccc2c(c1)[nH]c1ncnc(NCCCCN(C)C)c12] | 1.55 | 342.2 | C |
| 4 | 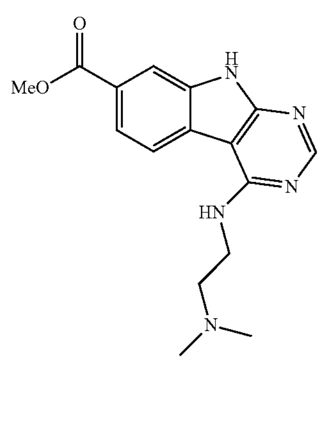 [SMILES: COC(=O)c1ccc2c(c1)[nH]c1ncnc(NCCN(C)C)c12] | 1.30 | 314.2 | D |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 5 | 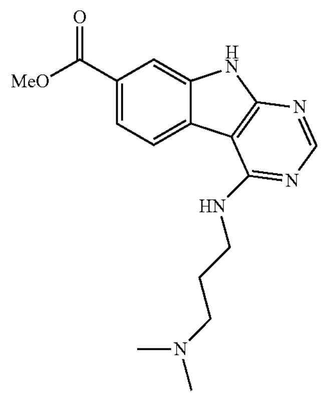 [SMILES: COC(=O)c1ccc2c(c1)[nH]c1ncnc(NCCCN(C)C)c12] | 1.29 | 328.2 | B |
| 6 | 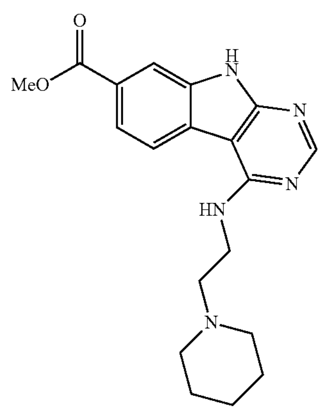 [SMILES: COC(=O)c1ccc2c(c1)[nH]c1ncnc(NCCN3CCCCC3)c12] | 1.41 | 354.2 | C |
| 7 | 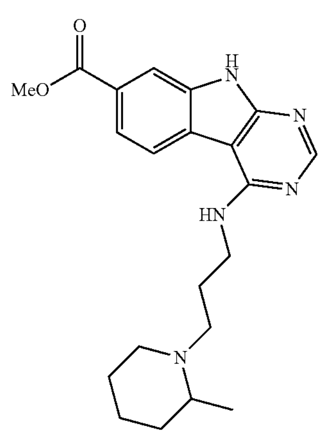 [SMILES: COC(=O)c1ccc2c(c1)[nH]c1ncnc(NCCCN3CCCCC3C)c12] | 1.43 | 382.2 | D |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 8 | 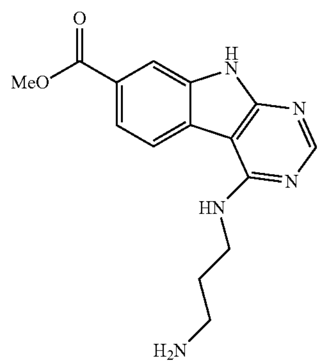 [SMILES: COC(=O)c1ccc2c(c1)[nH]c1ncnc(NCCCN)c12] | 1.34 | 300.2 | C |
| 9 | 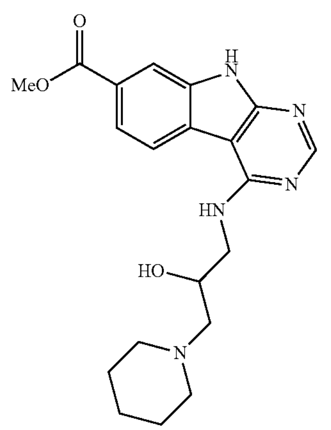 [SMILES: COC(=O)c1ccc2c(c1)[nH]c1ncnc(NCC(O)CN3CCCCC3)c12] | 1.35 | 384.2 | C |
| 10 | 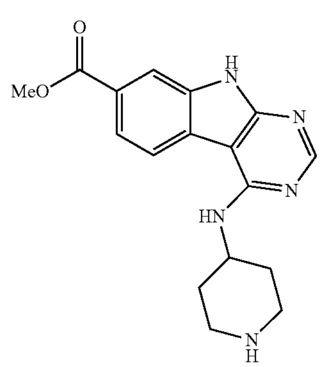 [SMILES: COC(=O)c1ccc2c(c1)[nH]c1ncnc(NC3CCNCC3)c12] | 1.34 | 326.2 | B |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 11 | 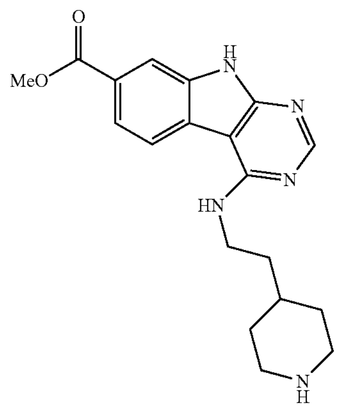 [SMILES: COC(=O)c1ccc2c(c1)[nH]c1ncnc(NCCC3CCNCC3)c12] | 1.40 | 354.2 | C |
| 12 | 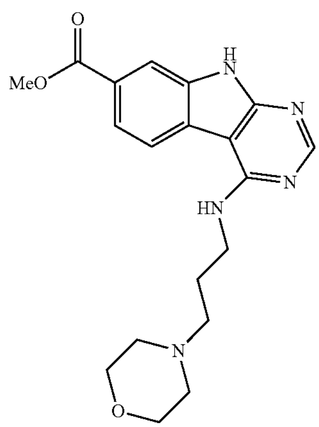 [SMILES: COC(=O)c1ccc2c(c1)[nH]c1ncnc(NCCCN3CCOCC3)c12] | 1.29 | 370.2 | A |
| 13 | 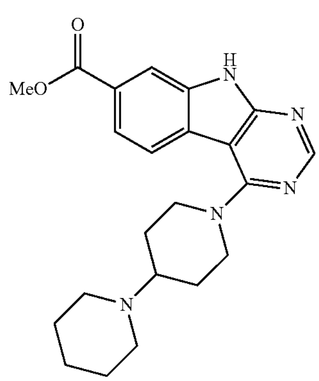 [SMILES: COC(=O)c1ccc2c(c1)[nH]c1ncnc(N3CCC(N4CCCCC4)CC3)c12] | 1.45 | 394.2 | D |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 14 | 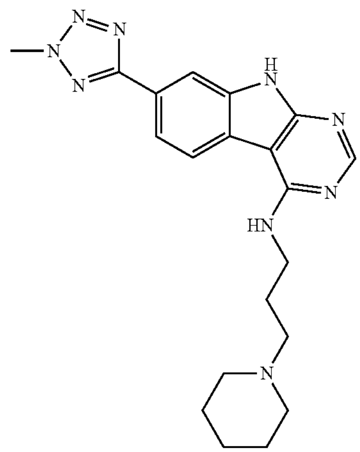 [SMILES: Cn1nnc(-c2ccc3c(c2)[nH]c2ncnc(NCCCN4CCCCC4)c23)n1] | 1.44 | 392.2 | D |
| 15 | 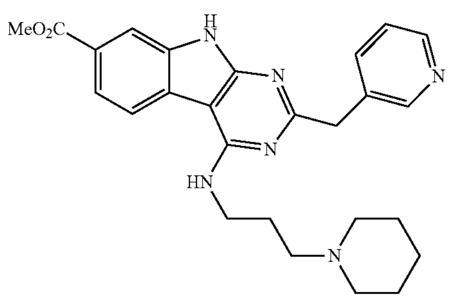 [SMILES: COC(=O)c1ccc2c(c1)[nH]c1nc(Cc3cccnc3)nc(NCCCN3CCCCC3)c12] | 1.43 | 459.2 | E |
| 16 | 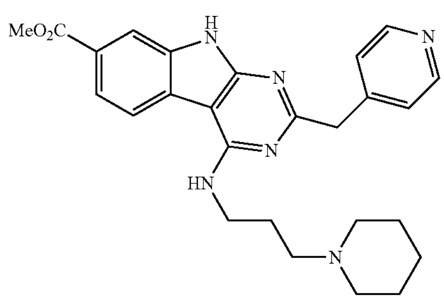 [SMILES: COC(=O)c1ccc2c(c1)[nH]c1nc(Cc3ccncc3)nc(NCCCN3CCCCC3)c12] | 1.78 | 459.2518 | C |
| 17 | 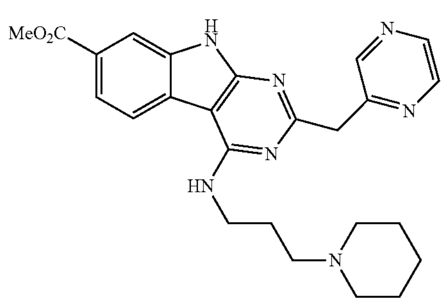 [SMILES: COC(=O)c1ccc2c(c1)[nH]c1nc(Cc3cnccn3)nc(NCCCN3CCCCC3)c12] | 1.54 | 460.2 | B |

TABLE 1-continued

Structure, analytical HPLC retention time, LCMS data and biological data of Examples.

| Compound number | Structure | HPLC $R_T$ (min) analytical | MS m/z $(M + H)^+$ | Biological data $(EC_{50})$* |
|---|---|---|---|---|
| 18 | 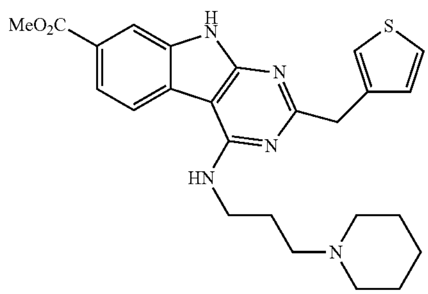 [SMILES: COC(=O)c1ccc2c(c1)[nH]c1nc(Cc3ccsc3)nc(NCCCN3CCCCC3)c12] | 2.068 | 464.2145 | E |
| 19 | 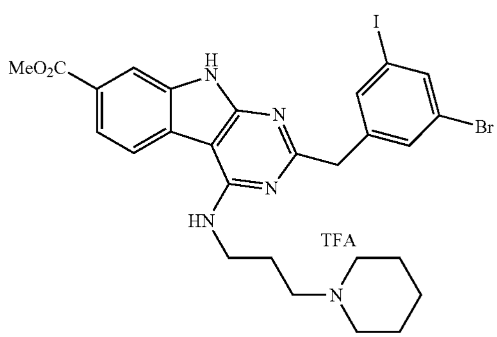 [SMILES: COC(=O)c1ccc2c(c1)[nH]c1nc(Cc3cc(Br)cc(I)c3)nc(NCCCN3CCCCC3)c12] | 2.349 | 662.063 | E |
| 20 | 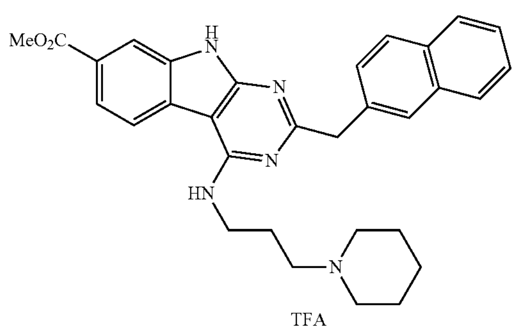 [SMILES: COC(=O)c1ccc2c(c1)[nH]c1nc(Cc3ccc4ccccc4c3)nc(NCCCN3CCCCC3)c12] | 2.206 | 508.2707 | D |
| 21 | 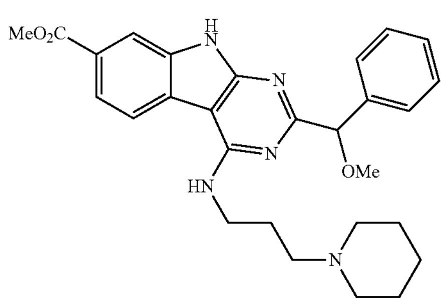 | 1.78 | 488.2665 | E |

TABLE 1-continued

Structure, analytical HPLC retention time, LCMS data and biological data of Examples.

| Compound number | Structure | HPLC $R_T$ (min) analytical | MS m/z $(M + H)^+$ | Biological data $(EC_{50})$* |
|---|---|---|---|---|
| 22 | 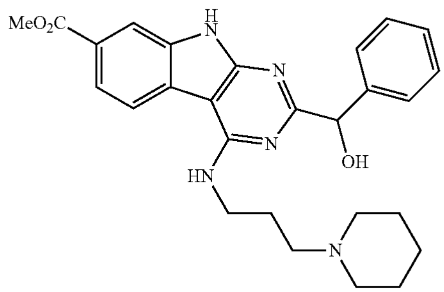 [SMILES: COC(=O)c1ccc2c(c1)[nH]c1nc(C(O)c3ccccc3)nc(NCCCN3CCCCC3)c12] | 1.68 | 474.2511 | F |
| 23 | 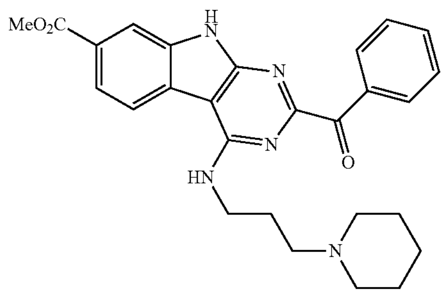 [SMILES: COC(=O)c1ccc2c(c1)[nH]c1nc(C(=O)c3ccccc3)nc(NCCCN3CCCCC3)c12] | 2.129 | 472.2342 | F |
| 24 | 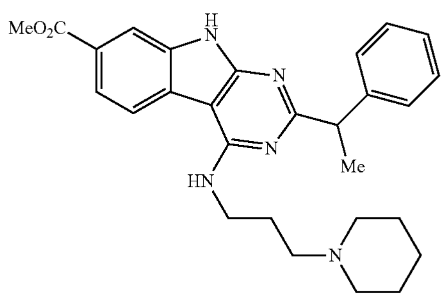 [SMILES: COC(=O)c1ccc2c(c1)[nH]c1nc(C(C)c3ccccc3)nc(NCCCN3CCCCC3)c12] | 2.083 | 472.2724 | E |
| 25 | 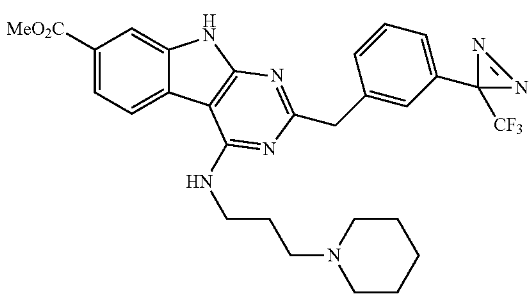 [SMILES: COC(=O)c1ccc2c(c1)[nH]c1nc(Cc3cccc(C4(C(F)(F)F)N=N4)c3)nc(NCCCN3CCCCC3)c12] | 2.05 | 566.2497 | E |
| 26 | 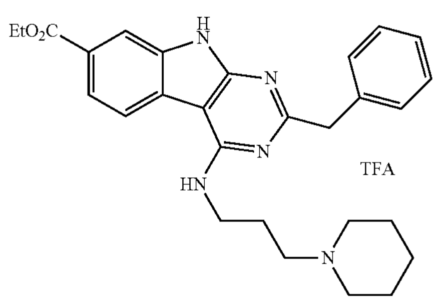 [SMILES: CCOC(=O)c1ccc2c(c1)[nH]c1nc(Cc3ccccc3)nc(NCCCN3CCCCC3)c12] | 2.152 | 472.2733 | F |

TABLE 1-continued
Structure, analytical HPLC retention time, LCMS data and biological data of Examples.
| Compound number | Structure | HPLC R$_T$ (min) analytical | MS m/z (M + H)$^+$ | Biological data (EC$_{50}$)* |
|---|---|---|---|---|
| 27 | 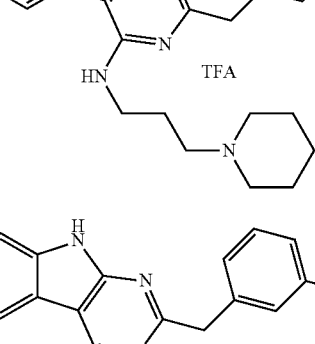 | 2.052 | 458.2598 | E |
| 28 | 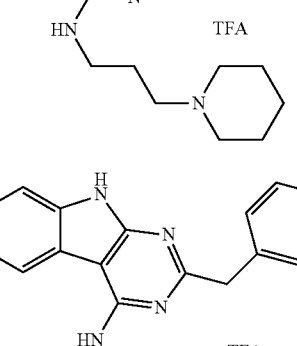 | 2.194 | 538.1670 | E |
| 29 | 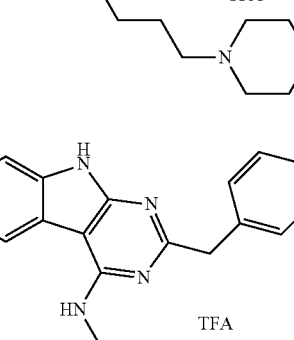 | 2.142 | 472.2756 | E |
| 30 | 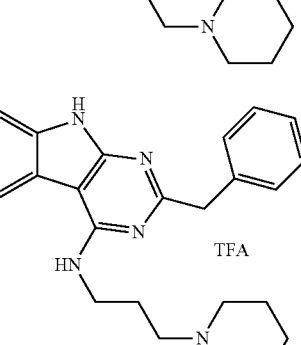 | 2.142 | 472.2740 | E |
| 31 | 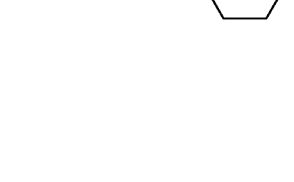 | 2.112 | 476.2499 | E |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 32 | 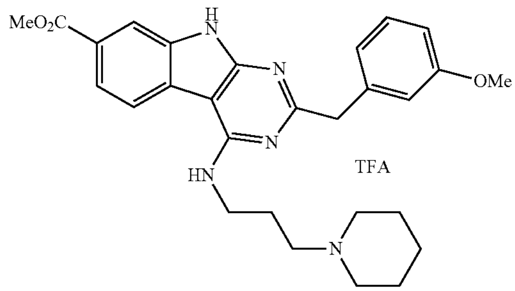 [SMILES: COC(=O)c1ccc2c(c1)[nH]c1nc(Cc3cccc(OC)c3)nc(NCCCN3CCCCC3)c12] | 2.070 | 488.2690 | E |
| 33 | 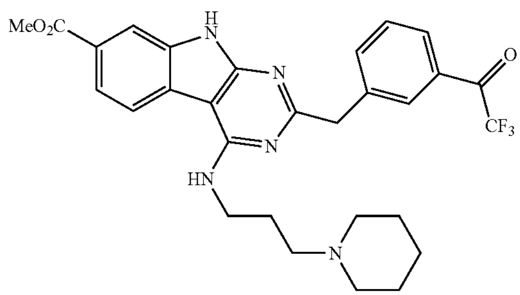 [SMILES: COC(=O)c1ccc2c(c1)[nH]c1nc(Cc3cccc(C(=O)C(F)(F)F)c3)nc(NCCCN3CCCCC3)c12] | 1.761.8 (hydrates) | 554.2384 | E |
| 34 | 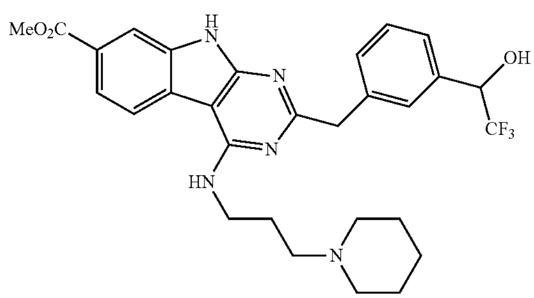 [SMILES: COC(=O)c1ccc2c(c1)[nH]c1nc(Cc3cccc(C(O)C(F)(F)F)c3)nc(NCCCN3CCCCC3)c12] | 2.142 | 554.2 | E |
| 35 | 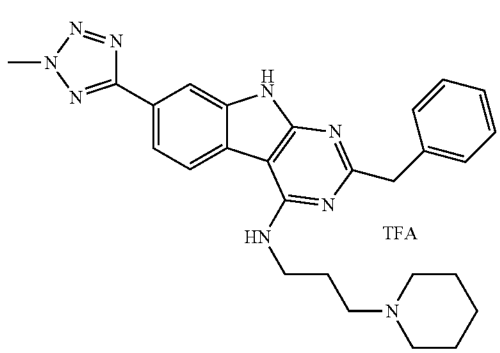 [SMILES: Cn1nnc(-c2ccc3c(c2)[nH]c2nc(Cc4ccccc4)nc(NCCCN4CCCCC4)c23)n1] | 2.063 | 482.28 | E |

TABLE 1-continued
Structure, analytical HPLC retention time, LCMS data and biological data of Examples.
| Compound number | Structure | HPLC $R_T$ (min) analytical | MS m/z $(M + H)^+$ | Biological data $(EC_{50})$* |
|---|---|---|---|---|
| 36 | 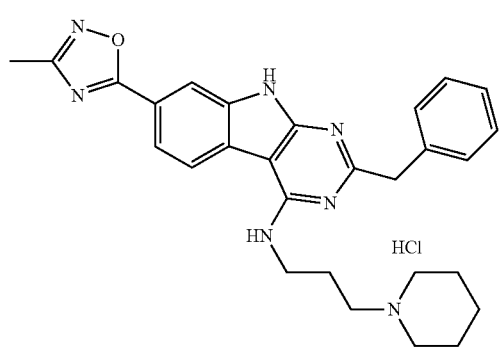 [SMILES: Cc1noc(-c2ccc3c(c2)[nH]c2nc(Cc4ccccc4)nc(NCCCN4CCCCC4)c23)n1 ; Cl] | 1.79 | 482.2663 | F |
| 37 | 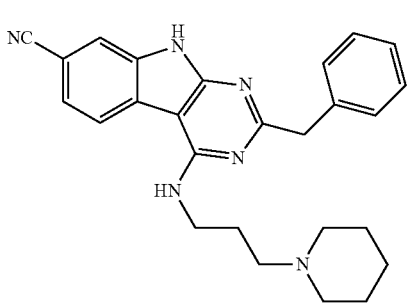 [SMILES: N#Cc1ccc2c(c1)[nH]c1nc(Cc3ccccc3)nc(NCCCN3CCCCC3)c12] | 1.68 | 425.2448 | C |
| 38 | 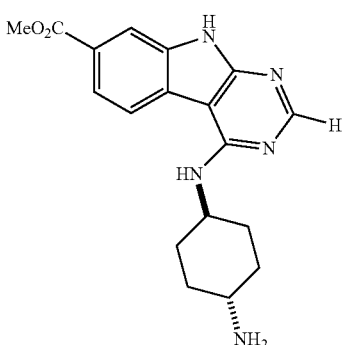 | 1.44 | 340.2 | D |
| 39 | 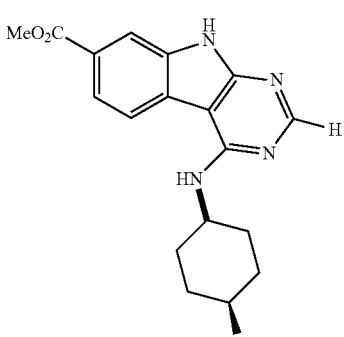 | 1.38 | 340.2 | C |

TABLE 1-continued

Structure, analytical HPLC retention time, LCMS data and biological data of Examples.

| Compound number | Structure | HPLC $R_T$ (min) analytical | MS m/z $(M + H)^+$ | Biological data $(EC_{50})$* |
|---|---|---|---|---|
| 40 | 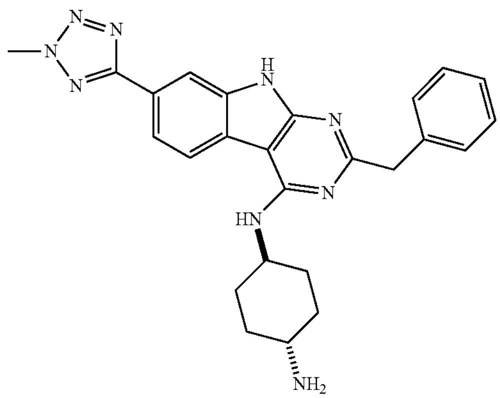 | 1.72 | 454.2 | E |
| 41 | 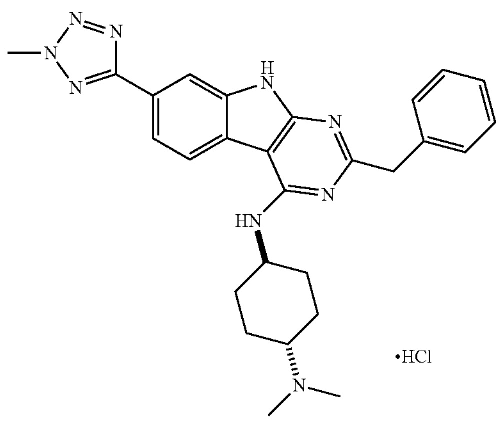 | 1.71 | 482.2785 | E |
| 42 | 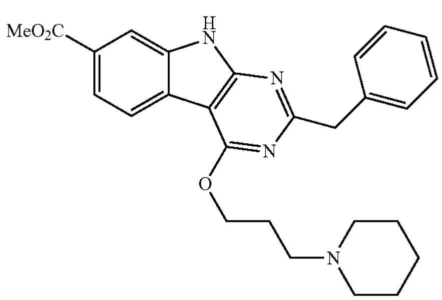 | 1.92 | 459.2392 | B |
| 43 | 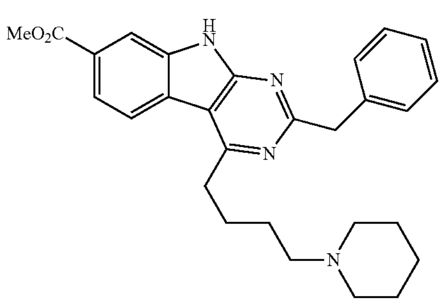 [SMILES: COC(=O)c1ccc2c(c1)[nH]c1nc(Cc3ccccc3)nc(CCCCN3CCCCC3)c12] | 1.75 | 457.2598 | F |

TABLE 1-continued

Structure, analytical HPLC retention time, LCMS data and biological data of Examples.

| Compound number | Structure | HPLC R$_T$ (min) analytical | MS m/z (M + H)$^+$ | Biological data (EC$_{50}$)* |
|---|---|---|---|---|
| 44 | 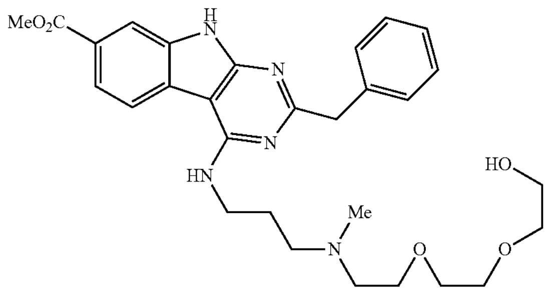 [SMILES: COC(=O)c1ccc2c(c1)[nH]c1nc(Cc3ccccc3)nc(NCCCN(C)CCOCCOCCO)c12] | 2.035 | 536.2867 | E |
| 45 | 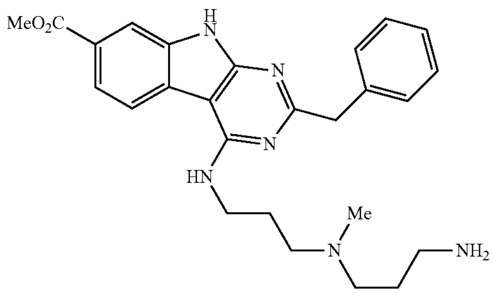 [SMILES: COC(=O)c1ccc2c(c1)[nH]c1nc(Cc3ccccc3)nc(NCCCN(C)CCCN)c12] | 1.63 | 461.2 | E |
| 46 | 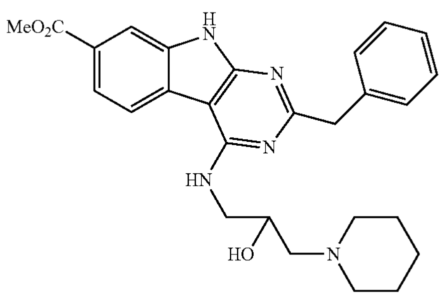 [SMILES: COC(=O)c1ccc2c(c1)[nH]c1nc(Cc3ccccc3)nc(NCC(O)CN3CCCCC3)c12] | 1.70 | 474.2476 | E |
| 47 | 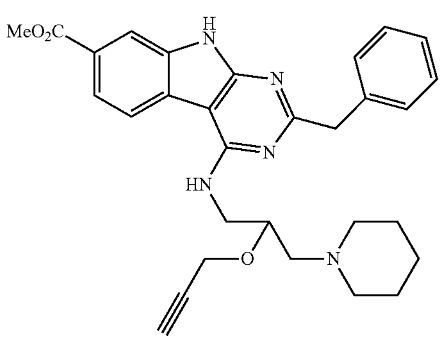 [SMILES: C#CCOC(CNc1nc(Cc2ccccc2)nc2[nH]c3cc(C(=O)OC)ccc3c12)CN1CCCCC1] | 1.85 | 512.2632 | E |
| 48 | 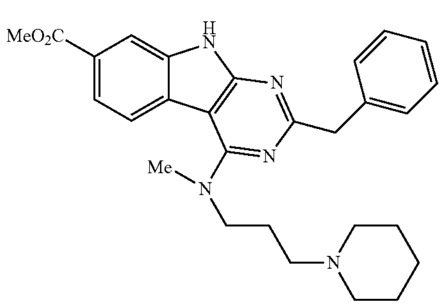 [SMILES: COC(=O)c1ccc2c(c1)[nH]c1nc(Cc3ccccc3)nc(N(C)CCCN3CCCCC3)c12] | 1.74 | 472.2717 | E |

TABLE 1-continued

Structure, analytical HPLC retention time, LCMS data and biological data of Examples.

| Compound number | Structure | HPLC $R_T$ (min) analytical | MS m/z $(M + H)^+$ | Biological data $(EC_{50})$* |
|---|---|---|---|---|
| 49 | 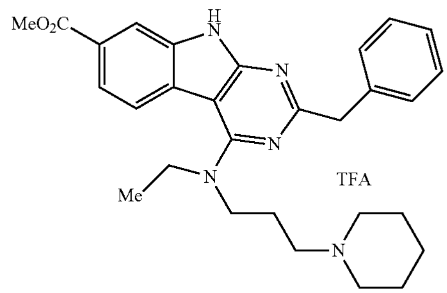 [SMILES: CCN(CCCN1CCCCC1)c1nc(Cc2ccccc2)nc2[nH]c3cc(C(=O)OC)ccc3c12] | 2.161 | 586.2839 | A |
| 50 | 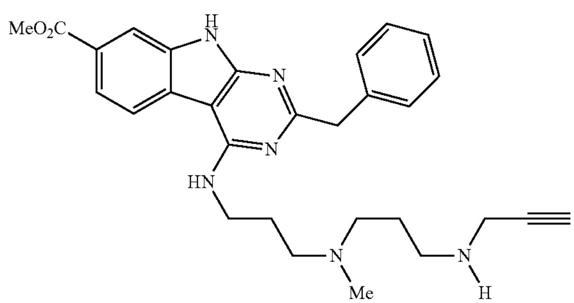 [SMILES: C#CCNCCCN(C)CCCNc1nc(Cc2ccccc2)nc2[nH]c3cc(C(=O)OC)ccc3c12] | 1.65 | 499.2823 | F |
| 51 | 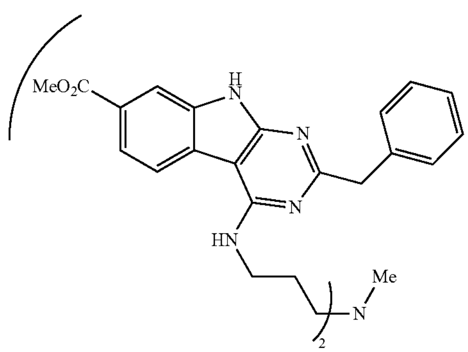 | 2.01 | 776.3 | E |
| 52 | 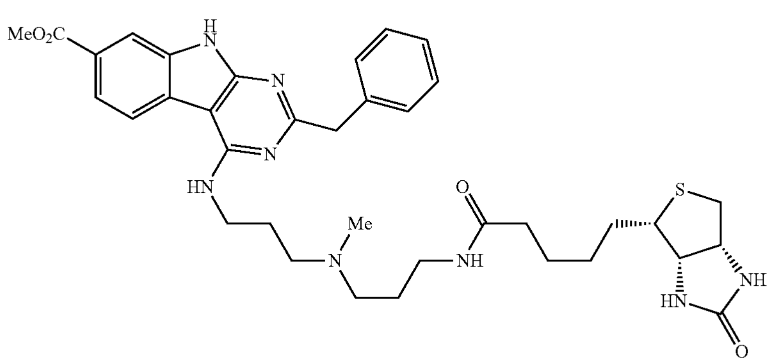 [SMILES: COC(=O)c1ccc2c(c1)[nH]c1nc(Cc3ccccc3)nc(NCCCN(C)CCCNC(=O)CCCC[C@@H]3SC[C@@H]4NC(=O)N[C@@H]43)c12] | 1.70 | 687.3 | C |

TABLE 1-continued

Structure, analytical HPLC retention time, LCMS data and biological data of Examples.

| Compound number | Structure | HPLC $R_T$ (min) analytical | MS m/z $(M + H)^+$ | Biological data $(EC_{50})$* |
|---|---|---|---|---|
| 53 | 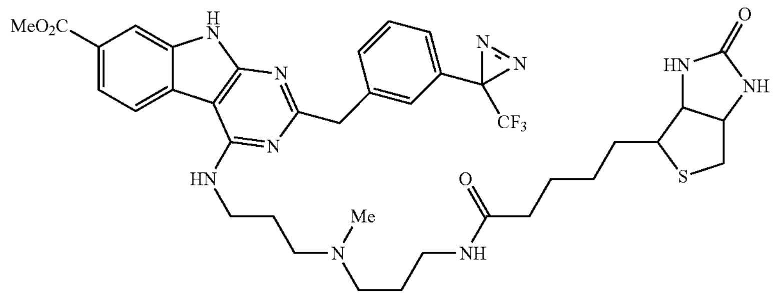 [SMILES: COC(=O)c1ccc2c(c1)[nH]c1nc(Cc3cccc(C4(C(F)(F)F)N=N4)c3)nc(NCCCN(C)CCCNC(=O)CCCCC3SCC4NC(=O)NC43)c12] | 2.06 | 795.3368 | F |
| 54 | 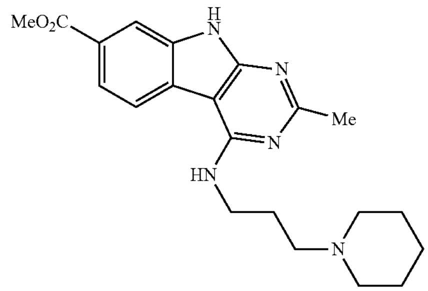 [SMILES: COC(=O)c1ccc2c(c1)[nH]c1nc(C)nc(NCCCN3CCCCC3)c12] | 1.46 | 382.2 | A |
| 55 | 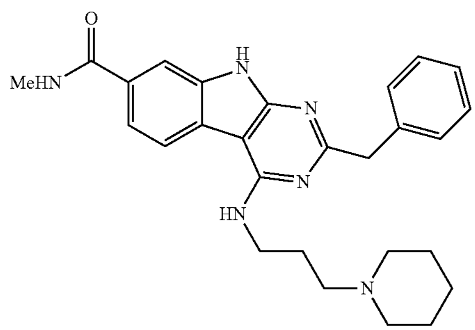 [SMILES: CNC(=O)c1ccc2c(c1)[nH]c1nc(Cc3ccccc3)nc(NCCCN3CCCCC3)c12] | 1.53 | 457.2708 | A |

The $EC_{50}$ is defined as the concentration that results in a 50% increase in CD34+CD45RA− cell count compared to vehicle cultures (DMSO). *$EC_{50}$: A>1000 nM; B=500-1000 nM; C=250-500 nM; D=100-250; E=<100 nM; F=compound showed >1.3 fold expansion.

Ex Vivo Functional Assay:

The ex vivo functionality of expanded cells was tested using the conventional colony-forming units in culture (CFU-C) assay. Untreated cells or cells incubated with DMSO, positive control or a compound of the invention were plated in methylcellulose medium in conventional conditions. As an example, Compound 1 (Table 1, Example 1) expands the number of multipotent hematopoietic progenitors. Methylcellulose culture of 1000 CD34+ mPB cells treated with Compound 1 for 10 days resulted in a 5-fold increase in multilineage granulocyte erythrocyte, macrophage and megakaryocyte (GEMM colonies) over input cells and a 10-fold increase compared to control cells. This suggests that Compound 1 promotes expansion of multipotent progenitor cells.

In Vivo Functional Assay:

CD34+ mPB cells cultured with compounds of the invention engraft immunodeficient strain NOD scid gamma (NSG) mice. The outcome of 2,000,000 and 500,000 CD34+ mPB cells cultured for 10 days with Compound 1 (Table 1, Example 1) or vehicle control conditions were transplanted in NSG mice. After 8 weeks post transplantation, human hematopoietic cell reconstitution was checked in the NSG bone marrow using antibody against human CD45. Cells treated with Compound 1 but not with vehicle were able to engraft NSG mice. Moreover, the reconstitution of the human myeloid and lymphoid compartments was also confirmed, as the bone marrow cells were positive for human CD33+ and CD19+ respectively. These results show that CD34+ mPB expanded with Compound 1 not only contribute to the engraftment but also retain in vivo multilineage repopulation potential.

Combination of Compounds:

CD34+ mPB cells cultured with compounds of the invention engraft immunodeficient strain NOD scid gamma (NSG) mice. The outcome of 2,000,000 and 500,000 CD34+ mPB cells cultured for 10 days with Compound 1 (Table 1, Example 1) or vehicle control conditions were transplanted in NSG mice. After 8 weeks post transplantation, human hematopoietic cell reconstitution was checked in the NSG bone marrow using antibody against human CD45. Cells treated with Compound 1 but not with vehicle were able to engraft NSG mice. Moreover, the reconstitution of the human myeloid and lymphoid compartments was also confirmed, as the bone marrow cells were positive for human CD33+ and CD19+ respectively. These results show that CD34+ mPB expanded with Compound 1 not only contribute to the engraftment but also retain in vivo multilineage repopulation potential.

It is understood that the examples and embodiments described herein are for illustrative purposes only and that various modifications or changes in light thereof will be suggested to persons skilled in the art and are to be included within the present discovery and scope of the appended claims.

The invention claimed is:
1. A compound of general formula I or II

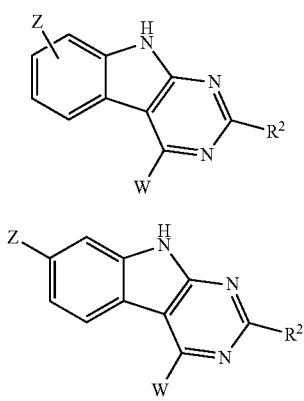

or a salt thereof,
wherein:
Z is
1) —P(O)(OR$^1$)(OR$^1$),
2) —C(O)OR$^1$,
3) —C(O)NHR$^1$,
4) —C(O)N(R$^1$)R$^1$,
5) —C(O)R$^1$,
6) —CN,
7) —SR$^1$,
8) —S(O)$_2$NH$_2$,
9) —S(O)$_2$NHR$^1$,
10) —S(O)$_2$N(R$^1$)R$^1$,
11) —S(O)R$^1$,
12) —S(O)$_2$R$^1$,
13) -L,
14) -benzyl optionally substituted with 1, 2 or 3 R$^A$ or R$^1$ substituents,
15) -L-heteroaryl optionally substituted with one or more R$^A$ or R$^1$ substituents attached on either or both the L and the heteroaryl groups,
16) -L-heterocyclyl optionally substituted with one or more R$^A$ or R$^1$ substituents attached on either one or both the L and the heterocyclyl groups,
17) -L-aryl optionally substituted with one or more R$^A$ or R$^1$ substituents attached on either or both the L and the heteroaryl groups,
18) -heteroaryl optionally substituted with one or more R$^A$ or R$^1$ substituents, or
19) -aryl optionally substituted with one or more R$^A$ or R$^1$ substituents, and wherein each substituent is optionally attached to the L group if it is not already present, and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the is substituted with one or more R$^1$ or R$^A$;

W is
1) —OR$^1$, wherein R$^1$ is —C$_{1-6}$ alkyl, —C$_{2-6}$ alkenyl, —C$_{2-6}$ alkynyl, C$_{3-7}$ cycloalkyl, —C$_{3-7}$ cycloalkenyl, —C$_{1-5}$ perfluorinated, -heterocyclyl, -aryl, -heteroaryl, -benzyl, or 5-[(3aS,4S,6aR)-2-oxohexahydro-1H-thieno[3,4-d]imidazol-4-yl]pentanoyl,
wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 R$^A$ or R$^1$ substituents;
2) -L-OH,
3) -L-OR$^1$,
4) —SR$^1$,
5) —CN,
6) —P(O)(OR$^1$)(OR$^1$),
7) —NHR$^1$,
8) —N(R$^1$)R$^1$,
9) -L-NH$_2$,
10) -L-NHR$^1$,
11) -L-N(R$^1$)R$^1$,
12) -L-SR$^1$,
13) -L-S(O)R$^1$,
14) -L-S(O)$_2$R$^1$,
15) -L-P(O)(OR$^1$)(OR$^1$),
16) —C(O)OR$^1$,
17) —C(O)NH$_2$,
18) —C(O)NHR$^1$,
19) —C(O)N(R$^1$)R$^1$,
20) —NHC(O)R$^1$,
21) —NR$^1$C(O)R$^1$,
22) —NHC(O)OR$^1$,
23) —NR$^1$C(O)OR$^1$,
24) —OC(O)NH$_2$,
25) —OC(O)NHR$^1$,
26) —OC(O)N(R$^1$)R$^1$,
27) —OC(O)R$^1$,
28) —C(O)R$^1$,
29) —NHC(O)NH$_2$,
30) —NHC(O)NHR$^1$,
31) —NHC(O)N(R$^1$)R$^1$,
32) —NR$^1$C(O)NH$_2$,
33) —NR$^1$C(O)NHR$^1$,
34) —NR$^1$C(O)N(R$^1$)R$^1$,
35) —NHS(O)$_2$R$^1$,
36) —NR$^1$S(O)$_2$R$^1$,
37) —S(O)$_2$NH$_2$,
38) —S(O)$_2$NHR$^1$,
39) —S(O)$_2$N(R$^1$)R$^1$,
40) —S(O)R$^1$,
41) —S(O)$_2$R$^1$,
42) —OS(O)$_2$R$^1$,
43) —S(O)$_2$OR$^1$,
44) -benzyl optionally substituted with 1, 2 or 3 R$^A$ or R$^1$ substituents,
45) -L-heteroaryl optionally substituted with one or more R$^A$ or R$^1$ substituents attached on either or both the L and the heteroaryl groups, 46) -L-heterocyclyl optionally substituted with one or more $R^4$ or $R^1$ substituents attached on either or both the L and the heterocyclyl groups,
47) -L-aryl optionally substituted with one or more $R^4$ or $R^1$ substituents attached on either or both the L and aryl groups,
48) -L-NR$^1$(R$^1$),
49) -(L-)$_2$NR$^1$,
50) -L-(N(R$^1$)-L)$_n$-N(R$^1$)R$^1$,
51) -L-(N(R$^1$)-L)$_n$- heteroaryl optionally substituted with one or more $R^4$ or $R^1$ substituents attached on either or both the L and heteroaryl groups,
52) -L-(N(R$^1$)-L)$_n$- heterocyclyl optionally substituted with one or more $R^4$ or $R^1$ substituents attached on either or both the L and heterocyclyl groups,
53) -L-(N(R$^1$)-L)$_n$- aryl optionally substituted with one or more $R^4$ or $R^1$ substituents attached on either or both the L and aryl groups,
54) —O-L-N(R$^1$)R$^1$,
55) —O-L- heteroaryl optionally substituted with one or more $R^4$ or $R^1$ substituents attached on either or both the L and heteroaryl groups,
56) —O-L- heterocyclyl optionally substituted with one or more $R^4$ or $R^1$ substituents attached on either or both the L and heterocyclyl groups,
57) —O-L- aryl optionally substituted with one or more $R^4$ or $R^1$ substituents attached on either or both the L and aryl groups,
58) —(O-L)$_2$-NR$^1$,
59) —O-L-(N(R$^1$)-L)$_n$-N(R$^1$)R$^1$,
60) —O-L-(N(R$^1$)-L)$_n$- heteroaryl optionally substituted with one or more $R^4$ or $R^1$ substituents attached on either or both the L and heteroaryl groups,
61) —O-L-(N(R$^1$)-L)$_n$- heterocyclyl optionally substituted with one or more $R^4$ or $R^1$ substituents attached on either or both the L and heterocyclyl groups,
62) —O-L-(N(R$^1$)-L)$_n$- aryl optionally substituted with one or more $R^4$ or $R^1$ substituents,
63) —S-L- heteroaryl optionally substituted with one or more $R^4$ or $R^1$ substituents,
64) —S-L- heterocyclyl optionally substituted with one or more $R^4$ or $R^1$ substituents,
65) —S-L- aryl optionally substituted with one or more $R^4$ or $R^1$ substituents attached on either or both the L and aryl groups,
66) —(S-L)$_2$NR$^1$,
67) —S-L-(N(R$^1$)-L)$_n$-N(R$^1$)R$^1$,
68) —S-L-(N(R$^1$)-L)$_n$- heteroaryl optionally substituted with one or more $R^4$ substituents,
69) —S-L-(N(R$^1$)-L)$_n$- heterocyclyl optionally substituted with one or more $R^4$ substituents,
70) —S-L-(N(R$^1$)-L)$_n$- aryl optionally substituted with one or more $R^4$ substituents,
71) —NR$^1$(R$^1$),
72) —(N(R$^1$)-L)$_n$-N(R$^1$)R$^1$,
73) —N(R$^1$)L)$_2$-NR$^1$,
74) —(N(R$^1$)-L)$_n$-N(R$^1$)R$^4$,
75) —(N(R$^1$)-L)$_n$- heteroaryl optionally substituted with one or more $R^4$ or $R^1$ substituents,
76) —(N(R$^1$)-L)$_n$- heterocyclyl optionally substituted with one or more $R^4$ or $R^1$ substituents,
77) —(N(R$^1$)-L)$_n$- aryl optionally substituted with one or more $R^4$ or $R^1$ substituents,
78) -heteroaryl optionally substituted with one or more $R^4$ substituents, or
79) -aryl optionally substituted with one or more $R^4$ substituents, and wherein each substituent is optionally attached to the L group if it is not already present,
and wherein when two $R^1$ substituents are present on the same nitrogen atom, then each $R^1$ substituent is independently selected from the list of $R^1$ values described thereafter,
and wherein n is an integer equal to either 0, 1, 2, 3, 4, or 5,
and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^4$;

L is
1) —C$_{1-6}$ alkyl,
2) —C$_{2-6}$ alkenyl,
3) —C$_{2-6}$ alkynyl,
4) —C$_{3-7}$ cycloalkyl,
5) —C$_{3-7}$ cycloalkenyl,
6) heterocyclyl,
7) —C$_{1-6}$ alkyl-C$_{3-7}$ cycloalkyl,
8) —C$_{1-6}$ alkyl-heterocyclyl,
9) aryl, or
10) heteroaryl,
and wherein the alkyl, the alkenyl, the alkynyl, the cycloalkyl, the cycloalkenyl, the heterocyclyl, the aryl and the heteroaryl groups are each independently optionally substituted with one or two $R^4$ substituent;

$R^1$ is
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl,
11) -benzyl, or
12) 5-[(3aS,4S,6aR)-2-oxohexahydro-1H-thieno[3,4-d]imidazol-4-yl]pentanoyl, and wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 $R^4$ or $R^1$ substituents;

$R^2$ is
1) —H,
2) —C$_{1-6}$ alkyl,
3) —SR$^1$,
4) —C(O)R$^1$,
5) —S(O)R$^1$,
6) —S(O)$_2$R$^1$,
7) -benzyl optionally substituted with 1, 2 or 3 $R^4$ or $R^1$ substituents,
8) -L-heteroaryl optionally substituted with one or more $R^4$ or $R^1$ substituents attached on either one or both the L and the heteroaryl groups,
9) -L-heterocyclyl optionally substituted with one or more $R^4$ or $R^1$ substituents attached on either one or both the L and the heterocyclyl groups,
10) -L-aryl optionally substituted with one or more $R^4$ or $R^1$ substituents attached on either one or both the L and the aryl groups,
11) -heteroaryl optionally substituted with one or more $R^4$ or $R^1$ substituents, or 12) -aryl optionally substituted with one or more $R^4$ or $R^1$ substituents, and wherein each substituent is optionally attached to the L group if it is not already present;

$R^4$ is
1) -halogen,
2) —$CF_3$,
3) —OH,
4) —$OR^1$,
5) -L-OH,
6) -L-$OR^1$,
7) —$OCF_3$,
8) —SH,
9) —SR1,
10) —CN,
11) —$NO_2$,
12) —$NH_2$,
13) —$NHR^1$,
14) —$NR^1R^1$,
15) -L-$NH_2$,
16) -L-$NHR^1$,
17) -L-$SR^1$,
18) -L-S(O)$R^1$,
19) -L-S(O)$_2R^1$,
20) —C(O)OH,
21) —C(O)$OR^1$,
22) —C(O)$NH_2$,
23) —C(O)$NHR^1$,
24) —C(O)N($R^1$)$R^1$,
25) —NHC(O)$R^1$,
26) —$NR^1$C(O)$R^1$,
27) —NHC(O)$OR^1$,
28) —$NR^1$C(O)$OR^1$,
29) —OC(O)$NH_2$,
30) —OC(O)$NHR^1$,
31) —OC(O)N($R^1$)$R^1$,
32) —OC(O)$R^1$,
33) —C(O)$R^1$,
34) —NHC(O)$NH_2$,
35) —NHC(O)$NHR^1$,
36) —NHC(O)N($R^1$)$R^1$,
37) —$NR^1$C(O)$NH_2$,
38) —$NR^1$C(O)$NHR^1$,
39) —$NR^1$C(O)N($R^1$)$R^1$,
40) —NHS(O)$_2R^1$,
41) —$NR^1$S(O)$_2R^1$,
42) —S(O)$_2NH_2$,
43) —S(O)$_2NHR^1$,
44) —S(O)$_2$N($R^1$)$R^1$,
45) —S(O)$R^1$,
46) —S(O)$_2R^1$,
47) —OS(O)$_2R^1$,
48) —S(O)$_2OR^1$,
49) -benzyl,
50) —$N_3$, or
51) —C(—N═N—)($CF_3$), and wherein the benzyl group is optionally substituted with 1, 2 or 3 $R^4$ or $R^1$ substituents provided that the compound of Formula (I) is other than

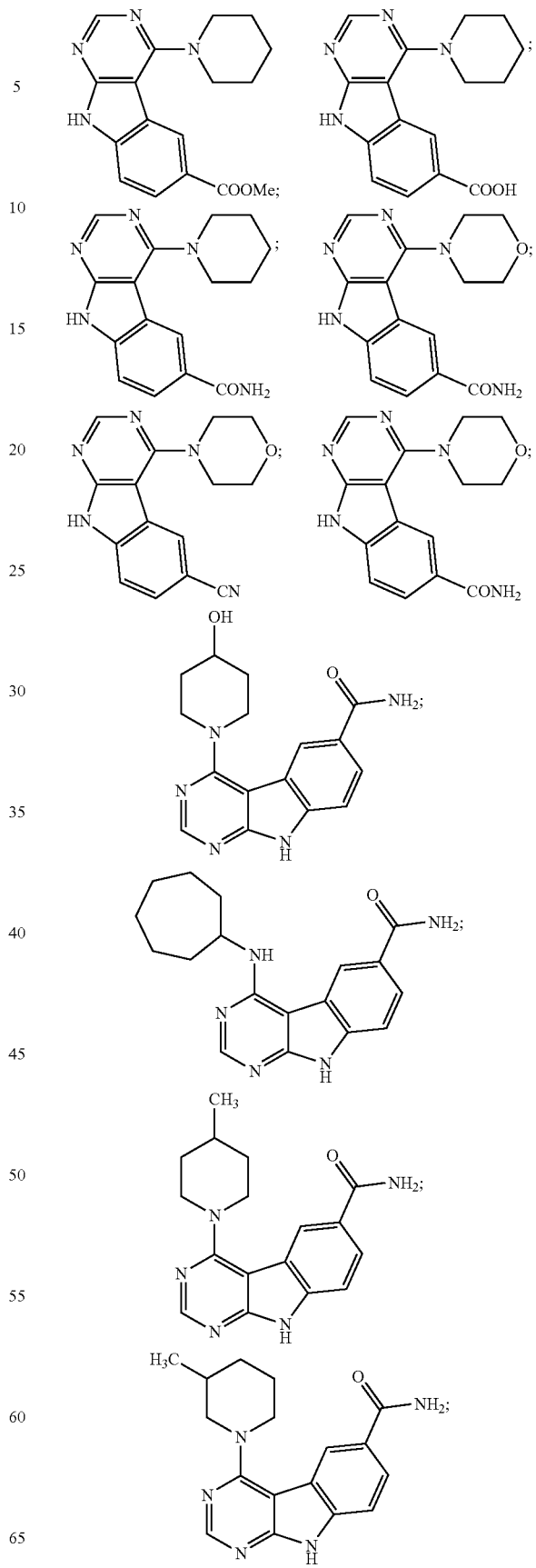

101
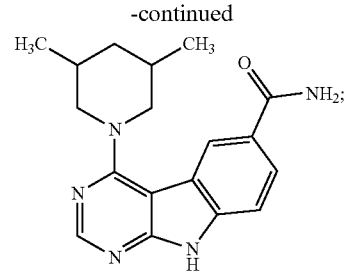
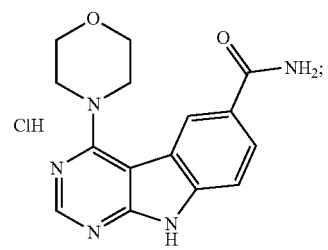
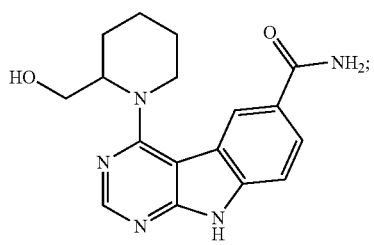
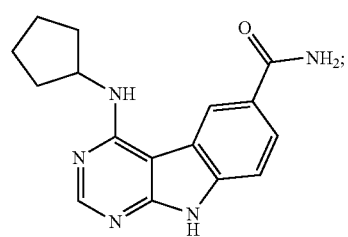
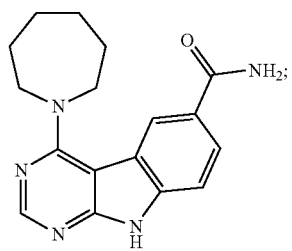
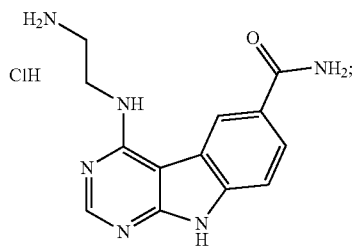
102
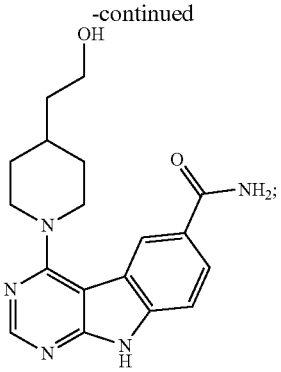
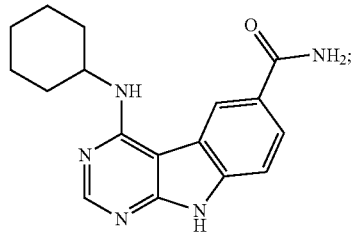
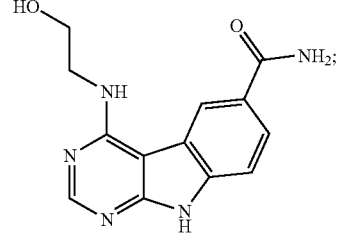
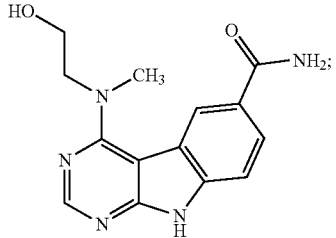
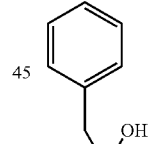
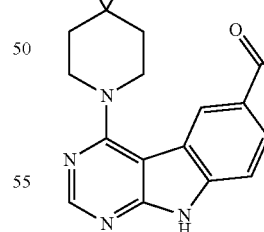
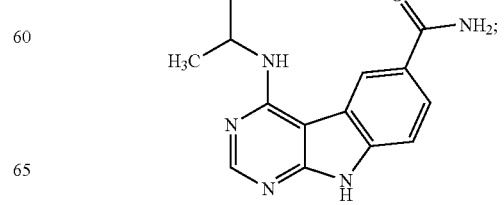

103
-continued
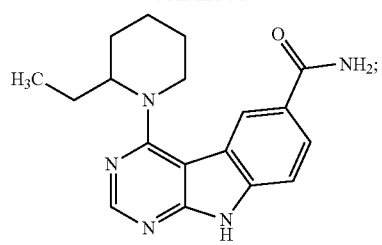
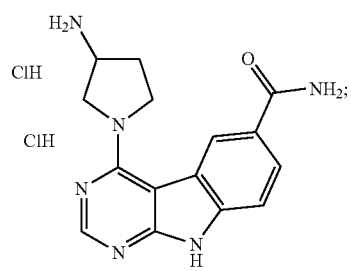
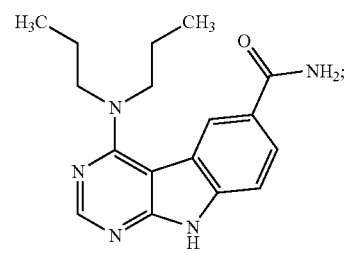
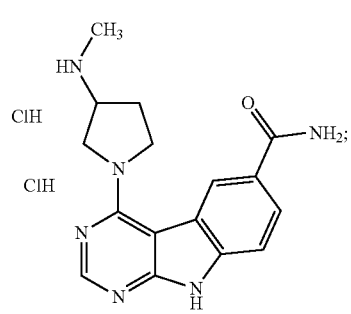
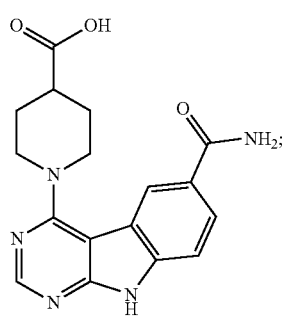
104
-continued
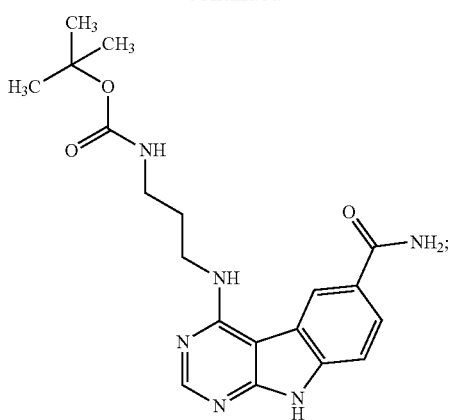

105
-continued
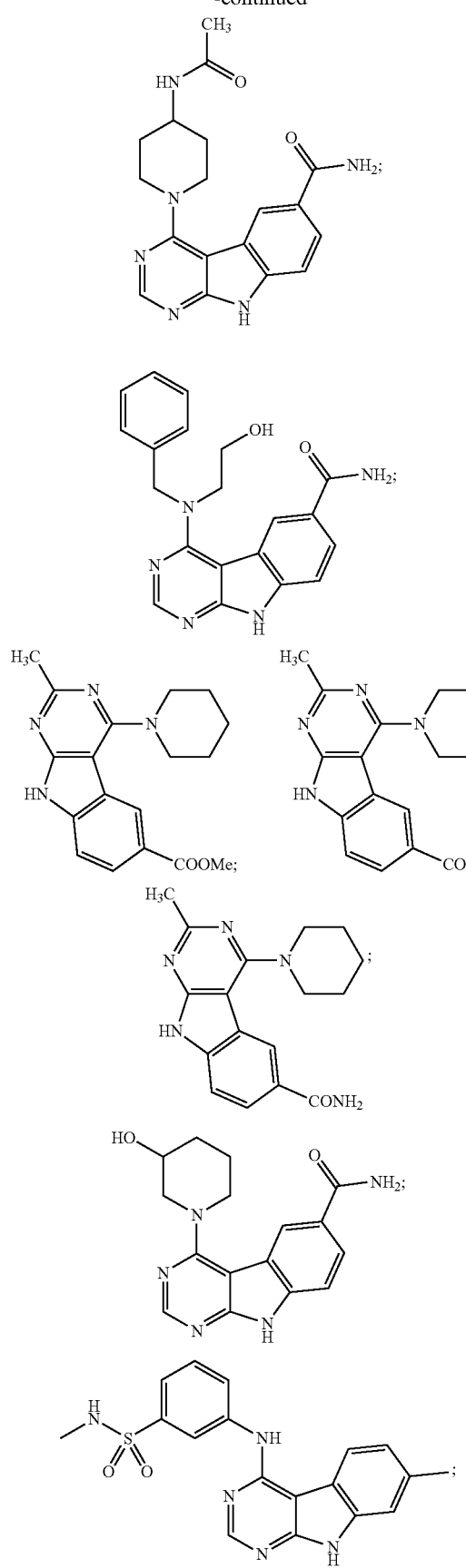
106
-continued
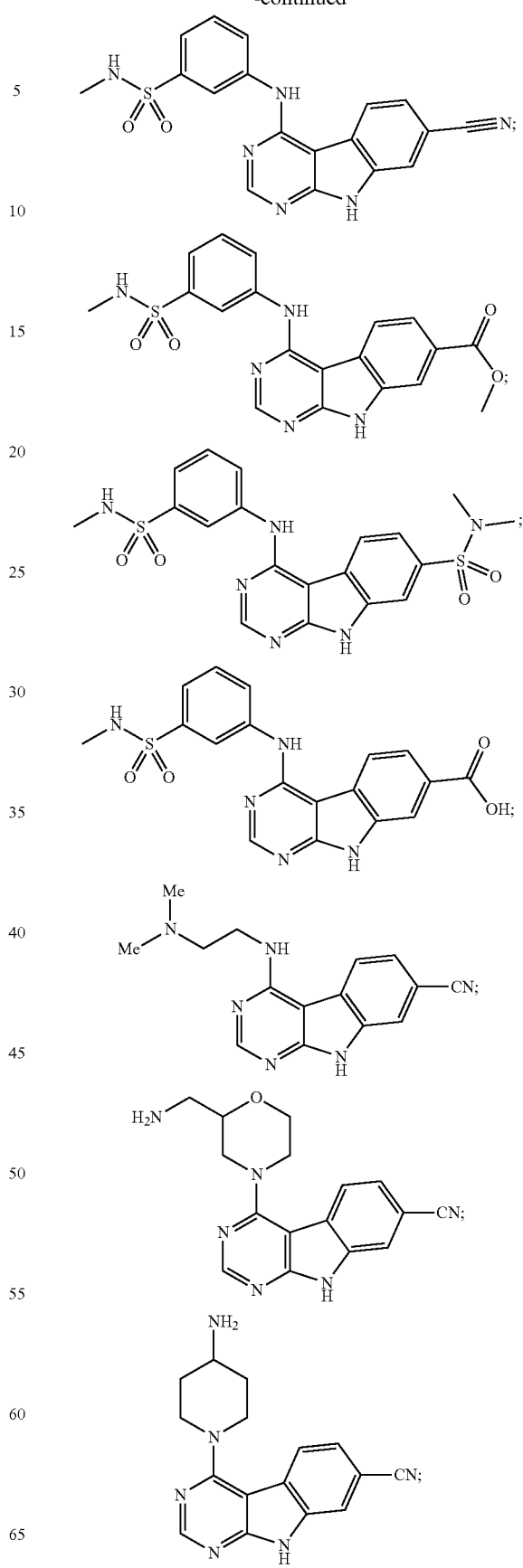

-continued
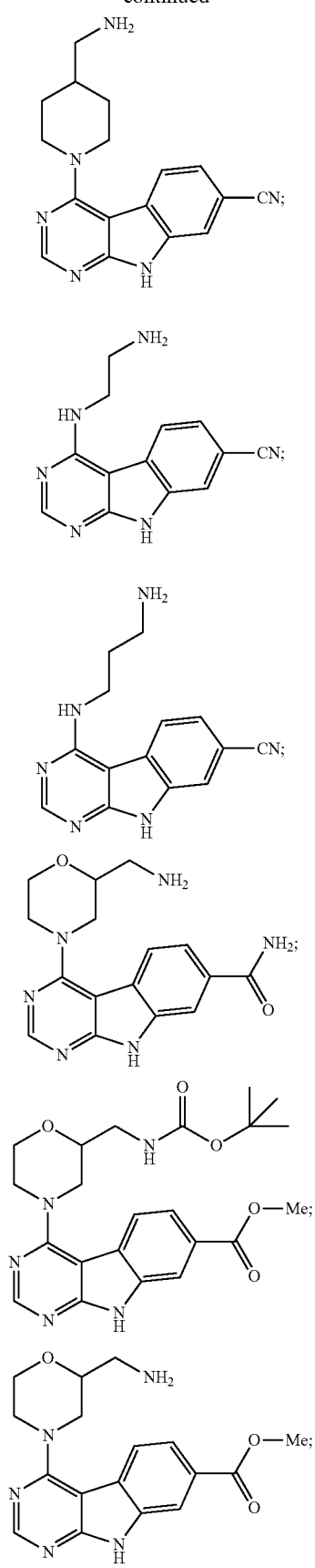
-continued
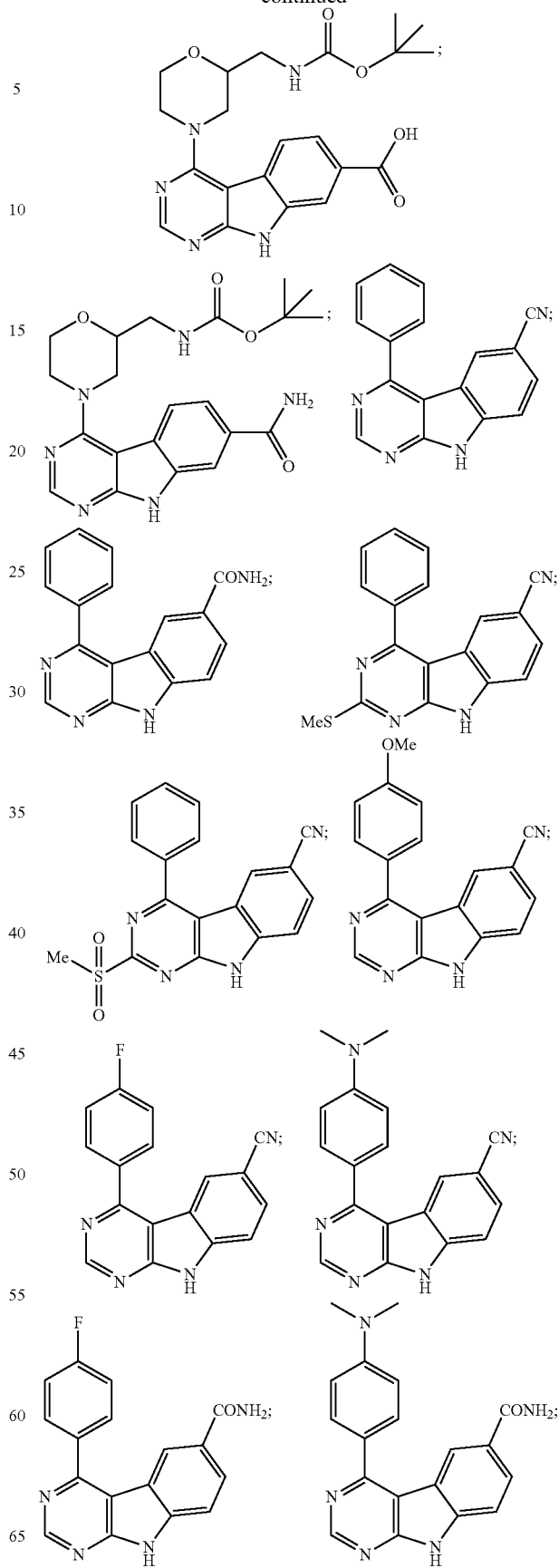

-continued

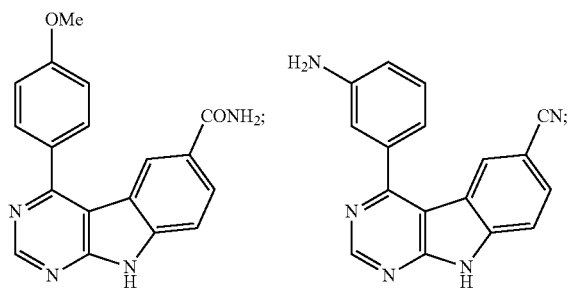

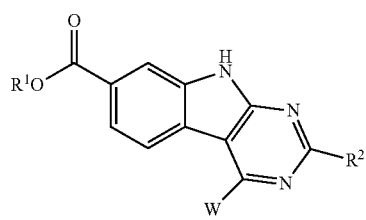

2. A compound according to claim 1, wherein the compound is of formula IIA, IIB or IIC or a salt thereof wherein Het is a 3 to 7-membered heterocycle, optionally substituted with one or more $R^1$ or $R^4$, and $R^5$ and $R^6$ are the same or different and are each independently L, or they join together with C to form a 5 to 7-membered ring which optionally includes one or more heteroatom selected from N, O and S, optionally the ring is substituted with one or more $R^1$ or $R^4$.

3. A compound according to claim 2, wherein the ring is a 5-membered ring, and the heteroatom is N.

4. A compound according to claim 1, wherein the compound is of formula or a salt thereof, wherein $R^3$ and $R^4$ are the same or different and are each independently H, or $R^1$, or $R^3$ and $R^4$ join together with N to which they are attached to form a 3 to 7-membered ring which optionally includes one or more other heteroatom selected from N, O and S, optionally the ring is substituted with one or more $R^1$ or $R^4$.

5. A compound according to claim 1, wherein:

Z is $CO_2Me$ or 2-methyl-2H-tetrazol-5-yl;

$R^2$ is benzyl or H; and

W is $NH-L-N(R^1)R^1$ wherein L is $C_{2-4}$ alkyl or $C_{3-7}$ cycloalkyl and $R^1$ and (R1) is $C_{1-4}$ alkyl or H; or ($R^1$) and $R^1$ join together with the nitrogen atom to which they are attached to form a 3 to 7-membered ring, which optionally includes one or more other heteroatom selected from N, O and S, optionally the ring is substituted with one or more $R^1$ or $R^4$.

6. A compound according to claim 1 which is:
| Compound number | Structure |
|---|---|
| 1 | 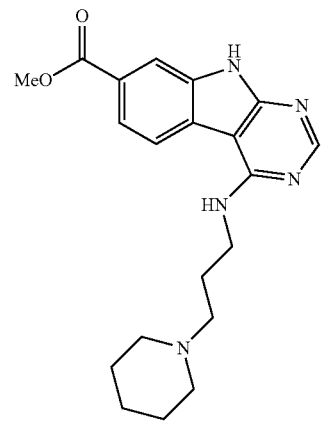 |
| 2 | 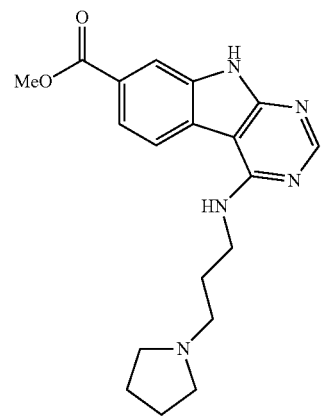 |
| 3 | 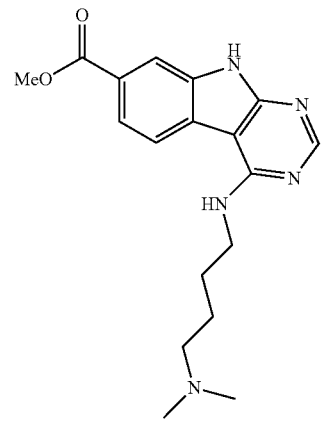 |

-continued
| Compound number | Structure |
|---|---|
| 4 | 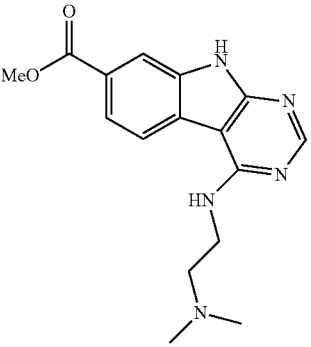 [SMILES: COC(=O)c1ccc2c(c1)[nH]c1ncnc(NCCN(C)C)c12] |
| 5 | 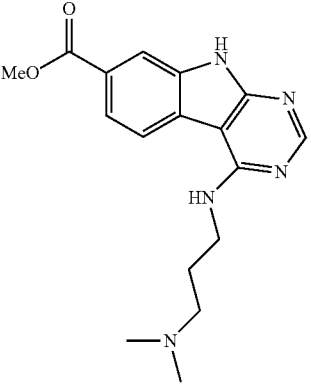 |
| 6 | 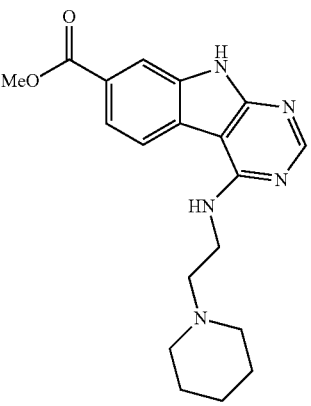 |
| 7 | 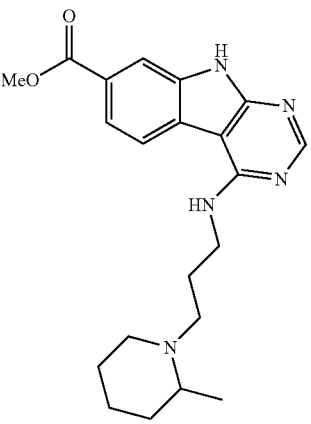 |

-continued
| Compound number | Structure |
|---|---|
| 8 | 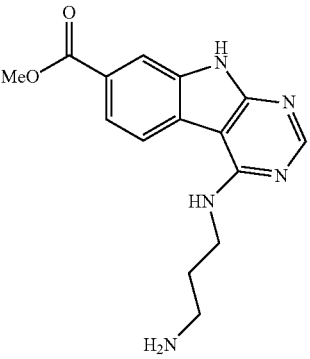 |
| 9 | 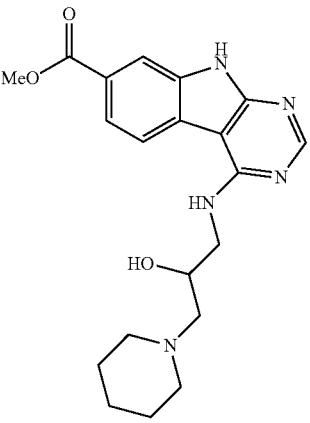 |
| 10 | 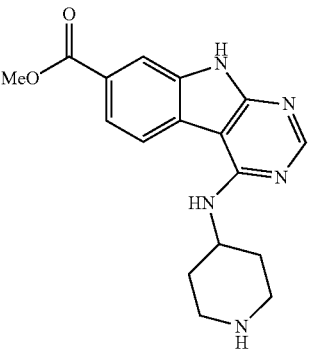 |
| 11 | 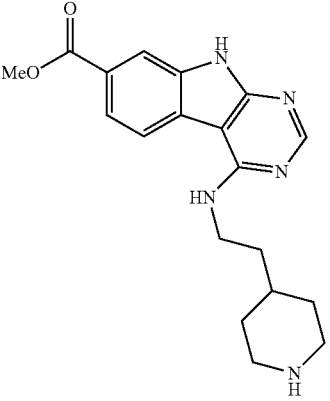 [SMILES: COC(=O)c1ccc2c(c1)[nH]c1ncnc(NCCC3CCNCC3)c12] |

-continued
| Compound number | Structure |
|---|---|
| 12 | 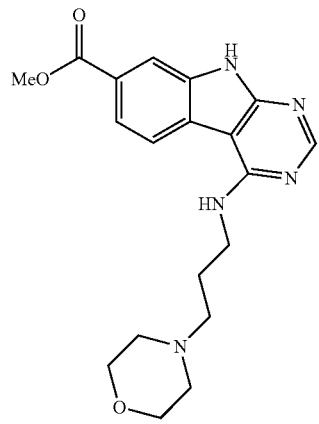 |
| 13 | 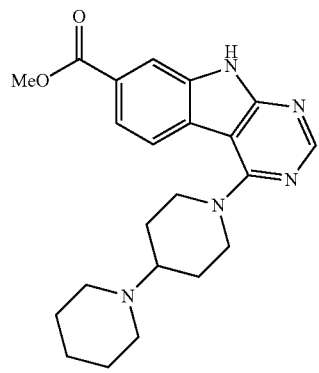 |
| 14 | 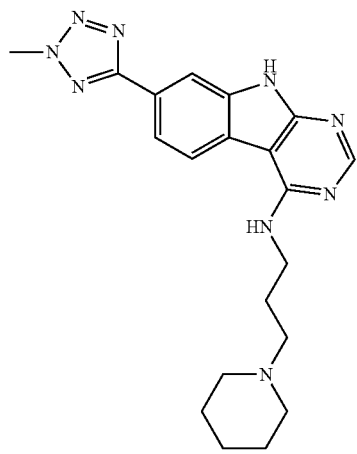 [SMILES: Cn1nnc(-c2ccc3c(c2)[nH]c2ncnc(NCCCN4CCCCC4)c23)n1] |
| 15 | 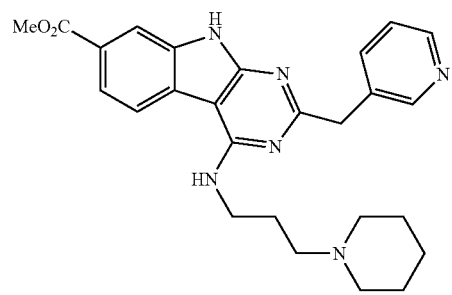 [SMILES: COC(=O)c1ccc2c(c1)[nH]c1nc(Cc3cccnc3)nc(NCCCN3CCCCC3)c12] |

-continued

| Compound number | Structure |
|---|---|
| 16 | 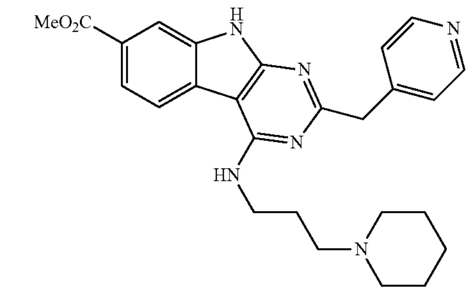 [SMILES: COC(=O)c1ccc2c(c1)[nH]c1nc(Cc3ccncc3)nc(NCCCN3CCCCC3)c12] |
| 17 | 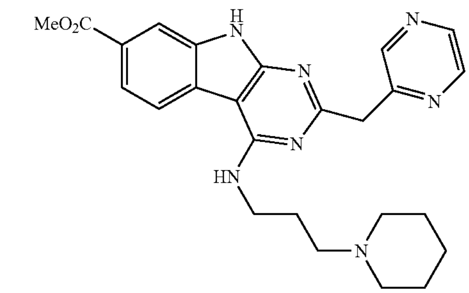 [SMILES: COC(=O)c1ccc2c(c1)[nH]c1nc(Cc3cnccn3)nc(NCCCN3CCCCC3)c12] |
| 18 | 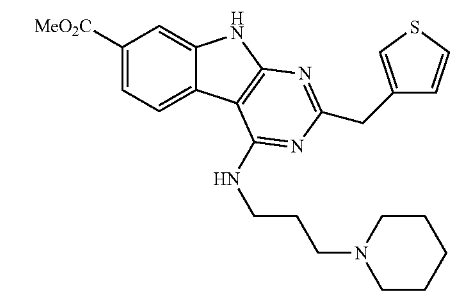 [SMILES: COC(=O)c1ccc2c(c1)[nH]c1nc(Cc3ccsc3)nc(NCCCN3CCCCC3)c12] |
| 19 | 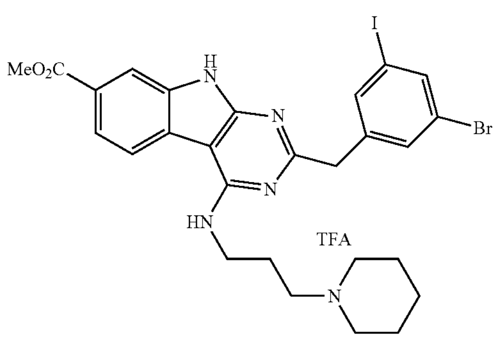 [SMILES: COC(=O)c1ccc2c(c1)[nH]c1nc(Cc3cc(Br)cc(I)c3)nc(NCCCN3CCCCC3)c12] |
| 20 | 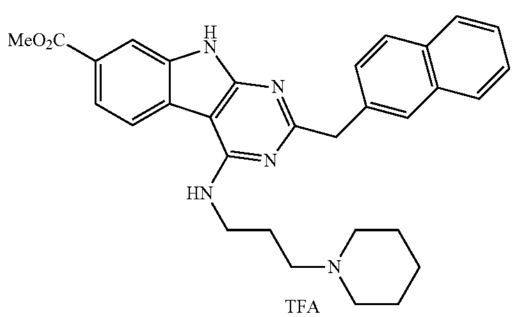 [SMILES: COC(=O)c1ccc2c(c1)[nH]c1nc(Cc3ccc4ccccc4c3)nc(NCCCN3CCCCC3)c12] |

-continued
| Compound number | Structure |
|---|---|
| 21 | 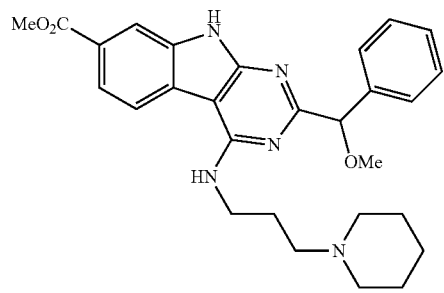 |
| 22 | 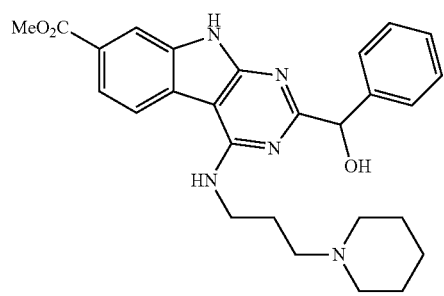 [SMILES: COC(=O)c1ccc2c(c1)[nH]c1nc(C(O)c3ccccc3)nc(NCCCN3CCCCC3)c12] |
| 23 | 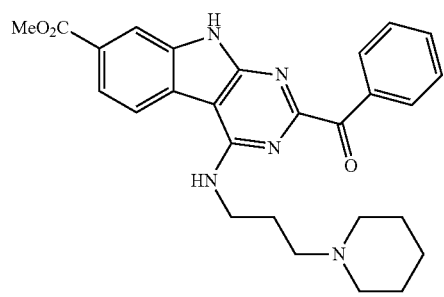 [SMILES: COC(=O)c1ccc2c(c1)[nH]c1nc(C(=O)c3ccccc3)nc(NCCCN3CCCCC3)c12] |
| 24 | 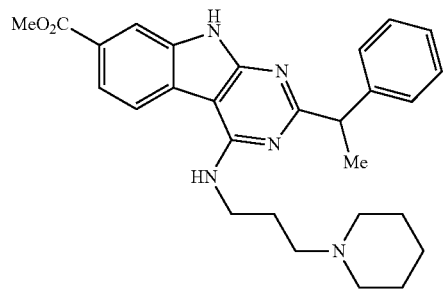 [SMILES: COC(=O)c1ccc2c(c1)[nH]c1nc(C(C)c3ccccc3)nc(NCCCN3CCCCC3)c12] |
| 25 | 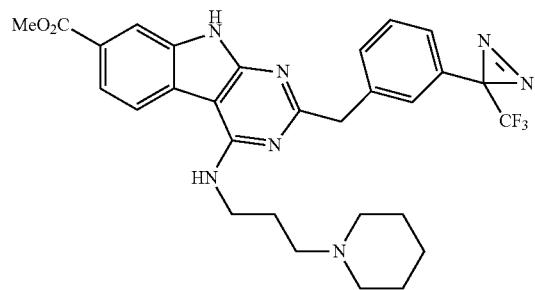 [SMILES: COC(=O)c1ccc2c(c1)[nH]c1nc(Cc3cccc(C4(C(F)(F)F)N=N4)c3)nc(NCCCN3CCCCC3)c12] |

-continued
| Compound number | Structure |
|---|---|
| 26 | 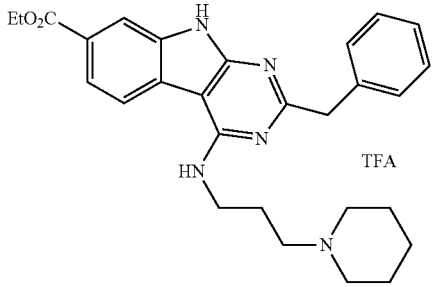 [SMILES: CCOC(=O)c1ccc2c(c1)[nH]c1nc(Cc3ccccc3)nc(NCCCN3CCCCC3)c12] |
| 27 | 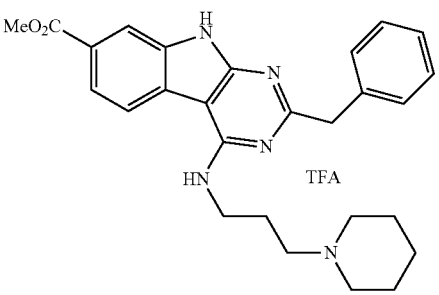 [SMILES: COC(=O)c1ccc2c(c1)[nH]c1nc(Cc3ccccc3)nc(NCCCN3CCCCC3)c12] |
| 28 | 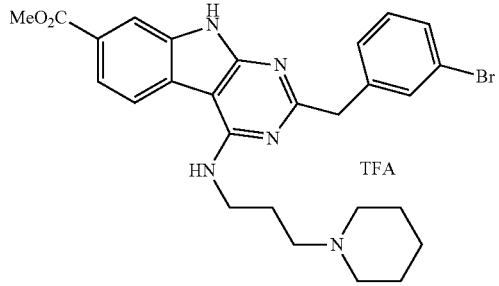 [SMILES: COC(=O)c1ccc2c(c1)[nH]c1nc(Cc3cccc(Br)c3)nc(NCCCN3CCCCC3)c12] |
| 29 | 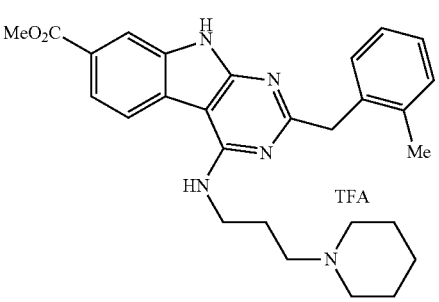 [SMILES: COC(=O)c1ccc2c(c1)[nH]c1nc(Cc3ccccc3C)nc(NCCCN3CCCCC3)c12] |
| 30 | 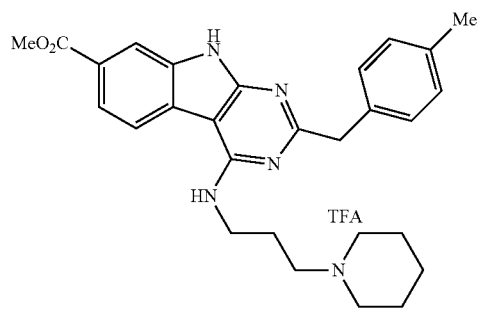 [SMILES: COC(=O)c1ccc2c(c1)[nH]c1nc(Cc3ccc(C)cc3)nc(NCCCN3CCCCC3)c12] |

| Compound number | Structure |
|---|---|
| 31 | (MeO₂C-substituted pyrimido-indole with 3-fluorobenzyl group and HN-propyl-piperidine side chain; TFA salt) |
| 32 | (MeO₂C-substituted pyrimido-indole with 3-methoxybenzyl group and HN-propyl-piperidine side chain; TFA salt) |
| 33 | (MeO₂C-substituted pyrimido-indole with 3-(trifluoroacetyl)benzyl group and HN-propyl-piperidine side chain) |
| 34 | (MeO₂C-substituted pyrimido-indole with 3-(1-hydroxy-2,2,2-trifluoroethyl)benzyl group and HN-propyl-piperidine side chain) |
| 35 | (2-methyltetrazolyl-substituted pyrimido-indole with benzyl group and HN-propyl-piperidine side chain; TFA salt) |

| Compound number | Structure |
|---|---|
| 36 | 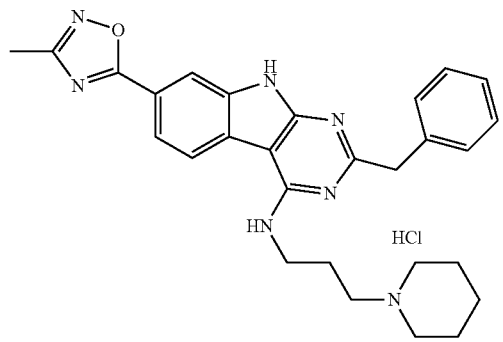 [SMILES: Cc1noc(-c2ccc3c(c2)[nH]c2nc(Cc4ccccc4)nc(NCCCN4CCCCC4)c23)n1 ; Cl] |
| 37 | 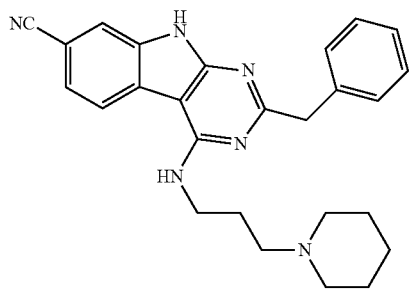 [SMILES: N#Cc1ccc2c(c1)[nH]c1nc(Cc3ccccc3)nc(NCCCN3CCCCC3)c12] |
| 38 | 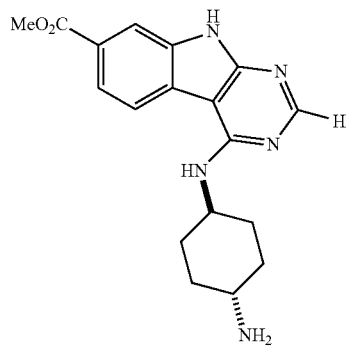 |
| 39 | 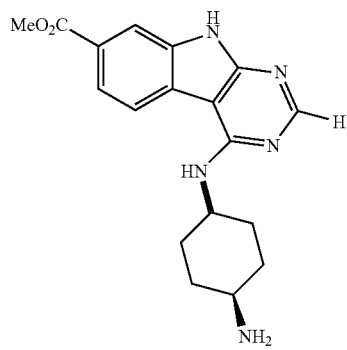 |

-continued
| Compound number | Structure |
|---|---|
| 40 | 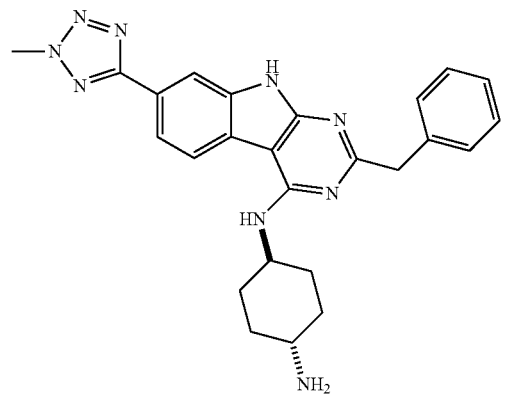 |
| 41 | 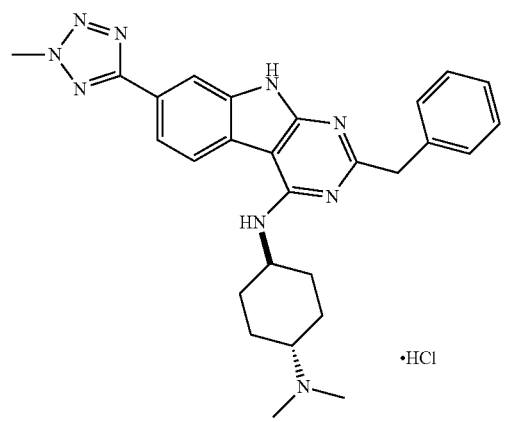 |
| 42 | 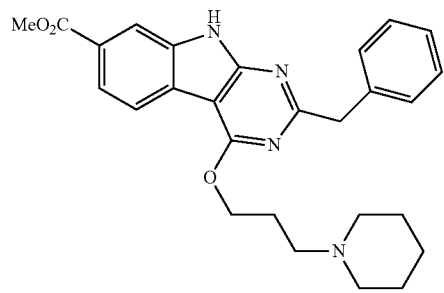 [SMILES: COC(=O)c1ccc2c(c1)[nH]c1nc(Cc3ccccc3)nc(OCCCN3CCCCC3)c12] |
| 43 | 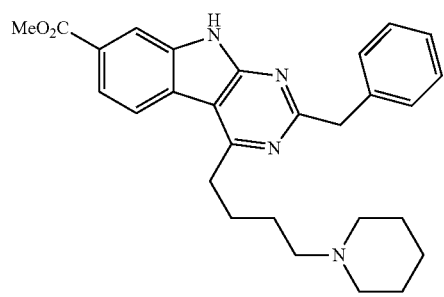 |

-continued
| Compound number | Structure |
|---|---|
| 44 | 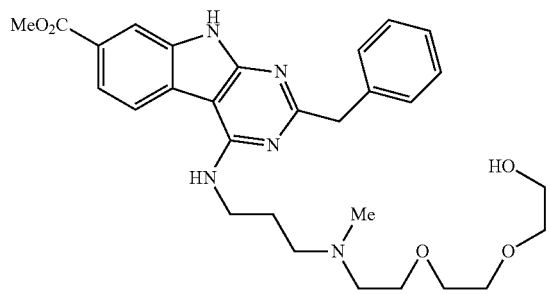 [SMILES: COC(=O)c1ccc2c(c1)[nH]c1nc(Cc3ccccc3)nc(NCCCN(C)CCOCCOCCO)c12] |
| 45 | 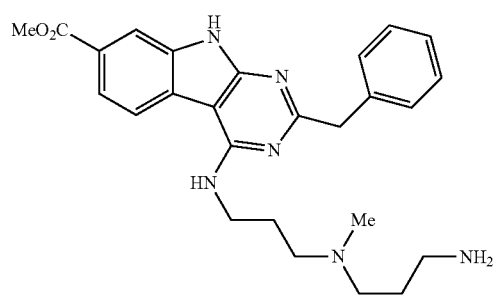 [SMILES: COC(=O)c1ccc2c(c1)[nH]c1nc(Cc3ccccc3)nc(NCCCN(C)CCCN)c12] |
| 46 | 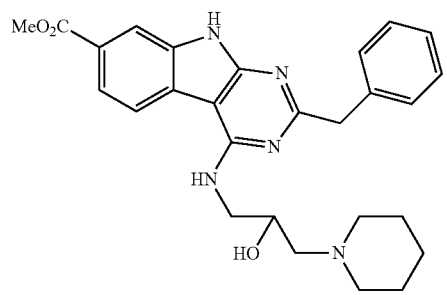 [SMILES: COC(=O)c1ccc2c(c1)[nH]c1nc(Cc3ccccc3)nc(NCC(O)CN3CCCCC3)c12] |
| 47 | 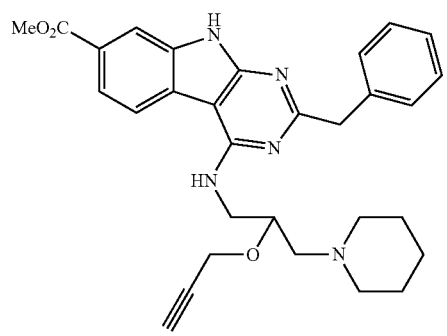 [SMILES: C#CCOC(CNc1nc(Cc2ccccc2)nc2[nH]c3cc(C(=O)OC)ccc3c12)CN1CCCCC1] |
| 48 | 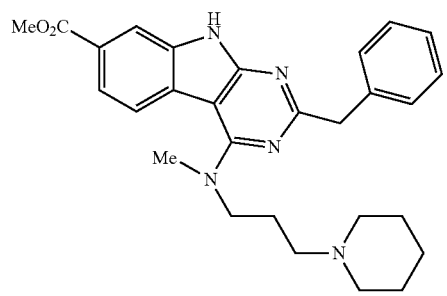 [SMILES: COC(=O)c1ccc2c(c1)[nH]c1nc(Cc3ccccc3)nc(N(C)CCCN3CCCCC3)c12] |

-continued
| Compound number | Structure |
|---|---|
| 49 | 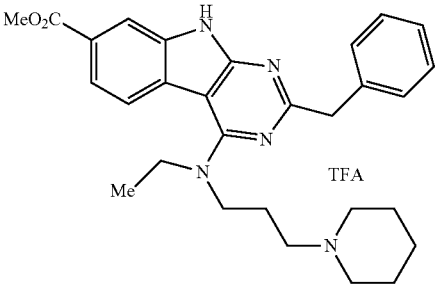 [SMILES: CCN(CCCN1CCCCC1)c1nc(Cc2ccccc2)nc2[nH]c3cc(C(=O)OC)ccc3c12] |
| 50 | 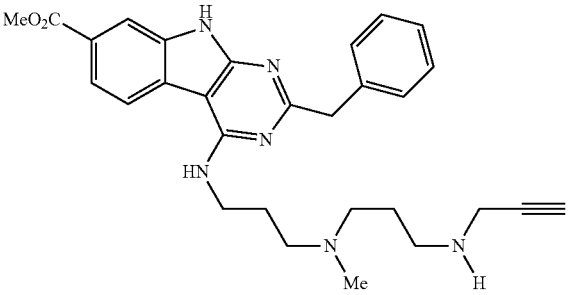 [SMILES: C#CCNCCCN(C)CCCNc1nc(Cc2ccccc2)nc2[nH]c3cc(C(=O)OC)ccc3c12] |
| 51 | 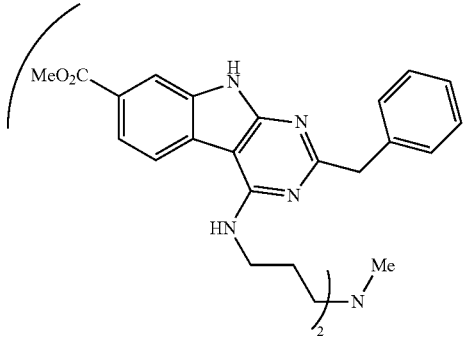 |
| 52 | 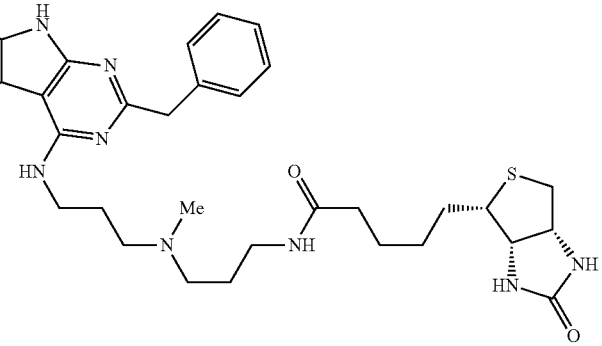 |
| 53 | 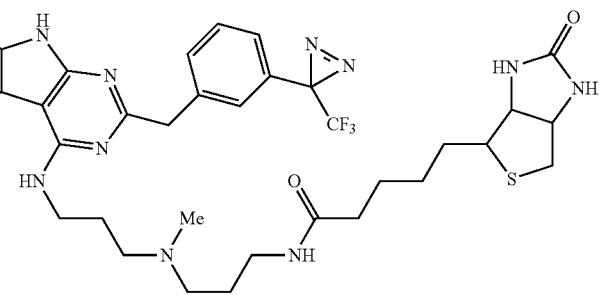 |

-continued

| Compound number | Structure |
|---|---|
| 54 | 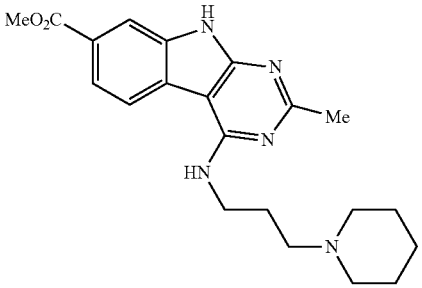 [SMILES: COC(=O)c1ccc2c(c1)[nH]c1nc(C)nc(NCCCN3CCCCC3)c12] |
| 55 | 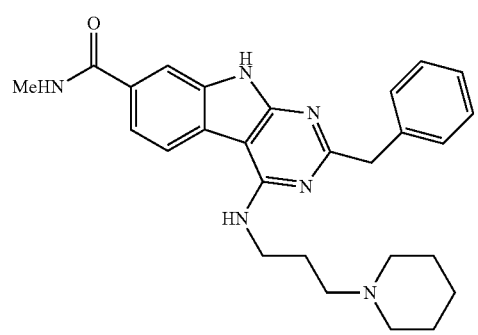 [SMILES: CNC(=O)c1ccc2c(c1)[nH]c1nc(Cc3ccccc3)nc(NCCCN3CCCCC3)c12] | or a salt thereof.

7. A method of treating a hematopoietic disorder/malignancy, an autoimmune disease and/or an inherited immunodeficient disease in a subject, comprising administering to the subject in need of such treatment, hematopoietic stem and/or progenitor cells expanded using a compound of general formula I or II

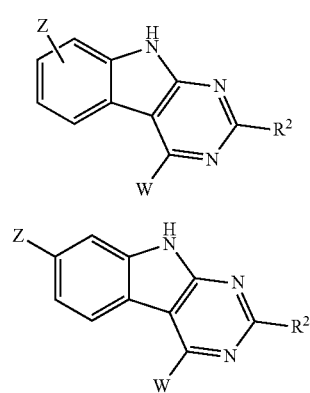

or a salt thereof,
wherein:
Z is
1) —P(O)(OR$^1$)(OR$^1$),
2) —C(O)OR$^1$,
3) —C(O)NHR$^1$,
4) —C(O)N(R$^1$)R$^1$,
5) —C(O)R$^1$,
6) —CN,
7) —SR$^1$,
8) —S(O)$_2$NH$_2$,
9) —S(O)$_2$NHR$^1$,
10) —S(O)$_2$N(R$^1$)R$^1$,
11) —S(O)R$^1$,
12) —S(O)$_2$R$^1$,
13) -L,
14) -benzyl optionally substituted with 1, 2 or 3 R$^A$ or R$^1$ substituents,
15) -L-heteroaryl optionally substituted with one or more R$^A$ or R$^1$ substituents attached on either or both the L and the heteroaryl groups,
16) -L-heterocyclyl optionally substituted with one or more R$^A$ or R$^1$ substituents attached on either one or both the L and the heterocyclyl groups,
17) -L-aryl optionally substituted with one or more R$^A$ or R$^1$ substituents attached on either or both the L and the heteroaryl groups,
18) -heteroaryl optionally substituted with one or more R$^A$ or R$^1$ substituents, or
19) -aryl optionally substituted with one or more R$^A$ or R$^1$ substituents,
and wherein each substituent is optionally attached to the L group if it is not already present, and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the is substituted with one or more R$^1$ or R$^A$;
W is
1) —H,
2) -halogen,
3) —OR$^1$,
4) -L-OH,
5) -L-OR$^1$,
6) —SR$^1$, 7) —CN,
8) —P(O)(OR$^1$)(OR$^1$),
9) —NHR$^1$,
10) —N(R$^1$)R$^1$,
11) -L-NH$_2$,
12) -L-NHR$^1$,
13) -L-N(R$^1$)R$^1$,
14) -L-SR$^1$,
15) -L-S(O)R$^1$,
16) -L-S(O)$_2$R$^1$,
17) -L-P(O)(OR$^1$)(OR$^1$),
18) —C(O)OR$^1$,
19) —C(O)NH$_2$,
20) —C(O)NHR$^1$,
21) —C(O)N(R$^1$)R$^1$,
22) —NHC(O)R$^1$,
23) —NR$^1$C(O)R$^1$,
24) —NHC(O)OR$^1$,
25) —NR$^1$C(O)OR$^1$,
26) —OC(O)NH$_2$,
27) —OC(O)NHR$^1$,
28) —OC(O)N(R$^1$)R$^1$,
29) —OC(O)R$^1$,
30) —C(O)R$^1$,
31) —NHC(O)NH$_2$,
32) —NHC(O)NHR$^1$,
33) —NHC(O)N(R$^1$)R$^1$,
34) —NR$^1$C(O)NH$_2$,
35) —NR$^1$C(O)NHR$^1$,
36) —NR$^1$C(O)N(R$^1$)R$^1$,
37) —NHS(O)$_2$R$^1$,
38) —NR$^1$S(O)$_2$R$^1$,
39) —S(O)$_2$NH$_2$,
40) —S(O)$_2$NHR$^1$,
41) —S(O)$_2$N(R$^1$)R$^1$,
42) —S(O)R$^1$,
43) —S(O)$_2$R$^1$,
44) —OS(O)$_2$R$^1$,
45) —S(O)$_2$OR$^1$,
46) -benzyl optionally substituted with 1, 2 or 3 R$^A$ or R$^1$ substituents,
47) -L-heteroaryl optionally substituted with one or more R$^A$ or R$^1$ substituents attached on either or both the L and the heteroaryl groups,
48) -L-heterocyclyl optionally substituted with one or more R$^A$ or R$^1$ substituents attached on either or both the L and the heterocyclyl groups,
49) -L-aryl optionally substituted with one or more R$^A$ or R$^1$ substituents attached on either or both the L and aryl groups,
50) -L-NR$^1$(R$^1$),
51) -(L-)$_2$NR$^1$,
52) -L-(N(R$^1$)-L)$_n$-N(R$^1$)R$^1$,
53) -L-(N(R$^1$)-L)$_n$- heteroaryl optionally substituted with one or more R$^A$ or R$^1$ substituents attached on either or both the L and heteroaryl groups,
54) -L-(N(R$^1$)-L)$_n$- heterocyclyl optionally substituted with one or more R$^A$ or R$^1$ substituents attached on either or both the L and heterocyclyl groups,
55) -L-(N(R$^1$)-L)$_n$- aryl optionally substituted with one or more R$^A$ or R$^1$ substituents attached on either or both the L and aryl groups,
56) —O-L-N(R$^1$)R$^1$,
57) —O-L- heteroaryl optionally substituted with one or more R$^A$ or R$^1$ substituents attached on either or both the L and heteroaryl groups,
58) —O-L- heterocyclyl optionally substituted with one or more R$^A$ or R$^1$ substituents attached on either or both the L and heterocyclyl groups,
59) —O-L- aryl optionally substituted with one or more R$^A$ or R$^1$ substituents attached on either or both the L and aryl groups,
60) —(O-L)$_2$-NR$^1$,
61) —O-L-(N(R$^1$)-L)$_n$-N(R$^1$)R$^1$,
62) —O-L-(N(R$^1$)-L)$_n$- heteroaryl optionally substituted with one or more R$^A$ or R$^1$ substituents attached on either or both the L and heteroaryl groups,
63) —O-L-(N(R$^1$)-L)$_n$- heterocyclyl optionally substituted with one or more R$^A$ or R$^1$ substituents attached on either or both the L and heterocyclyl groups,
64) —O-L-(N(R$^1$)-L)$_n$- aryl optionally substituted with one or more R$^A$ or R$^1$ substituents,
65) —S-L- heteroaryl optionally substituted with one or more R$^A$ or R$^1$ substituents,
66) —S-L- heterocyclyl optionally substituted with one or more R$^A$ or R$^1$ substituents,
67) —S-L- aryl optionally substituted with one or more R$^A$ or R$^1$ substituents attached on either or both the L and aryl groups,
68) —(S-L)$_2$NR$^1$,
69) —S-L-(N(R$^1$)-L)$_n$-N(R$^1$)R$^1$,
70) —S-L-(N(R$^1$)-L)$_n$- heteroaryl optionally substituted with one or more R$^A$ substituents,
71) —S-L-(N(R$^1$)-L)$_n$- heterocyclyl optionally substituted with one or more R$^A$ substituents,
72) —S-L-(N(R$^1$)-L)$_n$- aryl optionally substituted with one or more R$^A$ substituents,
73) —NR$^1$(R$^1$),
74) —(N(R$^1$)-L)$_n$-N(R$^1$)R$^1$,
75) —N(R$^1$)L)$_2$-NR$^1$,
76) —(N(R$^1$)-L)$_n$-N(R$^1$)R$^A$,
77) —(N(R$^1$)-L)$_n$- heteroaryl optionally substituted with one or more R$^A$ or R$^1$ substituents,
78) —(N(R$^1$)-L)$_n$- heterocyclyl optionally substituted with one or more R$^A$ or R$^1$ substituents,
79) —(N(R$^1$)-L)$_n$- aryl optionally substituted with one or more R$^A$ or R$^1$ substituents,
80) -heteroaryl optionally substituted with one or more R$^A$ substituents, or
81) -aryl optionally substituted with one or more R$^A$ substituents,
and wherein each substituent is optionally attached to the L group if it is not already present,
and wherein when two R$^1$ substituents are present on the same nitrogen atom, then each R$^1$ substituent is independently selected from the list of R$^1$ values described thereafter,
and wherein n is an integer equal to either 0, 1, 2, 3, 4, or 5,
and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the ring is substituted with one or more R$^1$ or R$^A$;

L is
1) —C$_{1-6}$ alkyl,
2) —C$_{2-6}$ alkenyl,
3) —C$_{2-6}$ alkynyl,
4) —C$_{3-7}$ cycloalkyl,
5) —C$_{3-7}$ cycloalkenyl,
6) heterocyclyl,
7) —C$_{1-6}$ alkyl-C$_{3-7}$ cycloalkyl,
8) —C$_{1-6}$ alkyl-heterocyclyl, 9) aryl, or
10) heteroaryl,
and wherein the alkyl, the alkenyl, the alkynyl, the cycloalkyl, the cycloalkenyl, the heterocyclyl, the aryl and the heteroaryl groups are each independently optionally substituted with one or two $R^4$ substituent;

$R^1$ is
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ perfluorinated,
8) -heterocyclyl,
9) -aryl,
10) -heteroaryl,
11) -benzyl, or
12) 5-[(3aS,4S,6aR)-2-oxohexahydro-1H-thieno[3,4-d]imidazol-4-yl]pentanoyl, and wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 $R^4$ or $R^1$ substituents;

$R^2$ is
1) —H,
2) —$C_{1-6}$ alkyl,
3) —$SR^1$,
4) —$C(O)R^1$,
5) —$S(O)R^1$,
6) —$S(O)_2R^1$,
7) -benzyl optionally substituted with 1, 2 or 3 $R^4$ or $R^1$ substituents,
8) -L-heteroaryl optionally substituted with one or more $R^4$ or $R^1$ substituents attached on either one or both the L and the heteroaryl groups,
9) -L-heterocyclyl optionally substituted with one or more $R^4$ or $R^1$ substituents attached on either one or both the L and the heterocyclyl groups,
10) -L-aryl optionally substituted with one or more $R^4$ or $R^1$ substituents attached on either one or both the L and the aryl groups,
11) -heteroaryl optionally substituted with one or more $R^4$ or $R^1$ substituents, or
12) -aryl optionally substituted with one or more $R^4$ or $R^1$ substituents,
and wherein each substituent is optionally attached to the L group if it is not already present;

$R^4$ is
1) -halogen,
2) —$CF_3$,
3) —OH,
4) —$OR^1$,
5) -L-OH,
6) -L-$OR^1$,
7) —$OCF_3$,
8) —SH,
9) —SR1,
10) —CN,
11) —$NO_2$,
12) —$NH_2$,
13) —$NHR^1$,
14) —$NR^1R^1$,
15) -L-$NH_2$,
16) -L-$NHR^1$,
17) -L-$SR^1$,
18) -L-$S(O)R^1$,
19) -L-$S(O)_2R^1$,
20) —C(O)OH,
21) —$C(O)OR^1$,
22) —$C(O)NH_2$,
23) —$C(O)NHR^1$,
24) —$C(O)N(R^1)R^1$,
25) —$NHC(O)R^1$,
26) —$NR^1C(O)R^1$,
27) —$NHC(O)OR^1$,
28) —$NR^1C(O)OR^1$,
29) —$OC(O)NH_2$,
30) —$OC(O)NHR^1$,
31) —$OC(O)N(R^1)R^1$,
32) —$OC(O)R^1$,
33) —$C(O)R^1$,
34) —$NHC(O)NH_2$,
35) —$NHC(O)NHR^1$,
36) —$NHC(O)N(R^1)R^1$,
37) —$NR^1C(O)NH_2$,
38) —$NR^1C(O)NHR^1$,
39) —$NR^1C(O)N(R^1)R^1$,
40) —$NHS(O)_2R^1$,
41) —$NR^1S(O)_2R^1$,
42) —$S(O)_2NH_2$,
43) —$S(O)_2NHR^1$,
44) —$S(O)_2N(R^1)R^1$,
45) —$S(O)R^1$,
46) —$S(O)_2R^1$,
47) —$OS(O)_2R^1$,
48) —$S(O)_2OR^1$,
49) -benzyl,
50) —$N_3$, or
51) —C(—N=N—)($CF_3$),
and wherein the benzyl group is optionally substituted with 1, 2 or 3 $R^4$ or $R^1$ substituents;

or a salt thereof.

8. A method according to claim 7, wherein the hematopoietic disorder/malignancy, the autoimmune disease and/or the inherited immunodeficient disease comprise bone marrow failure conditions, lupus, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, or inborn errors of metabolism.

9. A compound according to claim 2, wherein $R^2$ is benzyl or H.

10. A compound according to claim 2, wherein $R^5$ and $R^6$ join together with C to form:

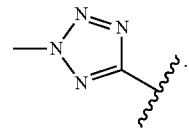

11. A compound according to claim 2, wherein W is

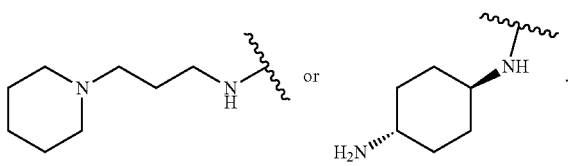 [SMILES: *NCCCN1CCCCC1 ; *N[C@H]1CC[C@H](N)CC1] or .

12. A method of increasing stem and progenitor cells, the method comprising; contacting a starting population in the presence of at least one compound, optionally together with at least one cell expanding factor which is a biologic or another small molecule, wherein said compound is of general formula I or II

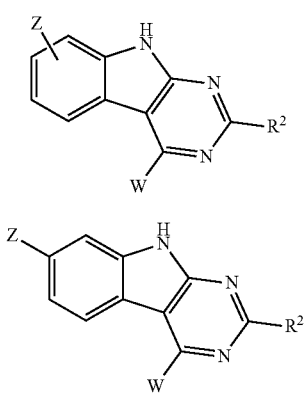

or a salt thereof,
wherein:
Z is
1) —P(O)(OR$^1$)(OR$^1$),
2) —C(O)OR$^1$,
3) —C(O)NHR$^1$,
4) —C(O)N(R$^1$)R$^1$,
5) —C(O)R$^1$,
6) —CN,
7) —SR$^1$,
8) —S(O)$_2$NH$_2$,
9) —S(O)$_2$NHR$^1$,
10) —S(O)$_2$N(R$^1$)R$^1$,
11) —S(O)R$^1$,
12) —S(O)$_2$R$^1$,
13) -L,
14) -benzyl optionally substituted with 1, 2 or 3 R$^A$ or R$^1$ substituents,
15) -L-heteroaryl optionally substituted with one or more R$^A$ or R$^1$ substituents attached on either or both the L and the heteroaryl groups,
16) -L-heterocyclyl optionally substituted with one or more R$^A$ or R$^1$ substituents attached on either one or both the L and the heterocyclyl groups,
17) -L-aryl optionally substituted with one or more R$^A$ or R$^1$ substituents attached on either or both the L and the heteroaryl groups,
18) -heteroaryl optionally substituted with one or more R$^A$ or R$^1$ substituents, or
19) -aryl optionally substituted with one or more R$^A$ or R$^1$ substituents, and wherein each substituent is optionally attached to the L group if it is not already present, and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the is substituted with one or more R$^1$ or R$^A$;
W is
1) —H,
2) -halogen,
3) —OR$^1$,
4) -L-OH,
5) -L-OR$^1$,
6) —SR$^1$,
7) —CN,
8) —P(O)(OR$^1$)(OR$^1$),
9) —NHR$^1$,
10) —N(R$^1$)R$^1$,
11) -L-NH$_2$,
12) -L-NHR$^1$,
13) -L-N(R$^1$)R$^1$,
14) -L-SR$^1$,
15) -L-S(O)R$^1$,
16) -L-S(O)$_2$R$^1$,
17) -L-P(O)(OR$^1$)(OR$^1$),
18) —C(O)OR$^1$,
19) —C(O)NH$_2$,
20) —C(O)NHR$^1$,
21) —C(O)N(R$^1$)R$^1$,
22) —NHC(O)R$^1$,
23) —NR$^1$C(O)R$^1$,
24) —NHC(O)OR$^1$,
25) —NR$^1$C(O)OR$^1$,
26) —OC(O)NH$_2$,
27) —OC(O)NHR$^1$,
28) —OC(O)N(R$^1$)R$^1$,
29) —OC(O)R$^1$,
30) —C(O)R$^1$,
31) —NHC(O)NH$_2$,
32) —NHC(O)NHR$^1$,
33) —NHC(O)N(R$^1$)R$^1$,
34) —NR$^1$C(O)NH$_2$,
35) —NR$^1$C(O)NHR$^1$,
36) —NR$^1$C(O)N(R$^1$)R$^1$,
37) —NHS(O)$_2$R$^1$,
38) —NR$^1$S(O)$_2$R$^1$,
39) —S(O)$_2$NH$_2$,
40) —S(O)$_2$NHR$^1$,
41) —S(O)$_2$N(R$^1$)R$^1$,
42) —S(O)R$^1$,
43) —S(O)$_2$R$^1$,
44) —OS(O)$_2$R$^1$,
45) —S(O)$_2$OR$^1$,
46) -benzyl optionally substituted with 1, 2 or 3 R$^A$ or R$^1$ substituents,
47) -L-heteroaryl optionally substituted with one or more R$^A$ or R$^1$ substituents attached on either or both the L and the heteroaryl groups,
48) -L-heterocyclyl optionally substituted with one or more R$^A$ or R$^1$ substituents attached on either or both the L and the heterocyclyl groups,
49) -L-aryl optionally substituted with one or more R$^A$ or R$^1$ substituents attached on either or both the L and aryl groups,
50) -L-NR$^1$(R$^1$),
51) -(L-)$_2$NR$^1$,
52) -L-(N(R$^1$)-L)$_n$-N(R$^1$)R$^1$, 53) -L-(N($R^1$)-L)$_n$- heteroaryl optionally substituted with one or more $R^A$ or $R^1$ substituents attached on either or both the L and heteroaryl groups,
54) -L-(N($R^1$)-L)$_n$- heterocyclyl optionally substituted with one or more $R^A$ or $R^1$ substituents attached on either or both the L and heterocyclyl groups,
55) -L-(N($R^1$)-L)$_n$- aryl optionally substituted with one or more $R^A$ or $R^1$ substituents attached on either or both the L and aryl groups,
56) —O-L-N($R^1$)$R^1$,
57) —O-L- heteroaryl optionally substituted with one or more $R^A$ or $R^1$ substituents attached on either or both the L and heteroaryl groups,
58) —O-L- heterocyclyl optionally substituted with one or more $R^A$ or $R^1$ substituents attached on either or both the L and heterocyclyl groups,
59) —O-L- aryl optionally substituted with one or more $R^A$ or $R^1$ substituents attached on either or both the L and aryl groups,
60) —(O-L)$_2$-N$R^1$,
61) —O-L-(N($R^1$)-L)$_n$-N($R^1$)$R^1$,
62) —O-L-(N($R^1$)-L)$_n$- heteroaryl optionally substituted with one or more $R^A$ or $R^1$ substituents attached on either or both the L and heteroaryl groups,
63) —O-L-(N($R^1$)-L)$_n$- heterocyclyl optionally substituted with one or more $R^A$ or $R^1$ substituents attached on either or both the L and heterocyclyl groups,
64) —O-L-(N($R^1$)-L)$_n$- aryl optionally substituted with one or more $R^A$ or $R^1$ substituents,
65) —S-L- heteroaryl optionally substituted with one or more $R^A$ or $R^1$ substituents,
66) —S-L- heterocyclyl optionally substituted with one or more $R^A$ or $R^1$ substituents,
67) —S-L- aryl optionally substituted with one or more $R^A$ or $R^1$ substituents attached on either or both the L and aryl groups,
68) —(S-L)$_2$N$R^1$,
69) —S-L-(N($R^1$)-L)$_n$-N($R^1$)$R^1$,
70) —S-L-(N($R^1$)-L)$_n$- heteroaryl optionally substituted with one or more $R^A$ substituents,
71) —S-L-(N($R^1$)-L)$_n$- heterocyclyl optionally substituted with one or more $R^A$ substituents,
72) —S-L-(N($R^1$)-L)$_n$- aryl optionally substituted with one or more $R^A$ substituents,
73) —N$R^1$($R^1$),
74) —(N($R^1$)-L)$_n$-N($R^1$)$R^1$,
75) —N($R^1$)L)$_2$-N$R^1$,
76) —(N($R^1$)-L)$_n$-N($R^1$)$R^A$,
77) —(N($R^1$)-L)$_n$- heteroaryl optionally substituted with one or more $R^A$ or $R^1$ substituents,
78) —(N($R^1$)-L)$_n$- heterocyclyl optionally substituted with one or more $R^A$ or $R^1$ substituents,
79) —(N($R^1$)-L)$_n$- aryl optionally substituted with one or more $R^A$ or $R^1$ substituents,
80) -heteroaryl optionally substituted with one or more $R^A$ substituents, or
81) -aryl optionally substituted with one or more $R^A$ substituents, and wherein each substituent is optionally attached to the L group if it is not already present,
and wherein when two $R^1$ substituents are present on the same nitrogen atom, then each $R^1$ substituent is independently selected from the list of $R^1$ values described thereafter,
and wherein n is an integer equal to either 0, 1, 2, 3, 4, or 5,
and wherein, when ($R^1$) and $R^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$;

L is
1) —$C_{1-6}$ alkyl,
2) —$C_{2-6}$ alkenyl,
3) —$C_{2-6}$ alkynyl,
4) —$C_{3-7}$ cycloalkyl,
5) —$C_{3-7}$ cycloalkenyl,
6) heterocyclyl,
7) —$C_{1-6}$ alkyl-$C_{3-7}$ cycloalkyl,
8) —$C_{1-6}$ alkyl-heterocyclyl,
9) aryl, or
10) heteroaryl, and wherein the alkyl, the alkenyl, the alkynyl, the cycloalkyl, the cycloalkenyl, the heterocyclyl, the aryl and the heteroaryl groups are each independently optionally substituted with one or two $R^A$ substituent;

$R^1$ is
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ perfluorinated,
8) -heterocyclyl,
9) -aryl,
10) -heteroaryl,
11) -benzyl, or
12) 5-[(3aS,4S,6aR)-2-oxohexahydro-1H-thieno[3,4-d]imidazol-4-yl]pentanoyl, and wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 $R^A$ or $R^1$ substituents;

$R^2$ is
1) —H,
2) —$C_{1-6}$ alkyl,
3) —S$R^1$,
4) —C(O)$R^1$,
5) —S(O)$R^1$,
6) —S(O)$_2R^1$,
7) -benzyl optionally substituted with 1, 2 or 3 $R^A$ or $R^1$ substituents,
8) -L-heteroaryl optionally substituted with one or more $R^A$ or $R^1$ substituents attached on either one or both the L and the heteroaryl groups,
9) -L-heterocyclyl optionally substituted with one or more $R^A$ or $R^1$ substituents attached on either one or both the L and the heterocyclyl groups,
10) -L-aryl optionally substituted with one or more $R^A$ or $R^1$ substituents attached on either one or both the L and the aryl groups,
11) -heteroaryl optionally substituted with one or more $R^A$ or $R^1$ substituents, or
12) -aryl optionally substituted with one or more $R^A$ or $R^1$ substituents, and wherein each substituent is optionally attached to the L group if it is not already present;

$R^A$ is
1) -halogen,
2) —CF$_3$,
3) —OH,
4) —O$R^1$,
5) -L-OH,

6) -L-OR¹,
7) —OCF₃,
8) —SH,
9) —SR1,
10) —CN,
11) —NO₂,
12) —NH₂,
13) —NHR¹,
14) —NR¹R¹,
15) -L-NH₂,
16) -L-NHR¹,
17) -L-SR¹,
18) -L-S(O)R¹,
19) -L-S(O)₂R¹,
20) —C(O)OH,
21) —C(O)OR¹,
22) —C(O)NH₂,
23) —C(O)NHR¹,
24) —C(O)N(R¹)R¹,
25) —NHC(O)R¹,
26) —NR¹C(O)R¹,
27) —NHC(O)OR¹,
28) —NR¹C(O)OR¹,
29) —OC(O)NH₂,
30) —OC(O)NHR¹,
31) —OC(O)N(R¹)R¹,
32) —OC(O)R¹,
33) —C(O)R¹,
34) —NHC(O)NH₂,
35) —NHC(O)NHR¹,
36) —NHC(O)N(R¹)R¹,
37) —NR¹C(O)NH₂,
38) —NR¹C(O)NHR¹,
39) —NR¹C(O)N(R¹)R¹,
40) —NHS(O)₂R¹,
41) —NR¹S(O)₂R¹,
42) —S(O)₂NH₂,
43) —S(O)₂NHR¹,
44) —S(O)₂N(R¹)R¹,
45) —S(O)R¹,
46) —S(O)₂R¹,
47) —OS(O)₂R¹,
48) —S(O)₂OR¹,
49) -benzyl,
50) —N₃, or
51) —C(—N=N—)(CF₃),
and wherein the benzyl group is optionally substituted with 1, 2 or 3 R⁴ or R¹ substituents.

13. The method of claim 12, which is ex vivo.

14. The method of claim 13, comprising contacting the starting population with at least one cell expanding factor which is a biologic.

15. The compound according to claim 1, wherein the compound is

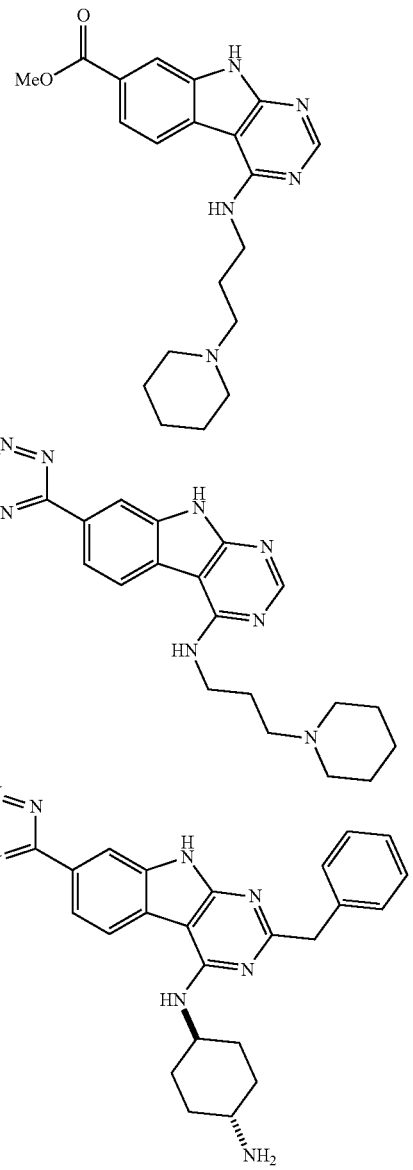

or a pharmaceutically acceptable salt thereof.

16. The compound of claim 1 which is a hydrochloride salt of

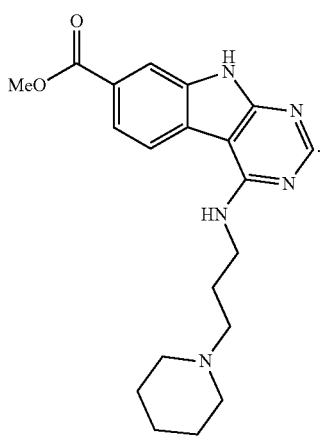 [SMILES: COC(=O)c1ccc2c(c1)[nH]c1ncnc(NCCCN3CCCCC3)c12]

17. The compound of claim 1 which is a hydrobromide salt of

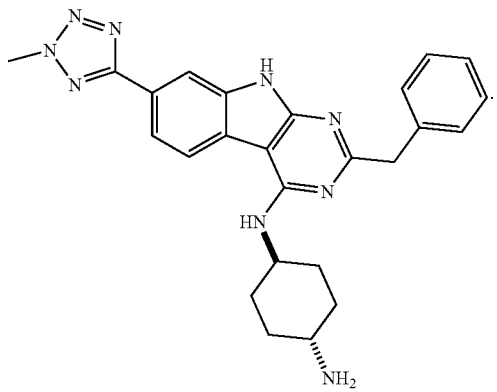

18. The method of claim 7, wherein the compound is of formula IIA, IIB or IIC

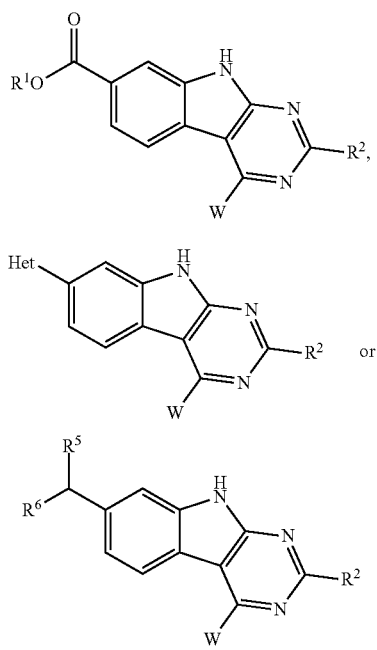

or a salt thereof, wherein Het is a 3 to 7-membered heterocycle, optionally substituted with one or more $R^1$ or $R^4$ and $R^5$ and $R^6$ join together with C to form a 5 to 7-membered ring which optionally includes one or more heteroatom selected from N, O and S, optionally the ring is substituted with one or more $R^1$ or $R^4$.

19. The method of claim 18, wherein the ring is a 5-membered ring, and the heteroatom is N.

20. The method of claim 7, wherein the compound is of formula

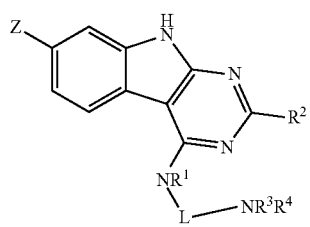

or a salt thereof, wherein $R^3$ and $R^4$ are the same or different and are each independently H or $R^1$, or $R^3$ and $R^4$ join together with N to which they are attached to form a 3 to 7-membered ring which optionally includes one or more other heteroatom selected from N, O and S, optionally the ring is substituted with one or more $R^1$ or $R^4$.

21. The method of claim 7, wherein:

Z is $CO_2Me$ or 2-methyl-2H-tetrazol-5-yl;

$R^2$ is benzyl, or H; and

W is $NH-L-N(R^1)R^1$ wherein L is $C_{2-4}$ alkyl or $C_{3-7}$ cycloalkyl and $R^1$ and (R1) is $C_{1-4}$ alkyl or H; or $(R^1)$ and $R^1$ join together with the nitrogen atom to which they are attached to form a 3 to 7-membered ring, which optionally includes one or more other heteroatom selected from N, O and S, optionally the ring is substituted with one or more $R^1$ or $R^4$.

22. The method of claim 7, wherein the compound is:

| Compound number | Structure |
|---|---|
| 1 | 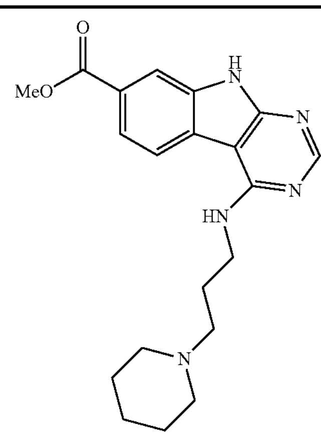 |

| Compound number | Structure |
|---|---|
| 2 | 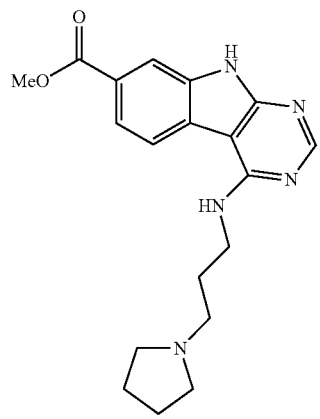 |
| 3 | 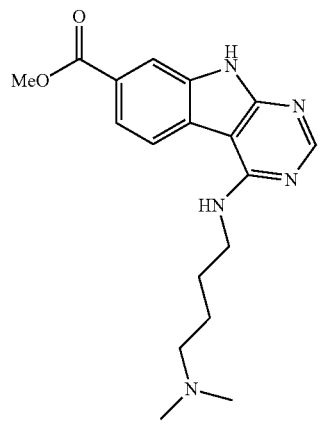 |
| 4 | 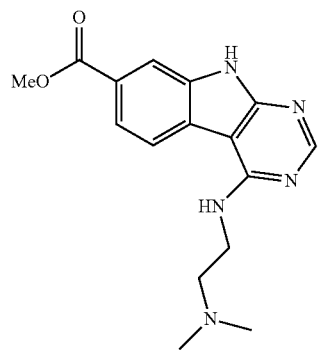 [SMILES: COC(=O)c1ccc2c(c1)[nH]c1ncnc(NCCN(C)C)c12] |

-continued

| Compound number | Structure |
|---|---|
| 5 | *(methyl 4-((3-(dimethylamino)propyl)amino)-9H-pyrimido[4,5-b]indole-7-carboxylate)* |
| 6 | *(methyl 4-((2-(piperidin-1-yl)ethyl)amino)-9H-pyrimido[4,5-b]indole-7-carboxylate)* |
| 7 | *(methyl 4-((3-(2-methylpiperidin-1-yl)propyl)amino)-9H-pyrimido[4,5-b]indole-7-carboxylate)* |
| 8 | *(methyl 4-((3-aminopropyl)amino)-9H-pyrimido[4,5-b]indole-7-carboxylate)* |

| Compound number | Structure |
|---|---|
| 9 | 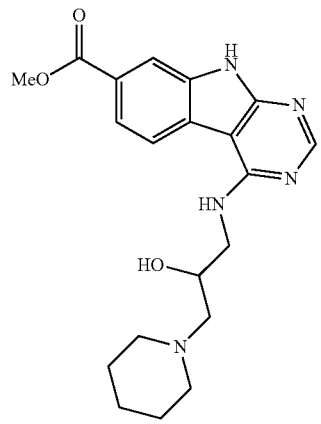 |
| 10 | 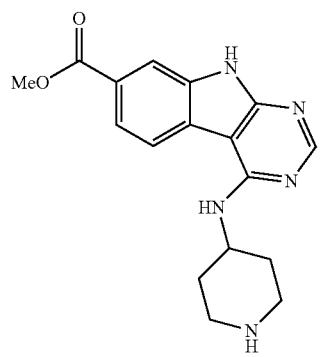 |
| 11 | 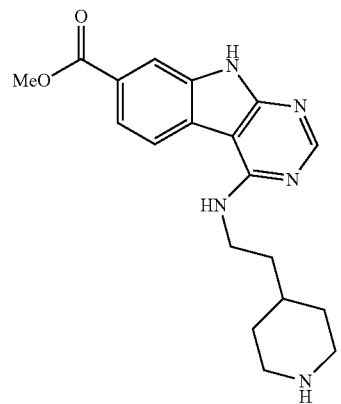 [SMILES: COC(=O)c1ccc2c(c1)[nH]c1ncnc(NCCC3CCNCC3)c12] |

| Compound number | Structure |
|---|---|
| 12 | 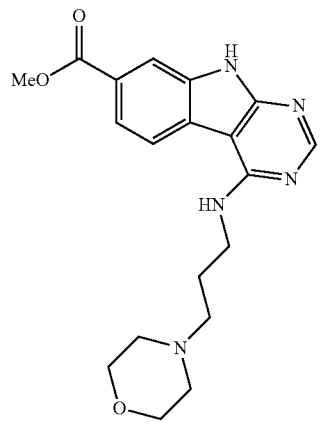 |
| 13 | 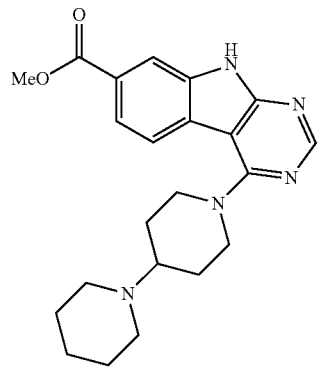 |
| 14 | 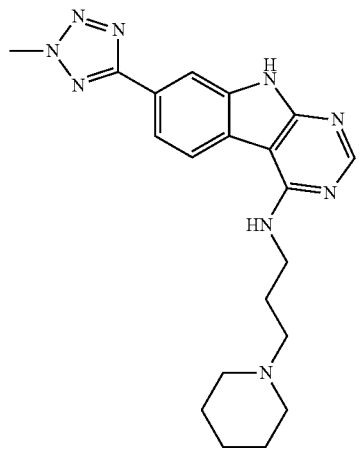 [SMILES: Cn1nnc(-c2ccc3c(c2)[nH]c2ncnc(NCCCN4CCCCC4)c23)n1] |
| 15 | 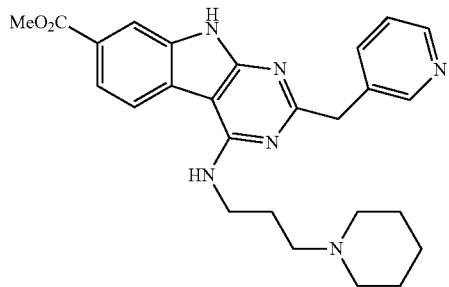 [SMILES: COC(=O)c1ccc2c(c1)[nH]c1nc(Cc3cccnc3)nc(NCCCN3CCCCC3)c12] |

-continued

| Compound number | Structure |
|---|---|
| 16 | MeO₂C-[tricyclic pyrimido-indole core with NH], 2-substituent: CH₂-(pyridin-4-yl); 4-substituent: NH-(CH₂)₃-piperidinyl |
| 17 | MeO₂C-[tricyclic pyrimido-indole core with NH], 2-substituent: CH₂-(pyrazin-2-yl); 4-substituent: NH-(CH₂)₃-piperidinyl |
| 18 | MeO₂C-[tricyclic pyrimido-indole core with NH], 2-substituent: CH₂-(thiophen-3-yl); 4-substituent: NH-(CH₂)₃-piperidinyl |
| 19 | MeO₂C-[tricyclic pyrimido-indole core with NH], 2-substituent: CH₂-(3-iodo-5-bromophenyl); 4-substituent: NH-(CH₂)₃-piperidinyl · TFA |
| 20 | MeO₂C-[tricyclic pyrimido-indole core with NH], 2-substituent: CH₂-(naphthalen-2-yl); 4-substituent: NH-(CH₂)₃-piperidinyl · TFA |

-continued
| Compound number | Structure |
|---|---|
| 21 | 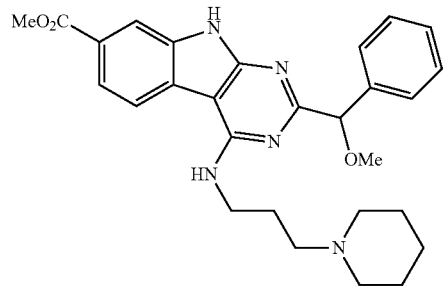 [SMILES: COC(=O)c1ccc2c(c1)[nH]c1nc(C(OC)c3ccccc3)nc(NCCCN3CCCCC3)c12] |
| 22 | 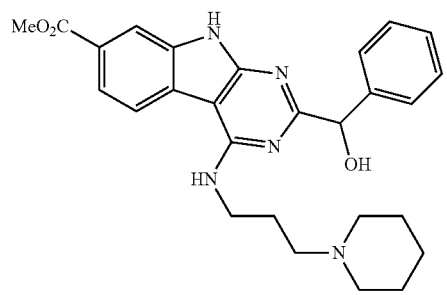 |
| 23 | 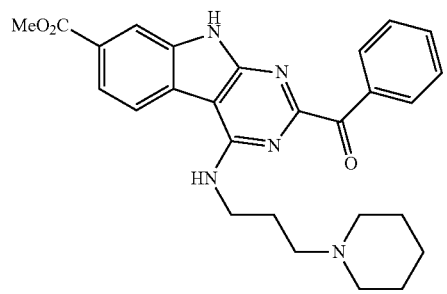 [SMILES: COC(=O)c1ccc2c(c1)[nH]c1nc(C(=O)c3ccccc3)nc(NCCCN3CCCCC3)c12] |
| 24 | 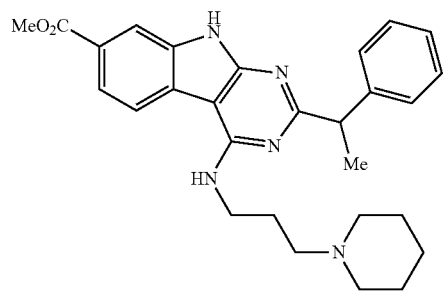 |
| 25 | 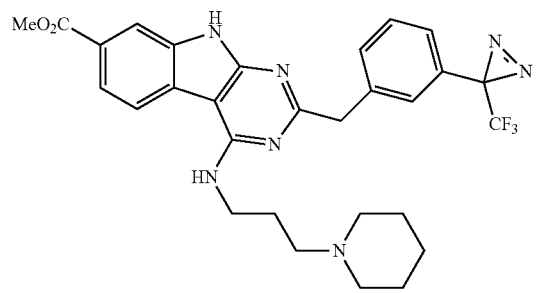 [SMILES: COC(=O)c1ccc2c(c1)[nH]c1nc(Cc3cccc(C4(C(F)(F)F)N=N4)c3)nc(NCCCN3CCCCC3)c12] |

-continued
| Compound number | Structure |
|---|---|
| 26 | 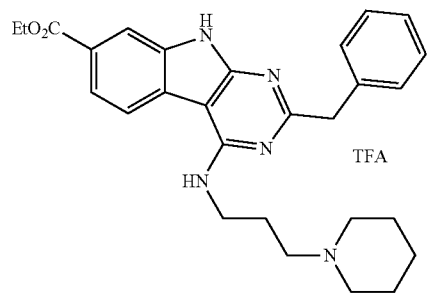 [SMILES: CCOC(=O)c1ccc2c(c1)[nH]c1nc(Cc3ccccc3)nc(NCCCN3CCCCC3)c12] |
| 27 | 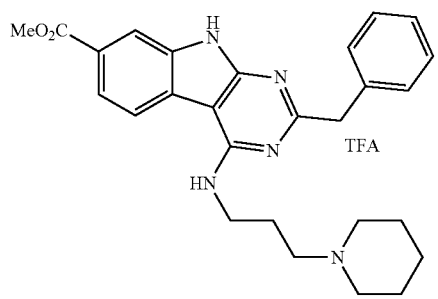 [SMILES: COC(=O)c1ccc2c(c1)[nH]c1nc(Cc3ccccc3)nc(NCCCN3CCCCC3)c12] |
| 28 | 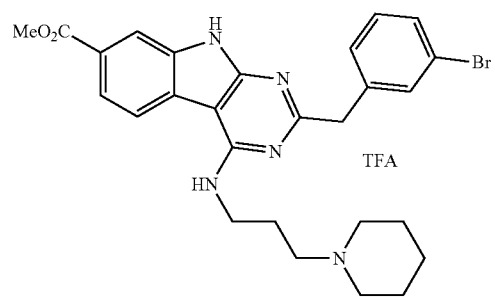 [SMILES: COC(=O)c1ccc2c(c1)[nH]c1nc(Cc3cccc(Br)c3)nc(NCCCN3CCCCC3)c12] |
| 29 | 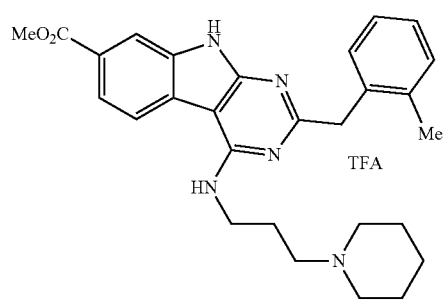 [SMILES: COC(=O)c1ccc2c(c1)[nH]c1nc(Cc3ccccc3C)nc(NCCCN3CCCCC3)c12] |
| 30 | 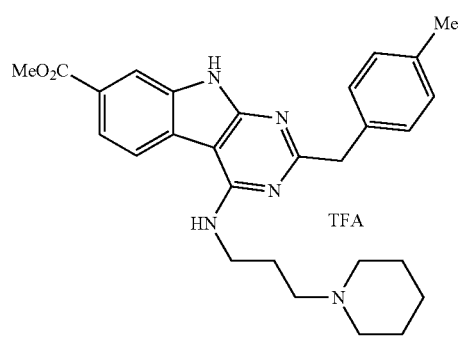 [SMILES: COC(=O)c1ccc2c(c1)[nH]c1nc(Cc3ccc(C)cc3)nc(NCCCN3CCCCC3)c12] |

-continued

| Compound number | Structure |
|---|---|
| 31 | (structure) |
| 32 | (structure) |
| 33 | (structure) |
| 34 | (structure) |
| 35 | (structure) |

| Compound number | Structure |
|---|---|
| 36 | 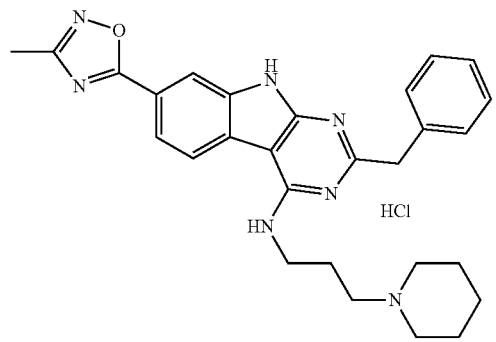 [SMILES: Cc1noc(-c2ccc3c(c2)[nH]c2nc(Cc4ccccc4)nc(NCCCN4CCCCC4)c23)n1 ; Cl] |
| 37 | 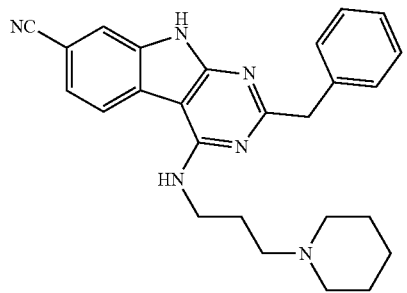 [SMILES: N#Cc1ccc2c(c1)[nH]c1nc(Cc3ccccc3)nc(NCCCN3CCCCC3)c12] |
| 38 | 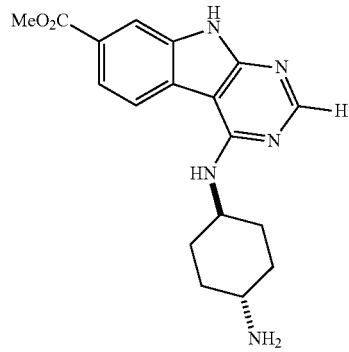 |
| 39 | 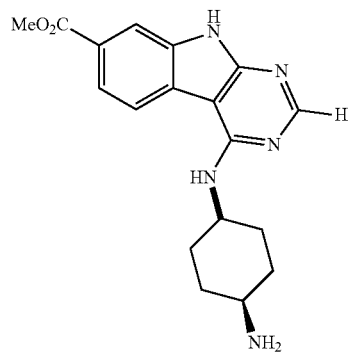 |

| Compound number | Structure |
|---|---|
| 40 | 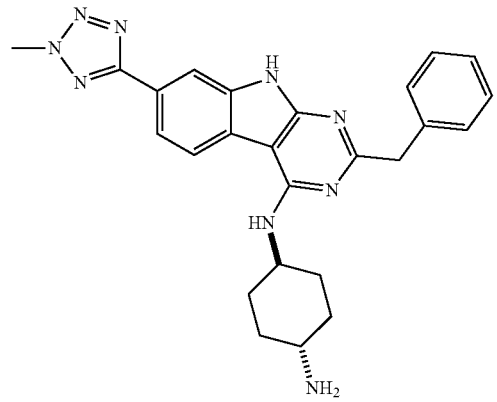 |
| 41 | 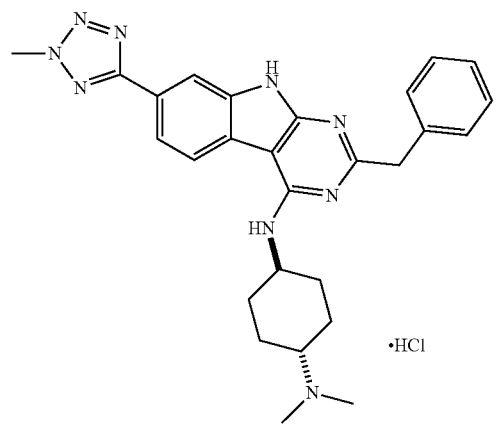 |
| 42 | 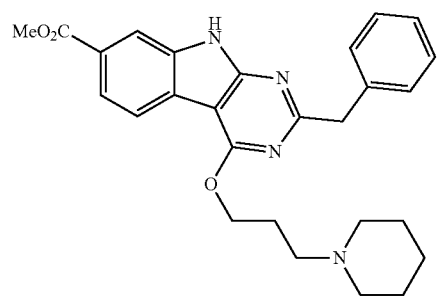 [SMILES: COC(=O)c1ccc2c(c1)[nH]c1nc(Cc3ccccc3)nc(OCCCN3CCCCC3)c12] |
| 43 | 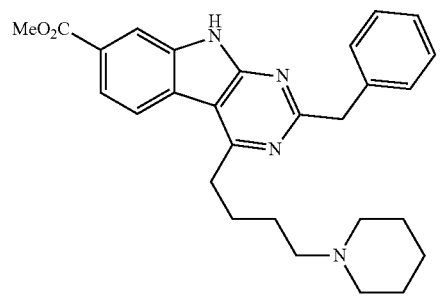 [SMILES: COC(=O)c1ccc2c(c1)[nH]c1nc(Cc3ccccc3)nc(CCCCN3CCCCC3)c12] |

-continued

| Compound number | Structure |
|---|---|
| 44 | 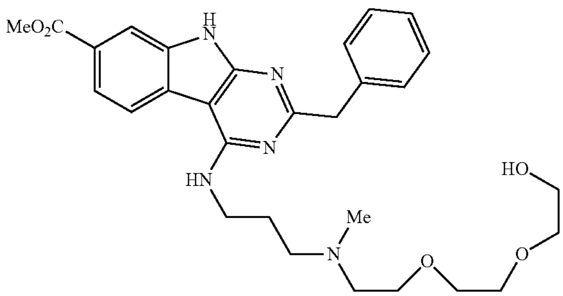 [SMILES: COC(=O)c1ccc2c(c1)[nH]c1nc(Cc3ccccc3)nc(NCCCN(C)CCOCCOCCO)c12] |
| 45 | 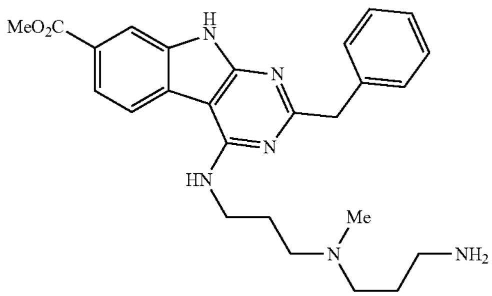 [SMILES: COC(=O)c1ccc2c(c1)[nH]c1nc(Cc3ccccc3)nc(NCCCN(C)CCCN)c12] |
| 46 | 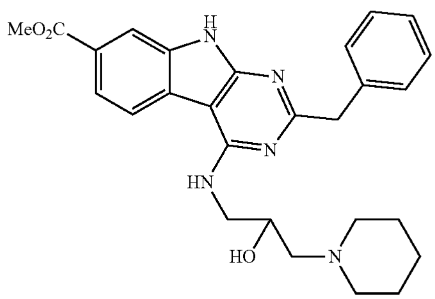 [SMILES: COC(=O)c1ccc2c(c1)[nH]c1nc(Cc3ccccc3)nc(NCC(O)CN3CCCCC3)c12] |
| 47 | 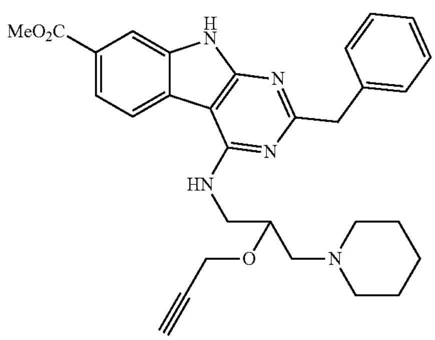 [SMILES: C#CCOC(CNc1nc(Cc2ccccc2)nc2[nH]c3cc(C(=O)OC)ccc3c12)CN1CCCCC1] |
| 48 | 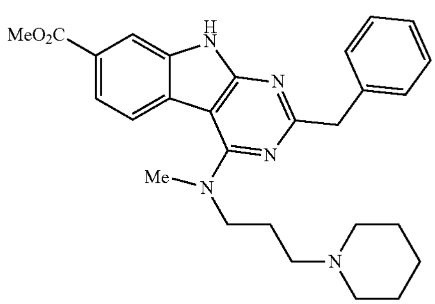 [SMILES: COC(=O)c1ccc2c(c1)[nH]c1nc(Cc3ccccc3)nc(N(C)CCCN3CCCCC3)c12] |

-continued

| Compound number | Structure |
|---|---|
| 49 | 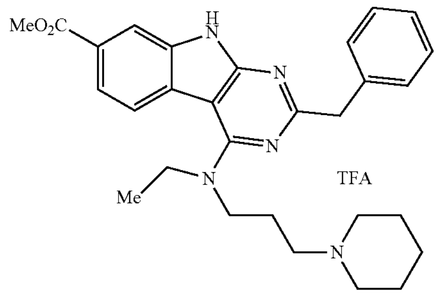 [SMILES: CCN(CCCN1CCCCC1)c1nc(Cc2ccccc2)nc2[nH]c3cc(C(=O)OC)ccc3c12] |
| 50 | 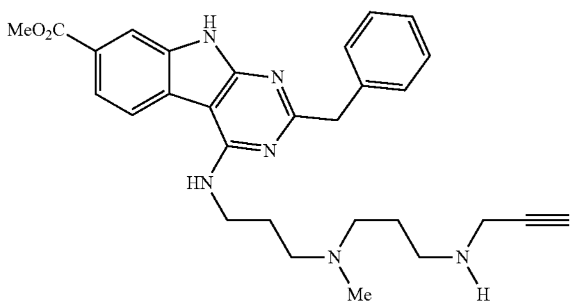 [SMILES: C#CCNCCCN(C)CCCNc1nc(Cc2ccccc2)nc2[nH]c3cc(C(=O)OC)ccc3c12] |
| 51 | 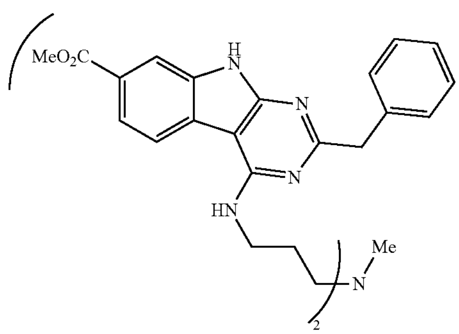 [SMILES: CNCCCNc1nc(Cc2ccccc2)nc2[nH]c3cc(C(=O)OC)ccc3c12] |
| 52 | 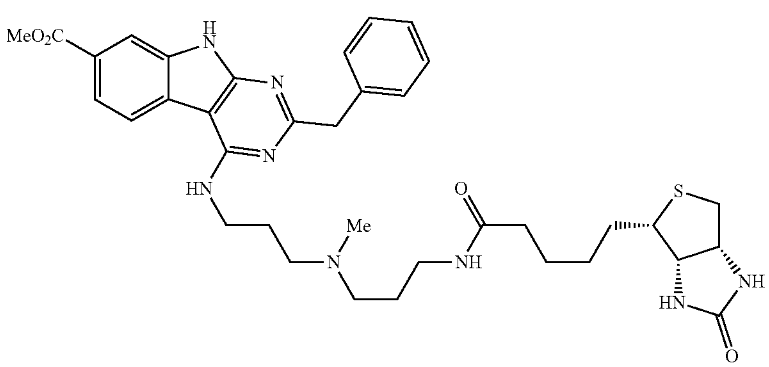 [SMILES: COC(=O)c1ccc2c(c1)[nH]c1nc(Cc3ccccc3)nc(NCCCN(C)CCCNC(=O)CCCC[C@@H]3SC[C@@H]4NC(=O)N[C@@H]43)c12] |

| Compound number | Structure |
|---|---|
| 53 | 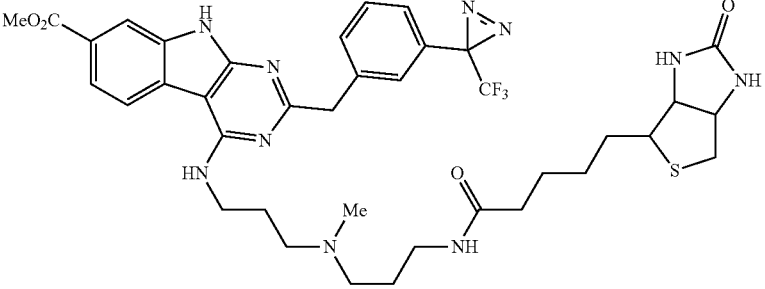 [SMILES: COC(=O)c1ccc2c(c1)[nH]c1nc(Cc3cccc(C4(C(F)(F)F)N=N4)c3)nc(NCCCN(C)CCCNC(=O)CCCCC3SCC4NC(=O)NC43)c12] |
| 54 | 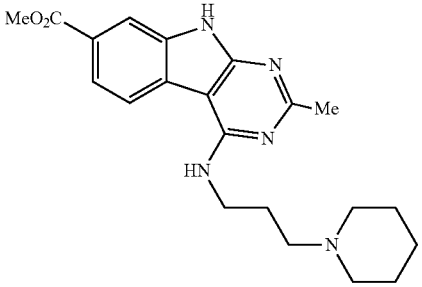 [SMILES: COC(=O)c1ccc2c(c1)[nH]c1nc(C)nc(NCCCN3CCCCC3)c12] |
| 55 | 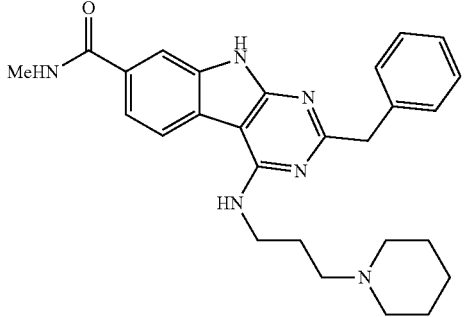 [SMILES: CNC(=O)c1ccc2c(c1)[nH]c1nc(Cc3ccccc3)nc(NCCCN3CCCCC3)c12] |
or a salt thereof.
23. The method of claim 18, wherein $R^2$ is benzyl or H.
24. The method of claim 18, wherein $R^5$ and $R^6$ join together with C to form:
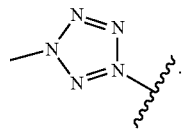
25. The method of claim 18, wherein W is
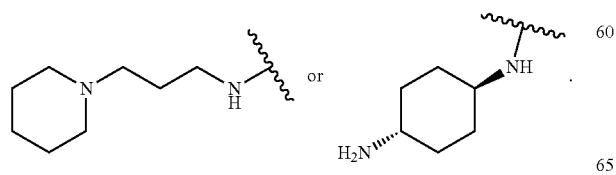
26. The method of claim 7, wherein the compound is
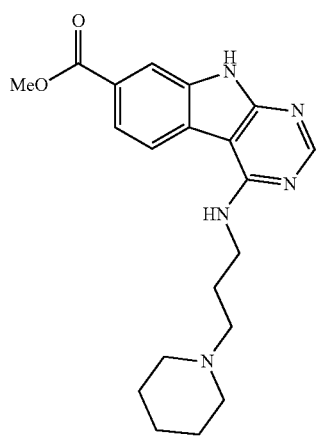

-continued

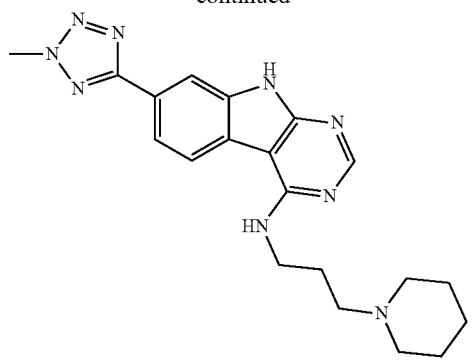

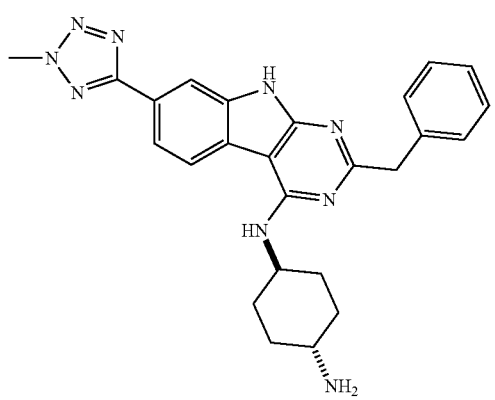

or a pharmaceutically acceptable salt thereof.

27. The method of claim 7, wherein the compound is a hydrochloride salt of

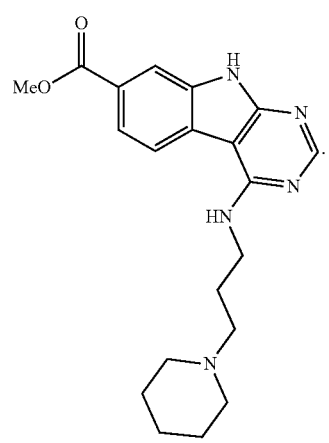 [SMILES: COC(=O)c1ccc2c(c1)[nH]c1ncnc(NCCCN3CCCCC3)c12]

28. The method of claim 7, wherein the compound is a hydrobromide salt of

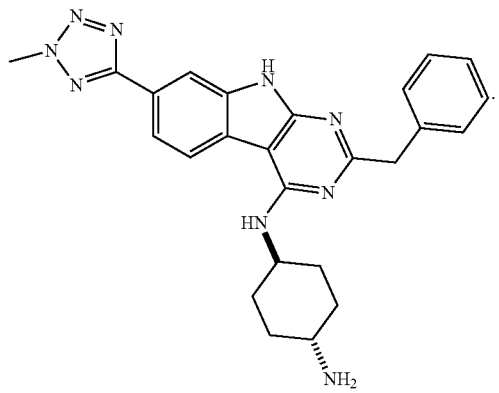

29. The method of claim 12, wherein the compound is of formula IIA, IIB or IIC

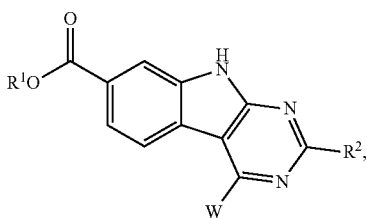
IIA

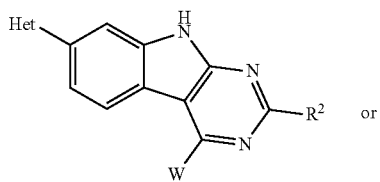
IIB

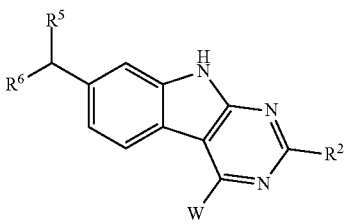
IIC or a salt thereof,
wherein Het is a 3 to 7-membered heterocycle, optionally substituted with one or more $R^1$ or $R^4$ and $R^5$ and $R^6$ join together with C to form a 5 to 7-membered ring which optionally includes one or more heteroatom selected from N, O and S, optionally the ring is substituted with one or more $R^1$ or $R^4$.

30. The method of claim 29, wherein the ring is a 5-membered ring, and the heteroatom is N.

31. The method of claim 12, wherein the compound is of formula

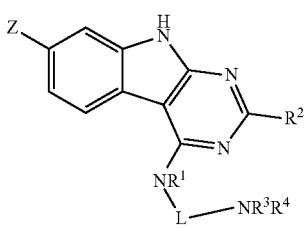

or a salt thereof,
wherein $R^3$ and $R^4$ are the same or different and are each independently H or $R^1$, or $R^3$ and $R^4$ join together with N to which they are attached to form a 3 to 7-membered ring which optionally includes one or more other heteroatom selected from N, O and S, optionally the ring is substituted with one or more $R^1$ or $R^A$.

32. The method of claim 12, wherein:
Z is $CO_2Me$ or 2-methyl-2H-tetrazol-5-yl;
$R^2$ is benzyl, or H; and
W is $NH-L-N(R^1)R^1$ wherein L is $C_{2-4}$ alkyl or $C_{3-7}$ cycloalkyl and $R^1$ and (R1) is $C_{1-4}$ alkyl or H; or
$(R^1)$ and $R^1$ join together with the nitrogen atom to which they are attached to form a 3 to 7-membered ring, which optionally includes one or more other heteroatom selected from N, O and S, optionally the ring is substituted with one or more $R^1$ or $R^A$.

33. The method of claim 12, wherein the compound is:

| Compound number | Structure |
|---|---|
| 1 | 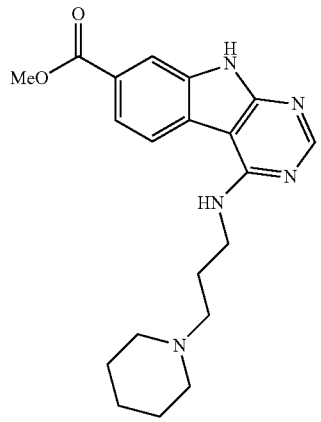 |
| 2 | 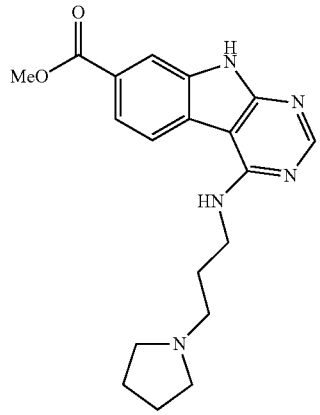 |

-continued
| Compound number | Structure |
|---|---|
| 3 | 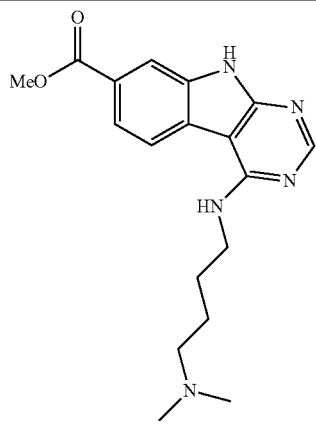 |
| 4 | 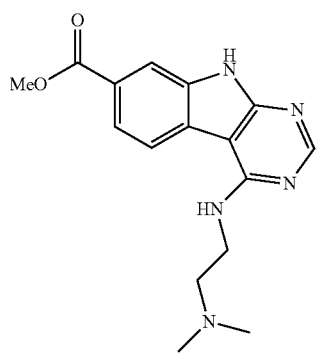 [SMILES: COC(=O)c1ccc2c(c1)[nH]c1ncnc(NCCN(C)C)c12] |
| 5 | 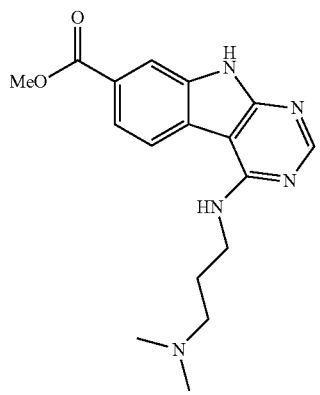 [SMILES: COC(=O)c1ccc2c(c1)[nH]c1ncnc(NCCCN(C)C)c12] |
| 6 | 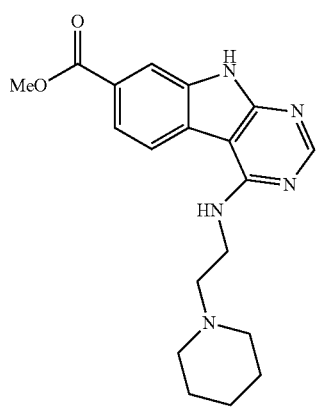 [SMILES: COC(=O)c1ccc2c(c1)[nH]c1ncnc(NCCN3CCCCC3)c12] |

-continued
| Compound number | Structure |
|---|---|
| 7 | 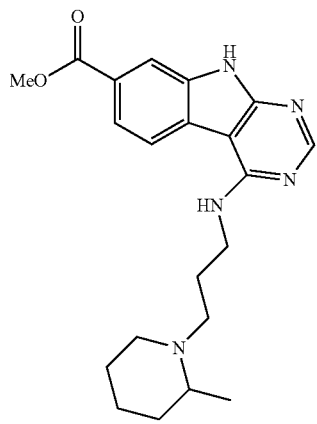 [SMILES: COC(=O)c1ccc2c(c1)[nH]c1ncnc(NCCCN3CCCCC3C)c12] |
| 8 | 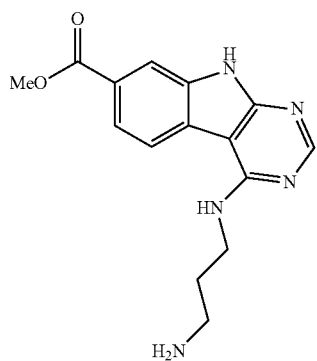 |
| 9 | 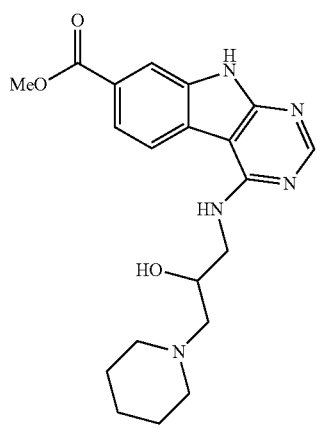 [SMILES: COC(=O)c1ccc2c(c1)[nH]c1ncnc(NCC(O)CN3CCCCC3)c12] |
| 10 | 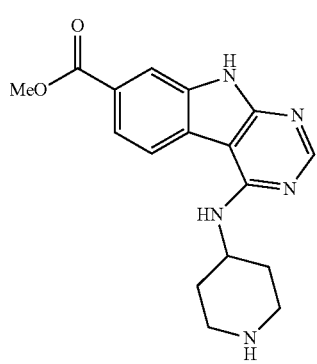 |

-continued
| Compound number | Structure |
|---|---|
| 11 | 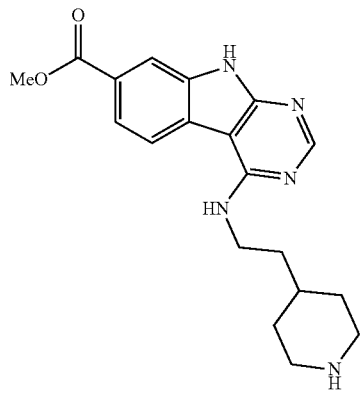 [SMILES: COC(=O)c1ccc2c(c1)[nH]c1ncnc(NCCC3CCNCC3)c12] |
| 12 | 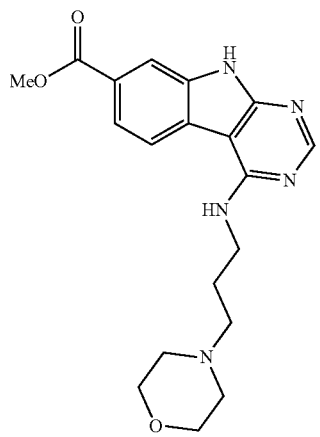 [SMILES: COC(=O)c1ccc2c(c1)[nH]c1ncnc(NCCCN3CCOCC3)c12] |
| 13 | 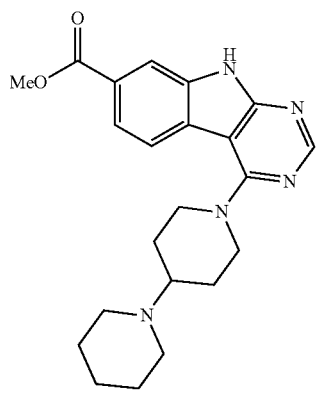 [SMILES: COC(=O)c1ccc2c(c1)[nH]c1ncnc(N3CCC(N4CCCCC4)CC3)c12] |

| Compound number | Structure |
|---|---|
| 14 | 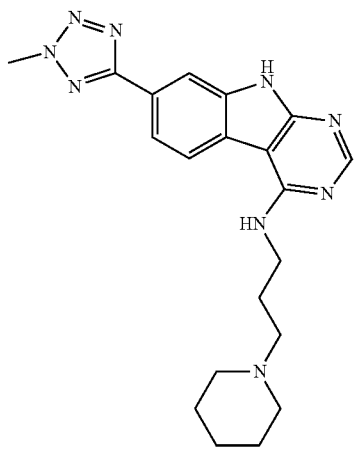 [SMILES: Cn1nnc(-c2ccc3c(c2)[nH]c2ncnc(NCCCN4CCCCC4)c23)n1] |
| 15 | 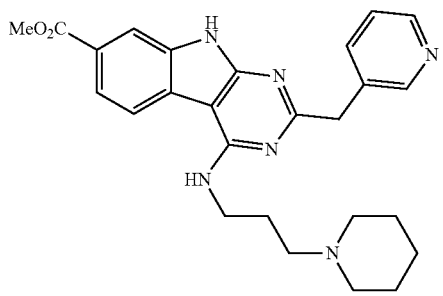 [SMILES: COC(=O)c1ccc2c(c1)[nH]c1nc(Cc3cccnc3)nc(NCCCN3CCCCC3)c12] |
| 16 | 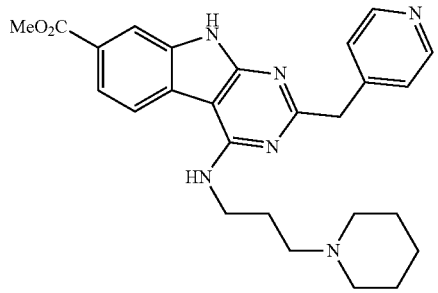 [SMILES: COC(=O)c1ccc2c(c1)[nH]c1nc(Cc3ccncc3)nc(NCCCN3CCCCC3)c12] |
| 17 | 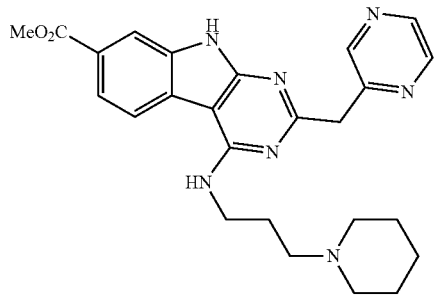 [SMILES: COC(=O)c1ccc2c(c1)[nH]c1nc(Cc3cnccn3)nc(NCCCN3CCCCC3)c12] |

-continued

| Compound number | Structure |
|---|---|
| 18 | *Structure: methyl ester-substituted pyrimido-indole with thiophen-3-ylmethyl group and HN-(CH2)3-piperidine substituent* |
| 19 | *Structure: methyl ester-substituted pyrimido-indole with 3-iodo-5-bromobenzyl group and HN-(CH2)3-piperidine substituent; TFA salt* |
| 20 | *Structure: methyl ester-substituted pyrimido-indole with naphthalen-2-ylmethyl group and HN-(CH2)3-piperidine substituent; TFA salt* |
| 21 | *Structure: methyl ester-substituted pyrimido-indole with phenyl(methoxy)methyl group and HN-(CH2)3-piperidine substituent* |
| 22 | *Structure: methyl ester-substituted pyrimido-indole with phenyl(hydroxy)methyl group and HN-(CH2)3-piperidine substituent* |

-continued
| Compound number | Structure |
|---|---|
| 23 | 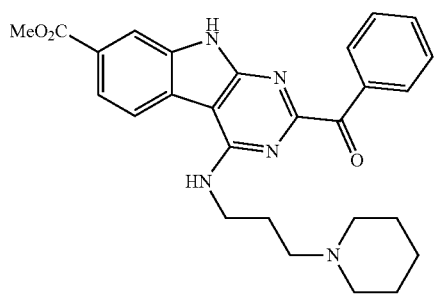 [SMILES: COC(=O)c1ccc2c(c1)[nH]c1nc(C(=O)c3ccccc3)nc(NCCCN3CCCCC3)c12] |
| 24 | 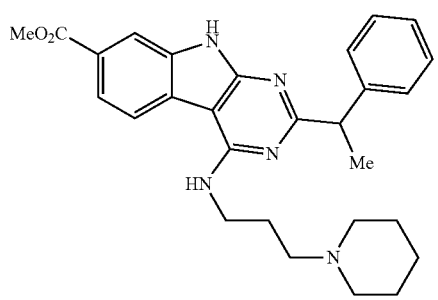 [SMILES: COC(=O)c1ccc2c(c1)[nH]c1nc(C(C)c3ccccc3)nc(NCCCN3CCCCC3)c12] |
| 25 | 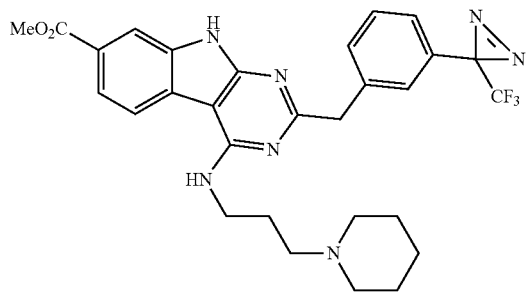 [SMILES: COC(=O)c1ccc2c(c1)[nH]c1nc(Cc3cccc(C4(C(F)(F)F)N=N4)c3)nc(NCCCN3CCCCC3)c12] |
| 26 | 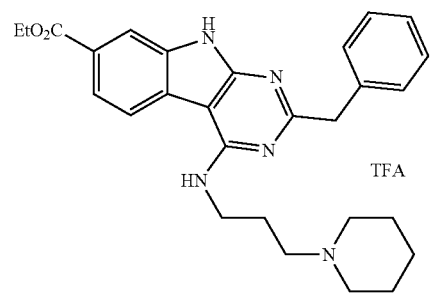 [SMILES: CCOC(=O)c1ccc2c(c1)[nH]c1nc(Cc3ccccc3)nc(NCCCN3CCCCC3)c12] |
| 27 | 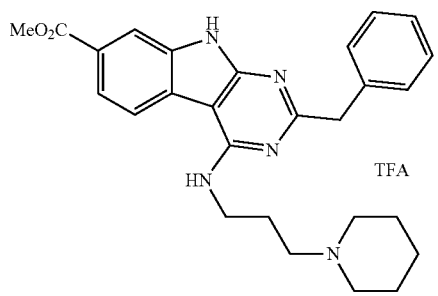 [SMILES: COC(=O)c1ccc2c(c1)[nH]c1nc(Cc3ccccc3)nc(NCCCN3CCCCC3)c12] |

-continued
| Compound number | Structure |
|---|---|
| 28 | 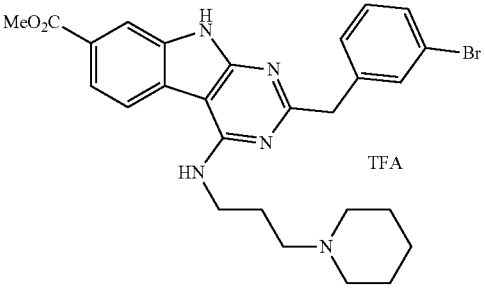 TFA |
| 29 | 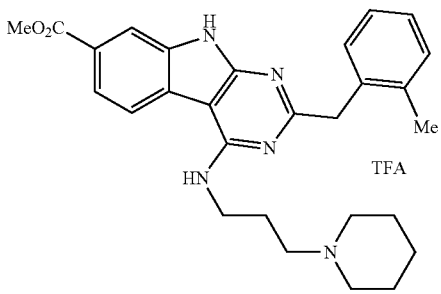 TFA |
| 30 | 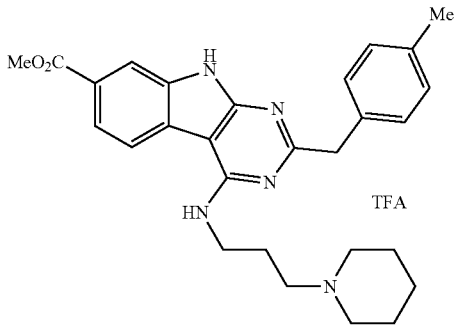 TFA |
| 31 | 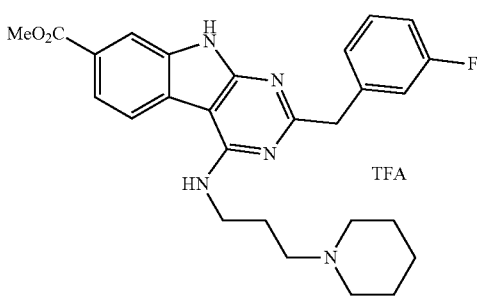 TFA |
| 32 | 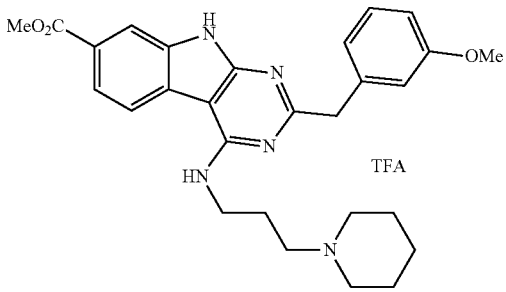 TFA |

-continued

| Compound number | Structure |
|---|---|
| 33 | (structure) |
| 34 | (structure) |
| 35 | (structure) TFA |
| 36 | (structure) HCl |
| 37 | (structure) |

-continued
| Compound number | Structure |
|---|---|
| 38 | 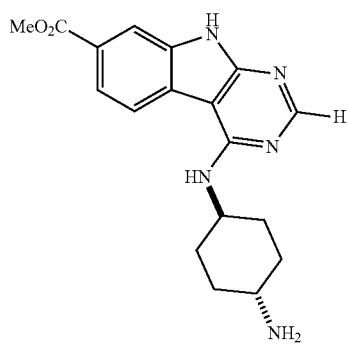 |
| 39 | 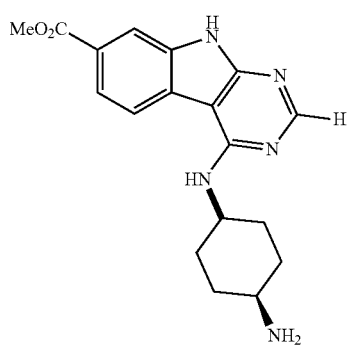 |
| 40 | 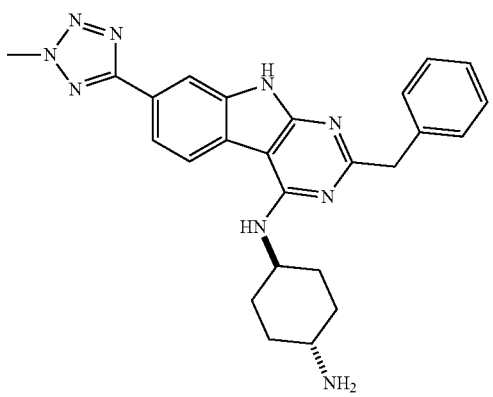 |
| 41 | 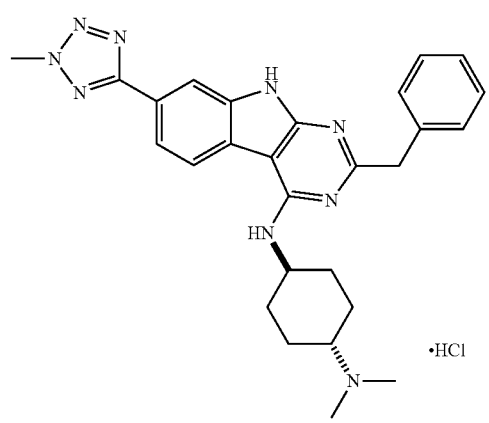 |

-continued
| Compound number | Structure |
|---|---|
| 42 | 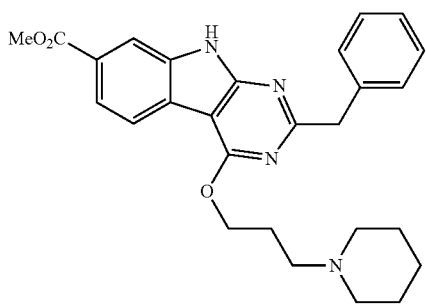 [SMILES: COC(=O)c1ccc2c(c1)[nH]c1nc(Cc3ccccc3)nc(CCCCN3CCCCC3)c12] |
| 43 | 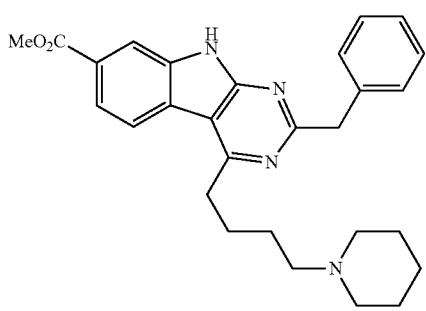 |
| 44 | 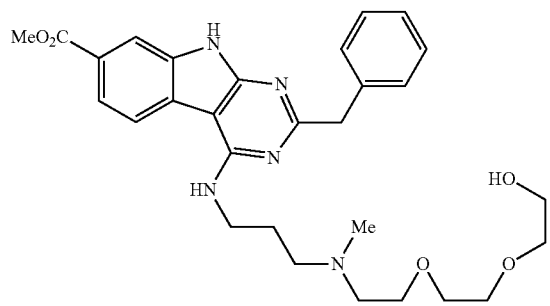 [SMILES: COC(=O)c1ccc2c(c1)[nH]c1nc(Cc3ccccc3)nc(NCCCN(C)CCOCCOCCO)c12] |
| 45 | 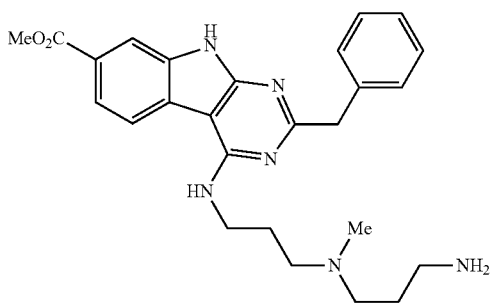 [SMILES: COC(=O)c1ccc2c(c1)[nH]c1nc(Cc3ccccc3)nc(NCCCN(C)CCCN)c12] |
| 46 | 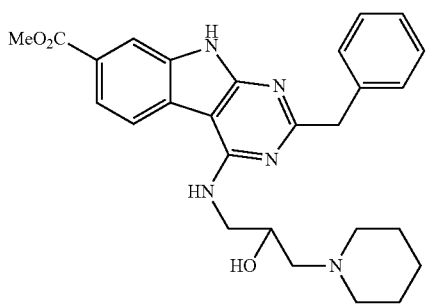 [SMILES: COC(=O)c1ccc2c(c1)[nH]c1nc(Cc3ccccc3)nc(NCC(O)CN3CCCCC3)c12] |

-continued
| Compound number | Structure |
|---|---|
| 47 | 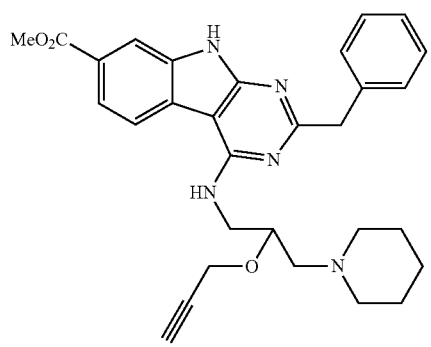 [SMILES: C#CCOC(CNc1nc(Cc2ccccc2)nc2[nH]c3cc(C(=O)OC)ccc3c12)CN1CCCCC1] |
| 48 | 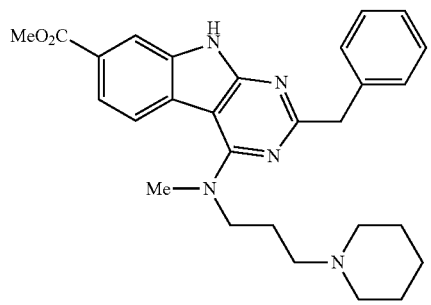 [SMILES: COC(=O)c1ccc2c(c1)[nH]c1nc(Cc3ccccc3)nc(N(C)CCCN3CCCCC3)c12] |
| 49 | 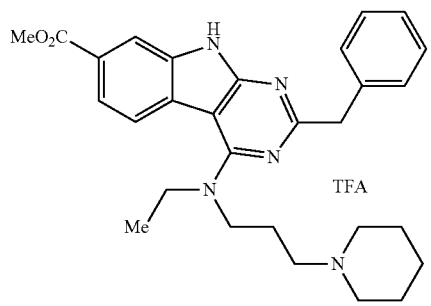 [SMILES: CCN(CCCN1CCCCC1)c1nc(Cc2ccccc2)nc2[nH]c3cc(C(=O)OC)ccc3c12] |
| 50 | 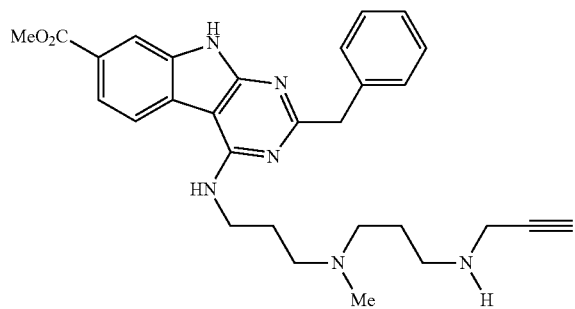 [SMILES: C#CCNCCCN(C)CCCNc1nc(Cc2ccccc2)nc2[nH]c3cc(C(=O)OC)ccc3c12] |

-continued

| Compound number | Structure |
|---|---|
| 51 | (structure) |
| 52 | (structure) |
| 53 | (structure) |
| 54 | (structure) |
| 55 | (structure) | or a salt thereof.

34. The method of claim 29, wherein $R^2$ is benzyl or H.

35. The method of claim 29, wherein $R^5$ and $R^6$ join together with C to form:

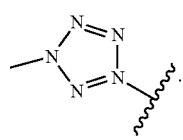

36. The method of claim 29, wherein W is

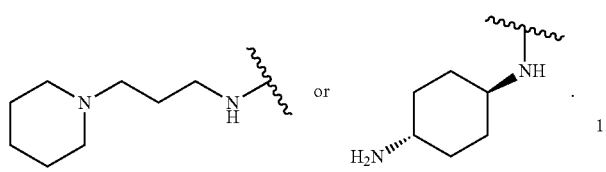

37. The method of claim 12, wherein the compound is

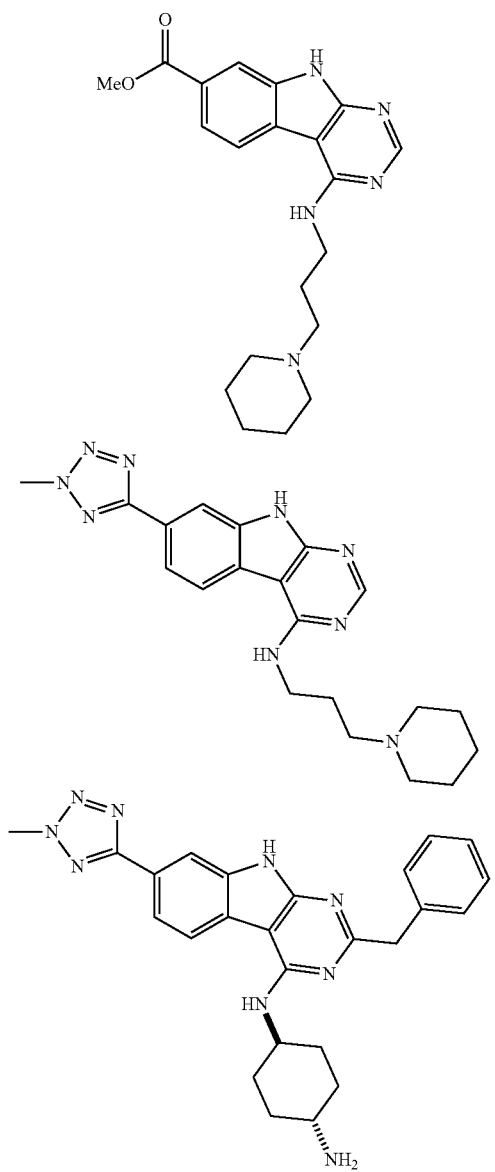

or a pharmaceutically acceptable salt thereof.

38. The method of claim 12, wherein the compound is a hydrochloride salt of

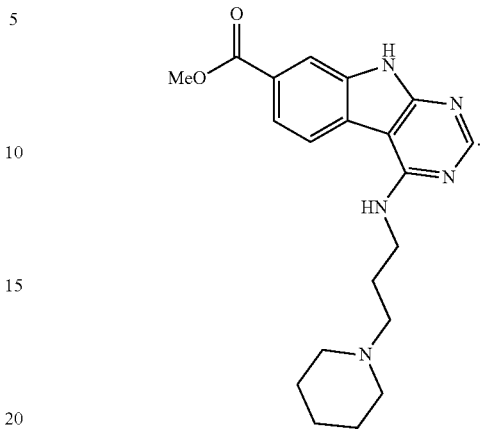

39. The method of claim 12, wherein the compound is a hydrobromide salt of

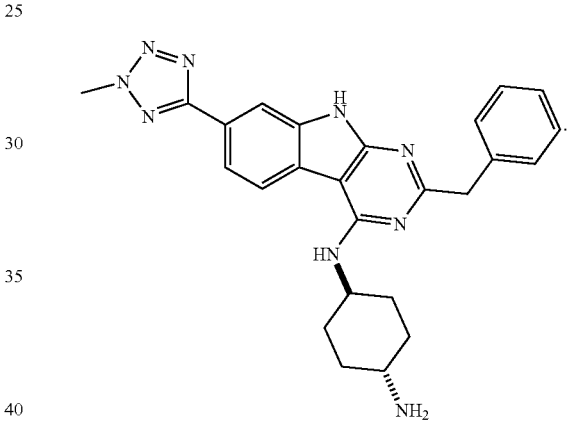

40. The method according to claim 12, wherein the stem and progenitor cells are human hematopoietic stem and progenitor cells.

41. The method according to claim 12, wherein the starting cell population includes CD34+ cells harvested from mobilized peripheral blood (mPB), bone marrow (BM) or umbilical cord blood (UCB).

42. The method according to claim 41, wherein the starting cell population includes CD34+ cells harvested from umbilical cord blood (UCB).

43. The method according to claim 12, wherein the starting cell population essentially consists of CD34+ cells purified from one or two umbilical cord blood units.

44. The method according to claim 43, comprising culturing the starting cell population in presence of said compound from about 2 days to about 21 days.

45. The method according to claim 43, comprising administering said compound to the starting cell population at a concentration between 1 nM and 3000 nM.

46. The method of claim 14, wherein the biologic comprises Interleukin-3 (IL-3), Granulocyte Macrophage Colony-Stimulating Factor (GM-CSF), Thrombopoietin (TPO), FMS-Like Tyrosine Kinase 3 Ligand (FLT3-L), Stem Cell Factor (SCF), Interleukin-6 (IL-6) or a combination thereof.

47. The method of claim 46, wherein the biologic comprises SCF, FLT3-L, TPO, IL-6 or a combination thereof.

48. The method of claim 12, wherein the other small molecule is StemRegenin 1 (SR1).

49. A cell population as expanded according to a method as defined in claim 12.

* * * * *